(12) United States Patent
Kennedy et al.

(10) Patent No.: US 10,236,078 B2
(45) Date of Patent: *Mar. 19, 2019

(54) METHODS FOR PROCESSING OR ANALYZING A SAMPLE OF THYROID TISSUE

(71) Applicant: VERACYTE, INC., South San Francisco, CA (US)

(72) Inventors: Giulia C. Kennedy, San Francisco, CA (US); Darya I. Chudova, San Jose, CA (US); Eric T. Wang, Milpitas, CA (US); Jonathan I. Wilde, Burlingame, CA (US)

(73) Assignee: Veracyte, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/661,496

(22) Filed: Jul. 27, 2017

(65) Prior Publication Data
US 2017/0329894 A1 Nov. 16, 2017

Related U.S. Application Data

(63) Continuation-in-part of application No. 15/274,492, filed on Sep. 23, 2016, now Pat. No. 9,856,537, which is a continuation of application No. 12/964,666, filed on Dec. 9, 2010, now Pat. No. 9,495,515, application No. 15/661,496, which is a continuation-in-part of application No. 13/589,022, filed on Aug. 17, 2012, which is a continuation of application No. 12/592,065, filed on Nov. 17, 2009, now Pat. No. 8,541,170.

(60) Provisional application No. 61/285,165, filed on Dec. 9, 2009, provisional application No. 61/199,585, filed on Nov. 17, 2008, provisional application No. 61/270,812, filed on Jul. 13, 2009.

(51) Int. Cl.

| | | |
|---|---|---|
| G06F 19/00 | (2018.01) |
| G06F 19/24 | (2011.01) |
| G06F 19/20 | (2011.01) |
| G01N 33/48 | (2006.01) |
| C12Q 1/68 | (2018.01) |
| C40B 30/04 | (2006.01) |
| G16B 25/00 | (2019.01) |
| G01N 33/50 | (2006.01) |
| C12Q 1/6886 | (2018.01) |
| G01N 33/574 | (2006.01) |
| G16H 10/40 | (2018.01) |
| G16H 15/00 | (2018.01) |
| G16H 50/20 | (2018.01) |
| G16H 40/63 | (2018.01) |
| G06N 20/00 | (2019.01) |

(52) U.S. Cl.
CPC ........... *G16B 25/00* (2019.02); *C12Q 1/6886* (2013.01); *G01N 33/5091* (2013.01); *G01N 33/57407* (2013.01); *G06F 19/00* (2013.01); *G06F 19/20* (2013.01); *G06F 19/24* (2013.01); *C12Q 2600/158* (2013.01); *G06N 20/00* (2019.01); *G16H 10/40* (2018.01); *G16H 15/00* (2018.01); *G16H 40/63* (2018.01); *G16H 50/20* (2018.01)

(58) Field of Classification Search
None
See application file for complete search history.

(56) References Cited

U.S. PATENT DOCUMENTS

| | | |
|---|---|---|
| 3,645,691 A | 2/1972 | Guenter et al. |
| 5,965,360 A | 10/1999 | Zain et al. |
| 5,989,815 A | 11/1999 | Skolnick et al. |
| 6,022,692 A | 2/2000 | Coulie et al. |
| 6,027,887 A | 2/2000 | Zavada et al. |
| 6,225,051 B1 | 5/2001 | Sugiyama et al. |
| 6,268,142 B1 | 7/2001 | Duff et al. |
| 6,436,642 B1 | 8/2002 | Gould-Rothberg et al. |
| 6,723,506 B2 | 4/2004 | Fletcher et al. |
| 7,186,514 B2 | 3/2007 | Zavada et al. |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,280,922 B2 | 10/2007 | Mei et al. |
| 7,300,788 B2 | 11/2007 | Matsuzaki et al. |
| 7,319,011 B2 | 1/2008 | Riggins et al. |
| 7,323,305 B2 | 1/2008 | Leamon et al. |

(Continued)

FOREIGN PATENT DOCUMENTS

| | | |
|---|---|---|
| CN | 101501214 A | 8/2009 |
| EP | 1975245 A1 | 10/2008 |

(Continued)

OTHER PUBLICATIONS

Wessels, et al., A protocol for building and evaluating predictors of disease state based on microarray data, Bioinformatics, 2005, 21:3755-3762.
Abrosimov et al. The cytoplasmic expression of MUC1 in papillary thyroid carcinoma of different histological variants and its correlation with cyclin D1 overexpression. Endocr Pathol. 2007;18(2):68-75.
Abubaker et al. Clinicopathological analysis of papillary thyroid cancer with PIK3CA alterations in a Middle Eastern population. J Clin Endocrinol Metab. 2008;93(2):611-8.

(Continued)

*Primary Examiner* — Channing S Mahatan
(74) *Attorney, Agent, or Firm* — Wilson, Sonsini, Goodrich & Rosati, PC

(57) ABSTRACT

The present disclosure provides methods for processing or analyzing a sample of tissue of a subject, to generate a classification of the sample of tissue as positive or negative for thyroid cancer. The present disclosure also provides algorithms and methods of classifying cancer, for example, thyroid cancer, methods of determining molecular profiles, and methods of analyzing results.

29 Claims, 113 Drawing Sheets

(56) References Cited

U.S. PATENT DOCUMENTS

| | | |
|---|---|---|
| 7,335,762 B2 | 2/2008 | Rothberg et al. |
| 7,358,061 B2 | 4/2008 | Yamamoto et al. |
| 7,361,488 B2 | 4/2008 | Fan et al. |
| 7,378,233 B2 | 5/2008 | Sidransky et al. |
| 7,407,755 B2 | 8/2008 | Lubinski et al. |
| 7,541,169 B2 | 6/2009 | Freimuth et al. |
| 7,598,052 B2 | 10/2009 | Giordano et al. |
| 7,767,391 B2 | 8/2010 | Scott et al. |
| 7,901,881 B2 | 3/2011 | Libutti et al. |
| 7,901,888 B2 | 3/2011 | Kebebew |
| 7,927,826 B2 | 4/2011 | Riggins et al. |
| 8,008,009 B2 | 8/2011 | Choquet-Kastylevsky et al. |
| 8,202,692 B2 | 6/2012 | Giordano et al. |
| 8,293,880 B2 | 10/2012 | Cote et al. |
| 8,354,228 B2 | 1/2013 | Ron |
| 8,465,914 B2 | 6/2013 | Brown et al. |
| 8,541,170 B2 | 9/2013 | Kennedy et al. |
| 8,568,971 B2 | 10/2013 | Brown et al. |
| 8,669,057 B2 | 3/2014 | Kennedy et al. |
| 8,802,599 B2 | 8/2014 | Aharonov et al. |
| 8,828,656 B2 | 9/2014 | Bullerdiek et al. |
| 8,877,445 B2 | 11/2014 | Shackney |
| 8,945,829 B2 | 2/2015 | Keutgen et al. |
| 9,040,286 B2 | 5/2015 | Zon et al. |
| 9,096,906 B2 | 8/2015 | Aharonov et al. |
| 9,157,123 B2 | 10/2015 | Xing |
| 9,175,352 B2 | 11/2015 | Keutgen et al. |
| 9,234,244 B2 | 1/2016 | Zeiger et al. |
| 9,495,515 B1 | 11/2016 | Kennedy et al. |
| 9,587,279 B2 | 3/2017 | Fahey, III et al. |
| 9,708,667 B2 | 7/2017 | Barnett-Itzhaki et al. |
| 9,856,537 B2 * | 1/2018 | Kennedy ............ C12Q 1/6886 |
| 2001/0051344 A1 | 12/2001 | Shalon et al. |
| 2002/0076735 A1 | 6/2002 | Williams et al. |
| 2002/0169137 A1 | 11/2002 | Reiner et al. |
| 2003/0186248 A1 | 10/2003 | Erlander et al. |
| 2003/0190602 A1 | 10/2003 | Pressman et al. |
| 2004/0019466 A1 | 1/2004 | Minor et al. |
| 2005/0042222 A1 | 2/2005 | Yamamoto et al. |
| 2005/0048533 A1 | 3/2005 | Sidransky et al. |
| 2005/0137805 A1 | 6/2005 | Lewin et al. |
| 2005/0240357 A1 | 10/2005 | Minor |
| 2005/0250125 A1 | 11/2005 | Novakoff |
| 2005/0266443 A1 | 12/2005 | Croce et al. |
| 2006/0019256 A1 | 1/2006 | Clarke et al. |
| 2006/0019615 A1 | 1/2006 | Ditmer |
| 2006/0035244 A1 | 2/2006 | Riggins et al. |
| 2006/0083744 A1 | 4/2006 | Chen et al. |
| 2006/0088851 A1 | 4/2006 | Erlander et al. |
| 2006/0094061 A1 | 5/2006 | Brys et al. |
| 2006/0105360 A1 | 5/2006 | Croce et al. |
| 2006/0127907 A1 | 6/2006 | Matsubara et al. |
| 2007/0020657 A1 | 1/2007 | Grebe et al. |
| 2007/0037186 A1 | 2/2007 | Jiang et al. |
| 2007/0048738 A1 | 3/2007 | Donkena et al. |
| 2007/0065833 A1 | 3/2007 | Gupta |
| 2007/0099209 A1 | 5/2007 | Clarke et al. |
| 2007/0105133 A1 | 5/2007 | Clarke et al. |
| 2007/0148667 A1 | 6/2007 | Williams et al. |
| 2007/0148687 A1 | 6/2007 | Bedingham et al. |
| 2007/0161004 A1 | 7/2007 | Brown et al. |
| 2007/0172844 A1 | 7/2007 | Lancaster et al. |
| 2007/0220621 A1 | 9/2007 | Clarke et al. |
| 2007/0238119 A1 | 10/2007 | Yu et al. |
| 2008/0028302 A1 | 1/2008 | Meschkat |
| 2008/0044824 A1 | 2/2008 | Giordano et al. |
| 2008/0124344 A1 | 5/2008 | Combs et al. |
| 2008/0131892 A1 | 6/2008 | Becker et al. |
| 2008/0145841 A1 | 6/2008 | Libutti et al. |
| 2008/0254470 A1 | 10/2008 | Berlin |
| 2008/0274457 A1 | 11/2008 | Eng et al. |
| 2008/0281568 A1 | 11/2008 | Kao et al. |
| 2009/0020433 A1 | 1/2009 | Cohen et al. |
| 2009/0191535 A1 | 7/2009 | Connelly et al. |
| 2009/0204333 A1 | 8/2009 | Friend et al. |
| 2010/0055704 A1 | 3/2010 | Giordano et al. |
| 2010/0099093 A1 | 4/2010 | Weaver et al. |
| 2010/0131286 A1 | 5/2010 | Houlgatte et al. |
| 2010/0131432 A1 | 5/2010 | Kennedy et al. |
| 2010/0178653 A1 | 7/2010 | Aharonov et al. |
| 2010/0285979 A1 | 11/2010 | Zeiger et al. |
| 2011/0092375 A1 | 4/2011 | Zamore et al. |
| 2011/0152110 A1 | 6/2011 | Vierlinger et al. |
| 2011/0212855 A1 | 9/2011 | Rafnar et al. |
| 2011/0230372 A1 | 9/2011 | Willman et al. |
| 2011/0287946 A1 | 11/2011 | Gudmundsson et al. |
| 2011/0312520 A1 | 12/2011 | Kennedy et al. |
| 2012/0015843 A1 | 1/2012 | Von et al. |
| 2012/0115743 A1 | 5/2012 | Davicioni et al. |
| 2012/0122718 A1 | 5/2012 | Reisman |
| 2012/0157334 A1 | 6/2012 | Beaudenon-Huibregtse et al. |
| 2012/0172243 A1 | 7/2012 | Davicioni et al. |
| 2012/0214165 A1 | 8/2012 | Walfish et al. |
| 2012/0220474 A1 | 8/2012 | Kennedy et al. |
| 2013/0142728 A1 | 6/2013 | Beaudenon-Huibregtse et al. |
| 2013/0150257 A1 | 6/2013 | Abdueva et al. |
| 2013/0172203 A1 | 7/2013 | Yeatman et al. |
| 2013/0225662 A1 | 8/2013 | Kennedy et al. |
| 2013/0231258 A1 | 9/2013 | Wilde et al. |
| 2013/0273543 A1 | 10/2013 | Gudmundsson et al. |
| 2014/0087961 A1 | 3/2014 | Sulem et al. |
| 2014/0121126 A1 | 5/2014 | Bivona et al. |
| 2014/0228237 A1 | 8/2014 | Kennedy et al. |
| 2014/0243240 A1 | 8/2014 | Soldin et al. |
| 2014/0315199 A1 | 10/2014 | Rhodes et al. |
| 2014/0315739 A1 | 10/2014 | Aharonov et al. |
| 2014/0349856 A1 | 11/2014 | Schnabel et al. |
| 2014/0349864 A1 | 11/2014 | Kennedy et al. |
| 2014/0371096 A1 | 12/2014 | Umbricht et al. |
| 2015/0038376 A1 | 2/2015 | Tian et al. |
| 2015/0099665 A1 | 4/2015 | Rosenfeld et al. |
| 2015/0141470 A1 | 5/2015 | Garraway et al. |
| 2015/0275306 A1 | 10/2015 | Bernards et al. |
| 2015/0299808 A1 | 10/2015 | Gonzalez et al. |
| 2015/0307947 A1 | 10/2015 | Basu et al. |
| 2015/0368724 A1 | 12/2015 | Aharonov et al. |
| 2016/0024586 A1 | 1/2016 | Delfour et al. |
| 2016/0032400 A1 | 2/2016 | Gomis et al. |
| 2016/0068915 A1 | 3/2016 | Kennedy et al. |
| 2016/0115546 A1 | 4/2016 | Rosenfeld et al. |
| 2016/0120832 A1 | 5/2016 | Rabinowitz et al. |
| 2016/0312305 A1 | 10/2016 | Kennedy et al. |
| 2016/0312306 A1 | 10/2016 | Kennedy et al. |
| 2016/0312307 A1 | 10/2016 | Kennedy et al. |
| 2016/0312308 A1 | 10/2016 | Kennedy et al. |
| 2017/0145513 A1 | 5/2017 | Kennedy et al. |
| 2017/0145514 A1 | 5/2017 | Kennedy et al. |
| 2017/0166980 A1 | 6/2017 | Fahey, III et al. |
| 2018/0122508 A1 * | 5/2018 | Wilde ................ G16H 10/40 |
| 2018/0127832 A1 * | 5/2018 | Kennedy ............ G06N 99/005 |

FOREIGN PATENT DOCUMENTS

| | | |
|---|---|---|
| EP | 1975252 A1 | 10/2008 |
| EP | 2366800 A1 | 9/2011 |
| JP | 2005168432 A | 6/2005 |
| WO | WO-2005005601 A2 | 1/2005 |
| WO | WO-2005005601 A3 | 4/2006 |
| WO | WO-2006062118 A1 | 6/2006 |
| WO | WO-2006127537 A2 | 11/2006 |
| WO | WO-2007038792 A2 | 4/2007 |
| WO | WO-2007038792 A3 | 11/2007 |
| WO | WO-2008104380 A2 | 9/2008 |
| WO | WO-2008119776 A1 | 10/2008 |
| WO | WO-2008104380 A3 | 11/2008 |
| WO | WO-2009020905 A2 | 2/2009 |
| WO | WO-2009026605 A2 | 3/2009 |
| WO | WO-2009029266 A2 | 3/2009 |
| WO | WO-2009037337 A1 | 3/2009 |
| WO | WO-2006127537 A3 | 4/2009 |
| WO | WO-2009042728 A1 | 4/2009 |
| WO | WO-2009126271 A1 | 10/2009 |
| WO | WO-2010056374 A2 | 5/2010 |
| WO | WO-2010073248 A2 | 7/2010 |

(56) References Cited

FOREIGN PATENT DOCUMENTS

| WO | WO-2010056374 A3 | 9/2010 |
|---|---|---|
| WO | WO-2010073248 A3 | 9/2010 |
| WO | WO-2011143361 A2 | 11/2011 |
| WO | WO-2013088457 A1 | 6/2013 |
| WO | WO-2015071876 A2 | 5/2015 |

OTHER PUBLICATIONS

ADAPT, The Peterson Institute for Cancer Research, probesets for ARSG, printed Jan. 10, 2013.
ADAPT, The Peterson Institute for Cancer Research, probesets for FREM2, printed Jan. 10, 2013.
ADAPT, The Peterson Institute for Cancer Research, probesets for GIMAP2, printed Jan. 10, 2013.
ADAPT, The Peterson Institute for Cancer Research, probesets for HRASLS3, printed Jan. 10, 2013.
ADAPT, The Peterson Institute for Cancer Research, probesets for PIGN, printed Jan. 10, 2013.
ADAPT website. Paterson Institute for Cancer Research. Probesets for AUTS2. Printed Jul. 1, 2014. 2 pages.
ADAPT website. Paterson Institute for Cancer Research. Probesets for FXYD6. Printed Jul. 1, 2014. 1 page.
Affymetrix: "Data Sheet Affymetrix(R) Genome-Wide Human SNP Array 6.0", 2007, pp. 1-4, XP002525407. Retrieved from the Internet: URL:http://www.affymetrix.com/support/technical/datasheets/genomewide_snp6_datasheet.pdf.
Affymetrix Technical Note: GeneChip® Gene 1.0 ST Array Design (created Sep. 5, 2007; downloaded from http://media.affymetrix.com/support/technical/technotes/gene_1_0_st_technote.pdf).
Affymetrix website for HG-U133A probe set list version 2004, Archived NetAffx Annotation Files (http://www.affymetrix.com/estore/catalog/131537/AFFY/Human+Genome+U133A+2.0+Array#1_3) printed Mar. 2015.
Afink, et al. Molecular characterization of iodotyrosine dehalogenase deficiency in patients with hypothyroidism. J Clin Endocrinol Metab. Dec. 2008;93(12):4894-901.
Aldred et al. Caveolin-1 and caveolin-2, together with three bone morphogenetic protein-related genes, may encode novel tumor suppressors down-regulated in sporadic follicular thyroid carcinogenesis. Cancer Res. 2003;63(11):2864-71.
Aldred et al. Papillary and follicular thyroid carcinomas show distinctly different microarray expression profiles and can be distinguished by a minimum of five genes. J Clin Oncol. 2004;22(17):3531-9.
Alexander, et al. Preoperative diagnosis of benign thyroid nodules with indeterminate cytology. N Engl J Med. Aug. 23, 2012;367(8):705-15. doi: 10.1056/NEJMoa1203208. Epub Jun. 25, 2012. with supplementary appendix.
Arnesen et al. Expression of N-acetyl transferase human and human Arrest defective 1 proteins in thyroid neoplasms. Thyroid. 2005;15(10):1131-6.
Bai et al. Mutational analysis of thyroid transcription factor-1 gene (TTF-1) in lung carcinomas. In Vitro Cell Dev Biol Anim. 2008;44(1-2):17-25.
Baldi; et al., "DNA microarrays and gene expression: from experiments to data analysis and modeling. Cambridge university press, 2002."
Baloch, et al. Our approach to follicular-patterned lesions of the thyroid. J Clin Pathol. Mar. 2007;60(3):244-50. Epub Jun. 23, 2006.
Banito et al. Aneuploidy and RAS mutations are mutually exclusive events in the development of well-differentiated thyroid follicular tumours. Clin Endocrinol (Oxf). 2007;67(5):706-11.
Barden et al. Classification of follicular thyroid tumors by molecular signature: results of gene profiling. Clin Cancer Res. 2003;9(5):1792-800.
Baris et al. Transcriptional profiling reveals coordinated up-regulation of oxidative metabolism genes in thyroid oncocytic tumors. J Clin Endocrinol Metab. 2004;89(2):994-1005.
Bessarabova, et al. Bimodal gene expression patterns in breast cancer. BMC Genomics. Feb. 10, 2010;11 Suppl 1:S8. doi: 10.1186/1471-2164-11-S1-S8.
Bonora et al. Novel germline variants identified in the inner mitochondrial membrane transporter TIMM44 and their role in predisposition to oncocytic thyroid carcinomas. Br J Cancer. 2006;95(11):1529-36.
Boulesteix, et al. Evaluating microarray-based classifiers: an overview. Cancer Inform. 2008;6:77-97. Epub Feb. 29, 2008.
Brasseur et al. Papillary thyroid carcinoma in a 9-year-old girl with ataxia-telangiectasia. Pediatr Blood Cancer. 2008;50(5):1058-60.
Brozek et al. Thyroid cancer in two siblings with FAP syndrome and APC mutation. Int J Colorectal Dis. 2008;23(3):331-2.
Bugalho et al. Mutation analysis of the RET proto-oncogene and early thyroidectomy: results of a Portuguese cancer centre. Surgery. 2007;141(1):90-5.
Cameselle-Teijeiro et al. Follicular thyroid carcinoma with an unusual glomeruloid pattern of growth. Hum Pathol. 2008;39(10):1540-7.
Carda et al. Anaplastic carcinoma of the thyroid with rhabdomyosarcomatous differentiation: a report of two cases. Virchows Arch. 2005;446(1):46-51.
Castro et al. Adenomas and follicular carcinomas of the thyroid display two major patterns of chromosomal changes. J Pathol. 2005;206(3):305-11.
Castro et al. PAX8-PPARgamma rearrangement is frequently detected in the follicular variant of papillary thyroid carcinoma. J Clin Endocrinol Metab. 2006;91(1):213-20.
Cerutti et al. A preoperative diagnostic test that distinguishes benign from malignant thyroid carcinoma based on gene expression. J Clin Invest. 2004;113(8):1234-42.
Cerutti et al. Diagnosis of suspicious thyroid nodules using four protein biomarkers. Clin Cancer Res. 2006;12(11 Pt 1):3311-8.
Chan, et al. Integrating Transcriptomics and Proteomics. Drug Discovery and Development. Apr. 1, 2006. 4 pages. Published in G&P magazine 2006 vol. 6 No. 3 pp. 20-26.
Chen et al. Restricted kappa/lambda light chain ratio by flow cytometry in germinal center B cells in Hashimoto thyroiditis. Am J Clin Pathol. 2006;125(1):42-8.
Cheung, et al. Immunohistochemical diagnosis of papillary thyroid carcinoma. Mod Pathol. Apr. 2001;14(4):338-42.
Chevillard et al. Gene expression profiling of differentiated thyroid neoplasms: diagnostic and clinical implications. Clin Cancer Res. 2004;10(19):6586-97.
Chiappetta et al. The antiapoptotic protein BAG3 is expressed in thyroid carcinomas and modulates apoptosis mediated by tumor necrosis factor-related apoptosis-inducing ligand. J Clin Endocrinol Metab. 2007;92(3):1159-63.
Chudova, et al. Molecular classification of thyroid nodules using high-dimensionality genomic data. J Clin Endocrinol Metab. Dec. 2010;95(12):5296-304. doi: 10.1210/jc.2010-1087. Epub Sep. 8, 2010.
Chung et al. Detection of BRAFV600E mutation on fine needle aspiration specimens of thyroid nodule refines cyto-pathology diagnosis, especially in BRAF600E mutation-prevalent area. Clin Endocrinol (Oxf). 2006;65(5):660-6.
Ciampi et al. BRAF copy number gains in thyroid tumors detected by fluorescence in situ hybridization. Endocr Pathol. 2005;16(2):99-105.
Cibas, et al. The Bethesda System for Reporting Thyroid Cytopathology. Am J Clin Pathol. Nov. 2009;132(5):658-65. doi: 10.1309/AJCPPHLWMI3JV4LA.
Clark et al. Discovery of tissue-specific exons using comprehensive human exon microarrays. Genome Biol. 2007;8(4):R64.
Cohen et al. Mutational analysis of BRAF in fine needle aspiration biopsies of the thyroid: a potential application for the preoperative assessment of thyroid nodules. Clin Cancer Res. 2004;10(8):2761-5.
Combined search report and examination report dated Oct. 1, 2013 for GB Application No. 1315760.7.
Cooper, et al. Management guidelines for patients with thyroid nodules and differentiated thyroid cancer. Thyroid. Feb. 2006;16(2):109-42.
Co-pending U.S. Appl. No. 15/618,656, filed Jun. 9, 2017.

(56) References Cited

OTHER PUBLICATIONS

Crescioli et al. Methimazole inhibits CXC chemokine ligand 10 secretion in human thyrocytes. J Endocrinol. 2007;195(1):145-55.
De Lellis et al. The pathobiology of the human calcitonin (C)-cell: a review. Pathol Annu. 1981;16(Pt 2):25-52.
Del Senno et al. c-myc oncogene alterations in human thyroid carcinomas. Cancer Detect Prev. 1987;10(3-4):159-66.
Delellis et al. C-cell hyperplasia. An ultrastructural analysis. Lab Invest. 1977;36(3):237-48.
Derringer, et al. Malignant lymphoma of the thyroid gland: a clinicopathologic study of 108 cases. Am J Surg Pathol. May 2000;24(5):623-39.
Dettori et al. Aneuploidy in oncocytic lesions of the thyroid gland: diffuse accumulation of mitochondria within the cell is associated with trisomy 7 and progressive numerical chromosomal alterations. Genes Chromosomes Cancer. 2003;38(1):22-31.
Diaz-Uriarte et al. Gene selection and classification of microarray data using random forest. BMC Bioinformatics. 2006;7:3.
Druckenthaner et al. Evidence for Somatostatin receptor 2 in thyroid tissue. Regul Pept. 2007;138(1):32-9.
Durand et al. Evaluation of gene expression profiles in thyroid nodule biopsy material to diagnose thyroid cancer. J Clin Endocrinol Metab. 2008;93(4):1195-202.
Elisei et al. RET genetic screening in patients with medullary thyroid cancer and their relatives: experience with 807 individuals at one center. J Clin Endocrinol Metab. 2007;92(12):4725-9.
Erdogan et al. The prevalence of RET/PTC mutations in papillary thyroid cancers in Turkish population and its relation between tumor histopathology and prognostic factors. Exp Clin Endocrinol Diabetes. 2008;116(4):225-30.
Esperante, et al. Identification and characterization of four PAX8 rare sequence variants (p. T225M, p. L233L, p. G336S and p. A439A) in patients with congenital hypothyroidism and dysgenetic thyroid glands. Clin Endocrinol (Oxf). May 2008;68(5):828-35.
Eszlinger et al. Gene expression analysis reveals evidence for inactivation of the TGF-beta signaling cascade in autonomously functioning thyroid nodules. Oncogene. 2004;23(3):795-804.
Eszlinger et al. Meta- and reanalysis of gene expression profiles of hot and cold thyroid nodules and papillary thyroid carcinoma for gene groups. J Clin Endocrinol Metab. 2006;91(5):1934-42.
Eszlinger et al. Perspectives and limitations of microarray-based gene expression profiling of thyroid tumors. Endocr Rev. 2007;28(3):322-38.
Eszlinger, et al. Perspectives for Improved and More Accurate Classification of Thyroid Epithelial Tumors. J Clin Endocrinol Metab. Sep. 2008;93(9):3286-94. Epub Jul. 1, 2008.
European search report and opinion dated Mar. 5, 2014 for EP Application No. 11781242.0.
European search report and opinion dated Apr. 28, 2016 for EP 16153243.7.
European search report and search opinion dated Jan. 28, 2013 for Application No. 10772919.6.
European search report and search opinion dated Nov. 27, 2012 for Application No. 09826462.5.
Ferrari, et al. An approach to estimate between- and within-group correlation coefficients in multicenter studies: plasma carotenoids as biomarkers of intake of fruits and vegetables. Am J Epidemiol. Sep. 15, 2005;162(6):591-8. Epub Aug. 10, 2005.
Finley et al. Advancing the molecular diagnosis of thyroid nodules: defining benign lesions by molecular profiling. Thyroid. 2005;15(6):562-8.
Finley et al. Discrimination of benign and malignant thyroid nodules by molecular profiling. Ann Surg. 2004;240(3):425-36; discussion 436-7.
Finley et al. Molecular analysis of Hurthle cell neoplasms by gene profiling. Surgery. 2004;136(6):1160-8.
Finley et al. Molecular profiling distinguishes papillary carcinoma from benign thyroid nodules. J Clin Endocrinol Metab. 2004;89(7):3214-23.
Finn, et al. Expression microarray analysis of papillary thyroid carcinoma and benign thyroid tissue: emphasis on the follicular variant and potential markers of malignancy. Virchows Arch. Mar. 2007;450(3):249-60.
Fishel, et al. Meta-analysis of gene expression data: a predictor-based approach. Bioinformatics. Jul. 1, 2007;23(13):1599-606. Epub Apr. 26, 2007.
Fontaine et al. Microarray analysis refines classification of non-medullary thyroid tumours of uncertain malignancy. Oncogene. 2008;27(15):2228-36.
Foppiani et al. Uncommon association of germline mutations of RET proto-oncogene and CDKN2A gene. Eur J Endocrinol. 2008;158(3):417-22.
Fryknas et al. Molecular markers for discrimination of benign and malignant follicular thyroid tumors. Tumour Biol. 2006;27(4):211-20.
Fujarewicz, et al. A multi-gene approach to differentiate papillary thyroid carcinoma from benign lesions: gene selection using support vector machines with bootstrapping. Endocr Relat Cancer. Sep. 2007;14(3):809-26.
Garcia-Lopez et al. Thyrocytes from autoimmune thyroid disorders produce the chemokines IP-10 and Mig and attract CXCR3+ lymphocytes. J Clin Endocrinol Metab. 2001;86(10):5008-16.
Gardina et al. Alternative splicing and differential gene expression in colon cancer detected by a whole genome exon array. BMC Genomics. 2006;7:325.
Gasparre et al. Disruptive mitochondrial DNA mutations in complex I subunits are markers of oncocytic phenotype in thyroid tumors. Proc Natl Acad Sci USA. 2007;104(21):9001-6.
Gene Annot Website. Array Probesets for HOMER2, printed Jan. 2016.
GeneAnnot website. Probesets for AKT1. Printed Aug. 30, 2016. 1 page.
GeneAnnot website. Probesets for ALK. Printed Aug. 30, 2016. 1 page.
GeneAnnot website. Probesets for BRAF. Printed Aug. 30, 2016. 1 page.
GeneAnnot website. Probesets for CALCA. Printed Aug. 30, 2016. 1 page.
GeneAnnot website. Probesets for CTNNB1. Printed Aug. 30, 2016. 1 page.
GeneAnnot website. Probesets for EIF1AY. Printed Aug. 30, 2016. 1 page.
GeneAnnot website. Probesets for IGF2BP2. Printed Aug. 30, 2016. 1 page.
GeneAnnot website. Probesets for KRAS. Printed Feb. 7, 2017. 2 pages.
GeneAnnot website. Probesets for KRT7. Printed Aug. 30, 2016. 1 page.
GeneAnnot website. Probesets for MET. Printed Aug. 30, 2016. 1 page.
GeneAnnot website. Probesets for NTRK2. Printed Aug. 30, 2016. 1 page.
GeneAnnot website. Probesets for NTRK3. Printed Aug. 30, 2016. 2 pages.
GeneAnnot website. Probesets for PIK3CA. Printed Aug. 30, 2016. 1 page.
GeneAnnot website. Probesets for PPARGC1A. Printed Aug. 30, 2016. 1 page.
GeneAnnot website. Probesets for PROS1. Printed Nov. 8, 2016. 1 page.
GeneAnnot website. Probesets for PTEN. Printed Aug. 30, 2016. 2 pages.
GeneAnnot website. Probesets for PTH. Printed Aug. 30, 2016. 1 page.
GeneAnnot website. Probesets for RASA1. Printed Aug. 30, 2016. 1 page.
GeneAnnot website. Probesets for RET. Printed Aug. 30, 2016. 1 page.
GeneAnnot website. Probesets for RXRG. Printed Nov. 8, 2016. 1 page.
GeneAnnot website. Probesets for TP53. Printed Aug. 30, 2016. 1 page.

(56) References Cited

OTHER PUBLICATIONS

GeneAnnot website. Probesets for TSHR. Printed Aug. 30, 2016. 1 page.
GeneAnnot website. Probesets for TTF1. Printed Aug. 30, 2016. 1 page.
Gereben et al. Pretranslational regulation of type 2 deiodinase. Thyroid. 2005;15(8):855-64.
Giordano et al. Delineation, functional validation, and bioinformatic evaluation of gene expression in thyroid follicular carcinomas with the PAX8-PPARG translocation. Clin Cancer Res. 2006;12(7 Pt 1):1983-93.
Giordano et al. Distinct transcriptional profiles of adrenocortical tumors uncovered by DNA microarray analysis. Am J Pathol. 2003;162(2):521-31.
Giordano et al. Molecular classification of papillary thyroid carcinoma: distinct BRAF, RAS, and RET/PTC mutation-specific gene expression profiles discovered by DNA microarray analysis. Oncogene. 2005;24(44):6646-56.
Giordano et al. Organ-specific molecular classification of primary lung, colon, and ovarian adenocarcinomas using gene expression profiles. Am J Pathol. 2001;159(4):1231-8.
Giordano. Genome-wide studies in thyroid neoplasia. Endocrinol Metab Clin North Am. 2008;37(2):311-31, vii-viii.
Gombos, et al. Characterization of microarray gene expression profiles of early stage thyroid tumours. Cancer Genomics Proteomics. Nov.-Dec. 2007;4(6):403-9.
Gonzalez-Campora et al. Blood group antigens in differentiated thyroid neoplasms. Arch Pathol Lab Med. 1998;122(11):957-65.
Gould et al. (1987). Synaptophysin expression in neuroendocrine neoplasms as determined by immunocytochemistry. Am J Pathol. 126(2):243-57.
Greenbaum, et al. Comparing protein abundance and mRNA expression levels on a genomic scale. Genome Biol. 2003;4(9):117. Epub Aug. 29, 2003.
Greenbaum, et al. Interrelating different types of genomic data, from proteome to secretome: 'oming in on function. Genome Res. Sep. 2001;11(9):1463-8.
Griffith et al. Meta-analysis and meta-review of thyroid cancer gene expression profiling studies identifies important diagnostic biomarkers. J Clin Oncol. 2006;24(31):5043-51.
Hadd, et al. Targeted, high-depth, next-generation sequencing of cancer genes in formalin-fixed, paraffin-embedded and fine-needle aspiration tumor specimens. J Mol Diagn. Mar. 2013;15(2):234-47. doi: 10.1016/j.jmoldx.2012.11.006. Epub Jan. 13, 2013.
Harach et al. Histology of familial thyroid tumours linked to a gene mapping to chromosome 19p13.2. J Pathol. 1999;189(3):387-93.
Hartigan, et al. The dip test of unimodality. Annals of Statistics. 1985; 13(1):70-84.
Haugen, et al. Development of a novel molecular classifier to accurately identify benign thyroid nodules in patients with indeterminate FNA cytology. Abstract presented at 14th International Thyroid Congress. Sep. 15, 2010.
Haugen et al. Increased expression of genes encoding mitochondrial proteins in papillary thyroid carcinomas. Thyroid. 2003;13(7):613-20.
Hawthorn, et al. TIMP1 and SERPIN-A overexpression and TFF3 and CRABP1 underexpression as biomarkers for papillary thyroid carcinoma. Head Neck. Dec. 2004;26(12):1069-83.
He, et al. A susceptibility locus for papillary thyroid carcinoma on chromosome 8q24. Cancer Res. Jan. 15, 2009;69(2):625-31.
He et al. The role of microRNA genes in papillary thyroid carcinoma. Proc Natl Acad Sci USA. 2005;102(52):19075-80.
Hellwig, et al. Comparison of scores for bimodality of gene expression distributions and genome-wide evaluation of the prognostic relevance of high-scoring genes. BMC Bioinformatics. May 25, 2010;11:276. doi: 10.1186/1471-2105-11-276.
Hemmer et al. Comparison of benign and malignant follicular thyroid tumours by comparative genomic hybridization. Br J Cancer. 1998;78(8):1012-7.
Hemmer, et al. DNA copy number changes in thyroid carcinoma. Am J Pathol. May 1999;154(5):1539-47.
Heuer et al. Different cytokine mRNA profiles in Graves' disease, Hashimoto's thyroiditis, and nonautoimmune thyroid disorders determined by quantitative reverse transcriptase polymerase chain reaction (RT-PCR). Thyroid. 1996;6(2):97-106.
Holden et al. Tyrosine kinase activating mutations in human malignancies: implications for diagnostic pathology. Exp Mol Pathol. 2008; 85(1):68-75.
Hoshikawa, et al. Hypoxia induces different genes in the lungs of rats compared with mice. Physiol Genomics. Feb. 6, 2003;12(3):209-19.
Hou et al. Genetic alterations and their relationship in the phosphatidylinositol 3-kinase/Akt pathway in thyroid cancer. Clin Cancer Res. 2007;13(4):1161-70.
Hsu et al. Characterization of a novel tripartite nuclear localization sequence in the EGFR family. J Biol Chem. 2007;282(14):10432-40.
Huang et al. A genome-wide approach to identify genetic variants that contribute to etoposide-induced cytotoxicity. Proc Natl Acad Sci USA. 2007;104(23):9758-63.
Huang et al. Gene expression in papillary thyroid carcinoma reveals highly consistent profiles. Proc Natl Acad Sci USA. 2001;98(26):15044-9.
Hunt, et al. A microdissection and molecular genotyping assay to confirm the identity of tissue floaters in paraffin-embedded tissue blocks Arch Pathol Lab Med. 2003; 127(2):213-217.
Inaji et al. Demonstration and diagnostic significance of pro-gastrin-releasing peptide in medullary thyroid carcinoma. Oncology. 2000;59(2):122-5.
International search report and written opinion dated Jan. 19, 2012 for PCT Application No. US2011/36143.
International search report and written opinion dated Feb. 25, 2011 for PCT Application No. US2010/034140.
International search report and written opinion dated Feb. 25, 2013 for PCT Application No. US2012/068804.
International search report and written opinion dated Apr. 17, 2015 for PCT/US2014/026411.
International search report and written opinion dated May 8, 2013 for PCT Application No. US2012/068587.
International search report dated Jul. 29, 2010 for PCT Application No. US2009/06162.
Irizarry, et al. Exploration, normalization, and summaries of high density oligonucleotide array probe level data. Biostatistics. Apr. 2003;4(2):249-64.
Ito, et al. Distant and lymph node metastases of thyroid nodules with no pathological evidence of malignancy: a limitation of pathological examination. Endocr J. Oct. 2008;55(5):889-94. Epub Jun. 14, 2008.
Ito et al. Simultaneous expression of keratan sulphate epitope (a sulphated poly-N-acetyllactosamine) and blood group ABH antigens in papillary carcinomas of the human thyroid gland. Histochem J. 1996;28(9):613-23.
Jacques et al. Two-step differential expression analysis reveals a new set of genes involved in thyroid oncocytic tumors. J Clin Endocrinol Metab. 2005;90(4):2314-20.
Jarzab et al. Gene Expression Profile of Papillary Thyroid Cancer: Sources of Variability and Diagnostic Implications. Cancer Res. 2005;65(4):1587-1597.
Jazdzewski et al. Common SNP in pre-miR-146a decreases mature miR expression and predisposes to papillary thyroid carcinoma. Proc Natl Acad Sci USA. 2008;105(20):7269-74.
Joseph et al. Lack of mutations in the thyroid hormone receptor (TR) alpha and beta genes but frequent hypermethylation of the TRbeta gene in differentiated thyroid tumors. J Clin Endocrinol Metab. 2007;92(12):4766-70.
Jovanovic et al. Most multifocal papillary thyroid carcinomas acquire genetic and morphotype diversity through subclonal evolution following the intra-glandular spread of the initial neoplastic clone. J Pathol. 2008;215(2):145-54.
Kakudo et al. Immunohistochemical study of substance P-like immunoreactivity in human thyroid and medullary carcinoma of the thyroid. J Submicrosc Cytol. 1983;15(2):563-8.

(56) References Cited

OTHER PUBLICATIONS

Kang et al. High prevalence of RET, RAS, and ERK expression in Hashimoto's thyroiditis and in papillary thyroid carcinoma in the Korean population. Thyroid. 2007;17(11):1031-8.

Kapadia, et al. Malignant lymphoma of the thyroid gland: a clinicopathologic study. Head Neck Surg. Mar.-Apr. 1982;4(4):270-80.

Kasraeian, et al. A comparison of fine-needle aspiration, core biopsy, and surgical biopsy in the diagnosis of extremity soft tissue masses. Clin Orthop Relat Res. Nov. 2010;468(11):2992-3002. doi: 10.1007/s11999-010-1401-x.

Katoh et al. Thyroid transcription factor-1 in normal, hyperplastic, and neoplastic follicular thyroid cells examined by immunohistochemistry and nonradioactive in situ hybridization. Mod Pathol. 2000;13(5):570-6.

Kebebew et al. Diagnostic and extent of disease multigene assay for malignant thyroid neoplasms. Cancer. 2006;106(12):2592-7.

Kebebew et al. Diagnostic and prognostic value of angiogenesis-modulating genes in malignant thyroid neoplasms. Surgery. Dec. 2005;138(6):1102-9; discussion 1109-10.

Kebebew, et al. The prevalence and prognostic value of BRAF mutation in thyroid cancer. Ann Surg. Sep. 2007;246(3):466-70; discussion 470-1.

Krause, et al. Characterisation of DEHAL1 expression in thyroid pathologies. Eur J Endocrinol. Mar. 2007;156(3):295-301.

Krawczak, et al. The mutational spectrum of single base-pair substitutions in mRNA splice junctions of human genes: causes and consequences. Hum Genet. Sep.-Oct. 1992;90(1-2):41-54.

Kreula, et al. Sample size in fine needle aspiration biopsy. Br J Surg. Dec. 1989;76(12):1270-2.

Kristensen, et al. Genetic variation in putative regulatory loci controlling gene expression in breast cancer. Proc Natl Acad Sci U S A. May 16, ;2006;103(20):7735-40. Epub May 9, 2006.

Kroese, et al. Genetic tests and their evaluation: can we answer the key questions? Genet Med. Nov.-Dec. 2004;6(6):475-80.

Kwan, et al. Heritability of alternative splicing in the human genome. Genome Res. Aug. 2007;17(8):1210-8.

Lacroix, et al. PAX8 and peroxisome proliferator-activated receptor gamma 1 gene expression status in benign and malignant thyroid tissues. Eur J Endocrinol. Sep. 2004;151(3):367-74.

Lau et al. Thyroid transcription factor-1: a review. Appl Immunohistochem Mol Morphol. 2002;10(2):97-102.

Lauter et al. Mutational analysis of CDKN1B, a candidate tumor-suppressor gene, in refractory secondary/tertiary hyperparathyroidism. Kidney Int. 2008;73(10):1137-40.

Lima et al. Thyroid Peroxidase and Thyroglobulin Expression in Normal Human Thyroid Glands. Endocr Pathol. 1998;9(1):333-338.

Lin et al. Expression of sodium iodide symporter in benign and malignant human thyroid tissues. Endocr Pathol. 2001;12(1):15-21.

Lin, et al. Thyroid ultrasonography with fine-needle aspiration cytology for the diagnosis of thyroid cancer. J Clin Ultrasound. Mar.-Apr. 1997;25(3):111-8.

Liu et al. Highly prevalent genetic alterations in receptor tyrosine kinases and phosphatidylinositol 3-kinase/akt and mitogen-activated protein kinase pathways in anaplastic and follicular thyroid cancers. J Clin Endocrinol Metab. 2008;93(8):3106-16.

Lubitz et al. 2006;Microarray analysis of thyroid nodule fine-needle aspirates accurately classifies benign and malignant lesions. J Mol Diagn. 8(4):490-8; quiz 528.

Lubitz et al. Molecular analysis of minimally invasive follicular carcinomas by gene profiling. Surgery. 2005;138(6):1042-8; discussion 1048-9.

Lucentini. Gene association studies typically wrong. The Scientist. 2004; 18(24):20.

Lui et al. 2008;CREB3L2-PPARgamma fusion mutation identifies a thyroid signaling pathway regulated by intramembrane proteolysis. Cancer Res. 68(17):7156-64.

Machens et al. Genotype-phenotype based surgical concept of hereditary medullary thyroid carcinoma. World J Surg. 2007;31(5):957-68.

Marsh, et al. Genome-wide copy number imbalances identified in familial and sporadic medullary thyroid carcinoma. J Clin Endocrinol Metab. Apr. 2003;88(4):1866-72.

Masini-Repiso et al. Ultrastructural localization of thyroid peroxidase, hydrogen peroxide-generating sites, and monoamine oxidase in benign and malignant thyroid diseases. Hum Pathol. 2004; 35(4):436-46.

Mason, et al. Bimodal distribution of RNA expression levels in human skeletal muscle tissue. BMC Genomics. Feb. 7, 2011;12:98. doi: 10.1186/1471-2164-12-98.

Matsubayashi et al. Gastrin-releasing peptide immunoreactivity in medullary thyroid carcinoma. Cancer. 1984;53(11):2472-7.

Maximo et al. Somatic and germline mutation in GRIM-19, a dual function gene involved in mitochondrial metabolism and cell death, is linked to mitochondrion-rich (Hurthle cell) tumours of the thyroid. Br J Cancer. 2005;92(10):1892-8.

Mazzanti, et al. Using gene expression profiling to differentiate benign versus malignant thyroid tumors. Cancer Res. Apr. 15, 2004;64(8):2898-903.

McCarroll, et al. Integrated detection and population-genetic analysis of SNPs and copy number variation. Nature Genetics 40, 1166-1174 (2008).

Mitomo et al. Downregulation of miR-138 is associated with overexpression of human telomerase reverse transcriptase protein in human anaplastic thyroid carcinoma cell lines. Cancer Sci. 2008;99(2):280-6.

Mizukami, et al. Late bone metastasis from an encapsulated follicular carcinoma of the thyroid without capsular and vascular invasion. Pathol Int. Jun. 1996;46(6):457-61.

Montero-Conde et al. Molecular profiling related to poor prognosis in thyroid carcinoma. Combining gene expression data and biological information. Oncogene. 2008;27(11):1554-61.

Moreno, et al. Mutations in the iodotyrosine deiodinase gene and hypothyroidism. N Engl J Med. Apr. 24, 2008;358(17):1811-8. doi: 10.1056/NEJMoa0706819.

Murphy et al. Identification of immunohistochemical biomarkers for papillary thyroid carcinoma using gene expression profiling. Hum Pathol. 2008;39(3):420-6.

Nakano et al. Apoptosis-induced decrease of intrathyroidal CD4(+)CD25(+) regulatory T cells in autoimmune thyroid diseases. Thyroid. 2007;17(1):25-31.

Nakashima et al. Foci formation of P53-binding protein 1 in thyroid tumors: activation of genomic instability during thyroid carcinogenesis. Int J Cancer. 2008;122(5):1082-91.

Nakashima et al. RET oncogene amplification in thyroid cancer: correlations with radiation-associated and high-grade malignancy. Hum Pathol. 2007;38(4):621-8.

Nakayama et al. High molecular weight caldesmon positive stromal cells in the capsule of thyroid follicular tumours and tumour-like lesions. J Clin Pathol. 2002;55(12):917-20.

Nam, et al. BRAF V600E mutation analysis of thyroid nodules needle aspirates in relation to their ultrasongraphic classification: a potential guide for selection of samples for molecular analysis. Thyroid. Mar. 2010;20(3):273-9. doi: 10.1089/thy.2009.0226.

National Cancer Institute web page: "Common Cancer Types", captured by WayBack machine on Dec. 4, 2011, http://www.cancer.gov/cancertopics/types/commoncancers.

Neonakis et al. Expression of calcitonin and somatostatin peptide and mRNA in medullary thyroid carcinoma. World J Surg. 1994;18(4):588-93.

Nikiforova et al. MicroRNA expression profiling of thyroid tumors: biological significance and diagnostic utility. J Clin Endocrinol Metab. 2008;93(5):1600-8.

Nikolova et al. Genome-wide gene expression profiles of thyroid carcinoma: Identification of molecular targets for treatment of thyroid carcinoma. 2008;Oncol Rep. 20(1):105-21.

Notice of allowance dated Jun. 13, 2013 for U.S. Appl. No. 12/592,065.

Notice of allowance dated Sep. 13, 2016 for U.S. Appl. No. 12/964,666.

Notice of allowance dated Oct. 18, 2013 for U.S. Appl. No. 13/318,751.

(56) References Cited

OTHER PUBLICATIONS

Oerntoft, et al. Genome-wide study of gene copy numbers, transcripts, and protein levels in pairs of non-invasive and invasive human transitional cell carcinomas. Mol Cell Proteomics. Jan. 2002;1(1):37-45.
Office action dated Jan. 5, 2015 for U.S. Appl. No. 14/086,716.
Office action dated Jan. 16, 2013 for U.S. Appl. No. 12/592,065.
Office action dated Jan. 22, 2016 for U.S. Appl. No. 13/708,439.
Office action dated Feb. 4, 2014 for U.S. Appl. No. 13/708,439.
Office Action dated Feb. 13, 2017 for U.S. Appl. No. 15/164,241.
Office action dated Feb. 27, 2015 for U.S. Appl. No. 13/710,134.
Office action dated Mar. 9, 2016 for U.S. Appl. No. 13/589,022.
Office Action dated Mar. 9, 2017 for U.S. Appl. No. 13/710,134.
Office Action dated Mar. 21, 2017 for U.S. Appl. No. 15/164,217.
Office Action dated Mar. 21, 2017 for U.S. Appl. No. 15/164,230.
Office Action dated Mar. 23, 2015 for U.S. Appl. No. 13/589,022.
Office Action dated Mar. 23, 2017 for U.S. Appl. No. 15/164,220.
Office Action dated Mar. 23, 2017 for U.S. Appl. No. 15/274,492.
Office action dated Apr. 6, 2012 for U.S. Appl. No. 12/964,666.
Office action dated Apr. 18, 2013 for U.S. Appl. No. 13/318,751.
Office action dated Apr. 27, 2015 for U.S. Appl. No. 12/964,666.
Office action dated May 8, 2014 for U.S. Appl. No. 13/105,756.
Office action dated May 9, 2016 for U.S. Appl. No. 12/964,666.
Office action dated May 16, 2016 for U.S. Appl. No. 14/153,219.
Office action dated May 27, 2015 for U.S. Appl. No. 13/105,756.
Office action dated Jun. 6, 2012 for U.S. Appl. No. 12/592,065.
Office action dated Jun. 10, 2014 for U.S. Appl. No. 13/708,439.
Office Action dated Jun. 12, 2017 for U.S. Appl. No. 13/105,756.
Office action dated Jun. 20, 2014 for U.S. Appl. No. 12/964,666.
Office Action dated Jun. 23, 2017 for U.S. Appl. No. 14/153,219.
Office Action dated Jul. 5, 2017 for U.S. Appl. No. 14/086,716.
Office action dated Jul. 6, 2011 for U.S. Appl. No. 12/964,666.
Office action dated Jul. 10, 2014 for U.S. Appl. No. 13/589,022.
Office action dated Jul. 26, 2016 for U.S. Appl. No. 13/710,134.
Office action dated Jul. 30, 2014 for U.S. Appl. No. 13/710,134.
Office action dated Aug. 10, 2016 for U.S. Appl. No. 14/086,716.
Office action dated Sep. 2, 2015 for U.S. Appl. No. 14/086,716.
Office action dated Sep. 8, 2016 for U.S. Appl. No. 15/164,241.
Office action dated Sep. 11, 2012 for U.S. Appl. No. 13/318,751.
Office action dated Sep. 19, 2016 for U.S. Appl. No. 15/164,217.
Office action dated Sep. 19, 2016 for U.S. Appl. No. 15/164,220.
Office action dated Sep. 19, 2016 for U.S. Appl. No. 15/164,230.
Office action dated Oct. 17, 2013 for U.S. Appl. No. 13/105,756.
Office action dated Nov. 7, 2016 for U.S. Appl. No. 13/105,756.
Office action dated Nov. 17, 2016 for U.S. Appl. No. 13/589,022.
Office action dated Nov. 18, 2016 for U.S. Appl. No. 14/153,219.
Office action dated Nov. 19, 2015 for U.S. Appl. No. 13/710,134.
Office action dated Nov. 29, 2013 for U.S. Appl. No. 13/710,134.
Office action dated Nov. 30, 2016 for U.S. Appl. No. 13/708,439.
Office action dated Dec. 17, 2015 for U.S. Appl. No. 13/105,756.
Owens, et al. Metastatic breast carcinoma involving the thyroid gland diagnosed by fine-needle aspiration: a case report. Diagn Cytopathol. Aug. 2005;33(2):110-5.
Pallante et al. MicroRNA deregulation in human thyroid papillary carcinomas. Endocr Relat Cancer. 2006;13(2):497-508.
Panicker et al. A common variation in deiodinase 1 gene DIO1 is associated with the relative levels of free thyroxine and triiodothyronine. J Clin Endocrinol Metab. 2008;93(8):3075-81.
Pavelic, et al. Molecular genetic alterations of FHIT and p53 genes in benign and malignant thyroid gland lesions. Mutat Res. Jul. 25, 2006;599(1-2):45-57. Epub May 15, 2006.
Phenekos et al. Th1 and Th2 serum cytokine profiles characterize patients with Hashimoto's thyroiditis (Th1) and Graves' disease (Th2). Neuroimmunomodulation. 2004;11(4):209-13.
Pinto et al. mRNA expression of tachykinins and tachykinin receptors in different human tissues. Eur J Pharmacol. 2004;494(2-3):233-9.
Pita et al. Gene expression profiling associated with the progression to poorly differentiated thyroid carcinomas. Br J Cancer. 2009;101(10):1782-1791.

Prasad et al. Identification of genes differentially expressed in benign versus malignant thyroid tumors. Clin Cancer Res. 2008;14(11):3327-37.
Puskas, et al. Gene profiling identifies genes specific for well-differentiated epithelial thyroid tumors. Cell Mol Biol (Noisy-le-grand). Sep. 5, 2005;51(2):177-86.
Qian, et al. Renal cell carcinoma metastatic to Hurthle cell adenoma of thyroid. Ann Diagn Pathol. Oct. 2004;8(5):305-8.
Ramzy; Ibrahim., "Clinical cytopathology and aspiration biopsy: Fundamental principles and practice. McGraw Hill Professional, 2001."
Reyes, et al. Identification of kallikrein 7, kallikrein 10 and secreted frizzled-related protein 2 as candidate molecular markers for papillary thyroid carcinoma using microarray analysis. Proc Amer Assoc Cancer Res. 2005, vol. 46, Abstract #38.
Ringel et al. Expression of the sodium iodide symporter and thyroglobulin genes are reduced in papillary thyroid cancer. Mod Pathol. 2001;14(4):289-96.
Robinson; et al., "A comparison of Affymetrix gene expression arrays. BMC bioinformatics 8.1 (2007): 449."
Rodrigues-Serpa, et al. Loss of heterozygosity in follicular and papillary thyroid carcinomas. Cancer Genet Cytogenet. Feb. 2003;141(1):26-31.
Roque, et al. Chromosome imbalances in thyroid follicular neoplasms: a comparison between follicular adenomas and carcinomas. Genes Chromosomes Cancer. Mar. 2003;36(3):292-302.
Rosai et al. Pitfalls in the diagnosis of thyroid neoplasms. Pathol Res Pract. 1987;182(2):169-79.
Rosen et al. A six-gene model for differentiating benign from malignant thyroid tumors on the basis of gene expression. Surgery. 2005;138(6):1050-6; discussion 1056-7.
Roura-Mir et al. Single-cell analysis of intrathyroidal lymphocytes shows differential cytokine expression in Hashimoto's and Graves' disease. Eur J Immunol. 1997;27(12):3290-302.
Saeys, et al. A review of feature selection techniques in bioinformatics. Bioinformatics. Oct. 1, 2007;23(19):2507-17. Epub Aug. 24, 2007.
Saiz et al. Immunohistochemical expression of cyclin D1, E2F-1, and Ki-67 in benign and malignant thyroid lesions. J Pathol. 2002;198(2):157-62.
Salvatore et al. A cell proliferation and chromosomal instability signature in anaplastic thyroid carcinoma. Cancer Res. 2007;67(21):10148-58.
Sambrook; et al., "Molecular Cloning: A Laboratory Manual. Second edition, Cold Spring Harbor Laboratory Press, 1989."
Santarpia et al. Phosphatidylinositol 3-kinase/akt and ras/raf-mitogen-activated protein kinase pathway mutations in anaplastic thyroid cancer. J Clin Endocrinol Metab. 2008;93(1):278-84.
Sapio, et al., Detection of RET/PTC, TRK and BRAF mutations in preoperative diagnosis of thyroid nodules with indeterminate cytological findings, C]Jnical Endocrjnology, 2007, 66: 678-683.
Satake et al. Overview of the primary structure, tissue-distribution, and functions of tachykinins and their receptors. Curr Drug Targets. 2006;7(8):963-74.
Savagner et al. Defective mitochondrial ATP synthesis in oxyphilic thyroid tumors. J Clin Endocrinol Metab. 2001;86(10):4920-5.
Savagner et al. PGC-1-related coactivator and targets are upregulated in thyroid oncocytoma. Biochem Biophys Res Commun. 2003;310(3):779-84.
Schiff, et al. Epidermal growth factor receptor (EGFR) is overexpressed in anaplastic thyroid cancer, and the EGFR inhibitor gefitinib inhibits the growth of anaplastic thyroid cancer. Clin Cancer Res. Dec. 15, 2004;10(24):8594-602.
Schroeder, et al. The RIN: an RNA integrity number for assigning integrity values to RNA measurements. BMC Mol Biol. Jan. 31, 2006;7:3.
Sheu et al. The C allele of the GNB3 C825T polymorphism of the G protein beta3-subunit is associated with an increased risk for the development of oncocytic thyroid tumours. J Pathol. 2007;211(1):60-6.
Shirasawa, S. Susceptibility genes for the development of autoimmune thyroid disease. Nippon Rinsho. Dec. 2006;64(12):2208-14. (Abstract only).

(56) References Cited

OTHER PUBLICATIONS

Shvero et al. Immunohistochemical profile and treatment of uncommon types of thyroid carcinomas. Oncol Rep. 2003;10(6):2075-8.
Singh et al. Screening for genetic aberrations in papillary thyroid cancer by using comparative genomic hybridization. Surgery. 2000;128(6):888-93;discussion 893-4.
Siragusa et al. MUC1 oncoprotein promotes refractoriness to chemotherapy in thyroid cancer cells. Cancer Res. 2007;67(11):5522-30.
Smith et al. Methylation status of genes in papillary thyroid carcinoma. Arch Otolaryngol Head Neck Surg. 2007;133(10):1006-11.
Smyth. Linear models and empirical bayes methods for assessing differential expression in microarray experiments. Stat Appl Genet Mol Biol. 2004;3:Article3. Epub Feb. 12, 2004.
Stanta et al. The biochemical and immunohistochemical profile of thyroid neoplasia. Pathol Annu. 1988;23 Pt 1: 129-57.
Subramaniam et al. Clonal characterization of sporadic cribriform-morular variant of papillary thyroid carcinoma by laser microdissection-based APC mutation analysis. Am J Clin Pathol. 2007;128(6):994-1001.
Symmans, et al. Total RNA Yield and Microarray Gene Expression Profiles from Fine-Needle Aspiration Biopsy and Core-Needle Biopsy Samples of Breast Carcinoma. 2003; Cancer 97(12): 2960-2971.
Takakura et al. Oncogenic role of miR-17-92 cluster in anaplastic thyroid cancer cells. Cancer Sci. 2008;99(6):1147-54.
Takano et al. Expression of oncofetal fibronectin messenger ribonucleic acid in fibroblasts in the thyroid: a possible cause of false positive results in molecular-based diagnosis of thyroid carcinomas. J Clin Endocrinol Metab. 2000;85(2):765-8.
Takano et al. Preoperative diagnosis of thyroid papillary and anaplastic carcinomas by real-time quantitative reverse transcription-polymerase chain reaction of oncofetal fibronectin messenger RNA. Cancer Res. 1999;59(18):4542-5.
Tamir et al. Expression and development of a functional plasmalemmal 5-hydroxytryptamine transporter by thyroid follicular cells. Endocrinology. 1996;137(10):4475-86.
Taniguchi et al. Differentiation of follicular thyroid adenoma from carcinoma by means of gene expression profiling with adapter-tagged competitive polymerase chain reaction. Oncology. 2005;69(5):428-35.
Terada. Brain metastasis from thyroid adenomatous nodules or an encapsulated thyroid follicular tumor without capsular and vascular invasion: a case report. Cases J. Jul. 17, 2009;2:7180. doi: 10.4076/1757-1626-2-7180.
Tetzlaff et al. Differential expression of miRNAs in papillary thyroid carcinoma compared to multinodular goiter using formalin fixed paraffin embedded tissues. Endocr Pathol. 2007;18(3):163-73.
Thompson et al. Primary smooth muscle tumors of the thyroid gland. Cancer. 1997;79(3):579-87.
Todaro et al. Autocrine production of interleukin-4 and interleukin-10 is required for survival and growth of thyroid cancer cells. Cancer Res. 2006;66(3):1491-9.
Tzen, et al. Is atypical follicular adenoma of the thyroid a preinvasive malignancy? Hum Pathol. Jul. 2003;34(7):666-9.
Ueda, et al. Analysis of PAX8 Gene in Congenital Hypothyroidism Mass Screening Positive Subjects. Folia Endocrinologica Japonica. Mar. 30, 2007, vol. 82, No. 4, p. 859. (in Japanese with English translation).
Unger et al. Array CGH demonstrates characteristic aberration signatures in human papillary thyroid carcinomas governed by RET/PTC. Oncogene. 2008;27(33):4592-602.
Vasko, et al. Gene expression and functional evidence of epithelial-to-mesenchymal transition in papillary thyroid carcinoma invasion. Proc Natl Acad Sci U S A. Feb. 20, 2007;104(8):2803-8. Epub Feb. 12, 2007.
Viale et al. Coexpression of cytokeratins and vimentin in normal and diseased thyroid glands. Lack of diagnostic utility of vimentin immunostaining. Am J Surg Pathol. 1989;13(12):1034-40.

Viney et al. Regulation of the cell-specific calcitonin/calcitonin gene-related peptide enhancer by USF and the Foxa2 forkhead protein. J Biol Chem. 2004;279(48):49948-55.
Visone et al. MicroRNAs (miR)-221 and miR-222, both overexpressed in human thyroid papillary carcinomas, regulate p27Kip1 protein levels and cell cycle. Endocr Relat Cancer. 2007;14(3):791-8.
Visone et al. Specific microRNAs are downregulated in human thyroid anaplastic carcinomas. Oncogene. 2007;26(54):7590-5.
Wang et al. Association of the T1799A BRAF mutation with tumor extrathyroidal invasion, higher peripheral platelet counts, and over-expression of platelet-derived growth factor-B in papillary thyroid cancer. Endocr Relat Cancer. 2008;15(1):183-90.
Wang et al. The expression analysis of ICOS-L on activated T cells and immature dendritic cells as well as malignant B cells and Grave's-disease-derived thyroid tissues by two novel mAbs against human ICOS-L. Tissue Antigens. 2007;69(1):62-72.
Watanabe et al. Decrease of intrathyroidal CD161+Valpha24+ Vbeta11+ NKT cells in Graves' disease. Endocr J. 2008; 55(1):199-203.
Wattel, et al. Gene expression in thyroid autonomous adenomas provides insight into their physiopathology. Oncogene. Oct. 20, 2005;24(46):6902-16.
Weber et al. A limited set of human MicroRNA is deregulated in follicular thyroid carcinoma. J Clin Endocrinol Metab. 2006;91(9):3584-91. Epub Jul. 5, 2006.
Weber et al. Genetic classification of benign and malignant thyroid follicular neoplasia based on a three-gene combination. J Clin Endocrinol Metab. 2005;90(5):2512-21.
Weber et al. Silencing of the maternally imprinted tumor suppressor ARHI contributes to follicular thyroid carcinogenesis. J Clin Endocrinol Metab. 2005;90(2):1149-55.
Wessagowit, et al. Normal and abnormal mechanisms of gene splicing and relevance to inherited skin diseases. J Dermatol Sci. Nov. 2005;40(2):73-84. Epub Jul. 27, 2005.
Whitehead, et al. Variation in tissue-specific gene expression among natural populations. Genome Biol. 2005;6(2):R13. Epub Jan. 26, 2005.
Wiseman et al. Molecular phenotyping of thyroid tumors identifies a Marker panel for differentiated thyroid cancer diagnosis. Ann Surg Oncol. 2008;15(10):2811-26.
Wreesmann et al. Genome-wide profiling of papillary thyroid cancer identifies MUC1 as an independent prognostic marker. Cancer Res. 2004;64(11):3780-9.
Wu, et al. A comparative study of 200 fine needle aspiration biopsies performed by clinicians and cytopathologists. Laryngoscope. Jul. 2006;116(7):1212-5.
Wu et al. Uncommon mutation, but common amplifications, of the PIK3CA gene in thyroid tumors. J Clin Endocrinol Metab. 2005;90(8):4688-93.
Xu et al. Differential expression of galectin-1 and galectin-3 in thyroid tumors. Potential diagnostic implications. Am J Pathol. 1995;147(3):815-22.
Yang et al. C-myc, N-myc, N-ras, and c-erb-B: lack of amplification or rearrangement in human medullary thyroid carcinoma and a derivative cell line. Anticancer Res. 1990;10(1):189-92.
Yano et al. Gene expression profiling identifies platelet-derived growth factor as a diagnostic molecular marker for papillary thyroid carcinoma. Clin Cancer Res. 2004;10(6):2035-43.
Yatabe et al. Epidermal growth factor receptor gene amplification is acquired in association with tumor progression of EGFR-mutated lung cancer. Cancer Res. 2008;68(7):2106-11.
Yeh et al. Differentiated thyroid cancer cell invasion is regulated through epidermal growth factor receptor-dependent activation of matrix metalloproteinase (MMP)-2/gelatinase A. Endocr Relat Cancer. 2006;13(4):1173-83.
Yeh et al. Somatic mitochondrial DNA (mtDNA) mutations in papillary thyroid carcinomas and differential mtDNA sequence variants in cases with thyroid tumours. Oncogene. 2000;19(16):2060-6.
Yoon et al. Identification of a novel noncoding RNA gene, NAMA, that is downregulated in papillary thyroid carcinoma with BRAF mutation and associated with growth arrest. Int J Cancer. 2007;121(4):767-75.

(56) References Cited

OTHER PUBLICATIONS

Zabel et al. S-100 protein and neuron-specific enolase in parathyroid glands and C-cells of the thyroid. Histochemistry. 1987;86(4):389-92.
Zanna et al. Trop-1 are conserved growth stimulatory molecules that mark early stages of tumor progression. Cancer. 2007;110(2):452-64.
Zeng et al. The contributions of oestrogen receptor isoforms to the development of papillary and anaplastic thyroid carcinomas. J Pathol. 2008;214(4):425-33.
Zhang, et al. Association between single-nucleotide polymorphisms of BRAF and papillary thyroid carcinoma in a Chinese population. Thyroid. Jan. 2013;23(1):38-44. doi: 10.1089/thy.2012.0228.
Zhang et al. Regulation of tumor necrosis factor-related apoptosis-inducing ligand-induced apoptosis by DJ-1 in thyroid cancer cells. Endocr Relat Cancer. 2008;15(2):535-44.
Zhou et al. RET proto-oncogene mutations are restricted to codons 634 and 918 in mainland Chinese families with MEN2A and MEN2B. Clin Endocrinol (Oxf). 2007;67(4):570-6.
Zhu et al. U1 snRNP-dependent function of TIAR in the regulation of alternative RNA processing of the human calcitonin/CGRP pre-mRNA. Mol Cell Biol. 2003;23(17):5959-71.
Abratani, Hiroyuki. Characteristic Diagnosis of Cancer by Gene Expression Profiling. Personalized Diagnosis of Cancer by Gene Expression Profiling. English Translation. Journal of Clinical and Experimental Medicine (IGAKU NO AYUMI), Jun. 1, 2002, vol. 201, No. 9, p. 687-692.
Durante, et al. BRAF mutations in papillary thyroid carcinomas inhibit genes involved in iodine metabolism. J Clin Endocrinol Metab. Jul. 2007;92(7):2840-3. Epub May 8, 2007.
Frattini, et al. Alternative mutations of BRAF, RET and NTRK1 are associated with similar but distinct gene expression patterns in papillary thyroid cancer. Oncogene. Sep. 23, 2004;23(44):7436-40.
Jo, et al. Influence of the BRAF V600E mutation on expression of vascular endothelial growth factor in papillary thyroid cancer. J Clin Endocrinol Metab. Sep. 2006;91(9):3667-70. Epub Jun. 13, 2006.
Johansson, et al. Confirmation of a BRAF mutation-associated gene expression signature in melanoma. Pigment Cell Res. Jun. 2007;20(3):216-21.
Kannengiesser, et al. Gene expression signature associated with BRAF mutations in human primary cutaneous melanomas. Mol Oncol. Apr. 2008;1(4):425-30. doi: 10.1016/j.molonc.2008.01.002. Epub Jan. 12, 2008.
Kawai, et al. Recent Advances of DNA chip application. Latest Situation in DNA Chip Applications. English Translation. Protein Nucleic Acid and Enzyme, Aug. 1, 2000, vol. 45, No. 11, p. 47-53.
Nucera, et al. Braf(V600E) mutation and the biology of papillary thyroid cancer. Endocr Relat Cancer. Mar. 2008;15(1):191-205. doi: 10.1677/ERC-7-0212.
Oler, et al. Gene expression profiling of papillary thyroid carcinoma identifies transcripts correlated with BRAF mutational status and lymph node metastasis. Clin Cancer Res. Aug. 1, 2008;14(15):4735-42. doi: 10.1158/1078-0432.CCR-07-4372.
Pavey, et al. Microarray expression profiling in melanoma reveals a BRAF mutation signature. Oncogene. May 20, 2004;23(23):4060-7.
Tian, et al. A combined oncogenic pathway signature of BRAF, KRAS and PI3KCA mutation improves colorectal cancer classification and cetuximab treatment prediction. Gut. Apr. 2013;62(4):540-9. doi: 10.1136/gutjnl-2012-302423. Epub Jul. 14, 2012.
Office Action dated Aug. 29, 2017 for U.S. Appl. No. 15/185,960.
Penland, et al. RNA expression analysis of formalin-fixed paraffin-embedded tumors. Lab Invest. Apr. 2007;87(4):383-91.
Adams, J.U., The Human Genome project set out to sequence all of the 3 billion nucleotides in the human genome. Exactly how was this daunting task done with such incredible speed and accuracy?DNA sequencing technologies. Nature Education, 2008; 1(1):193, pp. 1-6.
Ali et al. Use of the Affirma®Gene Expression Classifier for Preoperative Identification of Benign Thyroid Nodules with Indeterminate Fine Needle Aspiration Cytopathology. PLoS Currents 5:pp. 1-7 (2013).
Co-pending U.S. Appl. No. 16/174,769, filed Oct. 30, 2018, 118 pages.
Co-pending U.S. Appl. No. 16/174,784, filed Oct. 30, 2018, 255 pages.
Erkkila et al. Probabilistic analysis of gene expression measurements from heterogeneous tissues. Bioinformatics 26(20):2571-2577 (2010).
GeneAnnot Search for Affymetrix HG-U 133A microarray probesets for TIMP1, printed Dec. 2018, 1 page.
GeneAnnot Search for Affymetrix HG-U 133A microarray probesets for SLCA4, printed Dec. 2018, 2 pages.
Office Action dated Nov. 9, 2018 for U.S. Appl. No. 14/851,864, 22 pages.
Office Action dated Nov. 20, 2018 for U.S. Appl. No. 13/589,022, 37 pages.
Office Action dated Nov. 29, 2018 for U.S. Appl. No. 15/626,401, 11 pages.
Office Action dated Dec. 12, 2018 for U.S. Appl. No. 14/086,716, 27 pages.
Office action dated Dec. 13, 2018 for U.S. Appl. No. 14/153,219, 6 pages.
U.S. Appl. No. 15/185,960 Office Action dated Dec. 21, 2018, 24 pages.

* cited by examiner

| Input CEL File | Pathology |
|---|---|
| 151329HUEX1A11.CEL | Benign |
| 151345HUEX1A11.CEL | Benign |
| 151326HUEX1A11.CEL | Benign |
| 151380HUEX1A11.CEL | Benign |
| 151289HUEX1A11.CEL | Benign |
| 151338HUEX1A11.CEL | Benign |
| 151315HUEX1A11.CEL | Benign |
| 151306HUEX1A11.CEL | Benign |
| 151316HUEX1A11.CEL | Benign |
| 151276HUEX1A11.CEL | Benign |
| 151305HUEX1A11.CEL | Benign |
| 151330HUEX1A11.CEL | Benign |
| 151336HUEX1A11.CEL | Benign |
| 151275HUEX1A11.CEL | Benign |
| 151309HUEX1A11.CEL | Benign |
| 151284HUEX1A11.CEL | Benign |
| 151295HUEX1A11.CEL | Benign |
| 151279HUEX1A11.CEL | Benign |
| 151293HUEX1A11.CEL | Benign |
| 151359HUEX1A11.CEL | Benign |
| 151325HUEX1A11.CEL | Benign |
| 151283HUEX1A11.CEL | Benign |
| 151361HUEX1A11.CEL | Benign |
| 151294HUEX1A11.CEL | Benign |
| 151373HUEX1A11.CEL | Benign |
| 151364HUEX1A11.CEL | Benign |
| 151308HUEX1A11.CEL | Benign |
| 151291HUEX1A11.CEL | Benign |
| 151285HUEX1A11.CEL | Benign |
| 151363HUEX1A11.CEL | Malignant |
| 151347HUEX1A11.CEL | Malignant |

Figure 1

| | |
|---|---|
| 151346HUEX1A11.CEL | Malignant |
| 151288HUEX1A11.CEL | Malignant |
| 151340HUEX1A11.CEL | Malignant |
| 151334HUEX1A11.CEL | Malignant |
| 151300HUEX1A11.CEL | Malignant |
| 151323HUEX1A11.CEL | Malignant |
| 151319HUEX1A11.CEL | Malignant |
| 151358HUEX1A11.CEL | Malignant |
| 151365HUEX1A11.CEL | Malignant |
| 151348HUEX1A11.CEL | Malignant |
| 151320HUEX1A11.CEL | Malignant |
| 151278HUEX1A11.CEL | Malignant |
| 151304HUEX1A11.CEL | Malignant |
| 151341HUEX1A11.CEL | Malignant |
| 151281HUEX1A11.CEL | Malignant |
| 151321HUEX1A11.CEL | Malignant |
| 151339HUEX1A11.CEL | Malignant |
| 151277HUEX1A11.CEL | Malignant |
| 151286HUEX1A11.CEL | Malignant |
| 151362HUEX1A11.CEL | Malignant |
| 151382huex1a12.CEL | Malignant |
| 151379HUEX1A11.CEL | Malignant |
| 151376HUEX1A11.CEL | Malignant |
| 151318HUEX1A11.CEL | Malignant |
| 151352HUEX1A11.CEL | Malignant |
| 151384HUEX1A11.CEL | Malignant |
| 151354HUEX1A11.CEL | Malignant |
| 151353HUEX1A11.CEL | Malignant |
| 151344HUEX1A11.CEL | Malignant |
| 151368HUEX1A11.CEL | Malignant |
| 151324HUEX1A11.CEL | Malignant |
| 151350HUEX1A11.CEL | Malignant |
| 151317HUEX1A11.CEL | Malignant |

Figure 1 Continued

| | |
|---|---|
| 151375HUEX1A11.CEL | Malignant |
| 151367HUEX1A11.CEL | Malignant |
| 151311HUEX1A11.CEL | Normal |
| 151327HUEX1A11.CEL | Normal |
| 151298HUEX1A11.CEL | Normal |
| 151299HUEX1A11.CEL | Normal |
| 151310HUEX1A11.CEL | Normal |
| 151385HUEX1A11.CEL | Normal |
| 151349HUEX1A11.CEL | Normal |
| 151301HUEX1A11.CEL | Normal |
| 151351HUEX1A11.CEL | Normal |

Figure 1 Continued

| Gene | DE p-value | FDR DE p-value | Fold-change Malignant/ Benign | Fold-change Malignant/ Normal | Fold-change Benign/ Normal |
|---|---|---|---|---|---|
| MYOC | 6.40E-13 | 9.53E-09 | -1.06 | -2.45 | -2.32 |
| GPC3 | 5.31E-12 | 3.96E-08 | -1.08 | -2.23 | -2.07 |
| PLA2R1 | 3.11E-11 | 9.27E-08 | -1.93 | -3.36 | -1.74 |
| LMOD1 | 5.16E-11 | 1.10E-07 | -1.17 | -1.92 | -1.65 |
| MYEF2 | 6.15E-11 | 1.14E-07 | 1.69 | 2.42 | 1.43 |
| LRP1B | 1.74E-09 | 2.60E-06 | -1.93 | -2.42 | -1.25 |
| MPPED2 | 2.80E-09 | 3.47E-06 | -2.05 | -2.32 | -1.13 |
| GPM6A | 3.32E-09 | 3.80E-06 | -1.62 | -2.87 | -1.78 |
| TBC1D4 | 8.68E-09 | 8.63E-06 | -1.56 | -2.01 | -1.29 |
| STK32A | 9.74E-09 | 9.07E-06 | 2.54 | 3.26 | 1.29 |
| KHDRBS2 | 1.12E-08 | 9.85E-06 | -2.03 | -2.63 | -1.30 |
| FN1 | 1.24E-08 | 1.02E-05 | 3.96 | 5.84 | 1.47 |
| FLJ22655 | 1.28E-08 | 1.00E-05 | -1.07 | -1.86 | -1.73 |
| KIT | 1.51E-08 | 1.12E-05 | -1.88 | -2.10 | -1.12 |
| MATN2 | 2.03E-08 | 1.26E-05 | -1.91 | -3.12 | -1.63 |
| C9orf58 | 2.19E-08 | 1.31E-05 | -1.29 | -1.90 | -1.47 |
| ChGn | 2.56E-08 | 1.41E-05 | -2.27 | -2.99 | -1.32 |
| ANGPTL1 | 3.53E-08 | 1.88E-05 | -1.44 | -2.00 | -1.39 |
| FABP4 | 4.88E-08 | 2.42E-05 | -3.31 | -5.39 | -1.63 |
| SIPA1L2 | 8.59E-08 | 4.13E-05 | 1.56 | 1.92 | 1.23 |
| XPR1 | 9.26E-08 | 4.31E-05 | 1.53 | 2.09 | 1.36 |
| TBX22 | 9.39E-08 | 4.24E-05 | -1.61 | -2.43 | -1.51 |
| P4HA2 | 1.05E-07 | 4.48E-05 | 1.69 | 2.10 | 1.25 |
| TPO | 1.45E-07 | 5.83E-05 | -3.18 | -4.29 | -1.35 |
| TSC22D1 | 1.61E-07 | 6.31E-05 | 1.89 | 1.37 | -1.38 |
| JUN | 1.77E-07 | 6.59E-05 | -1.65 | -3.06 | -1.85 |
| DPT | 1.83E-07 | 6.67E-05 | -1.69 | -4.76 | -2.81 |
| GALNT7 | 2.59E-07 | 8.40E-05 | 1.82 | 2.08 | 1.14 |
| SLC26A4 | 2.80E-07 | 8.70E-05 | -3.22 | -4.27 | -1.33 |
| ADH1B | 2.91E-07 | 8.84E-05 | -1.36 | -3.48 | -2.56 |
| NRCAM | 4.32E-07 | 1.15E-04 | 1.80 | 3.16 | 1.76 |

Figure 2

| | | | | | |
|---|---|---|---|---|---|
| GABRB2 | 4.40E-07 | 1.15E-04 | 2.45 | 2.60 | 1.06 |
| DPP6 | 5.04E-07 | 1.23E-04 | -1.53 | -2.45 | -1.60 |
| MAFB | 6.56E-07 | 1.50E-04 | -1.45 | -1.87 | -1.29 |
| SDC4 | 6.85E-07 | 1.55E-04 | 2.13 | 1.95 | -1.09 |
| FOSB | 1.03E-06 | 2.10E-04 | -1.24 | -1.93 | -1.56 |
| EPHA3 | 1.06E-06 | 2.13E-04 | -1.20 | -2.11 | -1.75 |
| ARHGAP24 | 1.17E-06 | 2.27E-04 | -1.76 | -2.04 | -1.16 |
| C11orf74 | 1.39E-06 | 2.49E-04 | -1.73 | -2.50 | -1.45 |
| PI16 | 1.90E-06 | 3.22E-04 | -1.14 | -2.08 | -1.82 |
| CP | 1.94E-06 | 3.22E-04 | -2.48 | -3.28 | -1.32 |
| LRP2 | 2.03E-06 | 3.29E-04 | -2.14 | -2.07 | 1.03 |
| LIPH | 2.37E-06 | 3.64E-04 | 1.80 | 2.22 | 1.23 |
| RAB23 | 2.72E-06 | 4.06E-04 | -1.42 | -2.17 | -1.53 |
| TUSC3 | 2.79E-06 | 4.11E-04 | 1.94 | 2.43 | 1.26 |
| GLT8D2 | 3.34E-06 | 4.61E-04 | -1.54 | -3.07 | -1.99 |
| TRPC5 | 4.05E-06 | 5.29E-04 | 1.81 | 1.91 | 1.06 |
| TNIK | 4.10E-06 | 5.27E-04 | 1.34 | 1.99 | 1.48 |
| SCEL | 4.44E-06 | 5.56E-04 | 1.87 | 2.05 | 1.09 |
| TNFRSF11B | 4.54E-06 | 5.64E-04 | -1.73 | -2.41 | -1.39 |
| CAMK2N1 | 5.48E-06 | 6.48E-04 | 2.92 | 2.23 | -1.31 |
| LGALS3 | 5.85E-06 | 6.81E-04 | 1.95 | 1.81 | -1.08 |
| SCG5 | 6.09E-06 | 7.03E-04 | 3.16 | 2.81 | -1.13 |
| DPP4 | 6.98E-06 | 7.70E-04 | 2.55 | 3.30 | 1.29 |
| OGN | 6.99E-06 | 7.65E-04 | -1.21 | -2.05 | -1.69 |
| PGCP | 7.53E-06 | 8.07E-04 | -1.47 | -1.99 | -1.35 |
| NRIP1 | 7.92E-06 | 8.37E-04 | 1.73 | 1.86 | 1.08 |
| SDC2 | 9.39E-06 | 9.39E-04 | -1.67 | -2.64 | -1.58 |
| CD36 | 1.08E-05 | 1.04E-03 | -2.03 | -1.95 | 1.04 |
| CRABP1 | 1.14E-05 | 1.09E-03 | -2.65 | -6.83 | -2.58 |
| EFEMP1 | 1.17E-05 | 1.10E-03 | -1.56 | -2.43 | -1.56 |
| MFAP4 | 1.30E-05 | 1.18E-03 | -1.05 | -1.91 | -1.81 |
| ITGA2 | 1.36E-05 | 1.23E-03 | 1.73 | 2.20 | 1.27 |
| DUSP1 | 1.56E-05 | 1.36E-03 | -1.33 | -2.28 | -1.72 |

Figure 2 Continued

| | | | | | |
|---|---|---|---|---|---|
| EGR1 | 1.78E-05 | 1.51E-03 | -1.30 | -2.55 | -1.97 |
| EGR2 | 2.03E-05 | 1.66E-03 | -1.75 | -3.38 | -1.93 |
| SORBS2 | 2.15E-05 | 1.69E-03 | -1.67 | -2.06 | -1.23 |
| MET | 2.21E-05 | 1.72E-03 | 2.09 | 2.32 | 1.11 |
| CLDN16 | 2.27E-05 | 1.74E-03 | 2.48 | 3.55 | 1.44 |
| PSD3 | 2.76E-05 | 2.02E-03 | 1.76 | 2.13 | 1.21 |
| RABL3 | 3.17E-05 | 2.21E-03 | -1.97 | -1.94 | 1.02 |
| APOD | 3.17E-05 | 2.20E-03 | 1.05 | -3.54 | -3.70 |
| PCOLCE2 | 3.74E-05 | 2.52E-03 | -1.32 | -2.76 | -2.10 |
| ITM2A | 3.89E-05 | 2.57E-03 | -1.56 | -1.99 | -1.28 |
| ETV5 | 3.91E-05 | 2.56E-03 | 1.56 | 1.96 | 1.26 |
| PROS1 | 4.50E-05 | 2.79E-03 | 1.64 | 1.95 | 1.19 |
| HBB | 4.52E-05 | 2.79E-03 | -1.65 | -5.19 | -3.15 |
| CYR61 | 4.63E-05 | 2.83E-03 | -1.92 | -2.58 | -1.35 |
| NFE2L3 | 4.65E-05 | 2.83E-03 | 1.44 | 2.01 | 1.39 |
| FOS | 4.74E-05 | 2.86E-03 | -1.28 | -2.11 | -1.65 |
| DLG2 | 5.87E-05 | 3.32E-03 | -1.44 | -2.02 | -1.40 |
| PKHD1L1 | 5.91E-05 | 3.31E-03 | -2.55 | -3.84 | -1.50 |
| C9orf61 | 6.09E-05 | 3.39E-03 | -1.81 | -2.04 | -1.12 |
| AMIGO2 | 7.93E-05 | 4.21E-03 | 1.78 | 2.05 | 1.15 |
| ALDH1A1 | 9.36E-05 | 4.74E-03 | -1.81 | -2.15 | -1.19 |
| PSD3 | 1.06E-04 | 5.13E-03 | 1.43 | 1.91 | 1.33 |
| LIFR | 1.10E-04 | 5.23E-03 | -1.77 | -2.34 | -1.32 |
| C7orf24 | 1.30E-04 | 5.88E-03 | 1.58 | 1.96 | 1.24 |
| RAG2 | 1.37E-04 | 6.12E-03 | -1.86 | -1.55 | 1.20 |
| S100A2 | 1.45E-04 | 6.41E-03 | 2.42 | 1.39 | -1.74 |
| WDR72 | 1.47E-04 | 6.43E-03 | -1.92 | -2.51 | -1.31 |
| MT1G | 1.53E-04 | 6.55E-03 | -2.49 | -3.07 | -1.23 |
| DCN | 1.56E-04 | 6.65E-03 | -1.06 | -5.24 | -4.95 |
| ZNF804B | 1.62E-04 | 6.85E-03 | -1.20 | -2.21 | -1.85 |
| CTGF | 1.64E-04 | 6.86E-03 | -1.92 | -2.83 | -1.48 |
| RHOBTB3 | 1.65E-04 | 6.90E-03 | 1.68 | 1.99 | 1.18 |
| DNAJB4 | 1.65E-04 | 6.86E-03 | -1.31 | -2.13 | -1.62 |

Figure 2 Continued

| SERPINA1 | 1.65E-04 | 6.87E-03 | 2.89 | 3.08 | 1.07 |
| QPCT | 1.68E-04 | 6.90E-03 | 2.01 | 2.09 | 1.04 |
| TMEM171 | 2.46E-04 | 9.30E-03 | -1.51 | -2.92 | -1.93 |

Figure 2 Continued

| Gene | Alt. Exon p-value | Alt. Exon FDR p-value |
|---|---|---|
| TPO | 0.00E+00 | 0.00E+00 |
| DPP6 | 0.00E+00 | 0.00E+00 |
| LRP1B | 0.00E+00 | 0.00E+00 |
| KIT | 0.00E+00 | 0.00E+00 |
| CD36 | 0.00E+00 | 0.00E+00 |
| RHOBTB3 | 0.00E+00 | 0.00E+00 |
| CTSB | 0.00E+00 | 0.00E+00 |
| SLC4A4 | 0.00E+00 | 0.00E+00 |
| ANKS1B | 0.00E+00 | 0.00E+00 |
| MDM2 | 0.00E+00 | 0.00E+00 |
| ABCA8 | 0.00E+00 | 0.00E+00 |
| CDH6 | 0.00E+00 | 0.00E+00 |
| CENPJ | 0.00E+00 | 0.00E+00 |
| ABCA1 | 0.00E+00 | 0.00E+00 |
| DIO2 | 0.00E+00 | 0.00E+00 |
| PON2 | 0.00E+00 | 0.00E+00 |
| SLC20A1 | 0.00E+00 | 0.00E+00 |
| FBXL20 | 0.00E+00 | 0.00E+00 |
| PCNX | 0.00E+00 | 0.00E+00 |
| PGM2L1 | 0.00E+00 | 0.00E+00 |
| RASGRP3 | 0.00E+00 | 0.00E+00 |
| ZEB1 | 0.00E+00 | 0.00E+00 |
| AAK1 | 0.00E+00 | 0.00E+00 |
| AFAP1L2 | 0.00E+00 | 0.00E+00 |
| C12orf63 | 0.00E+00 | 0.00E+00 |
| DYX1C1 | 0.00E+00 | 0.00E+00 |
| MFSD11 | 0.00E+00 | 0.00E+00 |
| NUP93 | 0.00E+00 | 0.00E+00 |
| ATP10D | 0.00E+00 | 0.00E+00 |
| C12orf4 | 0.00E+00 | 0.00E+00 |
| EFTUD1 | 0.00E+00 | 0.00E+00 |

Figure 3

| | | |
|---|---|---|
| GTF3C3 | 0.00E+00 | 0.00E+00 |
| H2AFY | 0.00E+00 | 0.00E+00 |
| KLC1 | 0.00E+00 | 0.00E+00 |
| MGC29891 | 0.00E+00 | 0.00E+00 |
| SNAPC3 | 0.00E+00 | 0.00E+00 |
| VWF | 0.00E+00 | 0.00E+00 |
| ZZEF1 | 0.00E+00 | 0.00E+00 |
| ACSS1 | 0.00E+00 | 0.00E+00 |
| BRUNOL6 | 0.00E+00 | 0.00E+00 |
| EYA2 | 0.00E+00 | 0.00E+00 |
| ITPR3 | 0.00E+00 | 0.00E+00 |
| MLL3 | 0.00E+00 | 0.00E+00 |
| ORC2L | 0.00E+00 | 0.00E+00 |
| PCTK1 | 0.00E+00 | 0.00E+00 |
| RBM33 | 0.00E+00 | 0.00E+00 |
| TNS1 | 0.00E+00 | 0.00E+00 |
| FAM120A | 0.00E+00 | 0.00E+00 |
| FLJ10986 | 0.00E+00 | 0.00E+00 |
| CTSC | 6.68E-302 | 9.13E-300 |
| SETD4 | 8.65E-300 | 1.16E-297 |
| UAP1 | 1.16E-293 | 1.52E-291 |
| ATP2C2 | 2.78E-292 | 3.60E-290 |
| PSMF1 | 4.83E-292 | 6.20E-290 |
| CNTN5 | 7.41E-292 | 9.44E-290 |
| LONRF2 | 3.58E-290 | 4.52E-288 |
| DGKH | 5.82E-285 | 7.16E-283 |
| NFYC | 2.68E-284 | 3.28E-282 |
| FLJ20294 | 3.29E-284 | 3.98E-282 |
| ZFYVE21 | 1.52E-283 | 1.82E-281 |
| HECTD2 | 6.34E-282 | 7.56E-280 |
| WASF3 | 4.99E-276 | 5.81E-274 |
| KNTC1 | 8.88E-273 | 1.03E-270 |
| MPPED2 | 1.10E-265 | 1.24E-263 |

Figure 3 Continued

| | | |
|---|---|---|
| LRRC48 | 6.58E-260 | 7.32E-258 |
| EP400 | 7.62E-255 | 8.23E-253 |
| KCTD10 | 1.02E-244 | 1.04E-242 |
| SUSD1 | 2.04E-238 | 2.05E-236 |
| TNFAIP8 | 3.89E-237 | 3.89E-235 |
| FLJ10324 | 1.84E-235 | 1.80E-233 |
| DIO1 | 1.11E-232 | 1.08E-230 |
| ARHGAP6 | 1.22E-231 | 1.18E-229 |
| MYO1D | 8.30E-229 | 7.93E-227 |
| PER2 | 1.55E-228 | 1.47E-226 |
| ANXA9 | 3.78E-228 | 3.56E-226 |
| MYH14 | 1.26E-225 | 1.17E-223 |
| LTBP2 | 8.02E-224 | 7.33E-222 |
| AOX1 | 3.41E-219 | 3.04E-217 |
| PAK3 | 9.65E-219 | 8.56E-217 |
| CDK7 | 6.41E-218 | 5.62E-216 |
| SLC39A9 | 6.37E-217 | 5.55E-215 |
| SRF | 3.30E-208 | 2.79E-206 |
| LRRC50 | 2.08E-205 | 1.75E-203 |
| FTH1 | 2.32E-204 | 1.93E-202 |
| DOPEY2 | 1.22E-203 | 1.01E-201 |
| EGR2 | 7.02E-202 | 5.78E-200 |
| ITGA2 | 8.74E-202 | 7.15E-200 |
| FLJ21511 | 8.30E-200 | 6.72E-198 |
| KHDRBS2 | 1.06E-194 | 8.28E-193 |
| ABCC3 | 2.40E-191 | 1.85E-189 |
| PCSK6 | 4.70E-190 | 3.55E-188 |
| PDE6B | 5.87E-190 | 4.42E-188 |
| AUTS2 | 2.16E-183 | 1.58E-181 |
| KIAA1324 | 2.64E-182 | 1.92E-180 |
| ETV5 | 5.10E-182 | 3.69E-180 |
| POLE2 | 2.98E-179 | 2.13E-177 |
| CPEB2 | 3.75E-178 | 2.67E-176 |

Figure 3 Continued

| PKHD1L1 | 3.58E-176 | 2.52E-174 |
| CHRND | 5.54E-176 | 3.88E-174 |
| ZW10 | 3.17E-175 | 2.21E-173 |

Figure 3 Continued

| Gene | DE p-value | FDR DE p-value | Fold-change Malignant/Benign |
|---|---|---|---|
| SEMA3D | 1.02E-08 | 3.23E-04 | -11.18 |
| PDLIM4 | 4.57E-08 | 3.82E-04 | 3.51 |
| LRP1B | 7.45E-08 | 4.15E-04 | -14.82 |
| PLCD3 | 7.52E-08 | 4.15E-04 | 4.97 |
| FN1 | 9.57E-08 | 4.15E-04 | 10.71 |
| KIT | 1.35E-07 | 4.43E-04 | -4.75 |
| SPOCK1 | 1.45E-07 | 4.43E-04 | 5.04 |
| EPS8 | 1.57E-07 | 4.44E-04 | 3.17 |
| STK32A | 1.87E-07 | 4.61E-04 | 5.09 |
| IHPK3 | 1.94E-07 | 4.72E-04 | -3.06 |
| TCID-2526806 | 2.08E-07 | 4.80E-04 | 2.86 |
| MYEF2 | 2.11E-07 | 4.80E-04 | 3.61 |
| ARHGAP24 | 2.32E-07 | 4.89E-04 | -2.84 |
| MPPED2 | 3.43E-07 | 5.56E-04 | -4.49 |
| TGFA | 3.59E-07 | 5.56E-04 | 4.13 |
| KHDRBS2 | 4.99E-07 | 6.53E-04 | -4.28 |
| TPO | 7.17E-07 | 7.72E-04 | -5.28 |
| LGALS3 | 7.18E-07 | 7.72E-04 | 3.77 |
| SLC26A4 | 9.16E-07 | 8.86E-04 | -4.26 |
| GALE | 9.62E-07 | 9.19E-04 | 3.46 |
| GABRB2 | 1.18E-06 | 1.03E-03 | 10.65 |
| KLHDC8A | 1.35E-06 | 1.10E-03 | 4.64 |
| CDH3 | 1.72E-06 | 1.22E-03 | 6.67 |
| GALNT7 | 1.75E-06 | 1.22E-03 | 3.78 |
| CYSLTR2 | 2.53E-06 | 1.56E-03 | 7.40 |
| RAG1 | 3.49E-06 | 1.89E-03 | -9.03 |
| PSD3 | 4.08E-06 | 2.04E-03 | 4.19 |
| FABP4 | 4.18E-06 | 2.04E-03 | -11.06 |
| MATN2 | 4.23E-06 | 2.05E-03 | -2.87 |

Figure 4

| | | | |
|---|---|---|---|
| TRPC5 | 4.54E-06 | 2.14E-03 | 3.77 |
| LRP2 | 4.78E-06 | 2.17E-03 | -4.40 |
| MT1F | 4.93E-06 | 2.20E-03 | -5.00 |
| CDH16 | 5.19E-06 | 2.28E-03 | -2.86 |
| METTL7B | 6.09E-06 | 2.52E-03 | 3.20 |
| SYTL5 | 7.23E-06 | 2.82E-03 | 3.10 |
| CAMK2N1 | 7.45E-06 | 2.84E-03 | 3.82 |
| LIPH | 7.70E-06 | 2.90E-03 | 36.34 |
| AGTR1 | 8.16E-06 | 2.99E-03 | -3.41 |
| P2RY13 | 8.47E-06 | 3.06E-03 | 3.39 |
| SLC26A7 | 9.12E-06 | 3.22E-03 | -3.43 |
| LRRC7 | 9.97E-06 | 3.38E-03 | -2.91 |
| SPINK5 | 1.06E-05 | 3.53E-03 | -4.56 |
| TMEM166 | 1.34E-05 | 4.04E-03 | 6.87 |
| SCG5 | 1.46E-05 | 4.27E-03 | 5.53 |
| NPC2 | 1.52E-05 | 4.37E-03 | 2.78 |
| CD36 | 1.55E-05 | 4.41E-03 | -4.41 |
| RAG2 | 1.61E-05 | 4.49E-03 | -13.38 |
| COL9A3 | 1.64E-05 | 4.55E-03 | -6.08 |
| ELMO1 | 1.97E-05 | 5.17E-03 | -2.92 |
| PLA2R1 | 2.03E-05 | 5.26E-03 | -4.85 |
| 7A5 | 2.04E-05 | 5.28E-03 | 3.11 |
| MRO | 2.17E-05 | 5.45E-03 | -3.35 |
| DGKI | 2.45E-05 | 5.93E-03 | -3.38 |
| TUSC3 | 2.58E-05 | 6.13E-03 | 4.30 |
| TFF3 | 2.65E-05 | 6.21E-03 | -5.45 |
| TNFRSF10C | 2.78E-05 | 6.38E-03 | 2.85 |
| PROS1 | 2.80E-05 | 6.40E-03 | 2.72 |
| TCID-3430620 | 2.91E-05 | 6.55E-03 | -3.96 |
| ITGA2 | 3.09E-05 | 6.80E-03 | 3.42 |
| GPM6A | 3.10E-05 | 6.80E-03 | -3.86 |
| CDON | 3.28E-05 | 7.05E-03 | -2.73 |

Figure 4 Continued

| | | | |
|---|---|---|---|
| ARNTL | 3.49E-05 | 7.36E-03 | 2.84 |
| GDF15 | 3.58E-05 | 7.49E-03 | 6.64 |
| NRCAM | 3.77E-05 | 7.75E-03 | 4.02 |
| GSTM3 | 3.87E-05 | 7.90E-03 | -2.71 |
| ADAMTS9 | 3.89E-05 | 7.91E-03 | 2.85 |
| MED12L | 4.20E-05 | 8.33E-03 | 2.81 |
| LONRF2 | 4.29E-05 | 8.45E-03 | 3.73 |
| DNASE1L3 | 4.35E-05 | 8.54E-03 | -3.08 |
| TIPARP | 4.53E-05 | 8.72E-03 | 2.76 |
| DPP6 | 4.56E-05 | 8.73E-03 | -3.90 |
| DPP4 | 4.70E-05 | 8.89E-03 | 12.09 |
| TMEM100 | 4.71E-05 | 8.90E-03 | 4.37 |
| RYR2 | 4.75E-05 | 8.93E-03 | -3.76 |
| CLDN1 | 4.76E-05 | 8.93E-03 | 7.83 |
| RXRG | 4.80E-05 | 8.97E-03 | 3.09 |
| QPCT | 4.82E-05 | 9.00E-03 | 3.46 |
| SAMD4A | 5.00E-05 | 9.21E-03 | 2.80 |
| PKHD1L1 | 5.21E-05 | 9.49E-03 | -7.12 |
| MET | 5.26E-05 | 9.55E-03 | 3.10 |
| FAM114A1 | 5.30E-05 | 9.60E-03 | 2.79 |
| SCEL | 5.53E-05 | 9.85E-03 | 11.17 |
| SLA | 1.22E-04 | 1.58E-02 | -2.99 |
| RIMS2 | 2.01E-04 | 2.13E-02 | 2.97 |
| KIAA0408 | 2.44E-04 | 2.38E-02 | 2.75 |
| IL1RAP | 2.50E-04 | 2.42E-02 | 2.74 |
| SCNN1A | 2.72E-04 | 2.51E-02 | 2.98 |
| LIFR | 3.13E-04 | 2.74E-02 | -2.96 |
| FAM20A | 4.06E-04 | 3.18E-02 | 2.98 |
| PHF16 | 6.01E-04 | 4.00E-02 | 2.75 |
| SLC5A8 | 6.35E-04 | 4.14E-02 | -2.98 |
| ODZ1 | 6.43E-04 | 4.16E-02 | 2.97 |
| DLG2 | 7.11E-04 | 4.40E-02 | -2.74 |
| TBX22 | 7.82E-04 | 4.63E-02 | -2.73 |

Figure 4 Continued

| | | | |
|---|---|---|---|
| LAMB3 | 9.79E-04 | 5.30E-02 | 3.00 |
| AQP4 | 1.16E-03 | 5.85E-02 | -2.76 |
| SLPI | 1.22E-03 | 6.05E-02 | 2.93 |
| COL13A1 | 1.34E-03 | 6.37E-02 | 2.97 |
| SULF1 | 2.33E-03 | 8.77E-02 | 2.96 |
| CYP1B1 | 2.65E-03 | 9.43E-02 | 2.99 |

Figure 4 Continued

| Gene | DE FDR p-value | Alt. Exon FDR p-value | Fold-Change Malignant/Benign | Fold-Change Malignant/Normal | Fold-Change Benign/Normal |
|---|---|---|---|---|---|
| PLA2R1 | 9.27E-08 | 1.03E-54 | -1.93 | -3.36 | -1.74 |
| MYEF2 | 1.14E-07 | 9.58E-27 | 1.69 | 2.42 | 1.43 |
| LRP1B | 2.60E-06 | 0.00E+00 | -1.93 | -2.42 | -1.25 |
| MPPED2 | 3.47E-06 | 1.24E-263 | -2.05 | -2.32 | -1.13 |
| KHDRBS2 | 9.85E-06 | 8.28E-193 | -2.03 | -2.63 | -1.30 |
| FN1 | 1.02E-05 | 7.02E-127 | 3.96 | 5.84 | 1.47 |
| SPATS2 | 1.10E-05 | 2.79E-04 | 1.13 | 1.56 | 1.38 |
| KIT | 1.12E-05 | 0.00E+00 | -1.88 | -2.10 | -1.12 |
| MATN2 | 1.26E-05 | 1.21E-21 | -1.91 | -3.12 | -1.63 |
| C9orf58 | 1.31E-05 | 3.87E-16 | -1.29 | -1.90 | -1.47 |
| ChGn | 1.41E-05 | 5.54E-23 | -2.27 | -2.99 | -1.32 |
| ANGPTL1 | 1.88E-05 | 4.11E-32 | -1.44 | -2.00 | -1.39 |
| FABP4 | 2.42E-05 | 6.34E-105 | -3.31 | -5.39 | -1.63 |
| XPR1 | 4.31E-05 | 9.06E-05 | 1.53 | 2.09 | 1.36 |
| TPO | 5.83E-05 | 0.00E+00 | -3.18 | -4.29 | -1.35 |
| C10orf79 | 5.96E-05 | 5.75E-43 | -1.19 | -1.68 | -1.42 |
| TSC22D1 | 6.31E-05 | 6.19E-11 | 1.89 | 1.37 | -1.38 |
| GALNT7 | 8.40E-05 | 5.15E-10 | 1.82 | 2.08 | 1.14 |
| SLC26A4 | 8.70E-05 | 2.69E-05 | -3.22 | -4.27 | -1.33 |
| CYSLTR2 | 1.08E-04 | 3.75E-27 | 1.75 | 1.67 | -1.05 |
| GABRB2 | 1.15E-04 | 1.80E-56 | 2.45 | 2.60 | 1.06 |
| NRCAM | 1.15E-04 | 3.42E-17 | 1.80 | 3.16 | 1.76 |
| ADH1C | 1.16E-04 | 3.48E-18 | -1.12 | -1.60 | -1.43 |
| DPP6 | 1.23E-04 | 0.00E+00 | -1.53 | -2.45 | -1.60 |
| LINGO2 | 1.50E-04 | 3.74E-170 | -1.32 | -1.77 | -1.34 |
| SDC4 | 1.55E-04 | 8.65E-48 | 2.13 | 1.95 | -1.09 |
| ZFPM2 | 1.55E-04 | 5.60E-04 | -1.17 | -1.71 | -1.46 |
| ARHGAP24 | 2.27E-04 | 5.27E-18 | -1.76 | -2.04 | -1.16 |
| ARMCX3 | 2.28E-04 | 5.35E-03 | 1.50 | 1.68 | 1.12 |

Figure 5

| | | | | | |
|---|---|---|---|---|---|
| RUNX1T1 | 2.38E-04 | 1.58E-116 | -1.18 | -1.56 | -1.32 |
| C11orf74 | 2.49E-04 | 6.94E-07 | -1.73 | -2.50 | -1.45 |
| LRP2 | 3.29E-04 | 2.10E-93 | -2.14 | -2.07 | 1.03 |
| NPC2 | 3.64E-04 | 5.21E-19 | 1.39 | 1.61 | 1.16 |
| PLSCR4 | 3.69E-04 | 6.94E-12 | -1.31 | -1.77 | -1.35 |
| STK32A | 4.12E-04 | 3.12E-12 | 2.11 | | |
| TNIK | 5.27E-04 | 2.62E-35 | 1.34 | 1.99 | 1.48 |
| ANKRD37 | 5.34E-04 | 2.62E-93 | -1.27 | -1.61 | -1.27 |
| SCG5 | 7.03E-04 | 1.47E-03 | 3.16 | 2.81 | -1.13 |
| TBC1D4 | 7.08E-04 | 1.51E-16 | -1.61 | | |
| DPP4 | 7.70E-04 | 3.02E-138 | 2.55 | 3.30 | 1.29 |
| ELMO1 | 8.04E-04 | 7.58E-08 | -1.75 | -1.75 | 1.00 |
| PGCP | 8.07E-04 | 9.61E-03 | -1.47 | -1.99 | -1.35 |
| SDC2 | 9.39E-04 | 1.03E-10 | -1.67 | -2.64 | -1.58 |
| FAM20A | 9.45E-04 | 1.44E-127 | 1.29 | 1.61 | 1.25 |
| METTL7B | 9.70E-04 | 2.26E-13 | 1.58 | 1.65 | 1.05 |
| MAP2 | 9.94E-04 | 5.51E-08 | 1.50 | 1.58 | 1.05 |
| CD36 | 1.04E-03 | 0.00E+00 | -2.03 | -1.95 | 1.04 |
| CRABP1 | 1.09E-03 | 1.16E-10 | -2.65 | -6.83 | -2.58 |
| EFEMP1 | 1.10E-03 | 4.91E-04 | -1.56 | -2.43 | -1.56 |
| DCBLD2 | 1.11E-03 | 1.08E-06 | 1.59 | 1.68 | 1.05 |
| FLRT2 | 1.14E-03 | 1.66E-128 | -1.13 | -1.61 | -1.43 |
| ITGA2 | 1.23E-03 | 7.15E-200 | 1.73 | 2.20 | 1.27 |
| EGR1 | 1.51E-03 | 5.74E-13 | -1.30 | -2.55 | -1.97 |
| ASCC3 | 1.66E-03 | 4.30E-04 | 1.21 | 1.64 | 1.35 |
| EGR2 | 1.66E-03 | 5.78E-200 | -1.75 | -3.38 | -1.93 |
| MET | 1.72E-03 | 4.65E-09 | 2.09 | 2.32 | 1.11 |
| CLDN16 | 1.74E-03 | 1.27E-19 | 2.48 | 3.55 | 1.44 |
| HMGA2 | 1.82E-03 | 1.78E-11 | 1.47 | 1.79 | 1.21 |
| CENPJ | 2.13E-03 | 0.00E+00 | -1.44 | -1.60 | -1.12 |
| GPR125 | 2.17E-03 | 1.04E-11 | -1.43 | -1.67 | -1.17 |
| RABL3 | 2.21E-03 | 2.31E-21 | -1.97 | -1.94 | 1.02 |
| CD63 | 2.42E-03 | 7.85E-04 | 1.40 | 1.60 | 1.14 |

Figure 5 Continued

| | | | | | |
|---|---|---|---|---|---|
| P4HA2 | 2.49E-03 | 3.08E-13 | 1.71 | | |
| ETV5 | 2.56E-03 | 3.69E-180 | 1.56 | 1.96 | 1.26 |
| ITM2A | 2.57E-03 | 3.01E-07 | -1.56 | -1.99 | -1.28 |
| C9orf52 | 2.57E-03 | 3.76E-08 | 1.30 | 1.83 | 1.40 |
| 7A5 | 2.62E-03 | 5.07E-17 | 1.61 | | |
| ANKS1B | 2.71E-03 | 0.00E+00 | -1.31 | -1.68 | -1.29 |
| THRAP1 | 2.72E-03 | 1.06E-05 | 1.34 | 1.59 | 1.18 |
| PROS1 | 2.79E-03 | 2.25E-15 | 1.64 | 1.95 | 1.19 |
| NFE2L3 | 2.83E-03 | 2.91E-06 | 1.44 | 2.01 | 1.39 |
| CYR61 | 2.83E-03 | 2.07E-07 | -1.92 | -2.58 | -1.35 |
| ERO1LB | 2.99E-03 | 2.24E-03 | -1.61 | | |
| ACO1 | 3.03E-03 | 3.40E-10 | 1.32 | 1.73 | 1.31 |
| PKHD1L1 | 3.31E-03 | 2.52E-174 | -2.55 | -3.84 | -1.50 |
| DLG2 | 3.32E-03 | 2.35E-85 | -1.44 | -2.02 | -1.40 |
| C9orf61 | 3.39E-03 | 5.60E-08 | -1.81 | -2.04 | -1.12 |
| DEPDC6 | 4.09E-03 | 9.94E-11 | -1.53 | -1.69 | -1.10 |
| LRRC7 | 4.12E-03 | 7.23E-155 | -1.48 | -1.73 | -1.17 |
| MLLT3 | 4.64E-03 | 4.64E-03 | -1.41 | -1.71 | -1.21 |
| TUSC3 | 4.69E-03 | 1.31E-11 | 1.91 | | |
| ALDH1A1 | 4.74E-03 | 4.61E-08 | -1.81 | -2.15 | -1.19 |
| FBLN5 | 4.82E-03 | 3.18E-09 | -1.26 | -1.72 | -1.37 |
| SLA | 4.90E-03 | 4.03E-03 | -1.93 | -1.60 | 1.21 |
| LONRF2 | 4.97E-03 | 4.52E-288 | 1.85 | 1.49 | -1.24 |
| PSD3 | 5.13E-03 | 6.97E-19 | 1.43 | 1.91 | 1.33 |
| LIFR | 5.23E-03 | 2.95E-17 | -1.77 | -2.34 | -1.32 |
| C7orf24 | 5.88E-03 | 4.91E-05 | 1.58 | 1.96 | 1.24 |
| S100A2 | 6.41E-03 | 3.25E-115 | 2.42 | 1.39 | -1.74 |
| WDR72 | 6.43E-03 | 1.50E-16 | -1.92 | -2.51 | -1.31 |
| MT1G | 6.55E-03 | 1.96E-05 | -2.49 | -3.07 | -1.23 |
| LONRF2 | 6.60E-03 | 9.73E-05 | 1.91 | | |
| SLC4A4 | 6.75E-03 | 0.00E+00 | -1.72 | -1.76 | -1.03 |
| MT1H | 6.86E-03 | 8.57E-09 | -1.58 | -1.83 | -1.16 |
| DNAJB4 | 6.86E-03 | 1.92E-04 | -1.31 | -2.13 | -1.62 |

Figure 5 Continued

| CTGF | 6.86E-03 | 1.42E-11 | -1.92 | -2.83 | -1.48 |
| SERPINA1 | 6.87E-03 | 3.07E-04 | 2.89 | 3.08 | 1.07 |
| RHOBTB3 | 6.90E-03 | 0.00E+00 | 1.68 | 1.99 | 1.18 |
| QPCT | 6.90E-03 | 5.26E-07 | 2.01 | 2.09 | 1.04 |
| TMEM171 | 9.30E-03 | 7.78E-04 | -1.51 | -2.92 | -1.93 |

Figure 5 Continued

| TCID | GENE_na29 | TCID | GENE_na29 | TCID | GENE_na29 |
|---|---|---|---|---|---|
| 2337524 | 2337524 | 3914786 | ABCC13 | 2501697 | ACTR3 |
| 2357193 | 2357193 | 3260447 | ABCC2 | 2676901 | ACTR8 |
| 2383807 | 2383807 | 3726691 | ABCC3 | 2582562 | ACVR1 |
| 2406391 | 2406391 | 3446919 | ABCC9 | 3415148 | ACVR1B |
| 2472880 | 2472880 | 3450861 | ABCD2 | 2509557 | ACVR2A |
| 2489140 | 2489140 | 2777276 | ABCG2 | 3415109 | ACVRL1 |
| 2494151 | 2494151 | 2550755 | ABCG5 | 2623441 | ACY1 |
| 2506693 | 2506693 | 2474265 | ABHD1 | 3572263 | ACYP1 |
| 2641232 | 2641232 | 3535307 | ABHD12B | 3702382 | ADAD2 |
| 2649710 | 2649710 | 3607447 | ABHD2 | 3311832 | ADAM12 |
| 2652217 | 2652217 | 2523689 | ABI2 | 2539821 | ADAM17 |
| 2832019 | 2832019 | 2686458 | ABI3BP | 3011492 | ADAM22 |
| 2908499 | 2908499 | 3307939 | ABLIM1 | 3927446 | ADAMTS1 |
| 2908502 | 2908502 | 3739962 | ABR | 3641633 | ADAMTS17 |
| 3092561 | 3092561 | 3368940 | ABTB2 | 3700158 | ADAMTS18 |
| 3107603 | 3107603 | 3754469 | ACACA | 2889916 | ADAMTS2 |
| 3139557 | 3139557 | 3430959 | ACACB | 3927480 | ADAMTS5 |
| 3153400 | 3153400 | 3432030 | ACAD10 | 2859601 | ADAMTS6 |
| 3184925 | 3184925 | 2695648 | ACAD11 | 2680046 | ADAMTS9 |
| 3253452 | 3253452 | 2641341 | ACAD9 | 2977471 | ADAT2 |
| 3321980 | 3321980 | 2597347 | ACADL | 2800711 | ADCY2 |
| 3398455 | 3398455 | 3708306 | ACADVL | 3558168 | ADCY4 |
| 3511158 | 3511158 | 2712040 | ACAP2 | 3453252 | ADCY6 |
| 3619197 | 3619197 | 3723317 | ACBD4 | 3153718 | ADCY8 |
| 3749600 | 3749600 | 3279058 | ACBD7 | 3775906 | ADCYAP1 |
| 3777770 | 3777770 | 3328069 | ACCSL | 2558736 | ADD2 |
| 3881010 | 3881010 | 3730601 | ACE | 3263555 | ADD3 |
| 3893716 | 3893716 | 4000605 | ACE2 | 2779271 | ADH1A |
| 3895675 | 3895675 | 3164312 | ACER2 | 2779231 | ADH1A |
| 3958399 | 3958399 | 3528994 | ACIN1 | 2779199 | ADH1A |
| 3289445 | A1CF | 3528895 | ACIN1 | 2779271 | ADH1B |
| 3443348 | A2M | 3757433 | ACLY | 2779231 | ADH1B |
| 2558150 | AAK1 | 3013952 | ACN9 | 2779199 | ADH1B |
| 3697015 | AARS | 3166477 | ACO1 | 2779271 | ADH1C |
| 3070183 | AASS | 2394626 | ACOT7 | 2779231 | ADH1C |
| 3719362 | AATF | 4002741 | ACOT9 | 2779124 | ADH4 |
| 3218528 | ABCA1 | 3771215 | ACOX1 | 2387711 | ADH5 |
| 2756309 | ABCA10 | 2759857 | ACOX3 | 2779095 | ADH5 |
| 3768880 | ABCA10 | 2645387 | ACPL2 | 2779163 | ADH6 |
| 2756309 | ABCA11P | 3981164 | ACRC | 3252170 | ADK |
| 3768880 | ABCA11P | 3603199 | ACSBG1 | 3320123 | ADM |
| 3768969 | ABCA5 | 3726406 | ACSF2 | 3248824 | ADO |
| 3768791 | ABCA6 | 2796553 | ACSL1 | 2375596 | ADORA1 |
| 3815416 | ABCA7 | 4017810 | ACSL4 | 3940001 | ADORA2A |
| 3768627 | ABCA8 | 3651294 | ACSM5 | 3711869 | ADORA2B |
| 3768627 | ABCA9 | 3901696 | ACSS1 | 2427981 | ADORA3 |
| 3768703 | ABCA9 | 3424218 | ACSS3 | 3265047 | ADRB1 |
| 3060117 | ABCB1 | 2459837 | ACTA1 | 4049835 | ADRB3 |
| 3060182 | ABCB1 | 3299504 | ACTA2 | 3940631 | ADRBK2 |
| 2459924 | ABCB10 | 3569814 | ACTN1 | 2464353 | ADSS |
| 3060117 | ABCB4 | 2386943 | ACTN2 | 3607232 | AEN |
| 2599993 | ABCB6 | 3861503 | ACTN4 | 2834957 | AFAP1L1 |
| 4012949 | ABCB7 | 3832643 | ACTN4 | 3307851 | AFAP1L2 |
| 3690470 | ABCC11 | 3304406 | ACTR1A | 2399743 | AFARP1 |

Figure 6

| TCID | GENE_na29 |
|---|---|
| 2734784 | AFF1 |
| 3554592 | AFF1 |
| 2875555 | AFF4 |
| 2533670 | AGAP1 |
| 3031880 | AGAP3 |
| 3606682 | AGBL1 |
| 3372420 | AGBL2 |
| 2949830 | AGER |
| 2530599 | AGFG1 |
| 3083936 | AGPAT5 |
| 3095815 | AGPAT6 |
| 2734047 | AGPAT9 |
| 3039791 | AGR2 |
| 3039830 | AGR3 |
| 3695726 | AGRP |
| 3212728 | AGTPBP1 |
| 2647015 | AGTR1 |
| 2889486 | AGXT2L2 |
| 3023384 | AHCYL2 |
| 2975385 | AHI1 |
| 3375735 | AHNAK |
| 3581221 | AHNAK2 |
| 2991233 | AHR |
| 3545466 | AHSA1 |
| 2555277 | AHSA2 |
| 3522398 | AIDA |
| 2381876 | AIDA |
| 2457573 | AIDA |
| 4042837 | AIDA |
| 3191877 | AIF1L |
| 2439554 | AIM2 |
| 3226138 | AK1 |
| 2340315 | AK3L1 |
| 3728097 | AKAP1 |
| 3749086 | AKAP10 |
| 3487220 | AKAP11 |
| 2931569 | AKAP12 |
| 3606304 | AKAP13 |
| 3184408 | AKAP2 |
| 4008170 | AKAP4 |
| 3540068 | AKAP5 |
| 2925724 | AKAP7 |
| 3853299 | AKAP8 |
| 3012381 | AKAP9 |
| 2969201 | AKD2 |
| 3073981 | AKR1B1 |
| 3274758 | AKR1C1 |
| 3274758 | AKR1C2 |
| 3233049 | AKR1C3 |
| 3232944 | AKR1CL2 |
| 2399743 | AKR7A3 |
| 2399743 | AKR7L |
| 4009849 | ALAS2 |
| 3838522 | ALDH16A1 |

| TCID | GENE_na29 |
|---|---|
| 3209726 | ALDH1A1 |
| 3611625 | ALDH1A3 |
| 3169331 | ALDH1B1 |
| 3714068 | ALDH3A2 |
| 3337329 | ALDH3B1 |
| 3379091 | ALDH3B1 |
| 3337329 | ALDH3B2 |
| 3379091 | ALDH3B2 |
| 3571727 | ALDH6A1 |
| 2873785 | ALDH7A1 |
| 2975257 | ALDH8A1 |
| 3750767 | ALDOC |
| 3990566 | ALG11 |
| 3490504 | ALG11 |
| 3965393 | ALG12 |
| 2424148 | ALG14 |
| 2708407 | ALG3 |
| 2339682 | ALG6 |
| 3383164 | ALG8 |
| 3391149 | ALG9 |
| 2546409 | ALK |
| 3389878 | ALKBH8 |
| 2488785 | ALMS1 |
| 2488785 | ALMS1P |
| 3709417 | ALOX15B |
| 3244622 | ALOX5 |
| 2532314 | ALPI |
| 2532294 | ALPI |
| 3605884 | ALPK3 |
| 2532314 | ALPP |
| 2532294 | ALPP |
| 2532272 | ALPP |
| 2532294 | ALPPL2 |
| 2532272 | ALPPL2 |
| 2594773 | ALS2CR12 |
| 2852742 | AMACR |
| 3371544 | AMBRA1 |
| 3692856 | AMFR |
| 3393670 | AMICA1 |
| 3452478 | AMIGO2 |
| 4017961 | AMMECR1 |
| 3410322 | AMN1 |
| 4018454 | AMOT |
| 2696309 | AMOTL2 |
| 3046739 | AMPH |
| 2571075 | ANAPC1 |
| 2788143 | ANAPC10 |
| 3527597 | ANG |
| 3572782 | ANGEL1 |
| 3148463 | ANGPT1 |
| 3122489 | ANGPT2 |
| 2445982 | ANGPTL1 |
| 3819474 | ANGPTL4 |
| 3388517 | ANGPTL5 |

| TCID | GENE_na29 |
|---|---|
| 3850020 | ANGPTL6 |
| 2740067 | ANK2 |
| 3290875 | ANK3 |
| 3598199 | ANKDD1A |
| 3727787 | ANKFN1 |
| 3741997 | ANKFY1 |
| 2849469 | ANKH |
| 3349535 | ANKK1 |
| 3525679 | ANKRD10 |
| 3778252 | ANKRD12 |
| 3431376 | ANKRD13A |
| 3716151 | ANKRD13B |
| 2773023 | ANKRD17 |
| 3205834 | ANKRD18A |
| 3205834 | ANKRD18B |
| 2565559 | ANKRD23 |
| 3282117 | ANKRD26 |
| 2356273 | ANKRD35 |
| 2564816 | ANKRD36 |
| 2565935 | ANKRD36 |
| 2564816 | ANKRD36B |
| 2565935 | ANKRD36B |
| 2754673 | ANKRD37 |
| 3146661 | ANKRD46 |
| 3876142 | ANKRD5 |
| 2857488 | ANKRD55 |
| 2916825 | ANKRD6 |
| 2904329 | ANKS1A |
| 3467351 | ANKS1B |
| 3678279 | ANKS3 |
| 3217361 | ANKS6 |
| 3441542 | ANO2 |
| 3428333 | ANO4 |
| 3323748 | ANO5 |
| 2487082 | ANTXR1 |
| 2774971 | ANTXR2 |
| 3286975 | ANUBL1 |
| 3174816 | ANXA1 |
| 3627248 | ANXA2 |
| 3167110 | ANXA2 |
| 3627248 | ANXA2P1 |
| 2790109 | ANXA2P1 |
| 3167110 | ANXA2P2 |
| 3249171 | ANXA2P3 |
| 2732844 | ANXA3 |
| 2487412 | ANXA4 |
| 2784027 | ANXA5 |
| 2881747 | ANXA6 |
| 2358591 | ANXA9 |
| 3046062 | AOAH |
| 3722195 | AOC3 |
| 2522247 | AOX1 |
| 3754677 | AP1GBP1 |
| 3016177 | AP1S1 |

Figure 6 continued

| TCID | GENE_na29 | TCID | GENE_na29 | TCID | GENE_na29 |
|---|---|---|---|---|---|
| 2601287 | AP1S3 | 2734421 | ARHGAP24 | 3191074 | ASB6 |
| 3718682 | AP2B1 | 2833286 | ARHGAP26 | 2966636 | ASCC3 |
| 2655476 | AP2M1 | 3777263 | ARHGAP28 | 3429008 | ASCL1 |
| 2863730 | AP3B1 | 2423829 | ARHGAP29 | 3743371 | ASGR1 |
| 3636216 | AP3B2 | 3531479 | ARHGAP5 | 2437417 | ASH1L |
| 3295032 | AP3M1 | 3999568 | ARHGAP6 | 3094447 | ASH2L |
| 3096007 | AP3M2 | 3948259 | ARHGAP8 | 3966597 | ASMT |
| 2455418 | AP3S1 | 3445786 | ARHGDIB | 3137530 | ASPH |
| 3638665 | AP3S2 | 3642747 | ARHGDIG | 3214845 | ASPN |
| 2428855 | AP4B1 | 3352503 | ARHGEF12 | 2695295 | ASTE1 |
| 3593770 | AP4E1 | 2437801 | ARHGEF2 | 3881874 | ASXL1 |
| 2766893 | APBB2 | 2677723 | ARHGEF3 | 2544925 | ASXL2 |
| 2878368 | APBB3 | 2505833 | ARHGEF4 | 3069399 | ASZ1 |
| 2824198 | APC | 3029646 | ARHGEF5 | 3299255 | ATAD1 |
| 2622196 | APEH | 3029646 | ARHGEF5L | 3151534 | ATAD2 |
| 2434341 | APH1A | 3501661 | ARHGEF7 | 3716893 | ATAD5 |
| 3597521 | APH1B | 3537884 | ARID4A | 3310413 | ATE1 |
| 3369249 | APIP | 2461786 | ARID4B | 2588066 | ATF2 |
| 2486851 | APLF | 3600744 | ARIH1 | 2379132 | ATF3 |
| 3356115 | APLP2 | 2621827 | ARIH2 | 2949622 | ATF6B |
| 2361584 | APOA1BP | 2842530 | ARL10 | 3647827 | ATF7IP2 |
| 3945572 | APOBEC3C | 2632453 | ARL13B | 2818212 | ATG10 |
| 3945651 | APOBEC3F | 3767169 | ARL17P1 | 3769779 | ATG12 |
| 3945651 | APOBEC3G | 3334783 | ARL2 | 3578278 | ATG2B |
| 3835891 | APOC1 | 3304475 | ARL3 | 2339511 | ATG4C |
| 4054204 | APOD | 2931391 | ARL4A | 2526759 | ATIC |
| 3944404 | APOL1 | 2990464 | ARL4A | 2548776 | ATL2 |
| 3959350 | APOL3 | 2724853 | ARL4A | 3347658 | ATM |
| 2902531 | APOM | 3683037 | ARL6IP1 | 3390143 | ATM |
| 4002809 | APOO | 2628682 | ARL6IP5 | 3670668 | ATMIN |
| 3983105 | APOOL | 2451139 | ARL8A | 2726072 | ATP10D |
| 2833924 | APOOL | 2608765 | ARL8B | 2654855 | ATP11B |
| 2625606 | APPL1 | 3017080 | ARMC10 | 2711225 | ATP13A4 |
| 3469319 | APPL2 | 3238702 | ARMC3 | 2711205 | ATP13A4 |
| 3203311 | APTX | 2644461 | ARMC8 | 2353477 | ATP1A1 |
| 3802396 | AQP4 | 2531779 | ARMC9 | 2645764 | ATP1B3 |
| 3595594 | AQP9 | 3984945 | ARMCX3 | 3431483 | ATP2A2 |
| 3617757 | AQR | 4015838 | ARMCX6 | 3464983 | ATP2B1 |
| 3381241 | ARAP1 | 3321150 | ARNTL | 2375706 | ATP2B4 |
| 2785590 | ARAP2 | 3409127 | ARNTL2 | 2642325 | ATP2C1 |
| 2731542 | AREG | 3471198 | ARPC3 | 2695295 | ATP2C1 |
| 3453370 | ARF3 | 3188993 | ARPC5L | 3671727 | ATP2C2 |
| 3962587 | ARFGAP3 | 2616596 | ARPP-21 | 2351817 | ATP5F1 |
| 3139035 | ARFGEF1 | 2866704 | ARRDC3 | 2714200 | ATP5I |
| 3888055 | ARFGEF2 | 3768474 | ARSG | 3916576 | ATP5J |
| 2747893 | ARFIP1 | 2782694 | ARSJ | 3535125 | ATP5S |
| 2925841 | ARG1 | 2731928 | ART3 | 3996381 | ATP6AP1 |
| 3524618 | ARGLU1 | 3445723 | ART4 | 3105749 | ATP6V0D2 |
| 2746693 | ARHGAP10 | 3359881 | ART5 | 2841284 | ATP6V0E1 |
| 3283920 | ARHGAP12 | 3261923 | AS3MT | 2636589 | ATP6V1A |
| 2508611 | ARHGAP15 | 3395464 | ASAM | 3088544 | ATP6V1B2 |
| 2973694 | ARHGAP18 | 3153428 | ASAP1 | 2469529 | ATP6V1C2 |
| 3302187 | ARHGAP19 | 2468811 | ASAP2 | 2949038 | ATP6V1G2 |
| 3390641 | ARHGAP20 | 2553262 | ASB3 | 3982423 | ATP7A |

Figure 6 continued

| TCID | GENE_na29 | TCID | GENE_na29 | TCID | GENE_na29 |
|------|-----------|------|-----------|------|-----------|
| 2767378 | ATP8A1 | 2583014 | BAZ2B | 3256074 | BMPR1A |
| 3482274 | ATP8A2 | 3324453 | BBOX1 | 2523213 | BMPR2 |
| 3809826 | ATP8B1 | 3600960 | BBS4 | 3938817 | BMS1 |
| 3712835 | ATPAF2 | 2996321 | BBS9 | 2841528 | BNIP1 |
| 3617920 | ATPBD4 | 2634965 | BBX | 3314040 | BNIP3 |
| 2698844 | ATR | 3835777 | BCAM | 2761285 | BOD1L |
| 3874313 | ATRN | 3018535 | BCAP29 | 2536625 | BOK |
| 4013224 | ATRX | 4026669 | BCAP31 | 3683050 | BOLA2 |
| 3948754 | ATXN10 | 3729569 | BCAS3 | 2593838 | BOLL |
| 3471588 | ATXN2 | 3311775 | BCCIP | 3732448 | BPTF |
| 3576889 | ATXN3 | 3269662 | BCCIP | 2877257 | BRD8 |
| 2627390 | ATXN7 | 3454147 | BCDIN3D | 2798915 | BRD9 |
| 2456849 | AURKA | 2420808 | BCL10 | 2442858 | BRP44 |
| 2456849 | AURKAPS1 | 2554975 | BCL11A | 3842059 | BRSK1 |
| 3006572 | AUTS2 | 3811339 | BCL2 | 3267678 | BRWD2 |
| 2996033 | AVL9 | 3835198 | BCL2A1 | 4013730 | BRWD3 |
| 3459722 | AVPR1A | 3902489 | BCL2L1 | 3333595 | BSCL2 |
| 3063589 | AZGP1 | 2500275 | BCL2L11 | 3854417 | BST2 |
| 2667181 | AZI2 | 3936256 | BCL2L13 | 3836470 | BTBD1 |
| 3147591 | AZIN1 | 3405207 | BCL2L14 | 3363645 | BTBD10 |
| 2386418 | B3GALNT2 | 3386737 | BCL7B | 3430462 | BTBD11 |
| 2449104 | B3GALT2 | 2356818 | BCL9 | 3554592 | BTBD6 |
| 3375935 | B3GAT3 | 3348940 | BCO2 | 3577277 | BTBD7 |
| 3824596 | B3GNT3 | 2814527 | BDP1 | 2952497 | BTBD9 |
| 3475511 | B3GNT4 | 3758157 | BECN1 | 2773545 | BTC |
| 3418394 | B4GALNT1 | 2411799 | BEND5 | 2553771 | BTF3 |
| 3400236 | B4GALNT3 | 4016308 | BEX1 | 2375664 | BTG2 |
| 2440664 | B4GALT3 | 4016308 | BEX2 | 3926080 | BTG3 |
| 3908963 | B4GALT5 | 3649245 | BFAR | 2899372 | BTN3A1 |
| 3803120 | B4GALT6 | 3899111 | BFSP1 | 2899298 | BTN3A1 |
| 3110217 | BAALC | 2608725 | BHLHE40 | 2899372 | BTN3A2 |
| 3393257 | BACE1 | 3448088 | BHLHE41 | 2899298 | BTN3A2 |
| 3921933 | BACE2 | 2817251 | BHMT | 2899372 | BTN3A3 |
| 3981120 | BAG1 | 2817251 | BHMT2 | 2899298 | BTN3A3 |
| 2911372 | BAG2 | 3951927 | BID | 2844859 | BTNL8 |
| 3267314 | BAG3 | 3346548 | BIRC3 | 3261165 | BTRC |
| 3094494 | BAG4 | 3772187 | BIRC5 | 3014742 | BUD31 |
| 3924929 | BAGE | 2476219 | BIRC6 | 3764289 | BZRAP1 |
| 3924929 | BAGE2 | 3893250 | BIRC7 | 2690012 | BZW1 |
| 3924929 | BAGE3 | 3499585 | BIVM | 2522439 | BZW1 |
| 3924929 | BAGE4 | 3608298 | BLM | 2690012 | BZW1L1 |
| 3924929 | BAGE5 | 3751830 | BLMH | 2522439 | BZW1L1 |
| 3589947 | BAHD1 | 3301713 | BLNK | 3286776 | C10orf10 |
| 2912416 | BAI3 | 3303392 | BLOC1S2 | 3279089 | C10orf111 |
| 3737697 | BAIAP2 | 2366490 | BLZF1 | 3307795 | C10orf118 |
| 3240452 | BAMBI | 3619229 | BMF | 3309755 | C10orf119 |
| 2737596 | BANK1 | 3238491 | BMI1 | 3259087 | C10orf129 |
| 2949038 | BAT1 | 3089215 | BMP1 | 3259263 | C10orf131 |
| 2367154 | BAT2D1 | 2774817 | BMP2K | 3231846 | C10orf139 |
| 2949256 | BAT5 | 2958172 | BMP5 | 3280787 | C10orf140 |
| 3838067 | BAX | 2893895 | BMP6 | 3275132 | C10orf18 |
| 3560711 | BAZ1A | 2331558 | BMP8A | 3244539 | C10orf25 |
| 3056044 | BAZ1B | 2331511 | BMP8A | 3261886 | C10orf26 |
| 3457947 | BAZ2A | 2331511 | BMP8B | 3260099 | C10orf28 |

Figure 6 continued

| TCID | GENE_na29 | TCID | GENE_na29 | TCID | GENE_na29 |
|---|---|---|---|---|---|
| 3261923 | C10orf32 | 3550328 | C14orf129 | 2557549 | C1D |
| 3309124 | C10orf46 | 3550234 | C14orf132 | 4019967 | C1GALT1C1 |
| 3294959 | C10orf55 | 3563687 | C14orf138 | 2406735 | C1orf102 |
| 3254337 | C10orf57 | 3573933 | C14orf145 | 2443305 | C1orf114 |
| 3254488 | C10orf58 | 3573994 | C14orf145 | 2381249 | C1orf115 |
| 3241601 | C10orf68 | 3566949 | C14orf149 | 2453065 | C1orf116 |
| 3288518 | C10orf72 | 3543619 | C14orf169 | 2369609 | C1orf125 |
| 3305198 | C10orf79 | 3569778 | C14orf181 | 2407128 | C1orf149 |
| 3314720 | C10orf92 | 3571727 | C14orf45 | 2431886 | C1orf152 |
| 3314720 | C10orf93 | 3543979 | C14orf45 | 2391005 | C1orf159 |
| 3279410 | C10orf97 | 3540155 | C14orf50 | 2320392 | C1orf187 |
| 3334847 | C11orf2 | 3554523 | C14orf79 | 2436576 | C1orf189 |
| 3334446 | C11orf20 | 3554868 | C14orf80 | 2371547 | C1orf21 |
| 3358112 | C11orf35 | 3569285 | C14orf83 | 2406412 | C1orf216 |
| 3356417 | C11orf44 | 3633191 | C15orf17 | 2369325 | C1orf220 |
| 3325052 | C11orf46 | 3623472 | C15orf33 | 2364016 | C1orf226 |
| 3375999 | C11orf48 | 3629761 | C15orf44 | 2371738 | C1orf26 |
| 3329537 | C11orf49 | 3641597 | C15orf51 | 2436576 | C1orf43 |
| 3380996 | C11orf51 | 3619479 | C15orf57 | 2369325 | C1orf49 |
| 3396144 | C11orf61 | 3643114 | C16orf14 | 2358138 | C1orf51 |
| 3353441 | C11orf63 | 3649714 | C16orf45 | 2381876 | C1orf58 |
| 3390143 | C11orf65 | 3701433 | C16orf46 | 2402111 | C1orf63 |
| 2708855 | C11orf72 | 3695819 | C16orf48 | 2389718 | C1orf71 |
| 3343252 | C11orf73 | 3655708 | C16orf53 | 2359736 | C1orf77 |
| 3327166 | C11orf74 | 3644191 | C16orf73 | 2336963 | C1orf83 |
| 3386737 | C11orf75 | 3693511 | C16orf80 | 2438093 | C1orf85 |
| 3336486 | C11orf80 | 3678542 | C16orf89 | 3236786 | C1QL3 |
| 3368707 | C11orf91 | 3774975 | C17orf101 | 2852742 | C1QTNF3 |
| 3465188 | C12orf12 | 3744300 | C17orf44 | 2719440 | C1QTNF7 |
| 3430389 | C12orf23 | 3712098 | C17orf45 | 3403168 | C1S |
| 3424379 | C12orf26 | 3710277 | C17orf48 | 2902844 | C2 |
| 3421824 | C12orf28 | 3708201 | C17orf49 | 3876084 | C20orf103 |
| 3464622 | C12orf29 | 3724591 | C17orf57 | 3890109 | C20orf108 |
| 3471819 | C12orf30 | 3744254 | C17orf59 | 3893072 | C20orf11 |
| 3443434 | C12orf33 | 3766621 | C17orf72 | 3902764 | C20orf112 |
| 3410384 | C12orf35 | 3769969 | C17orf80 | 3899495 | C20orf12 |
| 3407849 | C12orf39 | 3735752 | C17orf86 | 3904797 | C20orf132 |
| 3441215 | C12orf4 | 3742627 | C17orf87 | 3746881 | C20orf191 |
| 3411234 | C12orf40 | 3740664 | C17orf91 | 3891723 | C20orf197 |
| 3453177 | C12orf41 | 3803500 | C18orf34 | 3895679 | C20orf27 |
| 3473331 | C12orf49 | 3791341 | C18orf49 | 3901665 | C20orf3 |
| 3401756 | C12orf5 | 3793588 | C18orf55 | 3896174 | C20orf30 |
| 3442249 | C12orf53 | 3795850 | C18orf56 | 3877221 | C20orf7 |
| 3403077 | C12orf57 | 3798829 | C18orf58 | 3900091 | C20orf74 |
| 3427282 | C12orf63 | 3828162 | C19orf2 | 3918104 | C21orf63 |
| 3410322 | C12orf72 | 3817651 | C19orf30 | 3926138 | C21orf91 |
| 3429857 | C12orf75 | 3832280 | C19orf33 | 3958045 | C22orf30 |
| 3471073 | C12orf76 | 3868330 | C19orf41 | 3965102 | C22orf34 |
| 3486956 | C13orf15 | 3822347 | C19orf53 | 3955357 | C22orf36 |
| 3480681 | C13orf3 | 3862785 | C19orf54 | 3952703 | C22orf39 |
| 3484117 | C13orf33 | 3864597 | C19orf61 | 3954764 | C22orf43 |
| 3485740 | C13orf36 | 3839400 | C19orf63 | 3963676 | C22orf9 |
| 3563372 | C14orf104 | 3850020 | C19orf66 | 3933331 | C2CD2 |
| 3528994 | C14orf119 | 3837664 | C19orf68 | 3381702 | C2CD3 |

Figure 6 continued

| TCID | GENE_na29 | TCID | GENE_na29 | TCID | GENE_na29 |
|---|---|---|---|---|---|
| 2525682 | C2orf21 | 2853642 | C5orf42 | 3086774 | C8orf79 |
| 2506335 | C2orf27A | 2858793 | C5orf43 | 3158812 | C8orf82 |
| 2506335 | C2orf27B | 3724591 | C5orf45 | 3140478 | C8orf84 |
| 2496628 | C2orf29 | 2844479 | C5orf45 | 3180717 | C9orf102 |
| 2482230 | C2orf30 | 2828564 | C5orf56 | 3226709 | C9orf114 |
| 2473831 | C2orf39 | 2854915 | C6 | 2549092 | C9orf126 |
| 2498274 | C2orf40 | 2951057 | C6orf1 | 3225224 | C9orf126 |
| 2477372 | C2orf56 | 2941972 | C6orf105 | 3179872 | C9orf129 |
| 2594313 | C2orf60 | 2951221 | C6orf106 | 3167684 | C9orf131 |
| 2566383 | C2orf64 | 2927967 | C6orf115 | 3195083 | C9orf142 |
| 2560317 | C2orf65 | 2986084 | C6orf120 | 3162529 | C9orf150 |
| 2597273 | C2orf67 | 2901841 | C6orf134 | 3216931 | C9orf156 |
| 2525852 | C2orf67 | 2956217 | C6orf138 | 3223903 | C9orf31 |
| 2559494 | C2orf7 | 2909772 | C6orf141 | 3213847 | C9orf33 |
| 2482440 | C2orf73 | 2960774 | C6orf147 | 3185618 | C9orf43 |
| 2556017 | C2orf86 | 2960399 | C6orf155 | 3037304 | C9orf51 |
| 2520069 | C2orf88 | 2916307 | C6orf165 | 3173974 | C9orf61 |
| 3848039 | C3 | 2966193 | C6orf168 | 3197231 | C9orf68 |
| 2662581 | C3orf10 | 2973232 | C6orf174 | 3193018 | C9orf7 |
| 2627080 | C3orf14 | 2984275 | C6orf176 | 3192580 | C9orf9 |
| 2688882 | C3orf17 | 2969350 | C6orf186 | 3192912 | C9orf96 |
| 2612012 | C3orf20 | 2974671 | C6orf192 | 3181240 | C9orf97 |
| 2663083 | C3orf31 | 2939593 | C6orf201 | 3867264 | CA11 |
| 2641577 | C3orf37 | 2902633 | C6orf26 | 3628498 | CA12 |
| 2619521 | C3orf41 | 2985342 | C6orf54 | 3105506 | CA13 |
| 2610417 | C3orf42 | 2945675 | C6orf62 | 3105600 | CA2 |
| 2700780 | C3orf44 | 2930753 | C6orf72 | 3729419 | CA4 |
| 2627368 | C3orf49 | 2931700 | C6orf97 | 3969855 | CA5B |
| 2636062 | C3orf52 | 3060051 | C7orf23 | 3969855 | CA5BP |
| 2674168 | C3orf62 | 3041409 | C7orf30 | 3137120 | CA8 |
| 2677653 | C3orf63 | 3005956 | C7orf42 | 3168066 | CA9 |
| 2681114 | C3orf64 | 3048134 | C7orf44 | 2531522 | CAB39 |
| 2902958 | C4A | 3022465 | C7orf54 | 3513752 | CAB39L |
| 2902958 | C4B | 3060450 | C7orf62 | 3939707 | CABIN1 |
| 2758076 | C4orf10 | 3011911 | C7orf63 | 3781531 | CABLES1 |
| 2734352 | C4orf12 | 2995491 | C7orf67 | 3400730 | CACNA1C |
| 2770427 | C4orf14 | 3037304 | C7orf70 | 2624385 | CACNA1D |
| 2791419 | C4orf18 | 3194969 | C8G | 3726618 | CACNA1G |
| 2765865 | C4orf19 | 3085933 | C8orf12 | 3643580 | CACNA1H |
| 2717757 | C4orf23 | 3124344 | C8orf16 | 3058991 | CACNA2D1 |
| 2743029 | C4orf29 | 3107234 | C8orf39 | 2675315 | CACNA2D2 |
| 2739714 | C4orf32 | 3095313 | C8orf4 | 3755580 | CACNB1 |
| 2766492 | C4orf34 | 3096271 | C8orf40 | 3237398 | CACNB2 |
| 2753994 | C4orf41 | 3130823 | C8orf41 | 2581349 | CACNB4 |
| 2730303 | C4orf7 | 3121198 | C8orf42 | 3959787 | CACNG2 |
| 2715440 | C4orf8 | 3101802 | C8orf44 | 3732092 | CACNG4 |
| 2875929 | C5orf15 | 3101765 | C8orf44 | 3841184 | CACNG6 |
| 2805176 | C5orf22 | 3086181 | C8orf49 | 2368198 | CACYBP |
| 2829542 | C5orf24 | 3151809 | C8orf54 | 3392332 | CADM1 |
| 2855578 | C5orf28 | 3119236 | C8orf55 | 3864519 | CADM4 |
| 2831519 | C5orf32 | 3089569 | C8orf58 | 2679406 | CADPS |
| 2853388 | C5orf33 | 3118651 | C8orf60 | 3364127 | CALCA |
| 2855614 | C5orf34 | 3099390 | C8orf71 | 3321592 | CALCB |
| 2882834 | C5orf4 | 3086809 | C8orf79 | 3456353 | CALCOCO1 |

Figure 6 continued

| TCID | GENE_na29 |
|---|---|
| 2591367 | CALCRL |
| 3025545 | CALD1 |
| 3304767 | CALHM2 |
| 2551924 | CALM2 |
| 3599280 | CALML4 |
| 3822049 | CALR |
| 3235516 | CAMK1D |
| 2782545 | CAMK2D |
| 3294854 | CAMK2G |
| 2400177 | CAMK2N1 |
| 2823880 | CAMK4 |
| 3229529 | CAMSAP1 |
| 2374345 | CAMSAP1L1 |
| 3420713 | CAND1 |
| 3772775 | CANT1 |
| 3861503 | CAPN12 |
| 3590853 | CAPN3 |
| 4018194 | CAPN6 |
| 2612278 | CAPN7 |
| 3831168 | CAPNS1 |
| 3326183 | CAPRIN1 |
| 2649182 | CAPRIN1 |
| 3389450 | CARD16 |
| 3389353 | CARD17 |
| 3866958 | CARD8 |
| 3820865 | CARM1 |
| 2814693 | CARTPT |
| 3447798 | CASC1 |
| 3266583 | CASC2 |
| 3590014 | CASC5 |
| 3013178 | CASD1 |
| 3644541 | CASKIN1 |
| 3389450 | CASP1 |
| 3389353 | CASP1 |
| 3389257 | CASP12 |
| 2796484 | CASP3 |
| 3389273 | CASP4 |
| 2781693 | CASP6 |
| 2916952 | CASP8AP2 |
| 2429556 | CASQ2 |
| 2638824 | CASR |
| 2868131 | CAST |
| 2821194 | CAST |
| 3326400 | CAT |
| 3378043 | CATSPER1 |
| 2825514 | CATSPER2 |
| 3020302 | CAV1 |
| 3020273 | CAV2 |
| 3293998 | CBARA1 |
| 3704567 | CBFA2T3 |
| 3665116 | CBFB |
| 3352070 | CBL |
| 3812864 | CBLN2 |
| 3910724 | CBLN4 |

| TCID | GENE_na29 |
|---|---|
| 3919834 | CBR3 |
| 3933923 | CBS |
| 2993639 | CBX3 |
| 3456630 | CBX5 |
| 3259367 | CC2D2B |
| 2619480 | CCBP2 |
| 3686587 | CCDC101 |
| 3251490 | CCDC109A |
| 2739160 | CCDC109B |
| 3941643 | CCDC117 |
| 3987607 | CCDC121 |
| 2545999 | CCDC121 |
| 3858794 | CCDC123 |
| 2860614 | CCDC125 |
| 2992963 | CCDC126 |
| 2670903 | CCDC13 |
| 3822287 | CCDC130 |
| 2692573 | CCDC14 |
| 2560149 | CCDC142 |
| 3765167 | CCDC144A |
| 3748400 | CCDC144A |
| 3009838 | CCDC146 |
| 2582701 | CCDC148 |
| 2855285 | CCDC152 |
| 2423264 | CCDC18 |
| 3367036 | CCDC34 |
| 2622026 | CCDC36 |
| 3731228 | CCDC45 |
| 2641449 | CCDC48 |
| 2657981 | CCDC50 |
| 3468225 | CCDC53 |
| 2343170 | CCDC55 |
| 3434193 | CCDC64 |
| 3413643 | CCDC65 |
| 3344685 | CCDC67 |
| 3808745 | CCDC68 |
| 2881860 | CCDC69 |
| 3241601 | CCDC7 |
| 2425173 | CCDC76 |
| 2348792 | CCDC76 |
| 2688813 | CCDC80 |
| 3387771 | CCDC82 |
| 3351733 | CCDC84 |
| 2553771 | CCDC88A |
| 2773407 | CCDC90B |
| 3817400 | CCDC94 |
| 2759393 | CCDC96 |
| 2840002 | CCDC99 |
| 2948821 | CCHCR1 |
| 3718204 | CCL13 |
| 3753966 | CCL14 |
| 3753966 | CCL15 |
| 3753956 | CCL16 |
| 3204285 | CCL19 |

| TCID | GENE_na29 |
|---|---|
| 3204301 | CCL21 |
| 2855542 | CCL28 |
| 3754070 | CCL3 |
| 3754070 | CCL3L1 |
| 3754070 | CCL3L3 |
| 3485674 | CCNA1 |
| 2741768 | CCNA2 |
| 2966371 | CCNC |
| 3380065 | CCND1 |
| 3338192 | CCND1 |
| 3401704 | CCND2 |
| 2953866 | CCND3 |
| 2838598 | CCNG1 |
| 3259400 | CCNJ |
| 2884578 | CCNJL |
| 2702307 | CCNL1 |
| 4041923 | CCNL2 |
| 2391532 | CCNL2 |
| 3453218 | CCNT1 |
| 2507209 | CCNT2 |
| 2620736 | CCR9 |
| 3213530 | CCRK |
| 3336351 | CCS |
| 3421630 | CCT2 |
| 3003193 | CCT6A |
| 3003193 | CCT6P1 |
| 3928070 | CCT8 |
| 2913694 | CD109 |
| 3316344 | CD151 |
| 2432714 | CD160 |
| 3442706 | CD163 |
| 3835035 | CD177 |
| 2860178 | CD180 |
| 3655109 | CD19 |
| 2362180 | CD1A |
| 2353669 | CD2 |
| 2636125 | CD200 |
| 3830359 | CD22 |
| 4035833 | CD24 |
| 3161082 | CD274 |
| 3601229 | CD276 |
| 2909404 | CD2AP |
| 3770305 | CD300A |
| 3770305 | CD300C |
| 3770361 | CD300LF |
| 2583254 | CD302 |
| 2453307 | CD34 |
| 3010503 | CD36 |
| 3838385 | CD37 |
| 3393744 | CD3D |
| 3836243 | CD3EAP |
| 3865378 | CD3EAP |
| 3992575 | CD40LG |
| 3326635 | CD44 |

Figure 6 continued

| TCID | GENE_na29 | TCID | GENE_na29 | TCID | GENE_na29 |
|---|---|---|---|---|---|
| 2377427 | CD46 | 2773719 | CDKL2 | 3920003 | CHAF1B |
| 2687739 | CD47 | 2905169 | CDKN1A | 3483159 | CHCHD2 |
| 2440354 | CD48 | 3201488 | CDKN2B | 3099089 | CHCHD7 |
| 3332729 | CD5 | 2871896 | CDO1 | 2356721 | CHD1L |
| 2326463 | CD52 | 3396770 | CDON | 3609138 | CHD2 |
| 2351572 | CD53 | 4024373 | CDR1 | 3709244 | CHD3 |
| 2377229 | CD55 | 3684782 | CDR2 | 3442054 | CHD4 |
| 3368707 | CD59 | 2734270 | CDS1 | 3906160 | CHD6 |
| 3457160 | CD63 | 3863669 | CEACAM1 | 3660858 | CHD9 |
| 3443868 | CD69 | 3834257 | CEACAM21 | 2676854 | CHDH |
| 2881370 | CD74 | 3834379 | CEACAM5 | 3354799 | CHEK1 |
| 3834502 | CD79A | 3834341 | CEACAM5 | 3479438 | CHFR |
| 3402315 | CD9 | 3834379 | CEACAM6 | 3549092 | CHGA |
| 2635741 | CD96 | 2321813 | CELA2A | 3875179 | CHGB |
| 3822657 | CD97 | 2321813 | CELA2B | 2451593 | CHI3L1 |
| 3966836 | CD99 | 2473991 | CENPA | 3358538 | CHID1 |
| 3489350 | CDADC1 | 2771654 | CENPC1 | 2607568 | CHL1 |
| 3235461 | CDC123 | 2780172 | CENPE | 4006841 | CHMP5 |
| 2348896 | CDC14A | 3505937 | CENPJ | 2994835 | CHN2 |
| 3503164 | CDC16 | 2859667 | CENPK | 3915569 | CHODL |
| 2857042 | CDC20B | 2444451 | CENPL | 3468080 | CHPT1 |
| 3221543 | CDC26 | 3187577 | CEP110 | 3428671 | CHPT1 |
| 3760625 | CDC27 | 2463864 | CEP170 | 4018080 | CHRDL1 |
| 2969467 | CDC2L6 | 2463864 | CEP170L | 3615791 | CHRFAM7A |
| 2921086 | CDC40 | 3779817 | CEP192 | 3359897 | CHRNA10 |
| 2324634 | CDC42 | 3464622 | CEP290 | 3129026 | CHRNA2 |
| 3119339 | CDC42 | 2369843 | CEP350 | 3913775 | CHRNA4 |
| 2459042 | CDC42BPA | 3258444 | CEP55 | 3603436 | CHRNA5 |
| 3580498 | CDC42BPB | 3345593 | CEP57 | 3615791 | CHRNA7 |
| 3335070 | CDC42EP2 | 2351632 | CEPT1 | 3708663 | CHRNB1 |
| 3770029 | CDC42EP4 | 2518272 | CERKL | 2360346 | CHRNB2 |
| 2434776 | CDC42SE1 | 3692701 | CES1 | 2532378 | CHRND |
| 3720896 | CDC6 | 3684982 | CES2 | 3742351 | CHRNE |
| 2346399 | CDC7 | 3692701 | CES4 | 2532399 | CHRNG |
| 2372967 | CDC73 | 3665049 | CES8 | 2567242 | CHST10 |
| 3402874 | CDCA3 | 4026263 | CETN2 | 2646125 | CHST2 |
| 2992243 | CDCA7L | 3662417 | CETP | 3802416 | CHST9 |
| 3040897 | CDCA7L | 2902844 | CFB | 2494447 | CIAO1 |
| 2671728 | CDCP1 | 2373336 | CFH | 3529877 | CIDEB |
| 3694657 | CDH11 | 2373406 | CFH | 3629529 | CILP |
| 3671202 | CDH13 | 2373336 | CFHR1 | 2737840 | CISD2 |
| 3695315 | CDH16 | 2373406 | CFHR1 | 2675504 | CISH |
| 3811949 | CDH19 | 2373406 | CFHR3 | 3474104 | CIT |
| 3802602 | CDH2 | 2373406 | CFHR4 | 4012178 | CITED1 |
| 3251068 | CDH23 | 2781736 | CFI | 2976768 | CITED2 |
| 3666366 | CDH3 | 2522616 | CFLAR | 3205659 | CKAP2 |
| 2805078 | CDH6 | 3508696 | CG030 | 3490655 | CKAP2 |
| 3417146 | CDK2 | 3867573 | CGB | 3371719 | CKAP5 |
| 3476097 | CDK2AP1 | 3867573 | CGB2 | 3580769 | CKB |
| 3458783 | CDK4 | 3867573 | CGB5 | 3664785 | CKLF |
| 3223425 | CDK5RAP2 | 3867573 | CGB7 | 3621351 | CKMT1A |
| 2813481 | CDK7 | 3867573 | CGB8 | 3178583 | CKS2 |
| 3482498 | CDK8 | 3595315 | CGNL1 | 2573641 | CLASP1 |
| 3563861 | CDKL1 | 3817501 | CHAF1A | 2668425 | CLASP2 |

Figure 6 continued

| TCID | GENE_na29 | TCID | GENE_na29 | TCID | GENE_na29 |
|---|---|---|---|---|---|
| 3862108 | CLC | 3815399 | CNN2 | 2451309 | COX7C |
| 2345023 | CLCA1 | 2424102 | CNN3 | 2700244 | CP |
| 2345095 | CLCA3P | 3260265 | CNNM1 | 3106559 | CP |
| 3378758 | CLCF1 | 3261971 | CNNM2 | 2647109 | CPA3 |
| 2751385 | CLCN3 | 3693673 | CNOT1 | 3716411 | CPD |
| 2320472 | CLCN6 | 3421897 | CNOT2 | 2750627 | CPE |
| 2710599 | CLDN1 | 3074362 | CNOT4 | 2719361 | CPEB2 |
| 3497195 | CLDN10 | 2844709 | CNOT6 | 2841699 | CPEB4 |
| 3012019 | CLDN12 | 2774565 | CNOT6L | 2842255 | CPLX2 |
| 2657808 | CLDN16 | 2963859 | CNR1 | 3461341 | CPM |
| 2932593 | CLDN20 | 3758157 | CNTD1 | 3105904 | CPNE3 |
| 3007960 | CLDN4 | 3331730 | CNTF | 2695453 | CPNE4 |
| 3952762 | CLDN5 | 3163728 | CNTLN | 3450655 | CPNE8 |
| 3743551 | CLDN7 | 3411721 | CNTN1 | 2524817 | CPO |
| 3928415 | CLDN8 | 3345940 | CNTN5 | 3158516 | CPSF1 |
| 3868987 | CLDND2 | 2607757 | CNTN6 | 2468920 | CPSF3 |
| 3443891 | CLEC2B | 3721989 | CNTNAP1 | 2315739 | CPSF3L |
| 3404436 | CLEC2D | 3029900 | CNTNAP2 | 3421446 | CPSF6 |
| 2620448 | CLEC3B | 3531163 | COCH | 3043648 | CPVL |
| 3443183 | CLEC4E | 3769969 | COG1 | 3895118 | CPXM1 |
| 3848525 | CLEC4G | 3488253 | COG3 | 2377427 | CR1L |
| 3848525 | CLEC4GP1 | 3067080 | COG5 | 2377283 | CR2 |
| 3076868 | CLEC5A | 2425756 | COL11A1 | 3603295 | CRABP1 |
| 3444009 | CLEC7A | 2961177 | COL12A1 | 2438458 | CRABP2 |
| 2787005 | CLGN | 3250486 | COL13A1 | 2660648 | CRBN |
| 2949330 | CLIC1 | 3181642 | COL15A1 | 2994558 | CREB5 |
| 4027769 | CLIC2 | 2404546 | COL16A1 | 3677795 | CREBBP |
| 3230594 | CLIC3 | 3762198 | COL1A1 | 2567647 | CREG2 |
| 2955638 | CLIC5 | 3013054 | COL1A2 | 2610136 | CRELD1 |
| 2955556 | CLIC5 | 2889542 | COL23A1 | 3950452 | CRELD2 |
| 3919278 | CLIC6 | 2781441 | COL25A1 | 2816536 | CRHBP |
| 3860229 | CLIP3 | 2642261 | COL29A1 | 3554818 | CRIP2 |
| 2475407 | CLIP4 | 2519577 | COL3A1 | 2956563 | CRISP3 |
| 2437329 | CLK2 | 3924424 | COL6A2 | 3720228 | CRKRS |
| 2437329 | CLK2P | 2673345 | COL7A1 | 3855104 | CRLF1 |
| 3577940 | CLMN | 2633390 | COL8A1 | 2759038 | CRMP1 |
| 3494502 | CLN5 | 2406579 | COL8A2 | 2398193 | CROCC |
| 3629494 | CLPX | 3892974 | COL9A3 | 2398193 | CROCCL1 |
| 2406420 | CLSPN | 3113133 | COLEC10 | 2398193 | CROCCL2 |
| 2395890 | CLSTN1 | 3518169 | COMMD6 | 3726772 | CROP |
| 3168415 | CLTA | 2768145 | COMMD8 | 3011317 | CROT |
| 2842530 | CLTB | 3369762 | COMMD9 | 3302572 | CRTAC1 |
| 3729172 | CLTC | 2363084 | COPA | 2616166 | CRTAP |
| 3129065 | CLU | 3855324 | COPE | 3469865 | CRY1 |
| 3775808 | CLUL1 | 2532064 | COPS7B | 3391149 | CRYAB |
| 2945882 | CMAH | 3761054 | COPZ2 | 2685776 | CRYBG3 |
| 3407926 | CMAS | 3417531 | COQ10A | 2418451 | CRYZ |
| 2668021 | CMTM6 | 2775965 | COQ2 | 3929821 | CRYZL1 |
| 2817464 | CMYA5 | 3571667 | COQ6 | 3457614 | CS |
| 3793760 | CNDP2 | 3470549 | CORO1C | 3444252 | CSDA |
| 2382419 | CNIH4 | 3751590 | CORO6 | 3444252 | CSDAP1 |
| 3971219 | CNKSR2 | 3711165 | COX10 | 2406783 | CSF3R |
| 2980516 | CNKSR3 | 3303109 | COX15 | 3126504 | CSGALNACT1 |
| 3821263 | CNN1 | 2772968 | COX18 | 3243908 | CSGALNACT2 |

Figure 6 continued

| TCID | GENE_na29 | TCID | GENE_na29 | TCID | GENE_na29 |
|---|---|---|---|---|---|
| 2880932 | CSNK1A1 | 3358950 | CTSD | 3910429 | CYP24A1 |
| 2880932 | CSNK1A1L | 3634811 | CTSH | 3258384 | CYP26A1 |
| 3960478 | CSNK1E | 2434609 | CTSK | 2559189 | CYP26B1 |
| 3629103 | CSNK1G1 | 3216671 | CTSL2 | 2528093 | CYP27A1 |
| 3629012 | CSNK1G1 | 2434575 | CTSS | 3458819 | CYP27B1 |
| 2826550 | CSNK1G3 | 3338552 | CTTN | 3862944 | CYP2A13 |
| 3894228 | CSNK2A1 | 3069470 | CTTNBP2 | 3862944 | CYP2A6 |
| 3894228 | CSNK2A1P | 3848644 | CTXN1 | 3862944 | CYP2A7 |
| 2902559 | CSNK2B | 3279698 | CUBN | 3862944 | CYP2A7P1 |
| 3101893 | CSPP1 | 3764022 | CUEDC1 | 3259019 | CYP2C19 |
| 2669930 | CSRNP1 | 3502497 | CUL4A | 3259019 | CYP2C9 |
| 3454662 | CSRNP2 | 4019900 | CUL4B | 2955761 | CYP39A1 |
| 2450865 | CSRP1 | 3347549 | CUL5 | 3063501 | CYP3A4 |
| 3463056 | CSRP2 | 2954355 | CUL7 | 3015040 | CYP3A43 |
| 3901333 | CST1 | 2954355 | CUL9 | 3063406 | CYP3A5 |
| 3901333 | CST4 | 2907754 | CUL9 | 3063406 | CYP3A5P2 |
| 3335894 | CST6 | 3310675 | CUZD1 | 3063501 | CYP3A7 |
| 2638869 | CSTA | 3389745 | CWF19L2 | 3551432 | CYP46A1 |
| 3934245 | CSTB | 2726542 | CWH43 | 2335048 | CYP4A11 |
| 3289631 | CSTF2T | 2773434 | CXCL1 | 2335048 | CYP4A22 |
| 3368520 | CSTF3 | 2773972 | CXCL11 | 3853658 | CYP4F11 |
| 4020137 | CT47A1 | 3286602 | CXCL12 | 3823340 | CYP4F12 |
| 4020137 | CT47A10 | 2732508 | CXCL13 | 2334986 | CYP4X1 |
| 4020137 | CT47A11 | 2876608 | CXCL14 | 3060994 | CYP51A1 |
| 4020137 | CT47A2 | 3863640 | CXCL17 | 3138204 | CYP7B1 |
| 4020137 | CT47A3 | 2773434 | CXCL2 | 2344888 | CYR61 |
| 4020137 | CT47A4 | 2773434 | CXCL3 | 4013460 | CYSLTR1 |
| 4020137 | CT47A5 | 2773947 | CXCL9 | 3489138 | CYSLTR2 |
| 4020137 | CT47A6 | 2578028 | CXCR4 | 3772525 | CYTH1 |
| 4020137 | CT47A7 | 4024420 | CXorf18 | 3837836 | CYTH2 |
| 4020137 | CT47A8 | 4003895 | CXorf21 | 3037251 | CYTH3 |
| 4020137 | CT47A9 | 4002011 | CXorf23 | 3940001 | CYTSA |
| 4020137 | CT47B1 | 3973891 | CXorf27 | 3714177 | CYTSB |
| 3533499 | CTAGE5 | 4006504 | CXorf36 | 3927392 | CYYR1 |
| 3029230 | CTAGE6 | 3981474 | CXorf50B | 3926138 | D21S2089E |
| 2417390 | CTBP2 | 3986230 | CXorf57 | 3517251 | DACH1 |
| 2420467 | CTBS | 3980264 | CXorf62 | 3538087 | DACT1 |
| 3665603 | CTCF | 3807809 | CXXC1 | 2622121 | DAG1 |
| 2527786 | CTDSP1 | 2831350 | CXXC5 | 2673830 | DALRD3 |
| 3458911 | CTDSP2 | 3709213 | CYB5D1 | 2848464 | DAP |
| 2617276 | CTDSPL | 3962530 | CYB5R3 | 2361036 | DAP3 |
| 3591909 | CTDSPL2 | 2915491 | CYB5R4 | 3628832 | DAPK2 |
| 2974330 | CTGF | 3973839 | CYBB | 2577958 | DARS |
| 2341663 | CTH | 2515240 | CYBRD1 | 4031834 | DAZ1 |
| 3110317 | CTHRC1 | 3613300 | CYFIP1 | 2664760 | DAZ2 |
| 2830946 | CTNNA1 | 2837266 | CYFIP2 | 4031834 | DAZ2 |
| 3292169 | CTNNA3 | 3660213 | CYLD | 2664760 | DAZ3 |
| 3219621 | CTNNAL1 | 3157217 | CYP11B1 | 4031834 | DAZ3 |
| 2618940 | CTNNB1 | 3157217 | CYP11B2 | 2664760 | DAZ4 |
| 4000839 | CTPS2 | 3304522 | CYP17A1 | 4031834 | DAZ4 |
| 3887117 | CTSA | 3261886 | CYP17A1OS | 3815834 | DAZAP1 |
| 3086206 | CTSB | 2548699 | CYP1B1 | 2664760 | DAZL |
| 3124537 | CTSB | 2523635 | CYP20A1 | 3223157 | DBC1 |
| 3385769 | CTSC | 2903034 | CYP21A2 | 2888800 | DBN1 |

Figure 6 continued

| TCID | GENE_na29 | TCID | GENE_na29 | TCID | GENE_na29 |
|---|---|---|---|---|---|
| 2425212 | DBT | 3847906 | DENND1C | 3513995 | DLEU2 |
| 2515183 | DCAF17 | 3118651 | DENND3 | 3513995 | DLEU2L |
| 2686023 | DCBLD2 | 3629811 | DENND4A | 3384704 | DLG2 |
| 3788560 | DCC | 3362263 | DENND5A | 3980643 | DLG3 |
| 3367788 | DCDC1 | 3449760 | DENND5B | 3708306 | DLG4 |
| 3367917 | DCDC1 | 3435490 | DENR | 3743393 | DLG4 |
| 2945440 | DCDC2 | 2858592 | DEPDC1B | 3082759 | DLGAP2 |
| 3367788 | DCDC5 | 3943101 | DEPDC5 | 3883819 | DLGAP4 |
| 3361072 | DCHS1 | 3113280 | DEPDC6 | 3565663 | DLGAP5 |
| 2790486 | DCHS2 | 3151401 | DERL1 | 3544346 | DLST |
| 3509473 | DCLK1 | 3742756 | DERL2 | 3544346 | DLSTP |
| 3465274 | DCN | 2528476 | DES | 2333794 | DMAP1 |
| 3440192 | DCP1B | 3638068 | DET1 | 4004044 | DMD |
| 2824354 | DCP2 | 3980482 | DGAT2L6 | 3859761 | DMKN |
| 3520934 | DCT | 3064501 | DGAT2L7 | 3159735 | DMRT3 |
| 2795819 | DCTD | 3039247 | DGKB | 2336809 | DMRTB1 |
| 2559967 | DCTN1 | 3487095 | DGKH | 3981474 | DMRTC1 |
| 3458614 | DCTN2 | 3074912 | DGKI | 3981474 | DMRTC1B |
| 2881554 | DCTN4 | 2413907 | DHCR24 | 3060051 | DMTF1 |
| 3092325 | DCTN6 | 2326496 | DHDDS | 2825514 | DMXL1 |
| 3683845 | DCUN1D3 | 2817837 | DHFR | 3624145 | DMXL2 |
| 2726828 | DCUN1D4 | 3667811 | DHODH | 2992243 | DNAH11 |
| 4018218 | DCX | 3558118 | DHRS1 | 3040897 | DNAH11 |
| 3824212 | DDA1 | 3719210 | DHRS11 | 2382781 | DNAH14 |
| 2420832 | DDAH1 | 3529237 | DHRS2 | 2849056 | DNAH5 |
| 3329649 | DDB2 | 2397025 | DHRS3 | 2491168 | DNAH6 |
| 3050388 | DDC | 3567187 | DHRS7 | 2491089 | DNAH6 |
| 3153633 | DDEF1IT1 | 3235373 | DHTKD1 | 2593013 | DNAH7 |
| 2321911 | DDI2 | 2763805 | DHX15 | 3690084 | DNAJA2 |
| 3251393 | DDIT4 | 3311775 | DHX32 | 3603247 | DNAJA4 |
| 2969350 | DDO | 3269662 | DHX32 | 3852783 | DNAJB1 |
| 2901970 | DDR1 | 3884922 | DHX35 | 2656569 | DNAJB11 |
| 2364231 | DDR2 | 2549007 | DHX57 | 3629811 | DNAJB14 |
| 3347831 | DDX10 | 3722554 | DHX8 | 2343289 | DNAJB4 |
| 2944068 | DDX18 | 3494502 | DHX9 | 3397461 | DNAJB6 |
| 3250055 | DDX21 | 3475511 | DIABLO | 3961699 | DNAJB7 |
| 3577513 | DDX24 | 3983962 | DIAPH2 | 3018866 | DNAJB9 |
| 3354896 | DDX25 | 3577870 | DICER1 | 3280902 | DNAJC1 |
| 3974838 | DDX3X | 2336891 | DIO1 | 3292413 | DNAJC12 |
| 3974838 | DDX3Y | 3573870 | DIO2 | 2642791 | DNAJC13 |
| 2829488 | DDX46 | 3924674 | DIP2A | 3457201 | DNAJC14 |
| 3766893 | DDX5 | 3414561 | DIP2B | 3619650 | DNAJC17 |
| 2476116 | DDX50 | 3273251 | DIP2C | 3590129 | DNAJC17 |
| 3754736 | DDX52 | 3214227 | DIRAS2 | 2806256 | DNAJC21 |
| 3203086 | DDX58 | 2417362 | DIRAS3 | 3367965 | DNAJC24 |
| 2450416 | DDX59 | 3598613 | DIS3L | 3184940 | DNAJC25 |
| 3393946 | DDX6 | 2385343 | DISC1 | 3184940 | DNAJC25-GNG10 |
| 2792800 | DDX60 | 2526980 | DKFZp434H1419 | | |
| 3358262 | DEAF1 | 2731636 | DKFZP564O0823 | 3497270 | DNAJC3 |
| 3122721 | DEFA4 | 2995320 | DKFZP586I1420 | 2340350 | DNAJC6 |
| 3122721 | DEFA8P | 3860912 | DKFZp761D1918 | 2847264 | DNAL4 |
| 3873091 | DEFB132 | 3348852 | DLAT | 2330723 | DNALI1 |
| 2382360 | DEGS1 | 3125116 | DLC1 | 3644664 | DNASE1L2 |
| 2944068 | DEK | 3489708 | DLEU1 | 2678298 | DNASE1L3 |

Figure 6 continued

| TCID | GENE_na29 | TCID | GENE_na29 | TCID | GENE_na29 |
|---|---|---|---|---|---|
| 2602770 | DNER | 3622239 | DUOXA2 | 2360633 | EFNA4 |
| 2600155 | DNPEP | 2887309 | DUSP1 | 2869880 | EFNA5 |
| 3259503 | DNTT | 2457261 | DUSP10 | 3557408 | EFS |
| 2423597 | DNTTIP2 | 3719515 | DUSP14 | 3635776 | EFTUD1 |
| 3269939 | DOCK1 | 3444958 | DUSP16 | 3759356 | EFTUD2 |
| 2601648 | DOCK10 | 2518729 | DUSP19 | 2739308 | EGF |
| 3988435 | DOCK11 | 2891241 | DUSP22 | 3969358 | EGFL6 |
| 2622970 | DOCK3 | 2362702 | DUSP23 | 2807195 | EGFLAM |
| 3090512 | DOCK5 | 3129731 | DUSP4 | 3002640 | EGFR |
| 3159330 | DOCK8 | 3263743 | DUSP5 | 2830861 | EGR1 |
| 3522398 | DOCK9 | 3464860 | DUSP6 | 3291601 | EGR2 |
| 3929821 | DONSON | 3593147 | DUT | 2484970 | EHBP1 |
| 3929775 | DONSON | 2391425 | DVL1 | 3837431 | EHD2 |
| 3919860 | DOPEY2 | 3552847 | DYNC1H1 | 3326461 | EHF |
| 3394192 | DPAGT1 | 3013565 | DYNC1I1 | 4031136 | EIF1AY |
| 2902089 | DPCR1 | 4037595 | DYNC1I2 | 3325052 | EIF2AK2 |
| 3913483 | DPH3B | 2515276 | DYNC1I2 | 2563654 | EIF2AK3 |
| 2584018 | DPP4 | 2981874 | DYNLT1 | 3544387 | EIF2B2 |
| 3032647 | DPP6 | 4004819 | DYNLT3 | 2409904 | EIF2B3 |
| 2688166 | DPPA2 | 2376894 | DYRK3 | 2330002 | EIF2C4 |
| 2688180 | DPPA4 | 2488252 | DYSF | 3903288 | EIF2S2 |
| 2443120 | DPT | 2596386 | DYTN | 3309215 | EIF3A |
| 3065546 | DPY19L2 | 3625391 | DYX1C1 | 2584712 | EIF3E |
| 3459801 | DPY19L2 | 3497195 | DZIP1 | 2483544 | EIF3F |
| 3065546 | DPY19L2P1 | 3521372 | DZIP1 | 3945056 | EIF3L |
| 3459801 | DPY19L2P1 | 2635263 | DZIP3 | 2655688 | EIF4G1 |
| 3065546 | DPY19L2P2 | 2401448 | E2F2 | 2400373 | EIF4G3 |
| 3459801 | DPY19L2P3 | 2612371 | EAF1 | 3008144 | EIF4H |
| 3107606 | DPY19L4 | 3111695 | EBAG9 | 3553607 | EIF5 |
| 2547386 | DPY30 | 2883878 | EBF1 | 3788270 | ELAC1 |
| 2424524 | DPYD | 3128411 | EBF2 | 3848689 | ELAVL1 |
| 2880292 | DPYSL3 | 3873923 | EBF4 | 4021433 | ELF4 |
| 3984702 | DRP2 | 3294242 | ECD | 3427098 | ELK3 |
| 3803020 | DSC1 | 2400518 | ECE1 | 3046197 | ELMO1 |
| 3802980 | DSC2 | 2413032 | ECHDC2 | 3907830 | ELMO2 |
| 3802924 | DSC3 | 2358360 | ECM1 | 2409310 | ELOVL1 |
| 3393311 | DSCAML1 | 3214867 | ECM2 | 2941721 | ELOVL2 |
| 3812074 | DSEL | 2652675 | ECT2 | 2962113 | ELOVL4 |
| 3783529 | DSG2 | 4011096 | EDA2R | 2781813 | ELOVL6 |
| 3904566 | DSN1 | 2386828 | EDARADD | 3784727 | ELP2 |
| 2893794 | DSP | 2608801 | EDEM1 | 3091628 | ELP3 |
| 2958325 | DST | 2447824 | EDEM3 | 2419432 | ELTD1 |
| 3878533 | DTD1 | 2865390 | EDIL3 | 2779543 | EMCN |
| 2378937 | DTL | 3891447 | EDN3 | 3865511 | EML2 |
| 3784208 | DTNA | 2562435 | EDNRB | 2478748 | EML4 |
| 2638962 | DTX3L | 3483159 | EEF1A1 | 3575371 | EML5 |
| 4046876 | DTYMK | 2960903 | EEF1A1 | 3679959 | EMP2 |
| 2636626 | DULLARD | 2960903 | EEF1AL7 | 3822657 | EMR2 |
| 2815139 | DULLARD | 2940920 | EEF1E1 | 3852832 | EMR3 |
| 3592214 | DUOX1 | 3962997 | EFCAB6 | 2458338 | ENAH |
| 3622176 | DUOX1 | 2554018 | EFEMP1 | 2382781 | ENAH |
| 3592214 | DUOX2 | 3087438 | EFHA2 | 2730503 | ENAM |
| 3622176 | DUOX2 | 2665472 | EFHB | 3345427 | ENDOD1 |
| 3622239 | DUOXA1 | 2360633 | EFNA3 | 3226709 | ENDOG |

Figure 6 continued

| TCID | GENE_na29 | TCID | GENE_na29 | TCID | GENE_na29 |
|---|---|---|---|---|---|
| 2395490 | ENO1 | 3445768 | ERP27 | 3644191 | FAHD1 |
| 2386828 | ENO1 | 3217736 | ERP44 | 2565753 | FAHD2A |
| 2733767 | ENOPH1 | 2395177 | ERRFI1 | 2494064 | FAHD2A |
| 3795866 | ENOSF1 | 3053380 | ERV3 | 2565753 | FAHD2B |
| 2925953 | ENPP1 | 3396107 | ESAM | 2494064 | FAHD2B |
| 2909020 | ENPP4 | 3800779 | ESCO1 | 2984835 | FAM103A1 |
| 2955673 | ENPP5 | 2856995 | ESM1 | 3769969 | FAM104A |
| 3259253 | ENTPD1 | 2534664 | ESPNL | 3278813 | FAM107B |
| 3230733 | ENTPD2 | 2931763 | ESR1 | 3869097 | FAM107B |
| 3571667 | ENTPD5 | 3568184 | ESR2 | 3331926 | FAM111A |
| 3260383 | ENTPD7 | 3107548 | ESRP1 | 3331903 | FAM111B |
| 3438772 | EP400 | 3696226 | ESRP2 | 2724094 | FAM114A1 |
| 3438772 | EP400NL | 2455933 | ESRRG | 3029230 | FAM115A |
| 2480383 | EPAS1 | 3633794 | ETFA | 3029230 | FAM115C |
| 2327677 | EPB41 | 3868963 | ETFB | 2678116 | FAM116A |
| 3883690 | EPB41L1 | 3864430 | ETHE1 | 3948543 | FAM118A |
| 2973995 | EPB41L2 | 2451870 | ETNK2 | 3355021 | FAM118B |
| 3797032 | EPB41L3 | 3397589 | ETS1 | 3418534 | FAM119B |
| 2870964 | EPB41L4A | 3039177 | ETV1 | 3179872 | FAM120A |
| 3219788 | EPB41L4B | 3758510 | ETV4 | 4009560 | FAM120C |
| 2503109 | EPB41L5 | 2709132 | ETV5 | 3490073 | FAM124A |
| 3284073 | EPC1 | 3405207 | ETV6 | 3189422 | FAM125B |
| 2997907 | EPDR1 | 2423017 | EVI5 | 3041294 | FAM126A |
| 2632225 | EPHA3 | 3355733 | EWSR1 | 2594627 | FAM126B |
| 2600689 | EPHA4 | 3941907 | EWSR1 | 4022925 | FAM127A |
| 2771342 | EPHA5 | 2938196 | EXOC2 | 3991889 | FAM127A |
| 2965206 | EPHA7 | 3025005 | EXOC4 | 4022925 | FAM127B |
| 2643592 | EPHB1 | 3771336 | EXOC7 | 3991889 | FAM127B |
| 2655845 | EPHB3 | 2396480 | EXOSC10 | 4022925 | FAM127C |
| 3028858 | EPHB6 | 3485863 | EXOSC8 | 3991889 | FAM127C |
| 2346625 | EPHX4 | 2741768 | EXOSC9 | 3225952 | FAM129B |
| 3772187 | EPR1 | 3150060 | EXT1 | 3077273 | FAM131B |
| 2456746 | EPRS | 3140037 | EYA1 | 2528275 | FAM134A |
| 3445908 | EPS8 | 3887479 | EYA2 | 2849992 | FAM134B |
| 3841949 | EPS8L1 | 2403335 | EYA3 | 2777487 | FAM13A |
| 3511698 | EPSTI1 | 3078348 | EZH2 | 3247977 | FAM13C |
| 3728588 | EPX | 3502437 | F10 | 3290649 | FAM13C |
| 2868131 | ERAP1 | 2755154 | F11 | 3360772 | FAM160A2 |
| 3720402 | ERBB2 | 2888741 | F12 | 3265432 | FAM160B1 |
| 3417249 | ERBB3 | 2816459 | F2R | 2638886 | FAM162A |
| 2597552 | ERBB4 | 2863363 | F2RL2 | 2369713 | FAM163A |
| 3865378 | ERCC1 | 2423907 | F3 | 3104323 | FAM164A |
| 3836217 | ERCC2 | 2443370 | F5 | 4051521 | FAM166A |
| 3288707 | ERCC6 | 4027639 | F8 | 2576281 | FAM168B |
| 4012142 | ERCC6L | 2334740 | FAAH | 2825796 | FAM170A |
| 2858752 | ERCC8 | 3979101 | FAAH2 | 3759105 | FAM171A2 |
| 3931765 | ERG | 2404418 | FABP3 | 2519294 | FAM171B |
| 3570049 | ERH | 3142381 | FABP4 | 3643347 | FAM173A |
| 3085065 | ERI1 | 3517694 | FABP5 | 2821981 | FAM174A |
| 3683845 | ERI2 | 3606304 | FABP5 | 2776088 | FAM175A |
| 3651509 | ERI2 | 2838116 | FABP6 | 2366941 | FAM175A |
| 3303255 | ERLIN1 | 3402571 | FADS1 | 2560625 | FAM176A |
| 3564790 | ERO1L | 3333226 | FADS2 | 3532353 | FAM177A1 |
| 2462329 | ERO1LB | 3603932 | FAH | 3260829 | FAM178A |

Figure 6 continued

| TCID | GENE_na29 | TCID | GENE_na29 | TCID | GENE_na29 |
|---|---|---|---|---|---|
| 2475348 | FAM179A | 3171425 | FAM75C1 | 3223605 | FBXW2 |
| 3534128 | FAM179B | 2820813 | FAM81B | 3230530 | FBXW5 |
| 3549436 | FAM181A | 3619595 | FAM82A2 | 2789957 | FBXW7 |
| 3649052 | FAM18B | 3143330 | FAM82B | 3433591 | FBXW8 |
| 2628482 | FAM19A1 | 3884892 | FAM83D | 2453036 | FCAMR |
| 3949722 | FAM19A5 | 3946146 | FAM83F | 3848492 | FCER2 |
| 3768535 | FAM20A | 2470470 | FAM84A | 3544216 | FCF1 |
| 3244742 | FAM21A | 3152558 | FAM84B | 3862188 | FCGBP |
| 3244742 | FAM21B | 3335338 | FAM89B | 2363689 | FCGR2A |
| 3244742 | FAM21C | 3114365 | FAM91A1 | 2363689 | FCGR2B |
| 3244742 | FAM21D | 3114365 | FAM91A2 | 2363689 | FCGR2C |
| 3310675 | FAM24B | 3107151 | FAM92A1 | 2440943 | FCGR3A |
| 3764738 | FAM33A | 3107151 | FAM92A2 | 2440943 | FCGR3B |
| 3256279 | FAM35A | 3107151 | FAM92A3 | 3838624 | FCGRT |
| 3256279 | FAM35B2 | 3589212 | FAM98B | 2815139 | FCHO2 |
| 3704376 | FAM38A | 2610241 | FANCD2 | 3381377 | FCHSD2 |
| 3798778 | FAM38B | 3607537 | FANCI | 3229338 | FCN1 |
| 3798829 | FAM38B2 | 3534248 | FANCM | 3229338 | FCN2 |
| 3921992 | FAM3B | 2584134 | FAP | 2363852 | FCRLA |
| 3070047 | FAM3C | 3321269 | FAR1 | 3086206 | FDFT1 |
| 2678468 | FAM3D | 3409605 | FAR2 | 3348189 | FDX1 |
| 2658785 | FAM43A | 3497881 | FARP1 | 3391149 | FDXACB1 |
| 2962383 | FAM46A | 2893130 | FARS2 | 3770457 | FDXR |
| 2353988 | FAM46C | 3257031 | FAS | 3333226 | FEN1 |
| 2731986 | FAM47E | 3257098 | FAS | 3396593 | FEZ1 |
| 3509910 | FAM48A | 3079336 | FASTK | 2612100 | FGD5 |
| 2528476 | FAM48A | 2586227 | FASTKD1 | 3708663 | FGF11 |
| 2541699 | FAM49A | 2797393 | FAT1 | 2710895 | FGF12 |
| 3996430 | FAM50A | 2742581 | FAT4 | 3523499 | FGF14 |
| 2757278 | FAM53A | 3862167 | FBL | 2742109 | FGF2 |
| 2830898 | FAM53C | 3948640 | FBLN1 | 3441168 | FGF23 |
| 2634091 | FAM55C | 3576749 | FBLN5 | 3593408 | FGF7 |
| 3705491 | FAM57A | 2500667 | FBLN7 | 3480885 | FGF9 |
| 4026560 | FAM58A | 3623031 | FBN1 | 2761829 | FGFBP1 |
| 3803290 | FAM59A | 2874371 | FBN2 | 3132016 | FGFR1 |
| 2368840 | FAM5B | 3656635 | FBXL19 | 3413950 | FGFR1OP2 |
| 2448710 | FAM5C | 3755655 | FBXL20 | 3310041 | FGFR2 |
| 3449700 | FAM60A | 3518455 | FBXL3 | 2338487 | FGGY |
| 3417371 | FAM62A | 2966078 | FBXL4 | 3057955 | FGL2 |
| 3082248 | FAM62B | 2761734 | FBXL5 | 2747961 | FHDC1 |
| 2434746 | FAM63A | 2802963 | FBXL7 | 3992408 | FHL1 |
| 2358591 | FAM63A | 2552153 | FBXO11 | 2568687 | FHL2 |
| 2423175 | FAM69A | 3813198 | FBXO15 | 3695541 | FHOD1 |
| 4019784 | FAM70A | 3129361 | FBXO16 | 3324447 | FIBIN |
| 3839400 | FAM71E1 | 2396750 | FBXO2 | 3377964 | FIBP |
| 2343170 | FAM73A | 3473480 | FBXO21 | 2727226 | FIP1L1 |
| 3190893 | FAM73B | 3602526 | FBXO22 | 3326826 | FJX1 |
| 3171425 | FAM75A1 | 3602526 | FBXO22OS | 3721452 | FKBP10 |
| 3171425 | FAM75A2 | 3368748 | FBXO3 | 3043936 | FKBP14 |
| 3171425 | FAM75A3 | 2978026 | FBXO30 | 2472955 | FKBP1B |
| 3171425 | FAM75A4 | 2531129 | FBXO36 | 3334339 | FKBP2 |
| 3171425 | FAM75A5 | 2980241 | FBXO5 | 3401119 | FKBP4 |
| 3171425 | FAM75A6 | 3943414 | FBXO7 | 2951567 | FKBP5 |
| 3171425 | FAM75A7 | 2886977 | FBXW11 | 3824963 | FKBP8 |

Figure 6 continued

| TCID | GENE_na29 | TCID | GENE_na29 | TCID | GENE_na29 |
|---|---|---|---|---|---|
| 3498315 | FKSG29 | 2366941 | FMO3 | 2854327 | FYB |
| 3355733 | FLI1 | 2433232 | FMO5 | 2969886 | FYN |
| 3748188 | FLII | 2451693 | FMOD | 2659887 | FYTTD1 |
| 3110217 | FLJ10489 | 3994100 | FMR1 | 3343452 | FZD4 |
| 4040117 | FLJ12120 | 2598261 | FN1 | 3385509 | FZD4 |
| 2738244 | FLJ20184 | 2526806 | FN1 | 2596763 | FZD5 |
| 3829638 | FLJ21369 | 3739147 | FN3K | 3110272 | FZD6 |
| 3358049 | FLJ23519 | 3227159 | FNBP1 | 2523045 | FZD7 |
| 3018011 | FLJ23834 | 3489212 | FNDC3A | 2378068 | G0S2 |
| 2369950 | FLJ23867 | 2652410 | FNDC3B | 2745547 | GAB1 |
| 3937967 | FLJ26056 | 2545953 | FNDC4 | 3383227 | GAB2 |
| 3953456 | FLJ26056 | 2405250 | FNDC5 | 3404636 | GABARAPL1 |
| 2460470 | FLJ30430 | 2350316 | FNDC7 | 3404636 | GABARAPL3 |
| 2617041 | FLJ31715 | 3343900 | FOLH1 | 3217242 | GABBR2 |
| 3489708 | FLJ31945 | 3372896 | FOLH1 | 3916576 | GABPA |
| 3346147 | FLJ32810 | 3343900 | FOLH1B | 2358700 | GABPB2 |
| 3415046 | FLJ33996 | 3372896 | FOLH1B | 2768056 | GABRA4 |
| 3301609 | FLJ34077 | 3339406 | FOLR1 | 2884845 | GABRB2 |
| 2716246 | FLJ35424 | 3544525 | FOS | 3614534 | GABRB3 |
| 2926447 | FLJ35700 | 3836266 | FOSB | 4054481 | GABRD |
| 2821761 | FLJ35946 | 2743085 | FOSL1 | 3585272 | GABRG3 |
| 2485257 | FLJ36848 | 3672609 | FOXF1 | 2964092 | GABRR1 |
| 3299782 | FLJ37201 | 3440598 | FOXM1 | 2341083 | GADD45A |
| 2536965 | FLJ38379 | 3715642 | FOXN1 | 3816509 | GADD45B |
| 2907396 | FLJ38717 | 2920475 | FOXO3 | 2765935 | GAFA3 |
| 3903461 | FLJ38773 | 2920475 | FOXO3B | 3575103 | GALC |
| 3724591 | FLJ39349 | 3019793 | FOXP2 | 2401581 | GALE |
| 2672629 | FLJ39534 | 2342176 | FPGT | 3593339 | GALK2 |
| 2564816 | FLJ40330 | 2342220 | FPGT | 3623472 | GALK2 |
| 2565935 | FLJ40330 | 3869237 | FPR1 | 3181600 | GALNT12 |
| 3887165 | FLJ40606 | 3839910 | FPR2 | 2511045 | GALNT13 |
| 2536996 | FLJ41327 | 2732655 | FRAS1 | 2384788 | GALNT2 |
| 3380647 | FLJ42102 | 3486096 | FREM2 | 2585129 | GALNT3 |
| 3380065 | FLJ42258 | 3212008 | FRMD3 | 3464912 | GALNT4 |
| 3338192 | FLJ42258 | 3278401 | FRMD4A | 2511603 | GALNT5 |
| 3636879 | FLJ43276 | 3621728 | FRMD5 | 2751936 | GALNT7 |
| 3981361 | FLJ44635 | 3287995 | FRMPD2 | 3401920 | GALNT8 |
| 3673661 | FLJ45121 | 3287995 | FRMPD2L1 | 3479015 | GALNT9 |
| 3549989 | FLJ45244 | 3287995 | FRMPD2L2 | 3363091 | GALNTL4 |
| 2812591 | FLJ46010 | 2590715 | FRZB | 3590853 | GANC |
| 3918953 | FLJ46020 | 3022422 | FSCN3 | 2637112 | GAP43 |
| 3097401 | FLJ46365 | 3183238 | FSD1L | 3402625 | GAPDH |
| 2481379 | FLJ46838 | 3815097 | FSTL3 | 3146661 | GAPDHL7 |
| 3722479 | FLJ77644 | 2875685 | FSTL4 | 3189110 | GAPVD1 |
| 4027176 | FLNA | 2791894 | FSTL5 | 3183238 | GARNL1 |
| 2625907 | FLNB | 2545841 | FTH1 | 3189714 | GARNL3 |
| 3546924 | FLRT2 | 2545841 | FTHL3P | 3929721 | GART |
| 3898355 | FLRT3 | 2419235 | FUBP1 | 3323891 | GAS2 |
| 3507282 | FLT1 | 3656904 | FUS | 3428268 | GAS2L3 |
| 3836556 | FLT3LG | 3837934 | FUT2 | 2444451 | GAS5 |
| 2387711 | FMN2 | 3540552 | FUT8 | 3781245 | GATA6 |
| 2510713 | FMNL2 | 3830166 | FXYD3 | 3825713 | GATAD2A |
| 3414104 | FMNL3 | 3830216 | FXYD5 | 3822386 | GATM |
| 3454006 | FMNL3 | 3393479 | FXYD6 | 2437205 | GBA |

Figure 6 continued

| TCID | GENE_na29 |
|------|-----------|
| 2437205 | GBAP |
| 2684187 | GBE1 |
| 3261544 | GBF1 |
| 3228523 | GBGT1 |
| 2421843 | GBP1 |
| 2421883 | GBP1 |
| 2421925 | GBP2 |
| 2421883 | GBP2 |
| 2421843 | GBP3 |
| 2421925 | GBP3 |
| 2421883 | GBP3 |
| 2421995 | GBP4 |
| 2421925 | GBP4 |
| 2422035 | GBP5 |
| 2345816 | GBP6 |
| 2421925 | GBP7 |
| 2512930 | GCA |
| 3945014 | GCAT |
| 2636062 | GCET2 |
| 2688605 | GCET2 |
| 3565524 | GCH1 |
| 3048468 | GCK |
| 2957560 | GCM1 |
| 3595441 | GCOM1 |
| 3701459 | GCSH |
| 3174510 | GDA |
| 3103607 | GDAP1 |
| 2430370 | GDAP2 |
| 3855285 | GDF1 |
| 3287789 | GDF10 |
| 3824993 | GDF15 |
| 3996404 | GDI1 |
| 3275132 | GDI2 |
| 3729014 | GDPD1 |
| 3382319 | GDPD5 |
| 3144934 | GEM |
| 2477980 | GEMIN6 |
| 2649640 | GFM1 |
| 2862716 | GFM2 |
| 2558045 | GFPT1 |
| 3308241 | GFRA1 |
| 3127156 | GFRA2 |
| 3685183 | GGA2 |
| 3770663 | GGA3 |
| 3044129 | GGCT |
| 3719161 | GGNBP2 |
| 3939914 | GGT1 |
| 3939009 | GGT1 |
| 3939914 | GGT2 |
| 3939009 | GGT2 |
| 3939914 | GGT3P |
| 3939009 | GGT3P |
| 3939914 | GGT8P |
| 3223967 | GGTA1 |

| TCID | GENE_na29 |
|------|-----------|
| 3939914 | GGTLC2 |
| 3939009 | GGTLC2 |
| 3939914 | GGTLC3 |
| 3939009 | GGTLC3 |
| 3031556 | GIMAP2 |
| 3031533 | GIMAP4 |
| 3031573 | GIMAP5 |
| 3079103 | GIMAP6 |
| 3031517 | GIMAP7 |
| 3031466 | GIMAP8 |
| 3880827 | GINS1 |
| 3703112 | GINS2 |
| 3471005 | GIT2 |
| 3656032 | GIYD1 |
| 3656032 | GIYD2 |
| 2923661 | GJA1 |
| 2407755 | GJA9 |
| 4054427 | GJB4 |
| 3504213 | GJB6 |
| 4015763 | GLA |
| 2668205 | GLB1 |
| 2989537 | GLCCI1 |
| 3197955 | GLDC |
| 3593931 | GLDN |
| 3698919 | GLG1 |
| 3047660 | GLI3 |
| 3422855 | GLIPR1 |
| 3422826 | GLIPR1L2 |
| 3197140 | GLIS3 |
| 3197014 | GLIS3 |
| 2749191 | GLRB |
| 3271018 | GLRX3 |
| 2520291 | GLS |
| 3437500 | GLT1D1 |
| 3824471 | GLT25D1 |
| 2676319 | GLT8D1 |
| 3468888 | GLT8D2 |
| 3451246 | GLT8D3 |
| 3978169 | GLTSCR2 |
| 2447066 | GLUL |
| 2487478 | GMCL1 |
| 2487478 | GMCL1L |
| 3914021 | GMEB2 |
| 3861948 | GMFG |
| 2898597 | GMNN |
| 2528620 | GMPPA |
| 3210737 | GNA14 |
| 3010439 | GNAI1 |
| 3779207 | GNAL |
| 3661940 | GNAO1 |
| 3210808 | GNAQ |
| 2391840 | GNB1 |
| 3402874 | GNB3 |
| 3184940 | GNG10 |

| TCID | GENE_na29 |
|------|-----------|
| 2417272 | GNG12 |
| 3535628 | GNG2 |
| 3333595 | GNG3 |
| 3845944 | GNG7 |
| 2948379 | GNL1 |
| 2858752 | GNL3L |
| 2858752 | GNL3LP |
| 2907513 | GNMT |
| 2385197 | GNPAT |
| 2879028 | GNPDA1 |
| 3564872 | GNPNAT1 |
| 3468103 | GNPTAB |
| 3460127 | GNS |
| 3225224 | GOLGA1 |
| 2617041 | GOLGA4 |
| 3617458 | GOLGA8A |
| 3617574 | GOLGA8A |
| 3617458 | GOLGA8B |
| 3617574 | GOLGA8B |
| 3212848 | GOLM1 |
| 3148871 | GOLSYN |
| 2451931 | GOLT1A |
| 2437645 | GON4L |
| 2971378 | GOPC |
| 2669888 | GORASP1 |
| 4049835 | GOT1L1 |
| 3707335 | GP1BA |
| 2711627 | GP5 |
| 3306984 | GPAM |
| 3829174 | GPATCH1 |
| 2402861 | GPATCH3 |
| 3759186 | GPATCH8 |
| 3063807 | GPC2 |
| 4022447 | GPC3 |
| 2615808 | GPD1L |
| 2511432 | GPD2 |
| 2987038 | GPER |
| 2794584 | GPM6A |
| 2474681 | GPN1 |
| 3191273 | GPR107 |
| 2955932 | GPR110 |
| 2955999 | GPR110 |
| 2473784 | GPR113 |
| 3094334 | GPR124 |
| 2763278 | GPR125 |
| 3581404 | GPR132 |
| 3438061 | GPR133 |
| 2386747 | GPR137B |
| 2505779 | GPR148 |
| 2587790 | GPR155 |
| 2651835 | GPR160 |
| 2442911 | GPR161 |
| 3978169 | GPR173 |
| 3982612 | GPR174 |

Figure 6 continued

| TCID | GENE_na29 |
|---|---|
| 2417390 | GPR177 |
| 3522644 | GPR18 |
| 3417767 | GPR182 |
| 3522662 | GPR183 |
| 3445028 | GPR19 |
| 3070873 | GPR37 |
| 2576988 | GPR39 |
| 2506570 | GPR39 |
| 3994964 | GPR50 |
| 3662808 | GPR56 |
| 4001654 | GPR64 |
| 2553262 | GPR75 |
| 3387010 | GPR83 |
| 2819779 | GPR98 |
| 3985260 | GPRASP1 |
| 3985305 | GPRASP2 |
| 3405587 | GPRC5A |
| 3683377 | GPRC5B |
| 2888385 | GPRIN1 |
| 2777639 | GPRIN3 |
| 2674229 | GPX1 |
| 3568603 | GPX2 |
| 2835715 | GPX3 |
| 3815538 | GPX4 |
| 2336439 | GPX7 |
| 2809831 | GPX8 |
| 2636626 | GRAMD1C |
| 2827057 | GRAMD3 |
| 3050462 | GRB10 |
| 2584712 | GRB14 |
| 3770743 | GRB2 |
| 2469825 | GREB1 |
| 2469157 | GRHL1 |
| 2325358 | GRHL3 |
| 2749222 | GRIA2 |
| 3989448 | GRIA3 |
| 4050485 | GRIN1 |
| 3770422 | GRIN2C |
| 3218151 | GRIN3A |
| 3595441 | GRINL1A |
| 3071063 | GRM8 |
| 3790529 | GRP |
| 2835006 | GRPEL2 |
| 2772614 | GRSF1 |
| 3755903 | GSDMB |
| 3445156 | GSG1 |
| 3741585 | GSG2 |
| 2691014 | GSK3B |
| 3187686 | GSN |
| 3903670 | GSS |
| 2738314 | GSTCD |
| 2350922 | GSTM1 |
| 2350981 | GSTM1 |
| 2350952 | GSTM1 |

| TCID | GENE_na29 |
|---|---|
| 2350922 | GSTM2 |
| 2351004 | GSTM2 |
| 2350981 | GSTM2 |
| 2350952 | GSTM2 |
| 2427208 | GSTM3 |
| 2350922 | GSTM4 |
| 2350981 | GSTM4 |
| 2350922 | GSTM5 |
| 2351004 | GSTM5 |
| 3262509 | GSTO1 |
| 3337168 | GSTP1 |
| 2727535 | GSX2 |
| 3574074 | GTF2A1 |
| 2481379 | GTF2A1L |
| 2421753 | GTF2B |
| 2861183 | GTF2H2 |
| 2861183 | GTF2H2B |
| 2861183 | GTF2H2C |
| 2861183 | GTF2H2D |
| 3435946 | GTF2H3 |
| 2902013 | GTF2H4 |
| 3008376 | GTF2I |
| 3008376 | GTF2IP1 |
| 3056656 | GTF2IRD2 |
| 3056656 | GTF2IRD2B |
| 3056656 | GTF2IRD2P |
| 3482888 | GTF3A |
| 2593352 | GTF3C3 |
| 2954771 | GTPBP2 |
| 2519480 | GULP1 |
| 2787958 | GYPB |
| 2787902 | GYPB |
| 2504328 | GYPC |
| 2787958 | GYPE |
| 2787902 | GYPE |
| 3446845 | GYS2 |
| 2809810 | GZMA |
| 3558375 | GZMB |
| 3558375 | GZMH |
| 2809793 | GZMK |
| 2876479 | H2AFY |
| 3250602 | H2AFY2 |
| 2946714 | H2BFS |
| 3770944 | H3F3B |
| 2664395 | HACL1 |
| 2473735 | HADHB |
| 3466687 | HAL |
| 3757288 | HAP1 |
| 2832052 | HARS |
| 2832052 | HARS2 |
| 2757621 | HAUS3 |
| 3360401 | HBB |
| 2878273 | HBEGF |
| 3360441 | HBG1 |

| TCID | GENE_na29 |
|---|---|
| 3360441 | HBG2 |
| 3018420 | HBP1 |
| 2975287 | HBS1L |
| 4026956 | HCFC1 |
| 3677356 | HCFC1R1 |
| 3429406 | HCFC2 |
| 2756309 | hCG_1771830 |
| 3621728 | hCG_1789710 |
| 2525852 | hCG_2024410 |
| 3871459 | hCG_2039146 |
| 2855963 | HCN1 |
| 2907173 | HCRP1 |
| 2328387 | HCRTR1 |
| 2606026 | HDAC4 |
| 4012204 | HDAC8 |
| 2991395 | HDAC9 |
| 3998444 | HDHD1A |
| 2462456 | HEATR1 |
| 2386867 | HEATR1 |
| 3659888 | HEATR3 |
| 3559690 | HEATR5A |
| 3765059 | HEATR6 |
| 3445123 | HEBP1 |
| 3559570 | HECTD1 |
| 3257750 | HECTD2 |
| 2409970 | HECTD3 |
| 2999334 | HECW1 |
| 2692909 | HEG1 |
| 3420497 | HELB |
| 3258910 | HELLS |
| 2776026 | HELQ |
| 3768015 | HELZ |
| 3217077 | HEMGN |
| 3628650 | HERC1 |
| 3614901 | HERC2 |
| 3585749 | HERC2 |
| 3614901 | HERC2P2 |
| 3585749 | HERC2P2 |
| 3614901 | HERC2P3 |
| 3585749 | HERC2P3 |
| 2735459 | HERC3 |
| 3292448 | HERC4 |
| 2735362 | HERC6 |
| 3662387 | HERPUD1 |
| 2605735 | HES6 |
| 3632152 | HEXA |
| 3738842 | HEXDC |
| 3774975 | HEXDC |
| 3723348 | HEXIM1 |
| 2924492 | HEY2 |
| 2422612 | HFM1 |
| 4047070 | HGD |
| 2745899 | HHIP |
| 2457496 | HHIPL2 |

Figure 6 continued

| TCID | GENE_na29 | TCID | GENE_na29 | TCID | GENE_na29 |
|---|---|---|---|---|---|
| 2635184 | HHLA2 | 2401275 | HNRNPR | 2916067 | HTR1E |
| 3938113 | HIC2 | 2864237 | HOMER1 | 3513147 | HTR2A |
| 3539070 | HIF1A | 3448152 | HOMER1 | 2655325 | HTR3C |
| 3836705 | HIF3A | 3096368 | HOOK3 | 2655325 | HTR3D |
| 2739160 | HIGD1A | 3042994 | HOXA13 | 2715820 | HTT |
| 3057370 | HIP1 | 3042816 | HOXA4 | 3049840 | HUS1 |
| 2352758 | HIPK1 | 3761441 | HOXB8 | 4009315 | HUWE1 |
| 3075778 | HIPK2 | 2516967 | HOXD1 | 3471327 | HVCN1 |
| 3325907 | HIPK3 | 2516853 | HOXD9 | 3697434 | HYDIN |
| 3952637 | HIRA | 2400322 | HP1BP3 | 2977621 | HYMAI |
| 3952703 | HIRA | 2408041 | HPCAL4 | 3394123 | HYOU1 |
| 2822407 | HISPPD1 | 2794408 | HPGD | 2539821 | IAH1 |
| 3621276 | HISPPD2A | 3830065 | HPN | 2380991 | IARS2 |
| 2946194 | HIST1H1A | 3991698 | HPRT1 | 2735129 | IBSP |
| 2946714 | HIST1H2BK | 2700244 | HPS3 | 2962525 | IBTK |
| 2946215 | HIST1H3B | 2647216 | HPS3 | 3038065 | ICA1 |
| 2899233 | HIST1H3E | 3358090 | HRAS | 3820443 | ICAM1 |
| 2899146 | HIST1H4C | 2658275 | HRASLS | 3766621 | ICAM2 |
| 2947081 | HIST1H4L | 3867708 | HRC | 3820469 | ICAM5 |
| 2895159 | HIVEP1 | 2656650 | HRG | 2394588 | ICMT |
| 2977265 | HIVEP2 | 3145980 | HRSP12 | 2401493 | ID3 |
| 3250278 | HK1 | 2345196 | HS2ST1 | 3300350 | IDE |
| 2948926 | HLA-B | 4022183 | HS6ST2 | 2597010 | IDH1 |
| 2948887 | HLA-B | 3671448 | HSBP1 | 3603199 | IDH3A |
| 2948926 | HLA-C | 3328069 | HSD17B12 | 3273601 | IDI1 |
| 2948887 | HLA-C | 3216195 | HSD17B3 | 3095223 | IDO1 |
| 2950263 | HLA-DMB | 3417703 | HSD17B6 | 3095257 | IDO2 |
| 2950329 | HLA-DPA1 | 2903488 | HSD17B8 | 4025339 | IDS |
| 2903401 | HLA-DPB1 | 3120358 | HSF1 | 2756831 | IDUA |
| 2950125 | HLA-DQB2 | 2923819 | HSF2 | 3226883 | IER5L |
| 2903189 | HLA-DRA | 4025485 | HSFX1 | 2362394 | IFI16 |
| 2901620 | HLA-E | 4025485 | HSFX2 | 2343511 | IFI44 |
| 3727583 | HLF | 3400034 | HSN2 | 2343473 | IFI44L |
| 3881282 | HM13 | 3580179 | HSP90AA1 | 2403261 | IFI6 |
| 3091848 | HMBOX1 | 3580179 | HSP90AA4P | 3257268 | IFIT5 |
| 3602873 | HMG20A | 2908474 | HSP90AB1 | 3315675 | IFITM1 |
| 3817040 | HMG20B | 2908474 | HSP90AB3P | 3201242 | IFNA10 |
| 3431483 | HMGA1 | 3429312 | HSP90B1 | 3201242 | IFNA16 |
| 3471198 | HMGA1 | 3429312 | HSP90B3P | 3201242 | IFNA17 |
| 3420316 | HMGA2 | 3874402 | HSPA12B | 3201242 | IFNA21 |
| 3994915 | HMGB3 | 3925439 | HSPA13 | 3201242 | IFNA4 |
| 2329386 | HMGB4 | 2902707 | HSPA1A | 3201242 | IFNA7 |
| 2958117 | HMGCLL1 | 2902707 | HSPA1B | 3918447 | IFNAR2 |
| 2815965 | HMGCR | 2949450 | HSPA1L | 3201359 | IFNE |
| 3944046 | HMGXB4 | 2828856 | HSPA4 | 2446198 | IFRG15 |
| 2838656 | HMMR | 2742935 | HSPA4L | 3676002 | IFT140 |
| 2841802 | HMP19 | 3225398 | HSPA5 | 3480411 | IFT88 |
| 3770606 | HN1 | 2413519 | HSPB11 | 3980455 | IGBP1 |
| 3754797 | HNF1B | 2692136 | HSPBAP1 | 3610804 | IGF1R |
| 2352609 | HNRNPA3 | 2593733 | HSPD1 | 2708922 | IGF2BP2 |
| 2843619 | HNRNPAB | 2400793 | HSPG2 | 3041409 | IGF2BP3 |
| 2775463 | HNRNPD | 3508330 | HSPH1 | 2934308 | IGF2R |
| 3861617 | HNRNPL | 2730194 | HTN3 | 3049292 | IGFBP3 |
| 4037595 | HNRNPM | 2401251 | HTR1D | 2598828 | IGFBP5 |

Figure 6 continued

| TCID | GENE_na29 |
|---|---|
| 3415744 | IGFBP6 |
| 2770469 | IGFBP7 |
| 2728448 | IGFBP7 |
| 3836614 | IGFL2 |
| 3375735 | IGHG1 |
| 2772566 | IGJ |
| 2563785 | IGK@ |
| 2563785 | IGKC |
| 2563785 | IGKV1-5 |
| 2563785 | IGKV3-15 |
| 2563785 | IGKV3-20 |
| 2563785 | IGKV3D-11 |
| 2563785 | IGKV3D-15 |
| 3954764 | IGLL3 |
| 4021777 | IGSF1 |
| 2701109 | IGSF10 |
| 3096092 | IKBKB |
| 2597867 | IKZF2 |
| 3755862 | IKZF3 |
| 2452948 | IL10 |
| 3167553 | IL11RA |
| 3988538 | IL13RA1 |
| 4018729 | IL13RA2 |
| 2624565 | IL17RB |
| 3391255 | IL18 |
| 2497119 | IL18R1 |
| 2571569 | IL1F8 |
| 2657831 | IL1RAP |
| 3972657 | IL1RAPL1 |
| 2497082 | IL1RL1 |
| 2497028 | IL1RL2 |
| 3832906 | IL28A |
| 3832906 | IL28B |
| 3832906 | IL29 |
| 3275729 | IL2RA |
| 2660617 | IL5RA |
| 2806468 | IL7R |
| 2731332 | IL8 |
| 2599303 | IL8RA |
| 2599303 | IL8RB |
| 2527580 | IL8RB |
| 2599303 | IL8RBP |
| 2527580 | IL8RBP |
| 3996971 | IL9R |
| 3367965 | IMMP1L |
| 2562685 | IMMT |
| 3142485 | IMPA1 |
| 3782166 | IMPACT |
| 3136413 | IMPAD1 |
| 3071700 | IMPDH1 |
| 2673873 | IMPDH2 |
| 3262129 | INA |
| 3554315 | INF2 |
| 2536757 | ING5 |

| TCID | GENE_na29 |
|---|---|
| 2596162 | INO80D |
| 2520113 | INPP1 |
| 2495446 | INPP4A |
| 2787459 | INPP4B |
| 3267382 | INPP5F |
| 3942766 | INPP5J |
| 3740264 | INPP5K |
| 3339423 | INPPL1 |
| 2502424 | INSIG2 |
| 3848243 | INSR |
| 3088405 | INTS10 |
| 2738314 | INTS12 |
| 3383081 | INTS4 |
| 3383081 | INTS4L1 |
| 3383081 | INTS4L2 |
| 3514488 | INTS6 |
| 2742829 | INTU |
| 2950823 | IP6K3 |
| 2980449 | IPCEF1 |
| 3853658 | IPMK |
| 2811812 | IPO11 |
| 3319840 | IPO7 |
| 2604998 | IQCA1 |
| 2328767 | IQCC |
| 3472274 | IQCD |
| 2713664 | IQCG |
| 3599059 | IQCH |
| 2649824 | IQCJ |
| 2816298 | IQGAP2 |
| 2366028 | IQWD1 |
| 2610359 | IRAK2 |
| 3412296 | IRAK4 |
| 2796384 | IRF2 |
| 2453881 | IRF6 |
| 2601995 | IRS1 |
| 3525234 | IRS2 |
| 4017694 | IRS4 |
| 2846522 | IRX2 |
| 3430776 | ISCU |
| 2438482 | ISG20L2 |
| 2808931 | ISL1 |
| 3621948 | ISLR |
| 2827709 | ISOC1 |
| 3882854 | ITCH |
| 3690193 | ITFG1 |
| 3401119 | ITFG2 |
| 3642707 | ITFG3 |
| 2809128 | ITGA1 |
| 2356218 | ITGA10 |
| 3630736 | ITGA11 |
| 2809245 | ITGA2 |
| 3759137 | ITGA2B |
| 3726154 | ITGA3 |
| 2518272 | ITGA4 |

| TCID | GENE_na29 |
|---|---|
| 2515627 | ITGA6 |
| 3457101 | ITGA7 |
| 2617188 | ITGA9 |
| 3741585 | ITGAE |
| 2519229 | ITGAV |
| 3852832 | ITGB1 |
| 3284188 | ITGB1 |
| 2539765 | ITGB1BP1 |
| 3724545 | ITGB3 |
| 2416218 | ITGB3BP |
| 2692816 | ITGB5 |
| 2583465 | ITGB6 |
| 2991860 | ITGB8 |
| 3499132 | ITGBL1 |
| 3276337 | ITIH5 |
| 4009751 | ITIH5L |
| 2837232 | ITK |
| 4013549 | ITM2A |
| 3874249 | ITPA |
| 2608469 | ITPR1 |
| 3448152 | ITPR2 |
| 2903782 | ITPR3 |
| 3918779 | ITSN1 |
| 3589905 | IVD |
| 2448073 | IVNS1ABP |
| 2931172 | IYD |
| 3160895 | JAK2 |
| 2880361 | JAKMIP2 |
| 3916527 | JAM2 |
| 3248986 | JMJD1C |
| 3291682 | JMJD1C |
| 2817291 | JMY |
| 3672886 | JPH3 |
| 3157060 | JRK |
| 3556990 | JUB |
| 2415084 | JUN |
| 2945440 | KAAG1 |
| 3998766 | KAL1 |
| 2639734 | KALRN |
| 3850676 | KANK2 |
| 3699757 | KARS |
| 2978957 | KATNA1 |
| 3507962 | KATNAL1 |
| 3787187 | KATNAL2 |
| 2514413 | KBTBD10 |
| 3389566 | KBTBD3 |
| 3511168 | KBTBD6 |
| 3511168 | KBTBD7 |
| 2628260 | KBTBD8 |
| 2427619 | KCNA3 |
| 2648991 | KCNAB1 |
| 3103062 | KCNB2 |
| 3462567 | KCNC2 |
| 3021009 | KCND2 |

Figure 6 continued

| TCID | GENE_na29 | TCID | GENE_na29 | TCID | GENE_na29 |
|---|---|---|---|---|---|
| 2428119 | KCND3 | 3829638 | KIAA0355 | 2672629 | KIF9 |
| 2613293 | KCNH8 | 2973232 | KIAA0408 | 3841756 | KIR2DL1 |
| 2762944 | KCNIP4 | 3681956 | KIAA0430 | 3841777 | KIR2DL1 |
| 2603960 | KCNJ13 | 2338719 | KIAA0485 | 4053056 | KIR2DL1 |
| 3920850 | KCNJ15 | 2393654 | KIAA0495 | 3841756 | KIR2DL2 |
| 3733238 | KCNJ16 | 3193870 | KIAA0649 | 3841777 | KIR2DL2 |
| 3733275 | KCNJ2 | 3329404 | KIAA0652 | 4053056 | KIR2DL2 |
| 3931495 | KCNJ6 | 3456955 | KIAA0748 | 3841756 | KIR2DL3 |
| 2385873 | KCNK1 | 3743119 | KIAA0753 | 3841777 | KIR2DL3 |
| 2379974 | KCNK2 | 2331213 | KIAA0754 | 4053056 | KIR2DL3 |
| 3334446 | KCNK4 | 3565739 | KIAA0831 | 3841777 | KIR2DL4 |
| 2952834 | KCNK5 | 3301263 | KIAA0894 | 3841756 | KIR2DS1 |
| 3296046 | KCNMA1 | 2437753 | KIAA0907 | 3841777 | KIR2DS1 |
| 2653673 | KCNMB2 | 2748198 | KIAA0922 | 4053056 | KIR2DS1 |
| 3421985 | KCNMB4 | 3429754 | KIAA1033 | 3841756 | KIR2DS2 |
| 3824666 | KCNN1 | 3255402 | KIAA1128 | 3841777 | KIR2DS2 |
| 2436826 | KCNN3 | 3238962 | KIAA1217 | 4053056 | KIR2DS2 |
| 3317352 | KCNQ1 | 3884640 | KIAA1219 | 3841756 | KIR2DS3 |
| 3154002 | KCNQ3 | 2927604 | KIAA1244 | 4053056 | KIR2DS3 |
| 2471384 | KCNS3 | 2432851 | KIAA1245 | 3841756 | KIR2DS4 |
| 3071878 | KCP | 3250093 | KIAA1279 | 3841777 | KIR2DS4 |
| 3470793 | KCTD10 | 3737488 | KIAA1303 | 4053056 | KIR2DS4 |
| 3687308 | KCTD13 | 3529951 | KIAA1305 | 3841756 | KIR2DS5 |
| 3383130 | KCTD14 | 2350489 | KIAA1324 | 3841777 | KIR2DS5 |
| 3944637 | KCTD17 | 3059942 | KIAA1324L | 4053056 | KIR2DS5 |
| 2594435 | KCTD18 | 3784999 | KIAA1328 | 3841756 | KIR3DL1 |
| 2380055 | KCTD3 | 2689286 | KIAA1407 | 3841777 | KIR3DL1 |
| 3128372 | KCTD9 | 3549264 | KIAA1409 | 4053056 | KIR3DL1 |
| 3128372 | KCTD9P2 | 3161167 | KIAA1432 | 3841756 | KIR3DL2 |
| 2827525 | KDELC1 | 3791168 | KIAA1468 | 3841777 | KIR3DL2 |
| 3867092 | KDELR1 | 3075431 | KIAA1549 | 3841777 | KIR3DL3 |
| 3945314 | KDELR3 | 2911257 | KIAA1586 | 3841777 | KIR3DP1 |
| 3817733 | KDM4B | 3308489 | KIAA1598 | 3841777 | KIR3DP1 |
| 3161566 | KDM4C | 3702499 | KIAA1609 | 4053056 | KIR3DP1 |
| 3439603 | KDM5A | 3737274 | KIAA1618 | 4053056 | KIR3DP1 |
| 2451309 | KDM5B | 3806126 | KIAA1632 | 3841777 | KIR3DS1 |
| 4009062 | KDM5C | 3961496 | KIAA1659 | 4053056 | KIR3DS1 |
| 3709153 | KDM6B | 2735815 | KIAA1680 | 3841357 | KIR3DX1 |
| 2769810 | KDR | 3854836 | KIAA1683 | 2727587 | KIT |
| 3593408 | KGFLP1 | 2588319 | KIAA1715 | 2724308 | KLB |
| 3593408 | KGFLP2 | 3164601 | KIAA1797 | 3553872 | KLC1 |
| 2960774 | KHDC1 | 2484457 | KIAA1841 | 3836217 | KLC3 |
| 2959039 | KHDRBS2 | 3258168 | KIF11 | 2954355 | KLC4 |
| 3117384 | KHDRBS3 | 3221822 | KIF12 | 3851840 | KLF1 |
| 3847814 | KHSRP | 3898796 | KIF16B | 2723997 | KLF3 |
| 2399620 | KIAA0090 | 3734292 | KIF19 | 3219215 | KLF4 |
| 3750872 | KIAA0100 | 2319661 | KIF1B | 3493543 | KLF5 |
| 3629103 | KIAA0101 | 3450775 | KIF21A | 3274361 | KLF6 |
| 2832963 | KIAA0141 | 3203935 | KIF24 | 2596514 | KLF7 |
| 3672368 | KIAA0182 | 3212232 | KIF27 | 3978943 | KLF8 |
| 2713555 | KIAA0226 | 2875419 | KIF3A | 3534886 | KLHDC1 |
| 3542145 | KIAA0247 | 3418298 | KIF5A | 2907568 | KLHDC3 |
| 3554452 | KIAA0284 | 3283991 | KIF5B | 2452440 | KLHDC8A |
| 2406139 | KIAA0319L | 2509900 | KIF5C | 2622006 | KLHDC8B |

Figure 6 continued

| TCID | GENE_na29 | TCID | GENE_na29 | TCID | GENE_na29 |
|---|---|---|---|---|---|
| 3721485 | KLHL10 | 2508520 | KYNU | 3944882 | LGALS1 |
| 2451428 | KLHL12 | 2339334 | L1TD1 | 3833183 | LGALS13 |
| 2750527 | KLHL2 | 3797295 | L3MBTL4 | 3960174 | LGALS2 |
| 3825260 | KLHL26 | 3597421 | LACTB | 3536706 | LGALS3 |
| 3562671 | KLHL28 | 3841506 | LAIR1 | 3861557 | LGALS4 |
| 2918037 | KLHL32 | 3841357 | LAIR2 | 2462456 | LGALS8 |
| 3983324 | KLHL4 | 3841506 | LAIR2 | 2386867 | LGALS8 |
| 2708066 | KLHL6 | 2925237 | LAMA2 | 3258713 | LGI1 |
| 2776998 | KLHL8 | 3913018 | LAMA5 | 3127352 | LGI3 |
| 3868828 | KLK10 | 3067302 | LAMB1 | 3859668 | LGI4 |
| 3868841 | KLK11 | 2674047 | LAMB2 | 3577078 | LGMN |
| 3868857 | KLK12 | 2453793 | LAMB3 | 3367096 | LGR4 |
| 3868783 | KLK7 | 3067408 | LAMB4 | 3422144 | LGR5 |
| 3444180 | KLRA1 | 2371065 | LAMC1 | 2375144 | LGR6 |
| 3443804 | KLRB1 | 2371139 | LAMC2 | 3867573 | LHB |
| 3444117 | KLRC1 | 4019849 | LAMP2 | 2552368 | LHCGR |
| 3444117 | KLRC2 | 2707876 | LAMP3 | 2863885 | LHFPL2 |
| 3444117 | KLRC3 | 3973768 | LANCL3 | 3224220 | LHX6 |
| 3444086 | KLRC4 | 2836738 | LARP1 | 2342475 | LHX8 |
| 3404660 | KLRD1 | 2743085 | LARP2 | 2854092 | LIFR |
| 3404030 | KLRG1 | 3414512 | LARP4 | 3718401 | LIG3 |
| 3444086 | KLRK1 | 2740005 | LARP7 | 3841545 | LILRA1 |
| 3272566 | KNDC1 | 4010860 | LAS1L | 3841357 | LILRA2 |
| 3435362 | KNTC1 | 3855285 | LASS1 | 3841545 | LILRB1 |
| 2691982 | KPNA1 | 3454296 | LASS5 | 3454331 | LIMA1 |
| 4041113 | KPNA2 | 2514122 | LASS6 | 2725061 | LIMCH1 |
| 2703217 | KPNA4 | 3008164 | LAT2 | 3893642 | LIME1 |
| 2922840 | KPNA5 | 2978989 | LATS1 | 3008108 | LIMK1 |
| 3724782 | KPNB1 | 3504526 | LATS2 | 3942838 | LIMK2 |
| 3030585 | KPNB1 | 3348568 | LAYN | 2574984 | LIMS2 |
| 3447863 | KRAS | 2458289 | LBR | 2838598 | LIN28B |
| 3422855 | KRR1 | 2382781 | LBR | 2775858 | LIN54 |
| 3462693 | KRR1 | 3599280 | LBXCOR1 | 3367183 | LIN7C |
| 3415576 | KRT18 | 2962026 | LCA5 | 3202528 | LINGO2 |
| 3757108 | KRT19 | 3696035 | LCAT | 3787855 | LIPG |
| 3415320 | KRT7 | 3653619 | LCMT1 | 2708855 | LIPH |
| 3455752 | KRT77 | 3190190 | LCN2 | 2868265 | LIX1 |
| 3455890 | KRT79 | 2762500 | LCORL | 2356142 | LIX1L |
| 3455516 | KRT8 | 3512874 | LCP1 | 3460584 | LLPH |
| 3455134 | KRT80 | 2886595 | LCP2 | 2565484 | LMAN2L |
| 3455344 | KRT82 | 2577856 | LCT | 3081624 | LMBR1 |
| 3923838 | KRTAP10-12 | 3304215 | LDB1 | 2660029 | LMLN |
| 3923838 | KRTAP10-4 | 2762088 | LDB2 | 2361279 | LMNA |
| 3923838 | KRTAP10-6 | 3446868 | LDHB | 2985342 | LMNA |
| 3923838 | KRTAP10-7 | 2400793 | LDLRAD2 | 3368814 | LMO2 |
| 3934623 | KRTAP12-1 | 4024420 | LDOC1 | 3446137 | LMO3 |
| 3934623 | KRTAP12-2 | 3963289 | LDOC1L | 2345286 | LMO4 |
| 3923881 | KRTAP12-3 | 2828796 | LEAP2 | 2451043 | LMOD1 |
| 3721279 | KRTAP9-2 | 2649182 | LEKR1 | 3008376 | LOC100093631 |
| 3721279 | KRTAP9-3 | 2452478 | LEMD1 | 3028011 | LOC100124692 |
| 3721279 | KRTAP9-4 | 3420079 | LEMD3 | 2366798 | LOC100127910 |
| 3721279 | KRTAP9-8 | 2340433 | LEPR | 3830216 | LOC100127972 |
| 3721279 | KRTAP9-9 | 2340433 | LEPROT | 3442054 | LOC100127974 |
| 2696415 | KY | 3414776 | LETMD1 | 3795184 | LOC100127994 |

Figure 6 continued

| TCID | GENE_na29 | TCID | GENE_na29 | TCID | GENE_na29 |
|---|---|---|---|---|---|
| 2321238 | LOC100128068 | 3987029 | LOC100130886 | 3735847 | LOC100133227 |
| 3913018 | LOC100128184 | 3946146 | LOC100130899 | 3930781 | LOC100133286 |
| 3777470 | LOC100128219 | 2540317 | LOC100130910 | 3279575 | LOC100133308 |
| 3302056 | LOC100128320 | 3275922 | LOC100130920 | 3056656 | LOC100133748 |
| 3872604 | LOC100128398 | 2861952 | LOC100130998 | 3309936 | LOC100133773 |
| 3817733 | LOC100128439 | 2602901 | LOC100131015 | 3171425 | LOC100133802 |
| 3836614 | LOC100128529 | 2533670 | LOC100131101 | 3841357 | LOC100133875 |
| 2933175 | LOC100128551 | 3110272 | LOC100131102 | 3746881 | LOC100133918 |
| 2606026 | LOC100128563 | 3848243 | LOC100131165 | 2565935 | LOC100133923 |
| 3848243 | LOC100128567 | 3814701 | LOC100131178 | 3223425 | LOC100133950 |
| 3890870 | LOC100128608 | 2542795 | LOC100131373 | 3976240 | LOC100133957 |
| 3020222 | LOC100128868 | 3754041 | LOC100131384 | 3514879 | LOC100134095 |
| 2321466 | LOC100129042 | 3754096 | LOC100131384 | 3759849 | LOC100134130 |
| 3396107 | LOC100129069 | 4040117 | LOC100131384 | 3287366 | LOC100134152 |
| 3765689 | LOC100129112 | 4040849 | LOC100131384 | 3227846 | LOC100134189 |
| 3759587 | LOC100129115 | 4025339 | LOC100131434 | 3274758 | LOC100134257 |
| 2601414 | LOC100129171 | 3464860 | LOC100131490 | 3754041 | LOC100134348 |
| 2900269 | LOC100129195 | 3868330 | LOC100131519 | 3754096 | LOC100134348 |
| 2404122 | LOC100129196 | 3875642 | LOC100131599 | 4040117 | LOC100134348 |
| 2869880 | LOC100129233 | 3227846 | LOC100131612 | 4040849 | LOC100134348 |
| 2604998 | LOC100129258 | 3259367 | LOC100131720 | 3050462 | LOC100134631 |
| 2691014 | LOC100129275 | 2994835 | LOC100131724 | 3636879 | LOC100134869 |
| 2587520 | LOC100129312 | 3756193 | LOC100131821 | 3325503 | LOC100190939 |
| 3696317 | LOC100129324 | 3754677 | LOC100131822 | 3652077 | LOC100190986 |
| 3623031 | LOC100129397 | 2779638 | LOC100131829 | 3279108 | LOC100192204 |
| 2969886 | LOC100129399 | 2622026 | LOC100131840 | 3260001 | LOC100270710 |
| 3050388 | LOC100129427 | 4027176 | LOC100131857 | 3683050 | LOC100271836 |
| 2889916 | LOC100129453 | 2984884 | LOC100131869 | 3724591 | LOC100272146 |
| 2746693 | LOC100129572 | 3155937 | LOC100131910 | 2993590 | LOC100272146 |
| 3090438 | LOC100129717 | 2364677 | LOC100131938 | 4025339 | LOC100272228 |
| 3128271 | LOC100129717 | 3513549 | LOC100131993 | 3454147 | LOC100286844 |
| 3290746 | LOC100129721 | 3681705 | LOC100131998 | 2881607 | LOC134466 |
| 3191273 | LOC100129785 | 3684782 | LOC100131998 | 3710681 | LOC139201 |
| 3400730 | LOC100129797 | 3684548 | LOC100131998 | 3542847 | LOC145474 |
| 3092415 | LOC100129846 | 2853642 | LOC100132000 | 3840857 | LOC147804 |
| 2409904 | LOC100129897 | 2824902 | LOC100132014 | 2468105 | LOC150622 |
| 3833183 | LOC100129935 | 3583541 | LOC100132025 | 2564816 | LOC150759 |
| 2577482 | LOC100129961 | 2984275 | LOC100132188 | 2575897 | LOC150776 |
| 3737697 | LOC100130078 | 4042198 | LOC100132235 | 2687739 | LOC151657 |
| 2563785 | LOC100130100 | 3650300 | LOC100132247 | 2880361 | LOC153469 |
| 2431595 | LOC100130131 | 3652077 | LOC100132247 | 2808180 | LOC153684 |
| 3439836 | LOC100130219 | 3922793 | LOC100132338 | 3220846 | LOC158402 |
| 2504328 | LOC100130248 | 3275132 | LOC100132353 | 3765167 | LOC162632 |
| 3742351 | LOC100130311 | 2431112 | LOC100132495 | 3748400 | LOC162632 |
| 2462693 | LOC100130331 | 3552729 | LOC100132532 | 3278234 | LOC168474 |
| 2614369 | LOC100130354 | 4040117 | LOC100132544 | 3402978 | LOC171220 |
| 2774817 | LOC100130356 | 2641341 | LOC100132731 | 3838809 | LOC199800 |
| 2942306 | LOC100130357 | 3392332 | LOC100132764 | 2927604 | LOC202451 |
| 3856720 | LOC100130518 | 2321466 | LOC100132942 | 3107606 | LOC203107 |
| 3826803 | LOC100130518 | 3855538 | LOC100133072 | 3280787 | LOC219688 |
| 3542145 | LOC100130542 | 3636879 | LOC100133144 | 3514879 | LOC220115 |
| 2662581 | LOC100130542 | 3017547 | LOC100133169 | 3533499 | LOC220429 |
| 3935016 | LOC100130597 | 3298924 | LOC100133190 | 3765167 | LOC220594 |
| 3739867 | LOC100130876 | 2342220 | LOC100133219 | 3748400 | LOC220594 |

Figure 6 continued

| TCID | GENE_na29 | TCID | GENE_na29 | TCID | GENE_na29 |
|---|---|---|---|---|---|
| 2906607 | LOC221442 | 3227846 | LOC441089 | 3681705 | LOC653390 |
| 3937967 | LOC26080 | 2995076 | LOC441208 | 3684782 | LOC653390 |
| 3953456 | LOC26080 | 3029230 | LOC441294 | 3684548 | LOC653390 |
| 3523499 | LOC283480 | 3641597 | LOC441734 | 3724698 | LOC653498 |
| 3487095 | LOC283508 | 2431595 | LOC51152 | 3754041 | LOC653498 |
| 3542847 | LOC283567 | 3948259 | LOC553158 | 3754096 | LOC653498 |
| 3613338 | LOC283683 | 3201345 | LOC554202 | 4040117 | LOC653498 |
| 3583541 | LOC283767 | 3819016 | LOC554363 | 4040849 | LOC653498 |
| 3941907 | LOC284685 | 3652077 | LOC595101 | 3206317 | LOC653501 |
| 3937967 | LOC284861 | 3683050 | LOC595101 | 2431886 | LOC653513 |
| 3953456 | LOC284861 | 3060994 | LOC613126 | 3591281 | LOC653566 |
| 2571075 | LOC285074 | 3652077 | LOC641298 | 2470470 | LOC653602 |
| 2781325 | LOC285456 | 3683050 | LOC641298 | 2575949 | LOC654264 |
| 2749380 | LOC285505 | 3938817 | LOC642311 | 2501317 | LOC654433 |
| 2791419 | LOC285505 | 2938196 | LOC642335 | 3358112 | LOC692247 |
| 2951567 | LOC285847 | 2506335 | LOC642669 | 4046876 | LOC727761 |
| 3031466 | LOC285972 | 3674504 | LOC643224 | 2628482 | LOC727775 |
| 3139882 | LOC286190 | 3405207 | LOC643287 | 3841756 | LOC727787 |
| 3650300 | LOC339047 | 2455418 | LOC643454 | 3841777 | LOC727787 |
| 2404958 | LOC339483 | 3281068 | LOC643475 | 3583541 | LOC727832 |
| 3205834 | LOC340508 | 3329069 | LOC644172 | 4026560 | LOC727895 |
| 2670903 | LOC348817 | 2506335 | LOC644525 | 2911903 | LOC727916 |
| 3686587 | LOC388242 | 3982423 | LOC644732 | 3635776 | LOC727963 |
| 3954729 | LOC388882 | 3982423 | LOC644756 | 2390518 | LOC728060 |
| 2472955 | LOC388931 | 3924929 | LOC645159 | 3504691 | LOC728099 |
| 3017080 | LOC389137 | 3583541 | LOC645162 | 3937967 | LOC728212 |
| 3212232 | LOC389765 | 2340350 | LOC645195 | 3953456 | LOC728212 |
| 3851651 | LOC389791 | 3583541 | LOC645202 | 3721279 | LOC728341 |
| 3704567 | LOC390748 | 3171425 | LOC645961 | 3029646 | LOC728377 |
| 2539869 | LOC392510 | 3283613 | LOC645984 | 3683050 | LOC728423 |
| 3826656 | LOC400680 | 3629811 | LOC646358 | 3471769 | LOC728543 |
| 2421883 | LOC400759 | 3203311 | LOC646808 | 2888103 | LOC728554 |
| 3960478 | LOC400927 | 3826803 | LOC646864 | 2487995 | LOC728731 |
| 2565935 | LOC400986 | 3621276 | LOC647471 | 2758602 | LOC728731 |
| 2576526 | LOC401010 | 3868330 | LOC647678 | 3223425 | LOC728779 |
| 4026560 | LOC401218 | 2525533 | LOC648149 | 3754041 | LOC728824 |
| 2994558 | LOC401317 | 2714200 | LOC649851 | 3754096 | LOC728824 |
| 3060994 | LOC401387 | 3621276 | LOC649956 | 4040117 | LOC728824 |
| 2988594 | LOC402509 | 2563785 | LOC650405 | 4040849 | LOC728824 |
| 3358950 | LOC402778 | 3939914 | LOC650860 | 3754070 | LOC728830 |
| 3244055 | LOC439911 | 2563785 | LOC652493 | 2431886 | LOC728989 |
| 3770944 | LOC440093 | 3642162 | LOC652595 | 4040117 | LOC729034 |
| 3583541 | LOC440243 | 2563785 | LOC652694 | 2619521 | LOC729085 |
| 3614901 | LOC440248 | 3692701 | LOC652708 | 2743085 | LOC729231 |
| 3585749 | LOC440248 | 2565935 | LOC652726 | 2565753 | LOC729234 |
| 4002011 | LOC440258 | 3841777 | LOC652779 | 2494064 | LOC729234 |
| 2593796 | LOC440258 | 2858134 | LOC653198 | 2500275 | LOC729312 |
| 3652077 | LOC440354 | 3937967 | LOC653264 | 3937967 | LOC729461 |
| 3683050 | LOC440354 | 3953456 | LOC653264 | 3953456 | LOC729461 |
| 3724698 | LOC440434 | 4015838 | LOC653354 | 3683050 | LOC729513 |
| 4040117 | LOC440434 | 3754041 | LOC653382 | 3652077 | LOC729602 |
| 2563785 | LOC440871 | 3754096 | LOC653382 | 2934308 | LOC729603 |
| 3173508 | LOC440897 | 4040117 | LOC653382 | 4002011 | LOC729609 |
| 2727226 | LOC441016 | 4040849 | LOC653382 | 2343823 | LOC729828 |

Figure 6 continued

| TCID | GENE_na29 | TCID | GENE_na29 | TCID | GENE_na29 |
|---|---|---|---|---|---|
| 2548274 | LOC729862 | 2672190 | LRRC2 | 2902559 | LY6G5B |
| 3855538 | LOC729991 | 3402984 | LRRC23 | 2949230 | LY6G5C |
| 3855538 | LOC729991-MEF2B | 3158812 | LRRC24 | 3119213 | LY6K |
| | | 2704763 | LRRC34 | 2583254 | LY75 |
| 2936857 | LOC730031 | 3665458 | LRRC36 | 2363248 | LY9 |
| 3681705 | LOC730092 | 3767169 | LRRC37A | 2566689 | LYG2 |
| 3684548 | LOC730092 | 3767169 | LRRC37A2 | 3098977 | LYN |
| 3826803 | LOC730110 | 3767169 | LRRC37A3 | 2576988 | LYPD1 |
| 2758602 | LOC731528 | 3767169 | LRRC37A4 | 2506570 | LYPD1 |
| 3717052 | LOC731788 | 3717452 | LRRC37B | 2510056 | LYPD6 |
| 2390518 | LOC731985 | 3717452 | LRRC37B2 | 2509988 | LYPD6B |
| 3721279 | LOC732428 | 2425173 | LRRC39 | 3135567 | LYPLA1 |
| 4031834 | LOC732447 | 2417737 | LRRC40 | 2380785 | LYPLAL1 |
| 3651509 | LOC81691 | 3712835 | LRRC48 | 3683845 | LYRM1 |
| 3248986 | LOC84989 | 3600212 | LRRC49 | 2916825 | LYRM2 |
| 2788800 | LOC90826 | 3370269 | LRRC4C | 3447863 | LYRM5 |
| 3954764 | LOC91316 | 3671607 | LRRC50 | 2828135 | LYRM7 |
| 3938817 | LOC96610 | 2365086 | LRRC52 | 2461999 | LYST |
| 3847356 | LONP1 | 3358090 | LRRC56 | 3362826 | LYVE1 |
| 3659306 | LONP2 | 3358112 | LRRC56 | 3421511 | LYZ |
| 3690470 | LONP2 | 3315907 | LRRC56 | 3403981 | M6PR |
| 2567167 | LONRF2 | 3154136 | LRRC6 | 3040518 | MACC1 |
| 3988638 | LONRF3 | 3106559 | LRRC69 | 2331213 | MACF1 |
| 2872848 | LOX | 2341387 | LRRC7 | 2576281 | MAD2L1 |
| 3302693 | LOXL4 | 2811812 | LRRC70 | 2396781 | MAD2L2 |
| 3220384 | LPAR1 | 3190778 | LRRC8A | 2714672 | MAEA |
| 3442137 | LPAR5 | 2345880 | LRRC8B | 3905875 | MAFB |
| 2845973 | LPCAT1 | 2345929 | LRRC8C | 3451814 | MAFG |
| 3661718 | LPCAT2 | 3538403 | LRRC9 | 2708610 | MAGEF1 |
| 3442427 | LPCAT3 | 3105430 | LRRCC1 | 3058209 | MAGI2 |
| 2343823 | LPHN2 | 2534456 | LRRFIP1 | 2352609 | MAGI3 |
| 2728938 | LPHN3 | 2669184 | LRRFIP2 | 3745525 | MAGOH2 |
| 3088486 | LPL | 3424705 | LRRIQ1 | 3444195 | MAGOHB |
| 3374402 | LPXN | 2418339 | LRRIQ3 | 3130823 | MAK16 |
| 2789266 | LRBA | 2608309 | LRRN1 | 7385515 | MALAT1 |
| 3488602 | LRCH1 | 3019158 | LRRN3 | 3790259 | MALT1 |
| 2659918 | LRCH3 | 3380996 | LRTOMT | 3174121 | MAMDC2 |
| 3336576 | LRFN4 | 2690012 | LSAMP | 2786732 | MAML3 |
| 3846831 | LRG1 | 3846831 | LSDP5 | 3994710 | MAMLD1 |
| 3025291 | LRGUK | 3131844 | LSM1 | 2971801 | MAN1A1 |
| 2680591 | LRIG1 | 3131205 | LSM12 | 2353881 | MAN1A2 |
| 3459120 | LRIG3 | 2746269 | LSM6 | 2326049 | MAN1C1 |
| 2739289 | LRIT3 | 3317071 | LSP1 | 2823551 | MAN2A1 |
| 3408505 | LRMP | 3830246 | LSR | 3608466 | MAN2A2 |
| 3528895 | LRP10 | 3529877 | LTB4R | 3633347 | MAN2C1 |
| 2979111 | LRP11 | 3529877 | LTB4R2 | 2779897 | MANBA |
| 2979187 | LRP11 | 2476510 | LTBP1 | 3884158 | MANBAL |
| 3147985 | LRP12 | 3571944 | LTBP2 | 2917767 | MANEA |
| 2578790 | LRP1B | 2672140 | LTF | 2330843 | MANEAL |
| 2586038 | LRP2 | 3674960 | LUC7L | 3975227 | MAOA |
| 2796847 | LRP2BP | 3465248 | LUM | 4006210 | MAOB |
| 3829242 | LRP3 | 3324162 | LUZP2 | 2814756 | MAP1B |
| 3158812 | LRRC14 | 2824902 | LVRN | 2525533 | MAP2 |
| 2898746 | LRRC16A | 3119339 | LY6E | 3710681 | MAP2K4 |

Figure 6 continued

| TCID | GENE_na29 | TCID | GENE_na29 | TCID | GENE_na29 |
|---|---|---|---|---|---|
| 3599162 | MAP2K5 | 2964350 | MDN1 | 3464417 | MGAT4C |
| 3733065 | MAP2K6 | 2962820 | ME1 | 2668425 | MGC12488 |
| 2574798 | MAP3K2 | 3385307 | ME3 | 4022690 | MGC16121 |
| 2403027 | MAP3K6 | 2847264 | MED10 | 3705135 | MGC16385 |
| 2930592 | MAP3K7IP2 | 2647898 | MED12L | 2658275 | MGC2889 |
| 2672966 | MAP4 | 3765689 | MED13 | 2877893 | MGC29506 |
| 2549260 | MAP4K3 | 4037595 | MED13L | 3528172 | MGC40069 |
| 2496727 | MAP4K4 | 3473083 | MED13L | 3011838 | MGC87042 |
| 2330289 | MAP7D1 | 3228635 | MED22 | 3304012 | MGEA5 |
| 3954238 | MAPK1 | 2974188 | MED23 | 3445741 | MGP |
| 2776670 | MAPK10 | 3838947 | MED25 | 3646277 | MGRN1 |
| 2904946 | MAPK13 | 3227846 | MED27 | 3406589 | MGST1 |
| 2904877 | MAPK14 | 3832964 | MED29 | 4042837 | MIA3 |
| 3788097 | MAPK4 | 3112713 | MED30 | 3320717 | MICAL2 |
| 3111561 | MAPK6 | 3707990 | MED31 | 3320819 | MICALCL |
| 3713874 | MAPK7 | 3855538 | MEF2B | 3999395 | MID1 |
| 3329069 | MAPK8IP1 | 2866225 | MEF2C | 2685776 | MINA |
| 2890605 | MAPK9 | 2827299 | MEGF10 | 3742351 | MINK1 |
| 2622912 | MAPKAPK3 | 3223551 | MEGF9 | 3950846 | MIOX |
| 3784344 | MAPRE2 | 2486178 | MEIS1 | 3496366 | MIRHG1 |
| 2792166 | MARCH1 | 3618333 | MEIS2 | 3707759 | MIS12 |
| 2801608 | MARCH6 | 3168508 | MELK | 2628785 | MITF |
| 3553690 | MARK3 | 2547332 | MEMO1 | 2383118 | MIXL1 |
| 3260001 | MARVELD1 | 2547332 | MEMO1 | 3312490 | MKI67 |
| 3667652 | MARVELD3 | 3039485 | MEOX2 | 3961496 | MKL1 |
| 2396415 | MASP2 | 3783788 | MEP1B | 3649052 | MKL2 |
| 2812690 | MAST4 | 2500550 | MERTK | 3076178 | MKRN1 |
| 3240012 | MASTL | 3020343 | MET | 3282463 | MKX |
| 2404122 | MATN1 | 3527745 | METT11D1 | 3434525 | MLEC |
| 3108526 | MATN2 | 3311342 | METTL10 | 2649609 | MLF1 |
| 3568667 | MAX | 3191074 | METTL11A | 2796510 | MLF1IP |
| 3808600 | MBD2 | 3375999 | METTL12 | 2616932 | MLH1 |
| 2694785 | MBD4 | 3556418 | METTL3 | 3572235 | MLH3 |
| 3497586 | MBNL2 | 3796244 | METTL4 | 2734784 | MLL |
| 2539607 | MBOAT2 | 3414739 | METTL7A | 3847703 | MLL |
| 3870570 | MBOAT7 | 3416895 | METTL7B | 3453592 | MLL2 |
| 3762625 | MBTD1 | 3651955 | METTL9 | 3924929 | MLL3 |
| 3971329 | MBTPS2 | 3808096 | MEX3C | 3017547 | MLL5 |
| 3674504 | MC1R | 3845296 | MEX3D | 3847703 | MLLT1 |
| 4024092 | MCF2 | 3748798 | MFAP4 | 3238231 | MLLT10 |
| 3924518 | MCM3AP | 3638204 | MFGE8 | 2358693 | MLLT11 |
| 3924518 | MCM3APAS | 2653932 | MFN1 | 3200982 | MLLT3 |
| 3097152 | MCM4 | 3735623 | MFSD11 | 2936857 | MLLT4 |
| 3063685 | MCM7 | 2331679 | MFSD2 | 3721886 | MLX |
| 3083778 | MCPH1 | 2376548 | MFSD4 | 2746164 | MMAA |
| 3609592 | MCTP2 | 2520138 | MFSD6 | 2334350 | MMACHC |
| 2948564 | MDC1 | 2714200 | MFSD7 | 3763270 | MMD |
| 3019981 | MDFIC | 2785035 | MFSD8 | 3388807 | MMP1 |
| 2485176 | MDH1 | 3028011 | MGAM | 3388893 | MMP13 |
| 2596386 | MDH1B | 2890859 | MGAT1 | 3528864 | MMP14 |
| 3329343 | MDK | 3534866 | MGAT2 | 3143643 | MMP16 |
| 3461164 | MDM1 | 3226883 | MGAT2 | 3143660 | MMP16 |
| 3421300 | MDM2 | 2566414 | MGAT4A | 3883236 | MMP24 |
| 2376037 | MDM4 | 2890239 | MGAT4B | 3753760 | MMP28 |

Figure 6 continued

| TCID | GENE_na29 | TCID | GENE_na29 | TCID | GENE_na29 |
|------|-----------|------|-----------|------|-----------|
| 2735759 | MMRN1 | 2817837 | MSH3 | 3428596 | MYBPC1 |
| 3298924 | MMRN2 | 2902633 | MSH5 | 3372129 | MYBPC3 |
| 3302360 | MMS19 | 2696764 | MSL2 | 2407755 | MYCBP |
| 2748163 | MND1 | 3979659 | MSN | 3518496 | MYCBP2 |
| 2362333 | MNDA | 3125571 | MSR1 | 2470838 | MYCN |
| 3625761 | MNS1 | 2674602 | MST1 | 2931970 | MYCT1 |
| 3202316 | MOBKL2B | 2835662 | MST150 | 3622934 | MYEF2 |
| 3784783 | MOCOS | 3992408 | MST159 | 3593014 | MYEF2 |
| 3064501 | MOGAT3 | 2674602 | MSTP2 | 3338060 | MYEOV |
| 2674963 | MON1A | 2674602 | MSTP9 | 3745351 | MYH1 |
| 3919952 | MORC3 | 3662106 | MT1A | 3744463 | MYH10 |
| 4017212 | MORC4 | 3662106 | MT1DP | 3682028 | MYH11 |
| 2794180 | MORF4 | 3662139 | MT1E | 3839206 | MYH14 |
| 2794180 | MORF4L1 | 3662201 | MT1F | 3745429 | MYH2 |
| 3475295 | MORN3 | 3692999 | MT1G | 3745351 | MYH2 |
| 2381309 | MOSC1 | 3662201 | MT1H | 3745429 | MYH3 |
| 4022833 | MOSPD1 | 3662236 | MT1IP | 3745429 | MYH4 |
| 3708874 | MPDU1 | 3662139 | MT1JP | 3745351 | MYH4 |
| 3198974 | MPDZ | 3662130 | MT1L | 3557504 | MYH6 |
| 3480013 | MPHOSPH8 | 3662150 | MT1M | 3557504 | MYH7 |
| 3476012 | MPHOSPH9 | 3662201 | MT1P2 | 3745429 | MYH8 |
| 2333107 | MPL | 3662150 | MT1P3 | 3745351 | MYH8 |
| 2594987 | MPP4 | 3662106 | MT1X | 3959451 | MYH9 |
| 3541073 | MPP5 | 3662247 | MT1X | 2597389 | MYL1 |
| 2993206 | MPP6 | 3662236 | MT1X | 2714200 | MYL5 |
| 3282601 | MPP7 | 3662150 | MT2A | 2651671 | MYNN |
| 3799167 | MPPE1 | 2952102 | MTCH1 | 2850071 | MYO10 |
| 3367673 | MPPED2 | 3060917 | MTERF | 2520429 | MYO1B |
| 3712363 | MPRIP | 2607020 | MTERFD2 | 3752709 | MYO1D |
| 2545653 | MPV17 | 3629378 | MTFMT | 3626826 | MYO1E |
| 3393720 | MPZL2 | 3101385 | MTFR1 | 3431071 | MYO1H |
| 2370317 | MR1 | 3540007 | MTHFD1 | 3624607 | MYO5A |
| 2915571 | MRAP2 | 2931391 | MTHFD1L | 3807595 | MYO5B |
| 2598496 | MREG | 2731417 | MTHFD2L | 2914070 | MYO6 |
| 3807965 | MRO | 3482888 | MTIF3 | 3631794 | MYO9A |
| 3480681 | MRP63 | 3994795 | MTM1 | 2443952 | MYOC |
| 3760945 | MRPL10 | 3994846 | MTMR1 | 3300597 | MYOF |
| 2955025 | MRPL14 | 3615985 | MTMR10 | 3796428 | MYOM1 |
| 3361116 | MRPL17 | 2434178 | MTMR11 | 2835619 | MYOZ3 |
| 3379708 | MRPL21 | 3615985 | MTMR15 | 3725779 | MYST2 |
| 3619479 | MRPL42P5 | 3764471 | MTMR4 | 3133135 | MYST3 |
| 3218067 | MRPL50 | 3511189 | MTRF1 | 2724585 | N4BP2 |
| 2664099 | MRPS25 | 3151970 | MTSS1 | 3508696 | N4BP2L2 |
| 2861952 | MRPS27 | 3125915 | MTUS1 | 2773872 | NAAA |
| 2808612 | MRPS30 | 2437118 | MUC1 | 3344142 | NAALAD2 |
| 3510925 | MRPS31 | 3366903 | MUC15 | 2653114 | NAALADL2 |
| 3409330 | MRPS35 | 3986168 | MUM1L1 | 2520225 | NAB1 |
| 3734760 | MRPS7 | 2676454 | MUSTN1 | 3417809 | NAB2 |
| 3188050 | MRRF | 3259019 | MUTYH | 3695268 | NAE1 |
| 2898452 | MRS2 | 3655723 | MVP | 3074912 | NAG20 |
| 3332403 | MS4A1 | 3997825 | MXRA5 | 2861616 | NAIP |
| 3374934 | MS4A4E | 2512701 | MXRA7 | 3066818 | NAMPT |
| 3374934 | MS4A6A | 3841076 | MYADM | 4012511 | NAP1L2 |
| 2480992 | MSH2 | 2547751 | MYADML | 4014759 | NAP1L3 |

Figure 6 continued

| TCID | GENE_na29 | TCID | GENE_na29 | TCID | GENE_na29 |
|---|---|---|---|---|---|
| 3359469 | NAP1L4 | 3839880 | NCRNA00085 | 2332013 | NFYC |
| 2777447 | NAP1L5 | 3656635 | NCRNA00095 | 3529156 | NGDN |
| 3901191 | NAPB | 2762944 | NCRNA00099 | 3985534 | NGFRAP1 |
| 3778823 | NAPG | 4028207 | NCRNA00105 | 2666566 | NGLY1 |
| 3868400 | NAPSA | 2390976 | NCRNA00115 | 2780060 | NHEDC1 |
| 3868400 | NAPSB | 3879372 | NCRNA00153 | 2780099 | NHEDC2 |
| 3486883 | NARG1L | 2363084 | NCSTN | 2363128 | NHLH1 |
| 3627363 | NARG2 | 4037595 | ND1 | 3265047 | NHLRC2 |
| 3809671 | NARS | 3776139 | NDC80 | 2674526 | NICN1 |
| 2334404 | NASP | 3495076 | NDFIP2 | 2462160 | NID1 |
| 4006210 | NAT13 | 3615556 | NDNL2 | 3564620 | NID2 |
| 3878934 | NAT5 | 3555736 | NDRG2 | 3693083 | NIP30 |
| 3323052 | NAV2 | 3294816 | NDST2 | 3613338 | NIPA1 |
| 2541230 | NBAS | 3825838 | NDUFA13 | 3613300 | NIPA2 |
| 3485292 | NBEA | 3458400 | NDUFA4L2 | 3146012 | NIPAL2 |
| 2506335 | NBEA | 2965674 | NDUFAF4 | 2325410 | NIPAL3 |
| 2523478 | NBEAL1 | 3341497 | NDUFC2 | 2806799 | NIPBL |
| 2621122 | NBEAL2 | 2363525 | NDUFS2 | 3956909 | NIPSNAP1 |
| 2752085 | NBLA00301 | 2331178 | NDUFS5 | 3182957 | NIPSNAP3A |
| 2432851 | NBPF1 | 3778207 | NDUFV2 | 3182957 | NIPSNAP3B |
| 2357217 | NBPF1 | 3922921 | NDUFV3 | 3218528 | NIPSNAP3B |
| 2432851 | NBPF10 | 2581000 | NEB | 2623859 | NISCH |
| 2357217 | NBPF10 | 2510485 | NEB | 2363389 | NIT1 |
| 2432851 | NBPF11 | 3106479 | NECAB1 | 2924081 | NKAIN2 |
| 2357217 | NBPF11 | 3625539 | NEDD4 | 2549092 | NKAP |
| 2432851 | NBPF12 | 3789947 | NEDD4L | 2666103 | NKIRAS1 |
| 2357217 | NBPF12 | 3128271 | NEFL | 2619344 | NKTR |
| 2432851 | NBPF14 | 3090436 | NEFM | 3980835 | NLGN3 |
| 2357217 | NBPF14 | 2418078 | NEGR1 | 3715368 | NLK |
| 2432851 | NBPF15 | 3086181 | NEIL2 | 2812359 | NLN |
| 2357217 | NBPF15 | 2666884 | NEK10 | 3662444 | NLRC5 |
| 2432851 | NBPF16 | 2642441 | NEK11 | 3319018 | NLRP14 |
| 2357217 | NBPF16 | 3715809 | NEK8 | 3636985 | NMB |
| 2432851 | NBPF20 | 3451814 | NELL2 | 2877231 | NME5 |
| 2357217 | NBPF20 | 2379068 | NENF | 2673136 | NME6 |
| 2432851 | NBPF8 | 2949471 | NEU1 | 2447324 | NMNAT2 |
| 2357217 | NBPF8 | 2343231 | NEXN | 2697902 | NMNAT3 |
| 2432851 | NBPF9 | 3717052 | NF1 | 3723264 | NMT1 |
| 2357217 | NBPF9 | 3696666 | NFAT5 | 3279108 | NMT2 |
| 3147173 | NCALD | 3795184 | NFATC1 | 2770039 | NMU |
| 3349293 | NCAM1 | 3666033 | NFATC3 | 2882325 | NMUR2 |
| 3915936 | NCAM2 | 3456666 | NFE2 | 2576526 | NOC2L |
| 3402571 | NCAPD2 | 2588827 | NFE2L2 | 3439013 | NOC4L |
| 2762500 | NCAPG | 3724591 | NFE2L3 | 3044072 | NOD1 |
| 3181302 | NCBP1 | 2993590 | NFE2L3 | 3803628 | NOL4 |
| 2713074 | NCBP2 | 2338719 | NFIA | 2942504 | NOL7 |
| 2590736 | NCKAP1 | 3199207 | NFIB | 3214749 | NOL8 |
| 2673648 | NCKIPSD | 3214451 | NFIL3 | 3261492 | NOLC1 |
| 2473149 | NCOA1 | 3561039 | NFKBIA | 3649320 | NOMO1 |
| 3139722 | NCOA2 | 2634091 | NFKBIZ | 3649320 | NOMO2 |
| 3887635 | NCOA3 | 3904189 | NFS1 | 3649320 | NOMO3 |
| 3903525 | NCOA6 | 2558118 | NFU1 | 3980887 | NONO |
| 2924514 | NCOA7 | 3166880 | NFX1 | 2758076 | NOP14 |
| 3746881 | NCOR1 | 2906607 | NFYA | 3442024 | NOP2 |

Figure 6 continued

| TCID | GENE_na29 | TCID | GENE_na29 | TCID | GENE_na29 |
|---|---|---|---|---|---|
| 2364016 | NOS1AP | 2334706 | NSUN4 | 3490892 | OLFM4 |
| 2514216 | NOSTRIN | 3280224 | NSUN6 | 3319119 | OLFML1 |
| 2431112 | NOTCH2 | 2724853 | NSUN7 | 3444043 | OLR1 |
| 2431112 | NOTCH2NL | 3045004 | NT5C3 | 2658346 | OPA1 |
| 2949901 | NOTCH4 | 3757399 | NT5C3L | 3301782 | OPALIN |
| 3113202 | NOV | 2915828 | NT5E | 3399004 | OPCML |
| 3558745 | NOVA1 | 3143330 | NTAN1 | 3181976 | OPHN1 |
| 4015481 | NOX1 | 3356539 | NTM | 2932219 | OPRM1 |
| 3385951 | NOX4 | 3466556 | NTN4 | 3353914 | OR10D1P |
| 3527514 | NP | 2361761 | NTRK1 | 3353876 | OR10G4 |
| 3347658 | NPAT | 3177111 | NTRK2 | 3353876 | OR10G7 |
| 3801411 | NPC1 | 3637818 | NTRK3 | 3353876 | OR10G8 |
| 3801411 | NPC1 | 2452405 | NUAK2 | 3353876 | OR10G9 |
| 3571904 | NPC2 | 3644162 | NUBP2 | 2465806 | OR14A16 |
| 3230697 | NPDC1 | 3531355 | NUBPL | 3188186 | OR1Q1 |
| 3891006 | NPEPL1 | 3322251 | NUCB2 | 2390180 | OR2AJ1 |
| 3724698 | NPEPPS | 2510713 | NUDC | 2900832 | OR2H1 |
| 4040117 | NPEPPS | 3148796 | NUDCD1 | 2465890 | OR2T12 |
| 2695648 | NPHP3 | 4008427 | NUDT10 | 4045946 | OR2T3 |
| 3650300 | NPIP | 4008427 | NUDT11 | 2465890 | OR2T33 |
| 3652077 | NPIP | 3581485 | NUDT14 | 4045946 | OR2T34 |
| 3652077 | NPIPL1 | 2642543 | NUDT16P | 2465890 | OR2T8 |
| 3652077 | NPIPL3 | 2432647 | NUDT17 | 2390180 | OR2W3 |
| 2370926 | NPL | 2951087 | NUDT3 | 3706617 | OR3A4 |
| 3774029 | NPLOC4 | 2355616 | NUDT4 | 3329983 | OR4B1 |
| 3404436 | NPM1 | 3235461 | NUDT5 | 3332008 | OR4D6 |
| 3089049 | NPM2 | 2742109 | NUDT6 | 2487995 | OR7E5P |
| 2738378 | NPNT | 2364438 | NUF2 | 2487995 | OR7E91P |
| 2359780 | NPR1 | 3512449 | NUFIP1 | 3380065 | ORAOV1 |
| 2805635 | NPR3 | 3571347 | NUMB | 2594569 | ORC2L |
| 2792127 | NPY1R | 2943808 | NUP153 | 2580304 | ORC4L |
| 3696666 | NQO1 | 4017281 | NUP62CL | 3658925 | ORC6L |
| 3756046 | NR1D1 | 3662265 | NUP93 | 2591942 | ORMDL1 |
| 2614142 | NR1D2 | 3359910 | NUP98 | 3416977 | ORMDL2 |
| 3855596 | NR2C2AP | 3654699 | NUPR1 | 3418436 | OS9 |
| 3610110 | NR2F2 | 2923060 | NUS1 | 2693217 | OSBPL11 |
| 2879312 | NR3C1 | 3590388 | NUSAP1 | 3801621 | OSBPL1A |
| 3415229 | NR4A1 | 3665857 | NUTF2 | 3041875 | OSBPL3 |
| 3181976 | NR4A3 | 3376155 | NXF1 | 2517588 | OSBPL6 |
| 3225096 | NR6A1 | 3739867 | NXN | 3555461 | OSGEP |
| 3067478 | NRCAM | 3305017 | OBFC1 | 2807359 | OSMR |
| 3023565 | NRF1 | 3417485 | OBFC2B | 2542420 | OSR1 |
| 3925639 | NRIP1 | 2383999 | OBSCN | 2968144 | OSTM1 |
| 2940145 | NRN1 | 2600237 | OBSL1 | 2758602 | OTOP1 |
| 3284302 | NRP1 | 3614774 | OCA2 | 2788195 | OTUD4 |
| 2524301 | NRP2 | 2768654 | OCIAD2 | 2434233 | OTUD7B |
| 2898371 | NRSN1 | 2375338 | OCR1 | 2485112 | OTX1 |
| 2552643 | NRXN1 | 2730281 | ODAM | 3566176 | OTX2 |
| 3545634 | NRXN3 | 2421121 | ODF2L | 2331511 | OXCT2 |
| 3088048 | NSAP11 | 4020655 | ODZ1 | 2408095 | OXCT2 |
| 2842951 | NSD1 | 3662041 | OGFOD1 | 2612625 | OXNAD1 |
| 3724197 | NSF | 3214800 | OGN | 3452664 | P11 |
| 3894637 | NSFL1C | 3981120 | OGT | 2701071 | P2RY13 |
| 2847292 | NSUN2 | 2587618 | OLA1 | 3513514 | P2RY5 |

Figure 6 continued

| TCID | GENE_na29 | TCID | GENE_na29 | TCID | GENE_na29 |
|---|---|---|---|---|---|
| 3294159 | P4HA1 | 2832467 | PCDHB18 | 2712754 | PCYT1A |
| 2875193 | P4HA2 | 2832325 | PCDHB19P | 3263944 | PDCD4 |
| 4041342 | P4HB | 2832310 | PCDHB2 | 2616317 | PDCD6IP |
| 2935311 | PACRG | 2832447 | PCDHB2 | 3358361 | PDDC1 |
| 2720732 | PACRGL | 2832297 | PCDHB2 | 2984275 | PDE10A |
| 3861978 | PAF1 | 2832310 | PCDHB3 | 2589017 | PDE11A |
| 2831209 | PAIP2 | 2832447 | PCDHB3 | 2590582 | PDE1A |
| 2659577 | PAK2 | 2832297 | PCDHB3 | 3416651 | PDE1B |
| 3987228 | PAK3 | 2832315 | PCDHB4 | 3044597 | PDE1C |
| 3184408 | PALM2 | 2832325 | PCDHB5 | 3381150 | PDE2A |
| 3184408 | PALM2-AKAP2 | 2832355 | PCDHB6 | 2340529 | PDE4B |
| 2822215 | PAM | 2832325 | PCDHB9 | 2858134 | PDE4D |
| 3457696 | PAN2 | 2832533 | PCDHGA1 | 2431886 | PDE4DIP |
| 3483159 | PAN3 | 2832533 | PCDHGA10 | 2783596 | PDE5A |
| 3874533 | PANK2 | 2832533 | PCDHGA11 | 2714132 | PDE6B |
| 3950602 | PANX2 | 2832533 | PCDHGA12 | 3138464 | PDE7A |
| 3543539 | PAPLN | 2832533 | PCDHGA2 | 3606034 | PDE8A |
| 2484305 | PAPOLG | 2832533 | PCDHGA3 | 2816681 | PDE8B |
| 2780999 | PAPSS1 | 2832533 | PCDHGA4 | 3922793 | PDE9A |
| 3256590 | PAPSS2 | 2832533 | PCDHGA5 | 2791197 | PDGFC |
| 2774817 | PAQR3 | 2832533 | PCDHGA6 | 3389077 | PDGFD |
| 2438016 | PAQR6 | 2832533 | PCDHGA7 | 2727226 | PDGFRA |
| 2983142 | PARK2 | 2832533 | PCDHGA8 | 3087703 | PDGFRL |
| 3441011 | PARP11 | 2832533 | PCDHGA9 | 3970833 | PDHA1 |
| 2639054 | PARP14 | 2832533 | PCDHGB1 | 3369249 | PDHX |
| 3527418 | PARP2 | 2832533 | PCDHGB2 | 2639225 | PDIA5 |
| 3505781 | PARP4 | 2832533 | PCDHGB3 | 2469529 | PDIA6 |
| 2808748 | PARP8 | 2832533 | PCDHGB4 | 2540317 | PDIA6 |
| 2692060 | PARP9 | 2832533 | PCDHGB5 | 3062082 | PDK4 |
| 2811145 | PART1 | 2832533 | PCDHGB6 | 3301218 | PDLIM1 |
| 3320865 | PARVA | 2832533 | PCDHGB7 | 2796951 | PDLIM3 |
| 3374746 | PATL1 | 2832533 | PCDHGB8P | 2828441 | PDLIM4 |
| 2571608 | PAX8 | 2832533 | PCDHGC3 | 2736322 | PDLIM5 |
| 3532793 | PAX9 | 2832533 | PCDHGC4 | 2766588 | PDS5A |
| 2976417 | PBOV1 | 2832533 | PCDHGC5 | 3484768 | PDS5B |
| 2364677 | PBX1 | 3342525 | PCF11 | 3650300 | PDXDC2 |
| 3855818 | PBX4 | 2560195 | PCGF1 | 3923257 | PDXK |
| 2829589 | PCBD2 | 2714230 | PCGF3 | 4011637 | PDZD11 |
| 2675801 | PCBP4 | 3887165 | PCIF1 | 2411173 | PDZK1IP1 |
| 2696802 | PCCB | 3059258 | PCLO | 3411810 | PDZRN4 |
| 2743800 | PCDH10 | 3059226 | PCLO | 3127610 | PEBP4 |
| 2878987 | PCDH12 | 3087813 | PCM1 | 3768796 | PECAM1 |
| 3516228 | PCDH20 | 2930863 | PCMT1 | 2939593 | PECI |
| 2722823 | PCDH7 | 3134922 | PCMTD1 | 2598496 | PECR |
| 3516639 | PCDH9 | 3542689 | PCNX | 3013255 | PEG10 |
| 2832423 | PCDHB10 | 2461037 | PCNXL2 | 3872053 | PEG3 |
| 2832431 | PCDHB11 | 2698996 | PCOLCE2 | 2556302 | PELI1 |
| 2832439 | PCDHB12 | 3921599 | PCP4 | 3537164 | PELI2 |
| 2832392 | PCDHB13 | 2868044 | PCSK1 | 2809128 | PELO |
| 2832447 | PCDHB13 | 4007550 | PCSK1N | 2605749 | PER2 |
| 2832325 | PCDHB14 | 3877892 | PCSK2 | 2976360 | PERP |
| 2832459 | PCDHB14 | 3642200 | PCSK6 | 3061191 | PEX1 |
| 2832297 | PCDHB14 | 3976124 | PCTK1 | 3753690 | PEX12 |
| 2832392 | PCDHB16 | 3466826 | PCTK2 | 2440117 | PEX19 |

Figure 6 continued

| TCID | GENE_na29 | TCID | GENE_na29 | TCID | GENE_na29 |
|---|---|---|---|---|---|
| 2465551 | PEX5 | 2905296 | PI16 | 3133233 | PLAT |
| 2707045 | PEX5L | 3259978 | PI4K2A | 3252036 | PLAU |
| 3709540 | PFAS | 2721777 | PI4K2B | 3294959 | PLAU |
| 2440612 | PFDN2 | 3953724 | PI4KA | 2475042 | PLB1 |
| 4009811 | PFKFB1 | 3953724 | PI4KAP1 | 3875642 | PLCB1 |
| 2377094 | PFKFB2 | 3953724 | PI4KAP2 | 3334372 | PLCB3 |
| 3233605 | PFKFB3 | 3599280 | PIAS1 | 3875908 | PLCB4 |
| 3413344 | PFKM | 2432647 | PIAS3 | 3759587 | PLCD3 |
| 2700585 | PFN2 | 3493448 | PIBF1 | 2527895 | PLCD4 |
| 3332780 | PGA3 | 3945180 | PICK1 | 3258477 | PLCE1 |
| 3332780 | PGA4 | 2602653 | PID1 | 2316605 | PLCH2 |
| 3332780 | PGA5 | 3428268 | PIGA | 2521574 | PLCL1 |
| 2593407 | PGAP1 | 4000512 | PIGA | 2612813 | PLCL2 |
| 2390518 | PGBD2 | 2551690 | PIGF | 3833443 | PLD3 |
| 3288707 | PGBD3 | 2714025 | PIGG | 3157901 | PLEC1 |
| 3108226 | PGCP | 3569339 | PIGH | 2486811 | PLEK |
| 2871685 | PGGT1B | 2418929 | PIGK | 3569257 | PLEK2 |
| 2339786 | PGM1 | 3811086 | PIGN | 3268274 | PLEKHA1 |
| 3381925 | PGM2L1 | 3391214 | PIH1D2 | 2517737 | PLEKHA3 |
| 3173508 | PGM5 | 3364759 | PIK3C2A | 3867458 | PLEKHA4 |
| 3173508 | PGM5P1 | 2697564 | PIK3CB | 3407096 | PLEKHA5 |
| 3173508 | PGM5P2 | 2395890 | PIK3CD | 3451988 | PLEKHA8 |
| 3824963 | PGPEP1 | 3018309 | PIK3CG | 2995189 | PLEKHA8 |
| 3988740 | PGRMC1 | 2813060 | PIK3R1 | 3451988 | PLEKHA9 |
| 2928930 | PHACTR2 | 2410470 | PIK3R3 | 2995189 | PLEKHA9 |
| 3891530 | PHACTR3 | 2525272 | PIKFYVE | 2505957 | PLEKHB2 |
| 3403981 | PHC1 | 3015442 | PILRB | 3107828 | PLEKHF2 |
| 3403981 | PHC1B | 3621728 | PIN4 | 3832992 | PLEKHG2 |
| 2405469 | PHC2 | 2400212 | PINK1 | 2798475 | PLEKHG4B |
| 2704894 | PHC3 | 3281068 | PIP4K2A | 3569339 | PLEKHH1 |
| 3971451 | PHEX | 3418303 | PIP4K2C | 2479433 | PLEKHH2 |
| 2903673 | PHF1 | 3300869 | PIP5K1A | 3759849 | PLEKHM1 |
| 2986084 | PHF10 | 3300869 | PIPSL | 3759849 | PLEKHM1P |
| 3489481 | PHF11 | 3957938 | PISD | 3598165 | PLEKHO2 |
| 3751184 | PHF12 | 3732230 | PITPNC1 | 2492659 | PLG |
| 2990043 | PHF14 | 3437801 | PIWIL1 | 2492659 | PLGLA |
| 2829337 | PHF15 | 3049700 | PKD1L1 | 2492659 | PLGLB1 |
| 3975893 | PHF16 | 3697933 | PKD1L3 | 2492659 | PLGLB2 |
| 2743315 | PHF17 | 2735221 | PKD2 | 3638546 | PLIN |
| 3116535 | PHF20L1 | 3111561 | PKHD1L1 | 2527196 | PLK1 |
| 2911944 | PHF3 | 3104260 | PKIA | 2858023 | PLK2 |
| 3991650 | PHF6 | 3631964 | PKM2 | 2923270 | PLN |
| 4009506 | PHF8 | 3822723 | PKN1 | 2699564 | PLOD2 |
| 4012299 | PHKA1 | 3922975 | PKNOX1 | 3977067 | PLP2 |
| 3659156 | PHKB | 3354535 | PKNOX2 | 2645906 | PLS1 |
| 3359461 | PHLDA2 | 3450234 | PKP2 | 3987996 | PLS3 |
| 2635906 | PHLDB2 | 2511820 | PKP4 | 2699623 | PLSCR4 |
| 3791482 | PHLPP | 3681488 | PLA2G10 | 3907524 | PLTP |
| 2428699 | PHTF1 | 3376529 | PLA2G16 | 3854417 | PLVAP |
| 3278198 | PHYH | 3960388 | PLA2G6 | 3755510 | PLXDC1 |
| 3190796 | PHYHD1 | 2955827 | PLA2G7 | 3073267 | PLXNA4 |
| 3127385 | PHYHIP | 2583374 | PLA2R1 | 2673181 | PLXNB1 |
| 3247977 | PHYHIPL | 3136178 | PLAG1 | 3426502 | PLXNC1 |
| 3290649 | PHYHIPL | 2977621 | PLAGL1 | 3911217 | PMEPA1 |

Figure 6 continued

| TCID | GENE_na29 | TCID | GENE_na29 | TCID | GENE_na29 |
|---|---|---|---|---|---|
| 3698081 | PMFBP1 | 3192033 | PPAPDC3 | 3444578 | PRB3 |
| 3962000 | PMM1 | 2763550 | PPARGC1A | 3444578 | PRB4 |
| 3647504 | PMM2 | 2773358 | PPBP | 3639031 | PRC1 |
| 2988459 | PMS2L3 | 2773407 | PPBPL2 | 3384270 | PRCP |
| 3009580 | PMS2L3 | 3338453 | PPFIA1 | 2919669 | PRDM1 |
| 2934191 | PNLDC1 | 3463821 | PPFIA2 | 3933243 | PRDM15 |
| 3571542 | PNMA1 | 3409211 | PPFIBP1 | 2316953 | PRDM16 |
| 3128731 | PNMA2 | 3319137 | PPFIBP2 | 2321238 | PRDM2 |
| 3316287 | PNPLA2 | 2357217 | PPIAL4A | 3470037 | PRDM4 |
| 3067592 | PNPLA8 | 2357217 | PPIAL4B | 3851776 | PRDX2 |
| 4042198 | PNRC2 | 2357217 | PPIAL4C | 3483885 | PRDX2 |
| 2336650 | PODN | 2357217 | PPIAL4G | 2367743 | PRDX6 |
| 3073013 | PODXL | 3628994 | PPIB | 2474265 | PREB |
| 2365496 | POGK | 2873105 | PPIC | 4053085 | PRELP |
| 3972093 | POLA1 | 2514441 | PPIG | 2550959 | PREPL |
| 3750825 | POLDIP2 | 3938244 | PPIL2 | 3102096 | PREX2 |
| 3563395 | POLE2 | 2978989 | PPIL4 | 3451375 | PRICKLE1 |
| 2489606 | POLE4 | 3678462 | PPL | 4007865 | PRICKLE3 |
| 3607537 | POLG | 3538555 | PPM1A | 3238962 | PRINS |
| 3766861 | POLG2 | 3954294 | PPM1F | 2337716 | PRKAA2 |
| 3788833 | POLI | 2623568 | PPM1M | 3434142 | PRKAB1 |
| 2757621 | POLN | 3107342 | PPM2C | 2433209 | PRKAB2 |
| 2562605 | POLR1A | 2475209 | PPP1CB | 3852529 | PRKACA |
| 2728448 | POLR2B | 3471374 | PPP1CC | 2344393 | PRKACB |
| 2655773 | POLR2H | 2948425 | PPP1R10 | 3453556 | PRKAG1 |
| 3065154 | POLR2J | 3463571 | PPP1R12A | 3732885 | PRKAR1A |
| 3065154 | POLR2J2 | 3580876 | PPP1R13B | 3018375 | PRKAR2B |
| 3065154 | POLR2J3 | 3865344 | PPP1R13L | 3653123 | PRKCB |
| 3009838 | POLR2J4 | 2931090 | PPP1R14C | 2624291 | PRKCD |
| 3065154 | POLR2J4 | 3838004 | PPP1R15A | 2480168 | PRKCE |
| 3109191 | POLR2K | 3884830 | PPP1R16B | 3538893 | PRKCH |
| 3296512 | POLR3A | 3416651 | PPP1R1A | 2651916 | PRKCI |
| 3430129 | POLR3B | 3720322 | PPP1R1B | 3275922 | PRKCQ |
| 2432647 | POLR3C | 2518488 | PPP1R1C | 4054481 | PRKCZ |
| 2432571 | POLR3GL | 3068688 | PPP1R3A | 3559192 | PRKD1 |
| 2988459 | POM121 | 2880051 | PPP2R2B | 2548500 | PRKD3 |
| 3057755 | POM121 | 2759205 | PPP2R2C | 3134034 | PRKDC |
| 3009580 | POM121 | 3271687 | PPP2R2D | 3246888 | PRKG1 |
| 3057755 | POM121C | 2643901 | PPP2R3A | 2775214 | PRKG2 |
| 2334602 | POMGNT1 | 3532353 | PPP2R3C | 3009580 | PRKRIP1 |
| 3057755 | POMZP3 | 3552729 | PPP2R5C | 3997946 | PRKX |
| 3061942 | PON1 | 3567984 | PPP2R5E | 3997946 | PRKY |
| 3061997 | PON2 | 2779638 | PPP3CA | 3838809 | PRMT1 |
| 3061964 | PON3 | 3294499 | PPP3CB | 3924783 | PRMT2 |
| 2690956 | POPDC2 | 3798291 | PPP4R1 | 3323443 | PRMT3 |
| 2967276 | POPDC3 | 3836760 | PPP5C | 2349848 | PRMT6 |
| 3009229 | POR | 3471300 | PPTC7 | 2459173 | PRO2012 |
| 3976639 | PORCN | 3814701 | PQLC1 | 3883207 | PROCR |
| 2365675 | POU2F1 | 4007765 | PRAF2 | 2682271 | PROK2 |
| 3352438 | POU2F3 | 2321058 | PRAMEF1 | 2486851 | PROKR1 |
| 2780522 | PPA2 | 2321058 | PRAMEF13 | 2761842 | PROM1 |
| 2857204 | PPAP2A | 2321058 | PRAMEF14 | 2685304 | PROS1 |
| 2414366 | PPAP2B | 2321058 | PRAMEF2 | 2379665 | PROX1 |
| 3160727 | PPAPDC2 | 3444578 | PRB1 | 2358171 | PRPF3 |

Figure 6 continued

| TCID | GENE_na29 | TCID | GENE_na29 | TCID | GENE_na29 |
|---|---|---|---|---|---|
| 2336383 | PRPF38A | 3960478 | psiTPTE22 | 2626802 | PTPRG |
| 3534201 | PRPF39 | 3935902 | psiTPTE22 | 3329983 | PTPRJ |
| 3221543 | PRPF4 | 3363979 | PSMA1 | 2973376 | PTPRK |
| 3414104 | PRPF40B | 3912861 | PSMA7 | 3777470 | PTPRM |
| 3454006 | PRPF40B | 2358906 | PSMB4 | 2600089 | PTPRN |
| 2892738 | PRPF4B | 2903285 | PSMB9 | 2327817 | PTPRU |
| 3413852 | PRPH | 3372209 | PSMC3 | 3757917 | PTRF |
| 3986514 | PRPS1 | 3721886 | PSMC3IP | 2838201 | PTTG1 |
| 3986514 | PRPS1L1 | 3833291 | PSMC4 | 2838201 | PTTG2 |
| 3771513 | PRPSAP1 | 3730941 | PSMC5 | 2404254 | PUM1 |
| 3838624 | PRR12 | 3315549 | PSMD13 | 2542816 | PUM2 |
| 3656318 | PRR14 | 2512701 | PSMD14 | 2831567 | PURA |
| 2994981 | PRR15 | 2655650 | PSMD2 | 2315739 | PUSL1 |
| 2984543 | PRR18 | 3300869 | PSMD4 | 3015442 | PVRIG |
| 3948259 | PRR5 | 3832383 | PSMD8 | 3394488 | PVRL1 |
| 3973692 | PRRG1 | 3722152 | PSME3 | 2688499 | PVRL2 |
| 2662473 | PRRT3 | 3873389 | PSMF1 | 2635641 | PVRL3 |
| 2366798 | PRRX1 | 3035408 | PSMG3 | 3134922 | PXDNL |
| 3028766 | PRSS1 | 2348060 | PTBP2 | 2626167 | PXK |
| 2899808 | PRSS16 | 3014742 | PTCD1 | 3880767 | PYGB |
| 3028766 | PRSS2 | 3215851 | PTCH1 | 3564210 | PYGL |
| 3343452 | PRSS23 | 3727787 | PTEN | 3625440 | PYGO1 |
| 3028766 | PRSS3 | 3727787 | PTENP1 | 2362351 | PYHIN1 |
| 3281703 | PRTFDC1 | 3236786 | PTER | 3302740 | PYROXD2 |
| 2358623 | PRUNE | 3535752 | PTGDR | 3443464 | PZP |
| 3210616 | PRUNE2 | 2353717 | PTGFRN | 3443348 | PZP |
| 3210497 | PRUNE2 | 3220673 | PTGR1 | 2762334 | QDPR |
| 4036437 | PRY | 2448382 | PTGS2 | 2477438 | QPCT |
| 4036437 | PRY2 | 3156307 | PTK2 | 3325768 | QSER1 |
| 3293762 | PSAP | 2907671 | PTK7 | 2369950 | QSOX1 |
| 3175971 | PSAT1 | 3405207 | PTMA | 3638204 | QTRT1 |
| 3126368 | PSD3 | 3402736 | PTMS | 3820727 | QTRT1 |
| 3126191 | PSD3 | 3074857 | PTN | 3458451 | R3HDM2 |
| 2501238 | PSD4 | 3839006 | PTOV1 | 3598482 | RAB11A |
| 3543467 | PSEN1 | 2911903 | PTP4A1 | 3131741 | RAB11FIP1 |
| 3863929 | PSG1 | 2404819 | PTP4A2 | 3642875 | RAB11FIP3 |
| 3863761 | PSG1 | 3118818 | PTP4A3 | 3223872 | RAB14 |
| 3863929 | PSG11 | 3180142 | PTPDC1 | 3568616 | RAB15 |
| 3863929 | PSG2 | 3279982 | PTPLA | 3890870 | RAB22A |
| 3863761 | PSG2 | 3164601 | PTPLAD2 | 2958670 | RAB23 |
| 3863761 | PSG3 | 2692411 | PTPLB | 2361257 | RAB25 |
| 3863929 | PSG4 | 3329886 | PTPMT1 | 3625271 | RAB27A |
| 3863761 | PSG4 | 3888721 | PTPN1 | 3788976 | RAB27B |
| 3863929 | PSG5 | 3009959 | PTPN12 | 3384321 | RAB30 |
| 3863761 | PSG5 | 2734629 | PTPN13 | 2929699 | RAB32 |
| 3863929 | PSG6 | 2455418 | PTPN14 | 3751002 | RAB34 |
| 3863761 | PSG6 | 2505529 | PTPN18 | 2810805 | RAB3C |
| 3863929 | PSG7 | 2428796 | PTPN22 | 2456849 | RAB3GAP2 |
| 3863761 | PSG7 | 2621333 | PTPN23 | 3421706 | RAB3IP |
| 3863929 | PSG8 | 3219885 | PTPN3 | 2905196 | RAB44 |
| 3863761 | PSG8 | 3874023 | PTPRA | 2641263 | RAB7A |
| 3863929 | PSG9 | 2373842 | PTPRC | 3707642 | RABEP1 |
| 3863761 | PSG9 | 3270270 | PTPRE | 3686750 | RABEP2 |
| 3881282 | PSIMCT-1 | 2333318 | PTPRF | 3188299 | RABGAP1 |

Figure 6 continued

| TCID | GENE_na29 | TCID | GENE_na29 | TCID | GENE_na29 |
|---|---|---|---|---|---|
| 2367963 | RABGAP1L | 2369110 | RASAL2 | 2395245 | RERE |
| 2342624 | RABGGTB | 3747792 | RASD1 | 3446297 | RERGL |
| 2989050 | RAC1 | 3944210 | RASD2 | 2728408 | REST |
| 3451960 | RACGAP1 | 2775259 | RASGEF1B | 3243846 | RET |
| 3454223 | RACGAP1 | 2817941 | RASGRF2 | 2566764 | REV1 |
| 3451960 | RACGAP1P | 3618736 | RASGRP1 | 2969677 | REV3L |
| 3454223 | RACGAP1P | 2476671 | RASGRP3 | 2766359 | RFC1 |
| 2852989 | RAD1 | 3867346 | RASIP1 | 3433747 | RFC5 |
| 2662020 | RAD18 | 3482845 | RASL11A | 2867788 | RFESD |
| 3183757 | RAD23B | 3286776 | RASSF4 | 3210457 | RFK |
| 2828564 | RAD50 | 3315952 | RASSF7 | 2593796 | RFTN2 |
| 3590086 | RAD51 | 3464405 | RASSF9 | 3625674 | RFX7 |
| 3728776 | RAD51C | 3489020 | RB1 | 3855596 | RFXANK |
| 3439836 | RAD52 | 2988459 | RBAK | 2779335 | RG9MTD2 |
| 3036476 | RADIL | 3653317 | RBBP6 | 2950590 | RGL2 |
| 2930957 | RAET1G | 4000944 | RBBP7 | 3639601 | RGMA |
| 2979187 | RAET1G | 3781429 | RBBP8 | 2821761 | RGMB |
| 2930957 | RAET1L | 3144760 | RBM12B | 2815488 | RGNEF |
| 2979187 | RAET1L | 3336402 | RBM14 | 2499158 | RGPD1 |
| 2663244 | RAF1 | 2675628 | RBM15B | 2499158 | RGPD2 |
| 3327143 | RAG1 | 3556888 | RBM23 | 2499158 | RGPD3 |
| 2360700 | RAG1AP1 | 3519119 | RBM26 | 2499158 | RGPD4 |
| 3369931 | RAG2 | 3976519 | RBM3 | 2499158 | RGPD5 |
| 3580234 | RAGE | 3033397 | RBM33 | 2499158 | RGPD6 |
| 3712675 | RAI1 | 2622469 | RBM5 | 2372781 | RGS1 |
| 4001223 | RAI2 | 2622469 | RBM6 | 3642707 | RGS11 |
| 2503200 | RALB | 3959203 | RBM9 | 2372812 | RGS13 |
| 3228523 | RALGDS | 3417583 | RBMS2 | 2447148 | RGS16 |
| 3105271 | RALYL | 2615060 | RBMS3 | 2372719 | RGS18 |
| 3438027 | RAN | 2697863 | RBP1 | 3914307 | RGS19 |
| 2499158 | RANBP2 | 2319550 | RBP7 | 2372858 | RGS2 |
| 3847538 | RANBP3 | 3092415 | RBPMS | 2441386 | RGS5 |
| 2853426 | RANBP3L | 3224366 | RC3H2 | 2463227 | RGS7 |
| 2942504 | RANBP9 | 3930235 | RCAN1 | 2447192 | RGS8 |
| 2351872 | RAP1A | 2325479 | RCAN3 | 3731543 | RGS9 |
| 2663244 | RAP1A | 3513794 | RCBTB1 | 2530330 | RHBDD1 |
| 2400655 | rap1GAP | 3513549 | RCBTB2 | 3009198 | RHBDD2 |
| 2736853 | RAP1GDS1 | 2398894 | RCC2 | 3674848 | RHBDF1 |
| 3497659 | RAP2A | 3336486 | RCE1 | 2674242 | RHOA |
| 4022032 | RAP2C | 3325503 | RCN1 | 2820925 | RHOBTB3 |
| 2749699 | RAPGEF2 | 3602723 | RCN2 | 2724671 | RHOH |
| 3452690 | RAPGEF3 | 2378584 | RCOR3 | 3717539 | RHOT1 |
| 2515783 | RAPGEF4 | 3103293 | RDH10 | 2384401 | RHOU |
| 3040967 | RAPGEF5 | 3416921 | RDH5 | 4019700 | RHOXF1 |
| 2595560 | RAPH1 | 3753896 | RDM1 | 3978295 | RIBC1 |
| 3720921 | RARA | 3390542 | RDX | 3430331 | RIC8B |
| 2614369 | RARB | 3158767 | RECQL4 | 3397877 | RICS |
| 3456081 | RARG | 3248999 | REEP3 | 2510485 | RIF1 |
| 3333899 | RARRES3 | 2871176 | REEP5 | 4052378 | RILPL1 |
| 2839671 | RARS | 2561201 | REG1P | 3476212 | RILPL1 |
| 2819044 | RASA1 | 2484358 | REL | 3476212 | RILPL2 |
| 2645579 | RASA2 | 2765865 | RELL1 | 3110395 | RIMS2 |
| 3065154 | RASA4 | 3065740 | RELN | 3378191 | RIN1 |
| 3065154 | RASA4B | 3970214 | REPS2 | 3781654 | RIOK3 |

Figure 6 continued

| TCID | GENE_na29 |
|---|---|
| 3555675 | RNASE1 |
| 3527597 | RNASE4 |
| 3527662 | RNASE6 |
| 2851965 | RNASEN |
| 2984884 | RNASET2 |
| 3453348 | RND1 |
| 2580802 | RND3 |
| 3434413 | RNF10 |
| 3130850 | RNF122 |
| 2647458 | RNF13 |
| 3059393 | RNF13 |
| 2857204 | RNF138 |
| 2857204 | RNF138P1 |
| 2468376 | RNF144A |
| 2897172 | RNF144B |
| 2884216 | RNF145 |
| 2924898 | RNF146 |
| 3927949 | RNF160 |
| 3133479 | RNF170 |
| 2790324 | RNF175 |
| 3221571 | RNF183 |
| 3146565 | RNF19A |
| 3036985 | RNF216 |
| 2988459 | RNF216L |
| 3036985 | RNF216L |
| 2924253 | RNF217 |
| 3895795 | RNF24 |
| 3205162 | RNF38 |
| 2715440 | RNF4 |
| 2963929 | RNGTT |
| 3358049 | RNH1 |
| 2672629 | RNU13P3 |
| 3403077 | RNU7 |
| 2683763 | ROBO1 |
| 3354293 | ROBO3 |
| 3220977 | ROD1 |
| 2640263 | ROPN1 |
| 2692640 | ROPN1 |
| 2640263 | ROPN1B |
| 2692640 | ROPN1B |
| 2339872 | ROR1 |
| 3627422 | RORA |
| 2435261 | RORC |
| 2721959 | ROS1 |
| 2971378 | ROS1 |
| 3098570 | RP1 |
| 2960774 | RP11-257K9.7 |
| 3674504 | RP11-631M21.2 |
| 3514879 | RP11-64P12.3 |
| 2432851 | RP11-9I2.2 |
| 2357217 | RP11-9I2.2 |
| 2321466 | RP1-21O18.1 |
| 3975869 | RP2 |
| 3896370 | RP5-1022P6.2 |

| TCID | GENE_na29 |
|---|---|
| 3045047 | RP9 |
| 3044938 | RP9 |
| 3045047 | RP9P |
| 3044938 | RP9P |
| 2346738 | RPAP2 |
| 2597273 | RPE |
| 2525852 | RPE |
| 4004878 | RPGR |
| 2374956 | RPL10 |
| 2331178 | RPL10 |
| 2904683 | RPL10A |
| 3674146 | RPL13 |
| 2618640 | RPL14 |
| 3294159 | RPL17 |
| 3309215 | RPL17 |
| 3867223 | RPL18 |
| 3309936 | RPL21 |
| 3309936 | RPL21P119 |
| 3309936 | RPL21P134 |
| 3309936 | RPL21P14 |
| 3309936 | RPL21P18 |
| 3309936 | RPL21P19 |
| 3309936 | RPL21P28 |
| 3309936 | RPL21P29 |
| 3309936 | RPL21P37 |
| 3309936 | RPL21P39 |
| 2769512 | RPL21P44 |
| 3309936 | RPL21P45 |
| 3309936 | RPL21P46 |
| 3309936 | RPL21P61 |
| 2898746 | RPL21P68 |
| 3309936 | RPL21P69 |
| 3309936 | RPL21P7 |
| 3309936 | RPL21P80 |
| 3309936 | RPL21P93 |
| 3309936 | RPL21P97 |
| 3309936 | RPL21P98 |
| 3036476 | RPL22 |
| 3729569 | RPL23A |
| 2390518 | RPL23AP7 |
| 2390518 | RPL23AP82 |
| 3174121 | RPL24 |
| 3842141 | RPL28 |
| 2604998 | RPL3 |
| 2694706 | RPL32 |
| 2694706 | RPL32P3 |
| 2527196 | RPL37A |
| 3391149 | RPL37AP8 |
| 2709606 | RPL39L |
| 2696309 | RPL39P5 |
| 3962587 | RPL5 |
| 2423175 | RPL5 |
| 3797450 | RPL6 |
| 3559570 | RPL9 |

| TCID | GENE_na29 |
|---|---|
| 2319340 | RPL9P11 |
| 3257559 | RPP30 |
| 3804143 | RPRD1A |
| 2358221 | RPRD2 |
| 3900470 | RPS15A |
| 2686717 | RPS18 |
| 2686717 | RPS18P12 |
| 2686717 | RPS18P5 |
| 3834465 | RPS19 |
| 3961253 | RPS19BP1 |
| 2331679 | RPS2 |
| 3383046 | RPS20P27 |
| 3892660 | RPS21 |
| 2850071 | RPS26 |
| 2850071 | RPS26P53 |
| 2850071 | RPS26P8 |
| 2330723 | RPS27 |
| 2531779 | RPS28 |
| 2326561 | RPS6KA1 |
| 2984655 | RPS6KA2 |
| 4002173 | RPS6KA3 |
| 3576284 | RPS6KA5 |
| 4014029 | RPS6KA6 |
| 3460467 | RPSAP52 |
| 2662397 | RPUSD3 |
| 2964231 | RRAGD |
| 3867965 | RRAS |
| 3363868 | RRAS2 |
| 3899173 | RRBP1 |
| 3318009 | RRM1 |
| 2469252 | RRM2 |
| 3681705 | RRN3 |
| 3684782 | RRN3 |
| 3684548 | RRN3 |
| 3962469 | RRP7A |
| 3947434 | RRP7A |
| 3947460 | RRP7A |
| 3962469 | RRP7B |
| 3947434 | RRP7B |
| 3947460 | RRP7B |
| 2675763 | RRP8 |
| 2428760 | RSBN1 |
| 3010030 | RSBN1L |
| 3865696 | RSHL1 |
| 3037100 | RSPH10B |
| 2989316 | RSPH10B |
| 3037100 | RSPH10B2 |
| 2989316 | RSPH10B2 |
| 2924851 | RSPO3 |
| 3662612 | RSPRY1 |
| 3279575 | RSU1 |
| 2348854 | RTCD1 |
| 2580076 | RTKN |
| 3567050 | RTN1 |

Figure 6 continued

| TCID | GENE_na29 | TCID | GENE_na29 | TCID | GENE_na29 |
| --- | --- | --- | --- | --- | --- |
| 2967650 | RTN4IP1 | 3633890 | SCAPER | 2355615 | SEC22B |
| 2657025 | RTP4 | 3091475 | SCARA3 | 3561952 | SEC23A |
| 2730554 | RUFY3 | 3129175 | SCARA5 | 3267455 | SEC23IP |
| 3930360 | RUNX1 | 2774049 | SCARB2 | 2829416 | SEC24A |
| 3144346 | RUNX1T1 | 3402571 | SCARNA10 | 2783316 | SEC24D |
| 2908762 | RUNX2 | 3442054 | SCARNA11 | 3235414 | SEC61A2 |
| 2401994 | RUNX3 | 2715076 | SCARNA22 | 2651782 | SEC62 |
| 3928040 | RWDD2B | 3972093 | SCARNA23 | 3779756 | SEH1L |
| 2749484 | RXFP1 | 2437753 | SCARNA4 | 3574207 | SEL1L |
| 3484393 | RXFP2 | 2703217 | SCARNA7 | 2764192 | SEL1L3 |
| 2805939 | RXFP3 | 2389789 | SCCPDH | 2443476 | SELE |
| 2442008 | RXRG | 3260586 | SCD | 2435005 | SELENBP1 |
| 3832457 | RYR1 | 3494629 | SCEL | 2473784 | SELI |
| 2387126 | RYR2 | 2769182 | SCFD2 | 2676901 | SELK |
| 4045676 | S100A1 | 2601230 | SCG2 | 2676927 | SELK |
| 2435383 | S100A10 | 3594003 | SCG3 | 2443450 | SELL |
| 2435410 | S100A11 | 3587495 | SCG5 | 2443417 | SELP |
| 2435981 | S100A12 | 2898934 | SCGN | 2647792 | SELT |
| 4045676 | S100A13 | 2649824 | SCHIP1 | 3058759 | SEMA3C |
| 4045665 | S100A14 | 2990404 | SCIN | 3059667 | SEMA3D |
| 4045643 | S100A16 | 2785282 | SCLT1 | 3059393 | SEMA3E |
| 2436088 | S100A2 | 2585400 | SCN2A | 2361342 | SEMA4A |
| 4045589 | S100A5 | 2584957 | SCN3A | 3607927 | SEMA4B |
| 4045577 | S100A6 | 3393622 | SCN4B | 2565592 | SEMA4C |
| 2435989 | S100A8 | 2585476 | SCN7A | 4051226 | SEMA4D |
| 2359664 | S100A9 | 3414969 | SCN8A | 2692199 | SEMA5B |
| 2329077 | S100PBP | 2585400 | SCN9A | 3592755 | SEMA6D |
| 3365249 | SAAL1 | 3441885 | SCNN1A | 2686646 | SENP7 |
| 2620685 | SACM1L | 3363868 | SCP2 | 3278234 | SEPHS1 |
| 3505319 | SACS | 2336585 | SCP2 | 2855285 | SEPP1 |
| 3691326 | SALL1 | 2794006 | SCRG1 | 2764054 | SEPSECS |
| 3150289 | SAMD12 | 3043895 | SCRN1 | 2569908 | SEPT10 |
| 3536434 | SAMD4A | 3760957 | SCRN2 | 2732273 | SEPT11 |
| 3252534 | SAMD8 | 3962839 | SCUBE1 | 3764527 | SEPT4 |
| 3061456 | SAMD9L | 3362191 | SCUBE2 | 3735847 | SEPT9 |
| 3480657 | SAP18 | 2904485 | SCUBE3 | 3837504 | SEPW1 |
| 3337618 | SAPS3 | 2780734 | SCYE1 | 2814424 | SERF1A |
| 3293244 | SAR1A | 3428131 | SCYL2 | 2814424 | SERF1B |
| 2876257 | SAR1B | 2594812 | SCYL2 | 3365136 | SERGEF |
| 2829416 | SAR1B | 2773907 | SDAD1 | 3947434 | SERHL |
| 3457201 | SARNP | 2542795 | SDC1 | 3947460 | SERHL |
| 3470253 | SART3 | 3108146 | SDC2 | 3947434 | SERHL2 |
| 2930243 | SASH1 | 2404209 | SDC3 | 3947460 | SERHL2 |
| 3564027 | SAV1 | 3907234 | SDC4 | 2328273 | SERINC2 |
| 3362468 | SBF2 | 3099750 | SDCBP | 3906942 | SERINC3 |
| 3476130 | SBNO1 | 3563459 | SDCCAG1 | 2864449 | SERINC5 |
| 3844978 | SBNO2 | 3229943 | SDCCAG3 | 3577612 | SERPINA1 |
| 2750594 | SC4MOL | 3092415 | SDHALP2 | 3577577 | SERPINA10 |
| 3352904 | SC5DL | 2987843 | SDK1 | 3577612 | SERPINA2 |
| 2817053 | SCAMP1 | 2592532 | SDPR | 3549757 | SERPINA3 |
| 3602004 | SCAMP5 | 3837934 | SEC1 | 3549740 | SERPINA3 |
| 3605780 | SCAND2 | 3790479 | SEC11C | 3549740 | SERPINA5 |
| 2621333 | SCAP | 3735752 | SEC14L1 | 2938972 | SERPINB1 |
| 2672712 | SCAP | 3942350 | SEC14L2 | 3791996 | SERPINB8 |

Figure 6 continued

| TCID | GENE_na29 | TCID | GENE_na29 | TCID | GENE_na29 |
|---|---|---|---|---|---|
| 2601414 | SERPINE2 | 3708919 | SHBG | 2828479 | SLC22A4 |
| 3331355 | SERPING1 | 2436985 | SHC1 | 3333831 | SLC22A9 |
| 2651165 | SERPINI1 | 3213847 | SHC3 | 2877861 | SLC23A1 |
| 3387259 | SESN3 | 2374926 | SHISA4 | 3622934 | SLC24A5 |
| 2589929 | SESTD1 | 2673270 | SHISA5 | 3593014 | SLC24A5 |
| 2672532 | SETD2 | 3418007 | SHMT2 | 3952543 | SLC25A1 |
| 3579205 | SETD3 | 2978050 | SHPRH | 2586845 | SLC25A12 |
| 3930781 | SETD4 | 2682568 | SHQ1 | 3062193 | SLC25A13 |
| 2609608 | SETD5 | 3968303 | SHROOM2 | 3488728 | SLC25A15 |
| 3489418 | SETDB2 | 3354174 | SIAE | 2909167 | SLC25A27 |
| 3228007 | SETX | 2636483 | SIDT1 | 2319340 | SLC25A33 |
| 3687277 | SEZ6L2 | 3839619 | SIGLEC12 | 2645275 | SLC25A36 |
| 3667281 | SF3B3 | 3869097 | SIGLEC6 | 3090006 | SLC25A37 |
| 3942998 | SFI1 | 3839619 | SIGLEC7 | 3377569 | SLC25A45 |
| 2676518 | SFMBT1 | 3839619 | SIGLEC9 | 3997360 | SLC25A6 |
| 2326774 | SFN | 3934111 | SIK1 | 2758831 | SLC26A1 |
| 3132782 | SFRP1 | 2877639 | SIL1 | 3418394 | SLC26A10 |
| 3966597 | SFRS17A | 3457336 | SILV | 2835300 | SLC26A2 |
| 3771800 | SFRS2 | 3542847 | SIPA1L1 | 3018605 | SLC26A4 |
| 2403740 | SFRS4 | 2460817 | SIPA1L2 | 3106559 | SLC26A7 |
| 3747324 | SFRS6 | 3894727 | SIRPA | 2452754 | SLC26A9 |
| 3886050 | SFRS6 | 3894727 | SIRPB1 | 3593575 | SLC27A2 |
| 2548970 | SFRS7 | 3249587 | SIRT1 | 2359885 | SLC27A3 |
| 2366156 | SFT2D2 | 3357785 | SIRT3 | 3872945 | SLC27A5 |
| 2948683 | SFTA2 | 3434308 | SIRT4 | 2827645 | SLC27A6 |
| 2562435 | SFTPB | 2895650 | SIRT5 | 3212420 | SLC28A3 |
| 2842101 | SFXN1 | 3042610 | SKAP2 | 2988594 | SLC29A4 |
| 3260985 | SFXN3 | 2651989 | SKIL | 2409104 | SLC2A1 |
| 2768981 | SGCB | 2902884 | SKIV2L | 2974935 | SLC2A12 |
| 2837029 | SGCD | 3154263 | SLA | 3450899 | SLC2A13 |
| 3061805 | SGCE | 2440327 | SLAMF1 | 4052021 | SLC2A6 |
| 2648535 | SGEF | 3570266 | SLC10A1 | 3622436 | SLC30A4 |
| 2340695 | SGIP1 | 3142485 | SLC10A5 | 2476116 | SLC30A6 |
| 2975014 | SGK1 | 2788511 | SLC10A7 | 2349043 | SLC30A7 |
| 3096545 | SGK196 | 3454576 | SLC11A2 | 2725381 | SLC30A9 |
| 3101802 | SGK3 | 2827525 | SLC12A2 | 2701927 | SLC33A1 |
| 3101765 | SGK3 | 3696057 | SLC12A4 | 2721959 | SLC34A2 |
| 3289235 | SGMS1 | 3696035 | SLC12A4 | 4007588 | SLC35A2 |
| 2738664 | SGMS2 | 3617312 | SLC12A6 | 2955061 | SLC35B2 |
| 3250863 | SGPL1 | 2638728 | SLC15A2 | 2940987 | SLC35B3 |
| 3568108 | SGPP1 | 3477917 | SLC15A4 | 3074039 | SLC35B4 |
| 2529421 | SGPP2 | 2921402 | SLC16A10 | 3329018 | SLC35C1 |
| 3431892 | SH2B3 | 3981959 | SLC16A2 | 3216276 | SLC35D2 |
| 3088213 | SH2D4A | 2427469 | SLC16A4 | 3389976 | SLC35F2 |
| 3921442 | SH3BGR | 3734648 | SLC16A5 | 2385967 | SLC35F3 |
| 3226804 | SH3GLB2 | 3768412 | SLC16A6 | 3076076 | SLC37A3 |
| 3717452 | SH3GLP1 | 3290746 | SLC16A8 | 3452417 | SLC38A4 |
| 3304970 | SH3PXD2A | 2960955 | SLC17A5 | 3769779 | SLC39A11 |
| 2887164 | SH3PXD2B | 3867842 | SLC17A7 | 3158581 | SLC39A4 |
| 2793137 | SH3RF1 | 3126694 | SLC18A1 | 3804195 | SLC39A6 |
| 2833924 | SH3RF2 | 3935016 | SLC19A1 | 3542063 | SLC39A9 |
| 3380365 | SHANK2 | 3160658 | SLC1A1 | 3333711 | SLC3A2 |
| 3158114 | SHARPIN | 2485836 | SLC1A4 | 2591837 | SLC40A1 |
| 3205659 | SHB | 2500919 | SLC20A1 | 2452691 | SLC41A1 |

Figure 6 continued

| TCID | GENE_na29 | TCID | GENE_na29 | TCID | GENE_na29 |
|---|---|---|---|---|---|
| 3469180 | SLC41A2 | 3454821 | SMAGP | 3693673 | SNORA46 |
| 3373845 | SLC43A3 | 3159946 | SMARCA2 | 3693673 | SNORA50 |
| 3183111 | SLC44A1 | 3820921 | SMARCA4 | 3359469 | SNORA54 |
| 2418570 | SLC44A5 | 2745646 | SMARCA5 | 3713951 | SNORA59A |
| 3713951 | SLC47A1 | 3457455 | SMARCC2 | 3713951 | SNORA59B |
| 2512790 | SLC4A10 | 3963754 | SMC1B | 2841284 | SNORA74B |
| 3895330 | SLC4A11 | 3182781 | SMC2 | 2375706 | SNORA77 |
| 2730746 | SLC4A4 | 3776193 | SMCHD1 | 3386814 | SNORA8 |
| 2559849 | SLC4A5 | 2553911 | SMEK2 | 2404254 | SNORD103A |
| 2831664 | SLC4A9 | 3683050 | SMG1 | 2949038 | SNORD117 |
| 3919033 | SLC5A3 | 2438042 | SMG5 | 3851651 | SNORD41 |
| 3467949 | SLC5A8 | 2371255 | SMG7 | 2342624 | SNORD45A |
| 3688878 | SLC6A10P | 2860898 | SMN1 | 2342624 | SNORD45C |
| 3439510 | SLC6A12 | 2814424 | SMN1 | 2444451 | SNORD47 |
| 3439549 | SLC6A13 | 2860898 | SMN2 | 3712098 | SNORD49A |
| 3988165 | SLC6A14 | 2814424 | SMN2 | 3386814 | SNORD5 |
| 3464276 | SLC6A15 | 2937144 | SMOC2 | 3542847 | SNORD56B |
| 3867734 | SLC6A16 | 3696317 | SMPD3 | 3386814 | SNORD6 |
| 2799030 | SLC6A19 | 2575897 | SMPD4 | 3371719 | SNORD67 |
| 2611848 | SLC6A6 | 2730404 | SMR3A | 2444451 | SNORD74 |
| 3688878 | SLC6A8 | 2730396 | SMR3A | 2444451 | SNORD76 |
| 2786322 | SLC7A11 | 2730404 | SMR3B | 2444451 | SNORD78 |
| 3087659 | SLC7A2 | 2730396 | SMR3B | 2444451 | SNORD80 |
| 3666146 | SLC7A6 | 3971387 | SMS | 2949038 | SNORD84 |
| 3666146 | SLC7A6OS | 3203382 | SMU1 | 4017961 | SNORD96B |
| 3557209 | SLC7A8 | 3014411 | SMURF1 | 2619666 | SNRK |
| 2497252 | SLC9A2 | 3766960 | SMURF2 | 2565262 | SNRNP200 |
| 3695541 | SLC9A5 | 2464909 | SMYD3 | 4052378 | SNRNP35 |
| 4006841 | SLC9A7 | 3740704 | SMYD4 | 3642162 | SNRPA1 |
| 2699145 | SLC9A9 | 3876245 | SNAP25 | 3903052 | SNTA1 |
| 2696113 | SLCO2A1 | 2962876 | SNAP91 | 3666601 | SNTB2 |
| 2869096 | SLCO4C1 | 3163136 | SNAPC3 | 3597857 | SNX1 |
| 3139580 | SLCO5A1 | 2777714 | SNCA | 3725083 | SNX11 |
| 2869124 | SLCO6A1 | 3022465 | SND1 | 3040073 | SNX13 |
| 3753568 | SLFN11 | 2607020 | SNED1 | 2963313 | SNX14 |
| 3753500 | SLFN11 | 3230332 | SNHG7 | 3334783 | SNX15 |
| 3753538 | SLFN12 | 3755198 | SNIP | 3142554 | SNX16 |
| 3753538 | SLFN12L | 2407163 | SNIP1 | 3398482 | SNX19 |
| 3753568 | SLFN13 | 3386814 | SNORA1 | 3597914 | SNX22 |
| 3753500 | SLFN13 | 3230332 | SNORA17 | 3628994 | SNX22 |
| 3718555 | SLFN5 | 3386814 | SNORA18 | 2826343 | SNX24 |
| 3302187 | SLIT1 | 3309215 | SNORA19 | 2754582 | SNX25 |
| 3302056 | SLIT1 | 3319840 | SNORA23 | 3830864 | SNX26 |
| 2720584 | SLIT2 | 3386814 | SNORA25 | 2359036 | SNX27 |
| 4024685 | SLITRK4 | 3553607 | SNORA28 | 2348437 | SNX7 |
| 3495968 | SLITRK5 | 3453177 | SNORA2A | 2369557 | SOAT1 |
| 3519840 | SLITRK6 | 3386814 | SNORA32 | 3772279 | SOCS3 |
| 2625793 | SLMAP | 3453177 | SNORA34 | 2721633 | SOD3 |
| 3779612 | SLMO1 | 2456849 | SNORA36B | 3301263 | SORBS1 |
| 3911814 | SLMO2 | 2558150 | SNORA36C | 2796995 | SORBS2 |
| 3907190 | SLPI | 3808600 | SNORA37 | 2797202 | SORBS2 |
| 3788302 | SMAD4 | 3386814 | SNORA40 | 3592109 | SORD |
| 3788270 | SMAD4 | 2437753 | SNORA42 | 3352948 | SORL1 |
| 3509842 | SMAD9 | 3230332 | SNORA43 | 2549092 | SOS1 |

Figure 6 continued

| TCID | GENE_na29 |
|---|---|
| 3960302 | SOX10 |
| 2897899 | SOX4 |
| 3447348 | SOX5 |
| 3364306 | SOX6 |
| 2603051 | SP110 |
| 2531310 | SP140 |
| 2531310 | SP140L |
| 2587520 | SP3 |
| 2587520 | SP3P |
| 2430422 | SPAG17 |
| 3742415 | SPAG7 |
| 2882098 | SPARC |
| 2777113 | SPARCL1 |
| 2420467 | SPATA1 |
| 3481543 | SPATA13 |
| 2380440 | SPATA17 |
| 2726910 | SPATA18 |
| 3909035 | SPATA2 |
| 2742134 | SPATA5 |
| 2867788 | SPATA9 |
| 3413950 | SPATS2 |
| 2522094 | SPATS2L |
| 2585933 | SPC25 |
| 3591281 | SPCS2 |
| 2752560 | SPCS3 |
| 2322103 | SPEN |
| 3621948 | SPG11 |
| 2834503 | SPINK5 |
| 3907320 | SPINLW1 |
| 3907335 | SPINLW1 |
| 3590164 | SPINT1 |
| 3799461 | SPIRE1 |
| 2404766 | SPOCD1 |
| 2876897 | SPOCK1 |
| 2735027 | SPP1 |
| 3623865 | SPPL2A |
| 3623472 | SPPL2A |
| 3589141 | SPRED1 |
| 2556752 | SPRED2 |
| 2742224 | SPRY1 |
| 3519309 | SPRY2 |
| 2319252 | SPSB1 |
| 3190558 | SPTAN1 |
| 2482505 | SPTBN1 |
| 3573152 | SPTLC2 |
| 3876990 | SPTLC3 |
| 3114832 | SQLE |
| 3592511 | SQRDL |
| 2890239 | SQSTM1 |
| 2844479 | SQSTM1 |
| 2551327 | SRBD1 |
| 3884191 | SRC |
| 3057668 | SRCRB4D |
| 2907730 | SRF |

| TCID | GENE_na29 |
|---|---|
| 3060300 | SRI |
| 3677969 | SRL |
| 3619165 | SRP14 |
| 3771297 | SRP68 |
| 2382781 | SRP9 |
| 2951674 | SRPK1 |
| 3066297 | SRPK2 |
| 3740998 | SRR |
| 3712098 | SRrp35 |
| 3802129 | SS18 |
| 2619323 | SS18L2 |
| 3027915 | SSBP1 |
| 2864849 | SSBP2 |
| 2413685 | SSBP3 |
| 2518428 | SSFA2 |
| 3408831 | SSPN |
| 2940551 | SSR1 |
| 2709750 | SST |
| 2391647 | SSU72 |
| 3976559 | SSX1 |
| 3976559 | SSX4 |
| 4007415 | SSX4 |
| 3976559 | SSX4B |
| 4007415 | SSX4B |
| 3976559 | SSX5 |
| 4007415 | SSX5 |
| 3976559 | SSX7 |
| 4007415 | SSX7 |
| 3976559 | SSX8 |
| 2699145 | ST13 |
| 3356175 | ST14 |
| 3135046 | ST18 |
| 3635198 | ST20 |
| 2562529 | ST3GAL5 |
| 2633256 | ST3GAL6 |
| 3361971 | ST5 |
| 2656837 | ST6GAL1 |
| 3771712 | ST6GALNAC1 |
| 3771675 | ST6GALNAC2 |
| 2342904 | ST6GALNAC5 |
| 3020496 | ST7 |
| 3020496 | ST7OT3 |
| 2868904 | ST8SIA4 |
| 3429159 | STAB2 |
| 2616804 | STAC |
| 2696802 | STAG1 |
| 3015338 | STAG3 |
| 3015338 | STAG3L1 |
| 3056705 | STAG3L1 |
| 3015338 | STAG3L2 |
| 3056705 | STAG3L2 |
| 3015338 | STAG3L3 |
| 3056705 | STAG3L3 |
| 3237088 | STAM |

| TCID | GENE_na29 |
|---|---|
| 3257031 | STAMBPL1 |
| 3094447 | STAR |
| 3508898 | STARD13 |
| 2870828 | STARD4 |
| 2565143 | STARD7 |
| 3457752 | STAT2 |
| 2592356 | STAT4 |
| 3721658 | STAT5A |
| 3721658 | STAT5B |
| 3458337 | STAT6 |
| 2731986 | STBD1 |
| 3011838 | STEAP1 |
| 3011861 | STEAP2 |
| 2502762 | STEAP3 |
| 2528386 | STK16 |
| 2593159 | STK17B |
| 2607262 | STK25 |
| 3146103 | STK3 |
| 2993029 | STK31 |
| 2834282 | STK32A |
| 3361811 | STK33 |
| 3409081 | STK38L |
| 2402459 | STMN1 |
| 3104489 | STMN2 |
| 3914050 | STMN3 |
| 3223928 | STOM |
| 2481379 | STON1 |
| 2481379 | STON1-GTF2A1L |
| 3574121 | STON2 |
| 3632806 | STRA6 |
| 3766284 | STRADA |
| 2522789 | STRADB |
| 3224591 | STRBP |
| 3621351 | STRC |
| 2548274 | STRN |
| 3531163 | STRN3 |
| 3852079 | STX10 |
| 2327219 | STX12 |
| 3891006 | STX16 |
| 3819016 | STXBP2 |
| 2350339 | STXBP3 |
| 2929870 | STXBP5 |
| 3558418 | STXBP6 |
| 3513293 | SUCLA2 |
| 2648098 | SUCNR1 |
| 3490741 | SUGT1 |
| 3486728 | SUGT1L1 |
| 3102372 | SULF1 |
| 3654669 | SULT1A1 |
| 3656032 | SULT1A1 |
| 3654669 | SULT1A2 |
| 3656032 | SULT1A2 |
| 3656032 | SULT1A3 |

Figure 6 continued

| TCID | GENE_na29 | TCID | GENE_na29 | TCID | GENE_na29 |
|---|---|---|---|---|---|
| 3656032 | SULT1A4 | 3151943 | TATDN1 | 3846280 | TBXA2R |
| 2498911 | SULT1C2 | 3422326 | TBC1D15 | 3027204 | TBXAS1 |
| 2498951 | SULT1C4 | 3217194 | TBC1D2 | 3576704 | TC2N |
| 3868785 | SULT2A1 | 2905432 | TBC1D22B | 2989537 | tcag7.903 |
| 2955282 | SUPT3H | 3754041 | TBC1D3 | 3985644 | TCEAL3 |
| 3764384 | SUPT4H1 | 3754096 | TBC1D3 | 3985644 | TCEAL6 |
| 3715703 | SUPT6H | 4040117 | TBC1D3 | 3985511 | TCEAL7 |
| 3228652 | SURF1 | 4040849 | TBC1D3 | 3969396 | TCEANC |
| 3228621 | SURF6 | 3754041 | TBC1D3B | 3140833 | TCEB1 |
| 3220846 | SUSD1 | 3754096 | TBC1D3B | 3590498 | TCEB1 |
| 4045426 | SUSD4 | 4040117 | TBC1D3B | 3595096 | TCF12 |
| 3236448 | SUV39H2 | 4040849 | TBC1D3B | 3962338 | TCF20 |
| 3379390 | SUV420H1 | 3754041 | TBC1D3C | 2926447 | TCF21 |
| 3716664 | SUZ12P | 3754096 | TBC1D3C | 3674434 | TCF25 |
| 2434139 | SV2A | 4040117 | TBC1D3C | 3808854 | TCF4 |
| 3608638 | SV2B | 4040849 | TBC1D3C | 2491386 | TCF7L1 |
| 3319997 | SWAP70 | 3754041 | TBC1D3D | 3264621 | TCF7L2 |
| 2894790 | SYCP2L | 3754096 | TBC1D3D | 3913483 | TCFL5 |
| 3468080 | SYCP3 | 4040117 | TBC1D3D | 3578152 | TCL1A |
| 3178952 | SYK | 4040849 | TBC1D3D | 3550139 | TCL1B |
| 2963407 | SYNCRIP | 3754041 | TBC1D3E | 3550139 | TCL6 |
| 2979871 | SYNE1 | 3754096 | TBC1D3E | 3374890 | TCN1 |
| 3539724 | SYNE2 | 4040117 | TBC1D3E | 3929237 | TCP10L |
| 3610982 | SYNM | 4040849 | TBC1D3E | 3368520 | TCP11L1 |
| 3294668 | SYNPO2L | 3724698 | TBC1D3F | 3471327 | TCTN1 |
| 4007899 | SYP | 3754041 | TBC1D3F | 3429365 | TDG |
| 3423622 | SYT1 | 3754096 | TBC1D3F | 2909167 | TDRD6 |
| 2361154 | SYT11 | 4040117 | TBC1D3F | 2435218 | TDRKH |
| 3336652 | SYT12 | 4040849 | TBC1D3F | 3320944 | TEAD1 |
| 3371114 | SYT13 | 3754041 | TBC1D3G | 3321055 | TEAD1 |
| 2378256 | SYT14 | 3754096 | TBC1D3G | 3401259 | TEAD4 |
| 3287366 | SYT15 | 4040117 | TBC1D3G | 2768396 | TEC |
| 3805614 | SYT4 | 4040849 | TBC1D3G | 2768396 | TEC |
| 3973891 | SYTL5 | 3754041 | TBC1D3H | 3553141 | TECPR2 |
| 3377474 | SYVN1 | 3754096 | TBC1D3H | 3165825 | TEK |
| 3014065 | TAC1 | 4040117 | TBC1D3H | 3415668 | TENC1 |
| 3292946 | TACR2 | 4040849 | TBC1D3H | 3555340 | TEP1 |
| 2414958 | TACSTD2 | 3754041 | TBC1D3P2 | 3020192 | TES |
| 3203199 | TAF1 | 3754096 | TBC1D3P2 | 3473436 | TESC |
| 3361021 | TAF10 | 4040117 | TBC1D3P2 | 3249886 | TET1 |
| 3671607 | TAF1C | 4040849 | TBC1D3P2 | 2738146 | TET2 |
| 3702382 | TAF1C | 3518086 | TBC1D4 | 3217807 | TEX10 |
| 3386814 | TAF1D | 2942306 | TBC1D7 | 3766716 | TEX2 |
| 3203199 | TAF1L | 3986291 | TBC1D8B | 3247784 | TFAM |
| 2907018 | TAF8 | 4002011 | TBC1D8B | 3247784 | TFAMP1 |
| 2635998 | TAGLN3 | 2709414 | TBCCD1 | 2329920 | TFAP2E |
| 2411198 | TAL1 | 2386418 | TBCE | 2573570 | TFCP2L1 |
| 3183348 | TAL2 | 2738378 | TBCKL | 4007734 | TFE3 |
| 3716048 | TAOK1 | 2780734 | TBCKL | 3069082 | TFEC |
| 2761941 | TAPT1 | 3419849 | TBK1 | 3933559 | TFF1 |
| 3046520 | TARP | 3354174 | TBRG1 | 3933536 | TFF3 |
| 3046708 | TARP | 3729834 | TBX2 | 3955875 | TFIP11 |
| 3027961 | TAS2R5 | 3982689 | TBX22 | 2591421 | TFPI |
| 3898126 | TASP1 | 3472755 | TBX3 | 3061621 | TFPI2 |

Figure 6 continued

| TCID | GENE_na29 |
|---|---|
| 3116614 | TG |
| 2558612 | TGFA |
| 2380590 | TGFB2 |
| 3181728 | TGFBR1 |
| 2615360 | TGFBR2 |
| 2422722 | TGFBR3 |
| 3776504 | TGIF1 |
| 2562198 | TGOLN2 |
| 3098935 | TGS1 |
| 2550542 | THADA |
| 3067644 | THAP5 |
| 3589458 | THBS1 |
| 3625391 | THEM4 |
| 2888103 | THOC3 |
| 3956854 | THOC5 |
| 3677356 | THOC6 |
| 3756046 | THRA |
| 2666147 | THRB |
| 3341497 | THRSP |
| 3514879 | THSD1 |
| 3514879 | THSD1P |
| 3600283 | THSD4 |
| 2558511 | TIA1 |
| 3309629 | TIAL1 |
| 3928668 | TIAM1 |
| 2932508 | TIAM2 |
| 2871821 | TICAM2 |
| 2333051 | TIE1 |
| 2782230 | TIFA |
| 2735598 | TIGD2 |
| 2883283 | TIMD4 |
| 2374956 | TIMM17A |
| 3289031 | TIMM23 |
| 3833093 | TIMM50 |
| 3976341 | TIMP1 |
| 3772661 | TIMP2 |
| 3943504 | TIMP3 |
| 2663130 | TIMP4 |
| 3558012 | TINF2 |
| 2649113 | TIPARP |
| 3693511 | TIPIN |
| 2366132 | TIPRL |
| 3355091 | TIRAP |
| 2908008 | TJAP1 |
| 3615579 | TJP1 |
| 3173880 | TJP2 |
| 3817116 | TJP3 |
| 3695107 | TK2 |
| 3751042 | TLCD1 |
| 3211579 | TLE1 |
| 3176209 | TLE4 |
| 3211579 | TLE4 |
| 2750753 | TLL1 |
| 3597125 | TLN2 |

| TCID | GENE_na29 |
|---|---|
| 2766192 | TLR10 |
| 2748346 | TLR2 |
| 2754937 | TLR3 |
| 2766262 | TLR6 |
| 3969115 | TLR8 |
| 2676009 | TLR9 |
| 2700365 | TM4SF1 |
| 2647315 | TM4SF4 |
| 3605268 | TM6SF1 |
| 3448481 | TM7SF3 |
| 3110608 | TM7SF4 |
| 3881686 | TM9SF4 |
| 3414186 | TMBIM6 |
| 3635578 | TMC3 |
| 3650762 | TMC7 |
| 2694931 | TMCC1 |
| 2376376 | TMCC2 |
| 3466206 | TMCC3 |
| 2442134 | TMCO1 |
| 3048778 | TMED4 |
| 2423264 | TMED5 |
| 2871821 | TMED7 |
| 3182229 | TMEFF1 |
| 2592598 | TMEFF2 |
| 3763390 | TMEM100 |
| 3722479 | TMEM106A |
| 2990342 | TMEM106B |
| 3413278 | TMEM106C |
| 2642995 | TMEM108 |
| 3471769 | TMEM116 |
| 3412345 | TMEM117 |
| 3388631 | TMEM123 |
| 2758658 | TMEM128 |
| 3478068 | TMEM132D |
| 3346147 | TMEM133 |
| 3397461 | TMEM135 |
| 3352485 | TMEM136 |
| 3029016 | TMEM139 |
| 2749380 | TMEM144 |
| 3830530 | TMEM147 |
| 2910364 | TMEM14A |
| 2701294 | TMEM14E |
| 2562387 | TMEM150 |
| 2766289 | TMEM156 |
| 2577482 | TMEM163 |
| 3987029 | TMEM164 |
| 3068476 | TMEM168 |
| 2815220 | TMEM171 |
| 2877990 | TMEM173 |
| 3031624 | TMEM176A |
| 2478269 | TMEM178 |
| 2537290 | TMEM18 |
| 2746645 | TMEM184C |
| 3659858 | TMEM188 |

| TCID | GENE_na29 |
|---|---|
| 3422231 | TMEM19 |
| 3039399 | TMEM195 |
| 3040465 | TMEM196 |
| 2925590 | TMEM200A |
| 3072435 | TMEM209 |
| 3166644 | TMEM215 |
| 3745525 | TMEM220 |
| 2961317 | TMEM30A |
| 2725332 | TMEM33 |
| 2690850 | TMEM39A |
| 2708817 | TMEM41A |
| 2611779 | TMEM43 |
| 2633891 | TMEM45A |
| 4004575 | TMEM47 |
| 2413423 | TMEM48 |
| 3929664 | TMEM50B |
| 2409770 | TMEM53 |
| 3144235 | TMEM55A |
| 2347732 | TMEM56 |
| 3825244 | TMEM59L |
| 3058156 | TMEM60 |
| 3591281 | TMEM62 |
| 3129948 | TMEM66 |
| 3136015 | TMEM68 |
| 2351632 | TMEM77 |
| 2427720 | TMEM77 |
| 3358262 | TMEM80 |
| 3316126 | TMEM80 |
| 3599669 | TMEM84 |
| 3620515 | TMEM87A |
| 2500615 | TMEM87B |
| 3709153 | TMEM88 |
| 2450668 | TMEM9 |
| 3571904 | TMEM90A |
| 3717870 | TMEM98 |
| 3181240 | TMOD1 |
| 3594031 | TMOD2 |
| 2668205 | TMPPE |
| 2729821 | TMPRSS11E |
| 2729821 | TMPRSS11E2 |
| 3393536 | TMPRSS13 |
| 3351200 | TMPRSS4 |
| 2491271 | TMSB10 |
| 4016193 | TMSB15A |
| 4016193 | TMSB15B |
| 3449068 | TMTC1 |
| 3425134 | TMTC3 |
| 3812206 | TMX3 |
| 3896976 | TMX4 |
| 3222170 | TNC |
| 3750625 | TNFAIP1 |
| 2825629 | TNFAIP8 |
| 3127703 | TNFRSF10B |
| 3089816 | TNFRSF10C |

Figure 6 continued

| TCID | GENE_na29 | TCID | GENE_na29 | TCID | GENE_na29 |
|---|---|---|---|---|---|
| 3150455 | TNFRSF11B | 3881443 | TPX2 | 3372896 | TRIM77 |
| 3645555 | TNFRSF12A | 3528172 | TRA@ | 3818515 | TRIP10 |
| 3648391 | TNFRSF17 | 3041519 | TRA2A | 2602901 | TRIP12 |
| 3441849 | TNFRSF1A | 2709062 | TRA2B | 2798915 | TRIP13 |
| 2956052 | TNFRSF21 | 3528172 | TRAC | 3597977 | TRIP4 |
| 2705706 | TNFSF10 | 3695433 | TRADD | 2408111 | TRIT1 |
| 3487299 | TNFSF11 | 3553337 | TRAF3 | 3896524 | TRMT6 |
| 3500787 | TNFSF13B | 2534810 | TRAF3IP1 | 2326846 | TRNP1 |
| 3222128 | TNFSF15 | 2969810 | TRAF3IP2 | 2660648 | TRNT1 |
| 2444239 | TNFSF18 | 3715839 | TRAF4 | 2645951 | TRPC1 |
| 2705266 | TNIK | 2378662 | TRAF5 | 3903708 | TRPC4AP |
| 3085270 | TNKS | 3369890 | TRAF6 | 4018327 | TRPC5 |
| 3373675 | TNKS1BP1 | 3644541 | TRAF7 | 3388438 | TRPC6 |
| 3257850 | TNKS2 | 3432267 | TRAFD1 | 3359267 | TRPM5 |
| 2342176 | TNNI3K | 3528172 | TRAJ17 | 3623771 | TRPM7 |
| 2342220 | TNNI3K | 2619120 | TRAK1 | 3149528 | TRPS1 |
| 2450762 | TNNT2 | 2594812 | TRAK2 | 3014411 | TRRAP |
| 3317117 | TNNT3 | 3139882 | TRAM1 | 3028766 | TRY6 |
| 3255402 | TNPO1 | 2957227 | TRAM2 | 3228373 | TSC1 |
| 3851651 | TNPO2 | 3843188 | TRAPPC2 | 3512294 | TSC22D1 |
| 3653398 | TNRC6A | 3843188 | TRAPPC2P1 | 2647647 | TSC22D2 |
| 3946192 | TNRC6B | 3865223 | TRAPPC6A | 3064039 | TSC22D4 |
| 2599153 | TNS1 | 3155937 | TRAPPC9 | 3365437 | TSG101 |
| 3049522 | TNS3 | 3528172 | TRAV20 | 2566586 | TSGA10 |
| 2949622 | TNXA | 3528172 | TRAV8-3 | 3546213 | TSHR |
| 2949622 | TNXB | 3528172 | TRD@ | 3794056 | TSHZ1 |
| 3762473 | TOB1 | 2953570 | TREM1 | 3889419 | TSHZ2 |
| 3907111 | TOMM34 | 2953501 | TREM2 | 3889624 | TSHZ2 |
| 3157385 | TOP1MT | 2906720 | TREML2 | 3858285 | TSHZ3 |
| 3756193 | TOP2A | 2906720 | TREML2P | 2503618 | TSN |
| 3748262 | TOP3A | 2906720 | TREML3 | 2334602 | TSPAN1 |
| 2695941 | TOPBP1 | 2906720 | TREML4 | 3069955 | TSPAN12 |
| 2446198 | TOR1AIP1 | 2954022 | TRERF1 | 2991150 | TSPAN13 |
| 2446198 | TOR1AIP2 | 2954025 | TRERF1 | 2842707 | TSPAN17 |
| 3136888 | TOX | 3046520 | TRGC2 | 3458783 | TSPAN31 |
| 2457842 | TP53BP2 | 3046708 | TRGV3 | 3316375 | TSPAN4 |
| 2544201 | TP53I3 | 3046520 | TRGV9 | 2778856 | TSPAN5 |
| 3145149 | TP53INP1 | 2641901 | TRH | 4015397 | TSPAN6 |
| 3883013 | TP53INP2 | 3115008 | TRIB1 | 3974019 | TSPAN7 |
| 3060095 | TP53TG1 | 3489644 | TRIM13 | 3461981 | TSPAN8 |
| 2317317 | TP73 | 3217123 | TRIM14 | 3978169 | TSPYL2 |
| 2915133 | TPBG | 3746845 | TRIM16 | 3740998 | TSR1 |
| 3141857 | TPD52 | 3746845 | TRIM16L | 2538480 | TSSC1 |
| 2924330 | TPD52L1 | 3318443 | TRIM22 | 3620799 | TTBK2 |
| 3204721 | TPM2 | 3360622 | TRIM22 | 2654306 | TTC14 |
| 2436526 | TPM3 | 2859734 | TRIM23 | 3327948 | TTC17 |
| 3823511 | TPM4 | 2948259 | TRIM26 | 2585236 | TTC21B |
| 2944025 | TPMT | 3128954 | TRIM35 | 2806186 | TTC23L |
| 2466554 | TPO | 2901503 | TRIM39 | 3721516 | TTC25 |
| 3361041 | TPP1 | 2901503 | TRIM39R | 3920385 | TTC3 |
| 3499453 | TPP2 | 2430126 | TRIM45 | 2589011 | TTC30A |
| 3643679 | TPSD1 | 3360622 | TRIM5 | 2588965 | TTC30A |
| 3006444 | TPST1 | 2845078 | TRIM52 | 2588965 | TTC30B |
| 3955915 | TPST2 | 2390180 | TRIM58 | 3111375 | TTC35 |

Figure 6 continued

| TCID | GENE_na29 | TCID | GENE_na29 | TCID | GENE_na29 |
|---|---|---|---|---|---|
| 2867693 | TTC37 | 2697372 | TXNDC6 | 2402601 | UBXN11 |
| 2412312 | TTC39A | 2644461 | TXNDC6 | 2472914 | UBXN2A |
| 3199662 | TTC39B | 3809324 | TXNL1 | 2507495 | UBXN4 |
| 3781980 | TTC39C | 3429460 | TXNRD1 | 2712858 | UBXN7 |
| 3333603 | TTC9C | 3775842 | TYMS | 2725013 | UCHL1 |
| 2500803 | TTL | 3795850 | TYMS | 2448971 | UCHL5 |
| 3761551 | TTLL6 | 3795866 | TYMS | 3381817 | UCP2 |
| 2420229 | TTLL7 | 3633794 | TYRO3 | 3365487 | UEVLD |
| 3906942 | TTPAL | 3590498 | TYRO3 | 2754673 | UFSP2 |
| 3783565 | TTR | 3633794 | TYRO3P | 2504883 | UGCGL1 |
| 3734236 | TTYH2 | 3590498 | TYRO3P | 3521484 | UGCGL2 |
| 3453837 | TUBA1A | 3293215 | TYSND1 | 2766456 | UGDH |
| 3453732 | TUBA1A | 3005995 | TYW1 | 2485257 | UGP2 |
| 3453837 | TUBA1B | 3055608 | TYW1 | 2853293 | UGT3A1 |
| 3453732 | TUBA1B | 3005995 | TYW1B | 2853325 | UGT3A2 |
| 3413787 | TUBA1B | 3055608 | TYW1B | 2740507 | UGT8 |
| 3413787 | TUBA1C | 3842345 | U2AF2 | 2364155 | UHMK1 |
| 2575949 | TUBA3C | 3631397 | UACA | 2904270 | UHRF1BP1 |
| 2506185 | TUBA3C | 2364189 | UAP1 | 2930957 | ULBP2 |
| 2575949 | TUBA3D | 3976062 | UBA1 | 2979187 | ULBP2 |
| 2506185 | TUBA3D | 3829768 | UBA2 | 3749010 | ULK2 |
| 2575949 | TUBA3E | 2345196 | UBA2 | 2670481 | ULK4 |
| 2506185 | TUBA3E | 2681195 | UBA3 | 3683549 | UMOD |
| 2528407 | TUBA4A | 2695648 | UBA5 | 2639874 | UMPS |
| 2528407 | TUBA4B | 2642911 | UBA5 | 3167731 | UNC13B |
| 3936515 | TUBA8 | 2771718 | UBA6 | 2986825 | UNC84A |
| 2901913 | TUBB | 2674762 | UBA7 | 2758602 | UNC93B3 |
| 3891342 | TUBB1 | 3498315 | UBAC2 | 3474697 | UNQ1887 |
| 2939232 | TUBB2A | 3203753 | UBAP2 | 2732339 | UNQ3028 |
| 2939232 | TUBB2B | 2360083 | UBAP2L | 3629103 | UNQ353 |
| 4050486 | TUBB2C | 3988874 | UBE2A | 2886535 | UNQ9374 |
| 4051521 | TUBB2C | 2613880 | UBE2E2 | 3277662 | UPF2 |
| 2901913 | TUBB2C | 3072276 | UBE2H | 3503224 | UPF3A |
| 3674504 | TUBB3 | 3643703 | UBE2I | 3351688 | UPK2 |
| 3847959 | TUBB4 | 3771543 | UBE2O | 3065154 | UPLP |
| 3674504 | TUBB4Q | 2436716 | UBE2Q1 | 3000953 | UPP1 |
| 3779579 | TUBB6 | 2451200 | UBE2T | 2511712 | UPP2 |
| 2901913 | TUBBP1 | 3097208 | UBE2V2 | 3652218 | UQCRC2 |
| 2901913 | TUBBP2 | 3725481 | UBE2Z | 2384705 | URB2 |
| 3764933 | TUBD1 | 3614087 | UBE3A | 2334279 | UROD |
| 3721926 | TUBG1 | 3431143 | UBE3B | 3854311 | USHBP1 |
| 3721926 | TUBG2 | 3033924 | UBE3C | 3775686 | USP14 |
| 3526151 | TUBGCP3 | 2319560 | UBE4B | 3936550 | USP18 |
| 2358993 | TUFT1 | 3653000 | UBFD1 | 3749498 | USP22 |
| 3401217 | TULP3 | 4027355 | UBL4A | 3391816 | USP28 |
| 3087167 | TUSC3 | 3820161 | UBL5 | 3685051 | USP31 |
| 4027769 | TWF1 | 2668351 | UBP1 | 3765167 | USP32 |
| 3451708 | TWF1 | 2437893 | UBQLN4 | 3748400 | USP32 |
| 2676009 | TWF2 | 3360553 | UBQLNL | 2419113 | USP33 |
| 3220156 | TXN | 3620880 | UBR1 | 2555277 | USP34 |
| 2412668 | TXNDC12 | 2907190 | UBR2 | 2604138 | USP40 |
| 2829562 | TXNDC15 | 2399409 | UBR4 | 3936550 | USP41 |
| 3707990 | TXNDC17 | 3147321 | UBR5 | 3466499 | USP44 |
| 3778589 | TXNDC2 | 3376023 | UBXN1 | 2966298 | USP45 |

Figure 6 continued

| TCID | GENE_na29 | TCID | GENE_na29 | TCID | GENE_na29 |
|---|---|---|---|---|---|
| 3320604 | USP47 | 3471264 | VPS29 | 3593770 | WDSOF1 |
| 2400718 | USP48 | 3475545 | VPS33A | 3886938 | WFDC2 |
| 3294576 | USP54 | 3689922 | VPS35 | 3907320 | WFDC6 |
| 3765167 | USP6 | 3475838 | VPS37B | 3907348 | WFDC8 |
| 3748400 | USP6 | 3620457 | VPS39 | 2715076 | WHSC1 |
| 3277468 | USP6NL | 7385683 | VPS41 | 3460198 | WIF1 |
| 3679564 | USP7 | 2357996 | VPS45 | 2587841 | WIPF1 |
| 3974708 | USP9X | 2556215 | VPS54 | 2995076 | WIPF3 |
| 3974708 | USP9Y | 2434892 | VPS72 | 3768474 | WIPI1 |
| 2930418 | UST | 3550485 | VRK1 | 3400034 | WNK1 |
| 3990566 | UTP14A | 3353914 | VWA5A | 4009604 | WNK3 |
| 3490504 | UTP14A | 3441685 | VWF | 2528159 | WNT10A |
| 3990566 | UTP14C | 3240340 | WAC | 2677356 | WNT5A |
| 3490504 | UTP14C | 3298738 | WAPAL | 2830598 | WNT8A |
| 3726992 | UTP18 | 3579546 | WARS | 3715109 | WSB1 |
| 2929168 | UTRN | 2969289 | WASF1 | 3430620 | WSCD2 |
| 3340697 | UVRAG | 3482572 | WASF3 | 2753732 | WWC2 |
| 3441941 | VAMP1 | 3445670 | WBP11 | 3968397 | WWC3 |
| 3744217 | VAMP2 | 3445670 | WBP11P1 | 3669650 | WWOX |
| 2443989 | VAMP4 | 3771037 | WBP2 | 3105777 | WWP1 |
| 4032755 | VAMP7 | 3985523 | WBP5 | 3977862 | XAGE1A |
| 2353237 | VANGL1 | 3056838 | WBSCR16 | 3977862 | XAGE1B |
| 3778601 | VAPA | 3007024 | WBSCR17 | 3977862 | XAGE1C |
| 2902013 | VARS2 | 2601341 | WDFY1 | 3977862 | XAGE1D |
| 3758291 | VAT1 | 3490251 | WDFY2 | 3977862 | XAGE1E |
| 3669552 | VAT1L | 2776372 | WDFY3 | 3956589 | XBP1 |
| 2426385 | VAV3 | 3565571 | WDHD1 | 3989678 | XIAP |
| 3996815 | VBP1 | 2760371 | WDR1 | 2513758 | XIRP2 |
| 3252071 | VCL | 2752478 | WDR17 | 4015548 | XKRX |
| 3998386 | VCX | 2724235 | WDR19 | 3216969 | XPA |
| 3998386 | VCX2 | 3553017 | WDR20 | 2663810 | XPC |
| 3998386 | VCX3A | 2725332 | WDR21B | 3946510 | XPNPEP3 |
| 3998386 | VCX3B | 3569926 | WDR22 | 3961699 | XPNPEP3 |
| 3998386 | VCY | 2458082 | WDR26 | 2555490 | XPO1 |
| 2875954 | VDAC1 | 2354082 | WDR3 | 3686339 | XPO6 |
| 3452818 | VDR | 2430422 | WDR3 | 3088983 | XPO7 |
| 2908179 | VEGFA | 3231846 | WDR37 | 2370123 | XPR1 |
| 2794792 | VEGFC | 3203855 | WDR40A | 2818454 | XRCC4 |
| 2610336 | VHL | 2863535 | WDR41 | 2526980 | XRCC5 |
| 2619265 | VIPR1 | 3988365 | WDR44 | 3879467 | XRN2 |
| 3082373 | VIPR2 | 2426840 | WDR47 | 3451264 | YAF2 |
| 2477203 | VIT | 2704143 | WDR49 | 2929870 | YAP1 |
| 3005266 | VKORC1L1 | 3464912 | WDR51B | 2405192 | YARS |
| 3160175 | VLDLR | 2489228 | WDR54 | 2329077 | YARS |
| 3872274 | VN1R1 | 2673830 | WDR6 | 3639601 | YBX2 |
| 2974592 | VNN1 | 3034449 | WDR60 | 2923060 | YDD19 |
| 2974635 | VNN2 | 2344731 | WDR63 | 2655168 | YEATS2 |
| 2974610 | VNN3 | 2332999 | WDR65 | 3832280 | YIF1B |
| 2675628 | VPRBP | 3730731 | WDR68 | 2413484 | YIPF1 |
| 3351806 | VPS11 | 3789442 | WDR7 | 2879509 | YIPF5 |
| 3108801 | VPS13B | 3625052 | WDR72 | 3825838 | YJEFN3 |
| 3627929 | VPS13C | 2417016 | WDR78 | 3240012 | YME1L1 |
| 2320762 | VPS13D | 2676041 | WDR82 | 3938244 | YPEL1 |
| 3874023 | VPS16A | 3607766 | WDR93 | 4024373 | YTHDC2 |

Figure 6 continued

| TCID | GENE_na29 | TCID | GENE_na29 | TCID | GENE_na29 |
|---|---|---|---|---|---|
| 2824483 | YTHDC2 | 3872053 | ZIM2 | 2745220 | ZNF330 |
| 2327630 | YTHDF2 | 3015147 | ZKSCAN1 | 3159013 | ZNF34 |
| 3886639 | YWHAB | 2706791 | ZMAT3 | 2642860 | ZNF346 |
| 3943207 | YWHAH | 3132616 | ZMAT4 | 3870135 | ZNF347 |
| 2539869 | YWHAQ | 3480129 | ZMYM2 | 3818842 | ZNF358 |
| 2437577 | YY1AP1 | 4011889 | ZMYM3 | 2862019 | ZNF366 |
| 2437645 | YY1AP1 | 2329752 | ZMYM4 | 3831475 | ZNF382 |
| 3971329 | YY2 | 2408929 | ZMYND12 | 3129361 | ZNF395 |
| 3813604 | ZADH2 | 3908149 | ZMYND8 | 3803882 | ZNF397 |
| 2704052 | ZBBX | 3053380 | ZNF117 | 3803882 | ZNF397OS |
| 2688499 | ZBED2 | 3849549 | ZNF121 | 3793888 | ZNF407 |
| 3349719 | ZBTB16 | 2465551 | ZNF124 | 3872335 | ZNF416 |
| 3989089 | ZBTB33 | 2808290 | ZNF131 | 3843275 | ZNF419 |
| 3458216 | ZBTB39 | 3872928 | ZNF132 | 3826656 | ZNF429 |
| 3189580 | ZBTB43 | 3843742 | ZNF135 | 3856720 | ZNF43 |
| 3398241 | ZBTB44 | 3855985 | ZNF14 | 3826306 | ZNF43 |
| 2571217 | ZC3H8 | 3319898 | ZNF143 | 3677592 | ZNF434 |
| 2412834 | ZCCHC11 | 3835318 | ZNF155 | 3283613 | ZNF438 |
| 3988596 | ZCCHC12 | 3976240 | ZNF157 | 3851454 | ZNF443 |
| 3703665 | ZCCHC14 | 2900195 | ZNF165 | 3991992 | ZNF449 |
| 3987607 | ZCCHC16 | 3819968 | ZNF177 | 3078774 | ZNF467 |
| 3791341 | ZCCHC2 | 3829857 | ZNF181 | 3842839 | ZNF470 |
| 3296981 | ZCCHC24 | 2900423 | ZNF187 | 3244055 | ZNF487 |
| 2721809 | ZCCHC4 | 2900372 | ZNF193 | 3826803 | ZNF492 |
| 2818079 | ZCCHC9 | 3359751 | ZNF195 | 3216476 | ZNF510 |
| 3063968 | ZCWPW1 | 2620160 | ZNF197 | 2474651 | ZNF512 |
| 3322958 | ZDHHC13 | 3717635 | ZNF207 | 3840795 | ZNF525 |
| 2933175 | ZDHHC14 | 3856646 | ZNF208 | 3843386 | ZNF530 |
| 3504691 | ZDHHC20 | 3856720 | ZNF208 | 3866649 | ZNF541 |
| 3199431 | ZDHHC21 | 3910260 | ZNF217 | 3843848 | ZNF544 |
| 3331433 | ZDHHC5 | 3244539 | ZNF22 | 3843188 | ZNF547 |
| 3307120 | ZDHHC6 | 3835318 | ZNF221 | 3843214 | ZNF548 |
| 4021341 | ZDHHC9 | 3835418 | ZNF224 | 3872441 | ZNF552 |
| 3241316 | ZEB1 | 3835494 | ZNF226 | 3819968 | ZNF559 |
| 2579572 | ZEB2 | 3835565 | ZNF233 | 3849797 | ZNF561 |
| 2528308 | ZFAND2B | 3835467 | ZNF234 | 3849797 | ZNF562 |
| 2905664 | ZFAND3 | 3285614 | ZNF25 | 3849549 | ZNF562 |
| 3462094 | ZFC3H1 | 3826041 | ZNF253 | 3860824 | ZNF569 |
| 3797015 | ZFP161 | 3872560 | ZNF256 | 3114820 | ZNF572 |
| 3842794 | ZFP28 | 3826803 | ZNF257 | 3864430 | ZNF575 |
| 3860954 | ZFP30 | 3392871 | ZNF259 | 3842315 | ZNF580 |
| 3569754 | ZFP36L1 | 3657367 | ZNF267 | 3842301 | ZNF581 |
| 3331730 | ZFP91 | 3004768 | ZNF273 | 3871903 | ZNF582 |
| 3331730 | ZFP91-CNTF | 3019401 | ZNF277 | 2390976 | ZNF596 |
| 3110789 | ZFPM2 | 4021508 | ZNF280C | 3213530 | ZNF598 |
| 3971923 | ZFX | 3625823 | ZNF280D | 3869714 | ZNF600 |
| 3971923 | ZFY | 3933399 | ZNF295 | 3872604 | ZNF606 |
| 2817731 | ZFYVE16 | 3063646 | ZNF3 | 3869714 | ZNF611 |
| 3619650 | ZFYVE19 | 2881607 | ZNF300 | 3747324 | ZNF624 |
| 3590129 | ZFYVE19 | 3829857 | ZNF302 | 3826041 | ZNF626 |
| 3553947 | ZFYVE21 | 3869714 | ZNF320 | 3826079 | ZNF626 |
| 3260018 | ZFYVE27 | 2946500 | ZNF322A | 2331903 | ZNF643 |
| 2757796 | ZFYVE28 | 2946500 | ZNF322B | 2422517 | ZNF644 |
| 3908062 | ZHX3 | 2947248 | ZNF323 | 3761737 | ZNF652 |

Figure 6 continued

| TCID | GENE_na29 |
|---|---|
| 3014904 | ZNF655 |
| 3206317 | ZNF658 |
| 3206317 | ZNF658B |
| 3826306 | ZNF66 |
| 2619521 | ZNF662 |
| 3871935 | ZNF667 |
| 2465493 | ZNF670 |
| 3857171 | ZNF675 |
| 3856720 | ZNF676 |
| 2402691 | ZNF683 |
| 3687910 | ZNF689 |
| 2465493 | ZNF695 |
| 3849549 | ZNF699 |
| 3657367 | ZNF720 |
| 3657318 | ZNF720 |
| 2756309 | ZNF721 |
| 3856720 | ZNF728 |
| 3078656 | ZNF746 |
| 3843275 | ZNF749 |
| 4023006 | ZNF75D |
| 3840795 | ZNF761 |
| 3840795 | ZNF765 |
| 3078656 | ZNF767 |
| 3872274 | ZNF772 |
| 3860999 | ZNF781 |
| 3030585 | ZNF783 |
| 3014808 | ZNF789 |
| 3851454 | ZNF799 |
| 3843906 | ZNF8 |
| 2518889 | ZNF804A |
| 3011675 | ZNF804B |
| 3872441 | ZNF814 |
| 3718382 | ZNF830 |
| 3871903 | ZNF835 |
| 3688381 | ZNF843 |
| 3840795 | ZNF845 |
| 3849549 | ZNF846 |
| 3826306 | ZNF85 |
| 3826079 | ZNF90 |
| 3005069 | ZNF92 |
| 3826079 | ZNF93 |
| 3826803 | ZNF98 |
| 3856720 | ZNF99 |
| 3826803 | ZNF99 |
| 2420958 | ZNHIT6 |
| 3668834 | ZNRF1 |
| 2995076 | ZNRF2 |
| 3057755 | ZP3 |
| 3057668 | ZP3 |
| 2462693 | ZP4 |
| 3050170 | ZPBP |
| 2577700 | ZRANB3 |
| 2900269 | ZSCAN16 |
| 3391769 | ZW10 |

| TCID | GENE_na29 |
|---|---|
| 3290210 | ZWINT |
| 2336539 | ZYG11A |
| 3741875 | ZZEF1 |

Figure 6 continued

| CEL File | Subtype Pathology | Simplified Pathology |
|---|---|---|
| 151276HUEX1A11.CEL | FA | B |
| 151279HUEX1A11.CEL | FA | B |
| 151326HUEX1A11.CEL | FA | B |
| 151329HUEX1A11.CEL | FA | B |
| 151345HUEX1A11.CEL | FA | B |
| 151356HUEX1A11.CEL | FA | B |
| 151359HUEX1A11.CEL | FA | B |
| 151361HUEX1A11.CEL | FA | B |
| 151364HUEX1A11.CEL | FA | B |
| 151793HUEX1A11.CEL | FA | B |
| 151794HUEX1A11.CEL | FA | B |
| 151795HUEX1A11.CEL | FA | B |
| 151797HUEX1A11.CEL | FA | B |
| 151798HUEX1A11.CEL | FA | B |
| 151799HUEX1A11.CEL | FA | B |
| 151800HUEX1A11.CEL | FA | B |
| 151801HUEX1A11.CEL | FA | B |
| 151802HUEX1A11.CEL | FA | B |
| 151803HUEX1A11.CEL | FA | B |
| 151804HUEX1A11.CEL | FA | B |
| 151805HUEX1A11.CEL | FA | B |
| 151806HUEX1A11.CEL | FA | B |
| 151285HUEX1A11.CEL | LCT | B |
| 151291HUEX1A11.CEL | LCT | B |
| 151294HUEX1A11.CEL | LCT | B |
| 151295HUEX1A11.CEL | LCT | B |
| 151305HUEX1A11.CEL | LCT | B |
| 151309HUEX1A11.CEL | LCT | B |
| 151316HUEX1A11.CEL | LCT | B |
| 151336HUEX1A11.CEL | LCT | B |
| 151338HUEX1A11.CEL | LCT | B |
| 151373HUEX1A11.CEL | LCT | B |
| 151860HUEX1A11.CEL | LCT | B |

Figure 7

| | | |
|---|---|---|
| 151862HUEX1A11.CEL | LCT | B |
| 151863HUEX1A11.CEL | LCT | B |
| 151864HUEX1A11.CEL | LCT | B |
| 151865HUEX1A11.CEL | LCT | B |
| 151868HUEX1A11.CEL | LCT | B |
| 151871HUEX1A11.CEL | LCT | B |
| 151872HUEX1A11.CEL | LCT | B |
| 151876HUEX1A11.CEL | LCT | B |
| 151881HUEX1A21.CEL | LCT | B |
| 151883HUEX1A11.CEL | LCT | B |
| 151890HUEX1A11.CEL | LCT | B |
| 151895HUEX1A11.CEL | LCT | B |
| 151896HUEX1A11.CEL | LCT | B |
| 151897HUEX1A11.CEL | LCT | B |
| 151899HUEX1A11.CEL | LCT | B |
| 151902HUEX1A11.CEL | LCT | B |
| 151908HUEX1A11.CEL | LCT | B |
| 151909HUEX1A11.CEL | LCT | B |
| 151911HUEX1A11.CEL | LCT | B |
| 151912HUEX1A11.CEL | LCT | B |
| 151913HUEX1A11.CEL | LCT | B |
| 151914HUEX1A11.CEL | LCT | B |
| 151915HUEX1A11.CEL | LCT | B |
| 151916HUEX1A11.CEL | LCT | B |
| 151918HUEX1A11.CEL | LCT | B |
| 151919HUEX1A11.CEL | LCT | B |
| 151920HUEX1A11.CEL | LCT | B |
| 151923HUEX1A11.CEL | LCT | B |
| 151275HUEX1A11.CEL | NHP | B |
| 151283HUEX1A11.CEL | NHP | B |
| 151284HUEX1A11.CEL | NHP | B |
| 151289HUEX1A11.CEL | NHP | B |
| 151293HUEX1A11.CEL | NHP | B |
| 151306HUEX1A11.CEL | NHP | B |

Figure 7 Continued

| | | |
|---|---|---|
| 151308HUEX1A11.CEL | NHP | B |
| 151315HUEX1A11.CEL | NHP | B |
| 151325HUEX1A11.CEL | NHP | B |
| 151330HUEX1A11.CEL | NHP | B |
| 151380HUEX1A11.CEL | NHP | B |
| 151751HUEX1A11.CEL | NHP | B |
| 151752HUEX1A11.CEL | NHP | B |
| 151753HUEX1A11.CEL | NHP | B |
| 151754HUEX1A11.CEL | NHP | B |
| 151757HUEX1A11.CEL | NHP | B |
| 151759HUEX1A11.CEL | NHP | B |
| 151760HUEX1A11.CEL | NHP | B |
| 151762HUEX1A11.CEL | NHP | B |
| 151763HUEX1A11.CEL | NHP | B |
| 151779HUEX1A11.CEL | NHP | B |
| 151787HUEX1A11.CEL | NHP | B |
| 151788HUEX1A11.CEL | NHP | B |
| 151875HUEX1A11.CEL | NHP | B |
| 151340HUEX1A11.CEL | ATC | M |
| 151354HUEX1A11.CEL | ATC | M |
| 151879HUEX1A11.CEL | ATC | M |
| 151886HUEX1A11.CEL | ATC | M |
| 151887HUEX1A11.CEL | ATC | M |
| 151278HUEX1A11.CEL | FC | M |
| 151281HUEX1A11.CEL | FC | M |
| 151317HUEX1A11.CEL | FC | M |
| 151323HUEX1A11.CEL | FC | M |
| 151334HUEX1A11.CEL | FC | M |
| 151362HUEX1A11.CEL | FC | M |
| 151365HUEX1A11.CEL | FC | M |
| 151840HUEX1A21.CEL | FC | M |
| 151842HUEX1A11.CEL | FC | M |
| 151843HUEX1A11.CEL | FC | M |
| 151844HUEX1A11.CEL | FC | M |

Figure 7 Continued

| | | |
|---|---|---|
| 151846HUEX1A11.CEL | FC | M |
| 151847HUEX1A11.CEL | FC | M |
| 151848HUEX1A11.CEL | FC | M |
| 151849HUEX1A11.CEL | FC | M |
| 151851HUEX1A11.CEL | FC | M |
| 151852HUEX1A11.CEL | FC | M |
| 151857HUEX1A11.CEL | FC | M |
| 151859HUEX1A11.CEL | FC | M |
| 151321HUEX1A11.CEL | FVPTC | M |
| 151339HUEX1A11.CEL | FVPTC | M |
| 151341HUEX1A11.CEL | FVPTC | M |
| 151347HUEX1A11.CEL | FVPTC | M |
| 151348HUEX1A11.CEL | FVPTC | M |
| 151358HUEX1A11.CEL | FVPTC | M |
| 151363HUEX1A11.CEL | FVPTC | M |
| 151367HUEX1A11.CEL | FVPTC | M |
| 151368HUEX1A11.CEL | FVPTC | M |
| 151819HUEX1A11.CEL | FVPTC | M |
| 151820HUEX1A11.CEL | FVPTC | M |
| 151824HUEX1A11.CEL | FVPTC | M |
| 151825HUEX1A11.CEL | FVPTC | M |
| 151828HUEX1A11.CEL | FVPTC | M |
| 151829HUEX1A11.CEL | FVPTC | M |
| 151831HUEX1A11.CEL | FVPTC | M |
| 151832HUEX1A11.CEL | FVPTC | M |
| 151834HUEX1A11.CEL | FVPTC | M |
| 151836HUEX1A11.CEL | FVPTC | M |
| 151850HUEX1A11.CEL | FVPTC | M |
| 151856HUEX1A11.CEL | FVPTC | M |
| 151277HUEX1A11.CEL | HC | M |
| 151318HUEX1A11.CEL | HC | M |
| 151352HUEX1A11.CEL | HC | M |
| 151375HUEX1A11.CEL | HC | M |
| 151780HUEX1A11.CEL | HC | M |

Figure 7 Continued

| | | |
|---|---|---|
| 151781HUEX1A11.CEL | HC | M |
| 151782HUEX1A11.CEL | HC | M |
| 151783HUEX1A11.CEL | HC | M |
| 151784HUEX1A11.CEL | HC | M |
| 151785HUEX1A11.CEL | HC | M |
| 151786HUEX1A11.CEL | HC | M |
| 151789HUEX1A11.CEL | HC | M |
| 151791HUEX1A11.CEL | HC | M |
| 151792HUEX1A11.CEL | HC | M |
| 151808HUEX1A11.CEL | HC | M |
| 151809HUEX1A11.CEL | HC | M |
| 151810HUEX1A11.CEL | HC | M |
| 151811HUEX1A11.CEL | HC | M |
| 151812HUEX1A11.CEL | HC | M |
| 151813HUEX1A11.CEL | HC | M |
| 151814HUEX1A11.CEL | HC | M |
| 151861HUEX1A21.CEL | HC | M |
| 151877HUEX1A11.CEL | HC | M |
| 151901HUEX1A11.CEL | HC | M |
| 151906HUEX1A11.CEL | HC | M |
| 151917HUEX1A11.CEL | HC | M |
| 151921HUEX1A11.CEL | HC | M |
| 151300HUEX1A11.CEL | MTC | M |
| 151304HUEX1A11.CEL | MTC | M |
| 151376HUEX1A11.CEL | MTC | M |
| 151773HUEX1A11.CEL | MTC | M |
| 151774HUEX1A11.CEL | MTC | M |
| 151775HUEX1A11.CEL | MTC | M |
| 151776HUEX1A11.CEL | MTC | M |
| 151777HUEX1A11.CEL | MTC | M |
| 151869HUEX1A11.CEL | MTC | M |
| 151874HUEX1A11.CEL | MTC | M |
| 151878HUEX1A11.CEL | MTC | M |
| 151880HUEX1A12.CEL | MTC | M |

Figure 7 Continued

| | | |
|---|---|---|
| 151882HUEX1A11.CEL | MTC | M |
| 151884HUEX1A11.CEL | MTC | M |
| 151888HUEX1A11.CEL | MTC | M |
| 151889HUEX1A11.CEL | MTC | M |
| 151891HUEX1A11.CEL | MTC | M |
| 151892HUEX1A11.CEL | MTC | M |
| 151893HUEX1A11.CEL | MTC | M |
| 151898HUEX1A11.CEL | MTC | M |
| 151903HUEX1A11.CEL | MTC | M |
| 151905HUEX1A11.CEL | MTC | M |
| 151286HUEX1A11.CEL | PTC | M |
| 151288HUEX1A11.CEL | PTC | M |
| 151297HUEX1A11.CEL | PTC | M |
| 151319HUEX1A11.CEL | PTC | M |
| 151320HUEX1A11.CEL | PTC | M |
| 151324HUEX1A11.CEL | PTC | M |
| 151344HUEX1A11.CEL | PTC | M |
| 151346HUEX1A11.CEL | PTC | M |
| 151350HUEX1A11.CEL | PTC | M |
| 151353HUEX1A11.CEL | PTC | M |
| 151379HUEX1A11.CEL | PTC | M |
| 151382HUEX1A12.CEL | PTC | M |
| 151384HUEX1A11.CEL | PTC | M |
| 151816HUEX1A11.CEL | PTC | M |
| 151817HUEX1A11.CEL | PTC | M |
| 151818HUEX1A11.CEL | PTC | M |
| 151821HUEX1A11.CEL | PTC | M |
| 151826HUEX1A11.CEL | PTC | M |
| 151827HUEX1A11.CEL | PTC | M |
| 151833HUEX1A11.CEL | PTC | M |
| 151835HUEX1A11.CEL | PTC | M |
| 151838HUEX1A11.CEL | PTC | M |
| 151839HUEX1A11.CEL | PTC | M |
| 151841HUEX1A11.CEL | PTC | M |

Figure 7 Continued

| | | |
|---|---|---|
| 151866HUEX1A21.CEL | PTC | M |
| 151894HUEX1A11.CEL | PTC | M |

Figure 7 Continued

| CEL File Name | Subtype Pathology | Simplified Pathology |
|---|---|---|
| F0012001 | B | B |
| F0012002 | B | B |
| F0012003 | B | B |
| F0012004 | B | B |
| F0012005 | FA | B |
| F0012006 | FA | B |
| F0012007 | FA | B |
| F0012008 | FA | B |
| F0012009 | FA | B |
| F0012010 | FA | B |
| F0012011 | FA | B |
| F0012012 | FA | B |
| F0012013 | FA | B |
| F0012014 | FA | B |
| F0012015 | FA | B |
| F0012016 | FA | B |
| F0012017 | FC | M |
| F0012018 | FC | M |
| F0012019 | FC | M |
| F0012020 | FC | M |
| F0012021 | FVPTC | M |
| F0012022 | FVPTC | M |
| F0012023 | FVPTC | M |
| F0012024 | HA | B |
| F0012025 | HA | B |
| F0012026 | HA | B |
| F0012027 | HC | M |
| F0012028 | MTC | M |
| F0012029 | NHP | B |
| F0012030 | NHP | B |
| F0012031 | NHP | B |
| F0012032 | NHP | B |
| F0012033 | NHP | B |

Figure 8

| | | |
|---|---|---|
| F0012034 | NHP | B |
| F0012035 | NHP | B |
| F0012036 | NHP | B |
| F0012037 | NHP | B |
| F0012038 | NHP | B |
| F0012039 | NHP | B |
| F0012040 | NHP | B |
| F0012041 | NHP | B |
| F0012042 | NHP | B |
| F0012043 | NHP | B |
| F0012044 | NHP | B |
| F0012045 | NHP | B |
| F0012046 | NHP | B |
| F0012047 | NHP | B |
| F0012048 | NHP | B |
| F0012049 | NHP | B |
| F0012050 | NHP | B |
| F0012051 | NHP | B |
| F0012052 | NHP | B |
| F0012053 | NHP | B |
| F0012054 | PTC | M |
| F0012055 | PTC | M |
| F0012056 | PTC | M |
| F0012057 | PTC | M |
| F0012058 | PTC | M |
| F0012059 | PTC | M |
| F0012060 | PTC | M |
| F0012061 | PTC | M |
| F0012062 | PTC | M |
| F0012063 | PTC | M |
| F0012064 | PTC | M |
| F0012065 | PTC | M |
| F0012066 | PTC | M |
| F0012067 | PTC | M |

Figure 8 Continued

| | | |
|---|---|---|
| F0012068 | PTC | M |
| F0012069 | PTC | M |
| F0012070 | PTC | M |
| F0012071 | PTC | M |
| F0012072 | PTC | M |
| F0012073 | PTC | M |
| F0012074 | PTC | M |

Figure 8 Continued

| Rank | Gene Symbol | TCID | Ref Seq |
|---|---|---|---|
| 1 | SEMA3D | 3059667 | NM_152754 |
| 2 | MT1G | 3692999 | NM_005950 |
| 3 | MGC26647 | 3060450 | BC028365 |
| 4 | CLDN16 | 2657808 | NM_006580 |
| 5 | DPP4 | 2584018 | NM_001935 |
| 6 | LIPH | 2708855 | NM_139248 |
| 7 | TM7SF4 | 3110608 | NM_030788 |
| 8 | RAG2 | 3369931 | NM_000536 |
| 9 | SLC26A4 | 3018605 | NM_000441 |
| 10 | STK32A | 2834282 | NM_001112724 |
| 11 | CD36 | 3010503 | NM_001001548 |
| 12 | PLA2R1 | 2583374 | NM_007366 |
| 13 | ELMO1 | 3046197 | NM_014800 |
| 14 | TCID2526806 | 2526806 | unknown |
| 15 | NELL2 | 3451814 | NM_006159 |
| 16 | CXCL9 | 2773947 | NM_002416 |
| 17 | CYSLTR2 | 3489138 | NM_020377 |
| 18 | LONRF2 | 2567167 | NM_198461 |
| 19 | TMSL8 | 4016193 | NM_021992 |
| 20 | CXCL13 | 2732508 | NM_006419 |
| 21 | RGS13 | 2372812 | NM_002927 |
| 22 | PSD3 | 3126191 | NM_015310 |
| 23 | TNFRSF17 | 3648391 | NM_001192 |
| 24 | TSPAN8 | 3461981 | NM_004616 |
| 25 | CXCL11 | 2773972 | NM_005409 |
| 26 | AIM2 | 2439554 | NM_004833 |
| 27 | ERO1LB | 2462329 | NM_019891 |
| 28 | TRPC5 | 4018327 | NM_012471 |
| 29 | TC2N | 3576704 | NM_152332 |
| 30 | PIP3-E | 2980449 | NM_015553 |
| 31 | ZMAT4 | 3132616 | NM_024645 |
| 32 | PTPRC | 2373842 | NM_002838 |
| 33 | RHOBTB3 | 2820925 | NM_014899 |

Figure 9

| | | | |
|---|---|---|---|
| 34 | TIMP1 | 3976341 | NM_003254 |
| 35 | MPZL2 | 3393720 | NM_144765 |
| 36 | IL7R | 2806468 | NM_002185 |
| 37 | SLC4A4 | 2730746 | NM_001098484 |
| 38 | MYEF2 | 3622934 | NM_016132 |
| 39 | LGALS2 | 3960174 | NM_006498 |
| 40 | KCNA3 | 2427619 | NM_002232 |
| 41 | PDE5A | 2783596 | NM_001083 |
| 42 | COP1 | 3389450 | NM_052889 |
| 43 | ANK2 | 2740067 | NM_001148 |
| 44 | EPS8 | 3445908 | NM_004447 |
| 45 | PLAG1 | 3136178 | NM_002655 |
| 46 | TLR10 | 2766192 | NM_030956 |
| 47 | IGF2BP2 | 2708922 | NM_006548 |
| 48 | PDK4 | 3062082 | NM_002612 |
| 49 | TMEM100 | 3763390 | NM_001099640 |
| 50 | SLC5A8 | 3467949 | NM_145913 |
| 51 | KLRG1 | 3404030 | NM_005810 |
| 52 | CP | 2700244 | NM_000096 |
| 53 | RYR2 | 2387126 | NM_001035 |
| 54 | TMEM171 | 2815220 | NM_173490 |
| 55 | BHLHB2 | 2608725 | NM_003670 |
| 56 | ARNTL | 3321150 | NM_001178 |
| 57 | GBP5 | 2422035 | NM_052942 |
| 58 | CYSLTR1 | 4013460 | NM_006639 |
| 59 | ACBD7 | 3279058 | NM_001039844 |
| 60 | LYPLA1 | 3135567 | NM_006330 |
| 61 | GABBR2 | 3217242 | NM_005458 |
| 62 | ITGA4 | 2518272 | NM_000885 |
| 63 | PLEKHF2 | 3107828 | NM_024613 |
| 64 | LOC401498 | 3166644 | NM_212558 |
| 65 | CASP1 | 3389353 | NM_033292 |
| 66 | MLLT3 | 3200982 | NM_004529 |
| 67 | CMAH | 2945882 | NR_002174 |

Figure 9 Continued

| | | | |
|---|---|---|---|
| 68 | ITPR1 | 2608469 | NM_001099952 |
| 69 | GLDC | 3197955 | NM_000170 |
| 70 | LRRN3 | 3019158 | NM_001099660 |
| 71 | TMEM156 | 2766289 | NM_024943 |
| 72 | ATP8A1 | 2767378 | NM_006095 |
| 73 | CSGALNACT1 | 3126504 | NM_018371 |
| 74 | PYHIN1 | 2362351 | NM_152501 |
| 75 | ZNF208 | 3856646 | ENST00000340708 |
| 76 | DOCK8 | 3159330 | NM_203447 |
| 77 | JAK2 | 3160895 | NM_004972 |
| 78 | SORBS2 | 2796995 | NM_021069 |
| 79 | CD2 | 2353669 | NM_001767 |
| 80 | RHOH | 2724671 | NM_004310 |
| 81 | PLEK | 2486811 | NM_002664 |
| 82 | ABCD2 | 3450861 | NM_005164 |
| 83 | PRICKLE1 | 3451375 | NM_153026 |
| 84 | KLRB1 | 3443804 | NM_002258 |
| 85 | STK17B | 2593159 | NM_004226 |
| 86 | CD69 | 3443868 | NM_001781 |
| 87 | PGCP | 3108226 | NM_016134 |
| 88 | NOD1 | 3044072 | NM_006092 |
| 89 | ENTPD1 | 3259253 | NM_001776 |
| 90 | C1orf34 | 2412312 | NM_001080494 |
| 91 | CCDC146 | 3009838 | NM_020879 |
| 92 | LRRN1 | 2608309 | NM_020873 |
| 93 | C12orf35 | 3410384 | NM_018169 |
| 94 | ANXA1 | 3174816 | NM_000700 |
| 95 | CAMK4 | 2823880 | NM_001744 |
| 96 | EFEMP1 | 2554018 | NM_004105 |
| 97 | SPP1 | 2735027 | NM_001040058 |
| 98 | C17orf87 | 3742627 | AY358809 |
| 99 | SEPP1 | 2855285 | NM_001093726 |
| 100 | PTPN22 | 2428796 | NM_015967 |

Figure 9 Continued

| Rank | Gene Symbol | TCID | P value | Fold Change |
|---|---|---|---|---|
| 1 | SCG3 | 3594003 | 5.77E-85 | 6.20 |
| 2 | SYT4 | 3805614 | 9.65E-75 | 4.17 |
| 3 | SCG2 | 2601230 | 3.63E-74 | 4.42 |
| 4 | DNAJC12 | 3292413 | 5.07E-74 | 3.19 |
| 5 | CHGB | 3875179 | 5.06E-73 | 5.88 |
| 6 | NEFM | 3090436 | 7.29E-71 | 4.39 |
| 7 | INA | 3262129 | 2.30E-70 | 3.95 |
| 8 | KIAA1409 | 3549264 | 3.73E-70 | 2.55 |
| 9 | CALCA | 3364127 | 1.40E-68 | 5.73 |
| 10 | CEACAM5 | 3834341 | 3.01E-67 | 5.55 |
| 11 | ASCL1 | 3429008 | 4.03E-66 | 3.61 |
| 12 | SNAP25 | 3876245 | 1.66E-65 | 3.59 |
| 13 | RAB3C | 2810805 | 3.32E-65 | 3.53 |
| 14 | SCN9A | 2585400 | 7.04E-62 | 3.02 |
| 15 | RGS7 | 2463227 | 2.08E-61 | 1.66 |
| 16 | ST18 | 3135046 | 1.42E-60 | 2.82 |
| 17 | SCGN | 2898934 | 2.82E-60 | 3.54 |
| 18 | PCSK1 | 2868044 | 1.02E-59 | 2.76 |
| 19 | NRXN1 | 2552643 | 2.31E-59 | 2.61 |
| 20 | PRUNE2 | 3210497 | 1.82E-58 | 3.59 |
| 21 | C19orf30 | 3817651 | 3.45E-58 | 2.35 |
| 22 | C6orf117 | 2915571 | 5.01E-58 | 2.60 |
| 23 | SLC2A12 | 2974935 | 6.94E-57 | 2.57 |
| 24 | FMN2 | 2387711 | 1.73E-56 | 3.36 |
| 25 | OR10G9 | 3353876 | 9.70E-56 | 3.20 |
| 26 | NOL4 | 3803628 | 1.75E-54 | 2.87 |
| 27 | JAKMIP2 | 2880361 | 2.69E-54 | 2.35 |
| 28 | DNAJC6 | 2340350 | 3.61E-54 | 1.98 |
| 29 | SYT1 | 3423622 | 4.31E-54 | 3.36 |
| 30 | CYP3A5 | 3063406 | 4.63E-54 | 1.78 |
| 31 | HMP19 | 2841802 | 1.19E-53 | 2.68 |
| 32 | GRP | 3790529 | 1.80E-53 | 2.40 |

Figure 10

| | | | | |
|---|---|---|---|---|
| 33 | RET | 3243846 | 3.10E-53 | 1.51 |
| 34 | KIAA1244 | 2927604 | 9.26E-53 | 1.44 |
| 35 | CNTN1 | 3411721 | 4.37E-52 | 3.20 |
| 36 | GRIA3 | 3989448 | 1.14E-51 | 3.33 |
| 37 | TSHZ2 | 3889419 | 2.00E-51 | 2.79 |
| 38 | PRUNE2 | 3210616 | 2.04E-51 | 3.06 |
| 39 | FSTL5 | 2791894 | 6.58E-51 | 3.82 |
| 40 | EDN3 | 3891447 | 9.93E-51 | 2.76 |
| 41 | LGR5 | 3422144 | 1.11E-50 | 2.72 |
| 42 | PBOV1 | 2976417 | 1.80E-50 | 2.78 |
| 43 | GALNT13 | 2511045 | 2.24E-50 | 3.28 |
| 44 | CADPS | 2679406 | 1.85E-49 | 1.77 |
| 45 | PHYHIPL | 3247977 | 1.88E-49 | 2.51 |
| 46 | GRM8 | 3071063 | 5.28E-49 | 2.00 |
| 47 | CNKSR3 | 2980516 | 2.30E-48 | 1.22 |
| 48 | MEIS2 | 3618333 | 1.00E-47 | 1.99 |
| 49 | HPGD | 2794408 | 2.06E-47 | 3.40 |
| 50 | DCX | 4018218 | 3.69E-47 | 1.72 |
| 51 | CA8 | 3137120 | 4.13E-47 | 1.55 |
| 52 | FGF9 | 3480885 | 5.66E-47 | 2.32 |
| 53 | DNER | 2602770 | 5.94E-47 | 1.12 |
| 54 | NCALD | 3147173 | 9.64E-47 | 2.43 |
| 55 | TMEM16D | 3428333 | 1.65E-46 | 2.58 |
| 56 | AMPH | 3046739 | 4.08E-46 | 1.19 |
| 57 | SLC4A10 | 2512790 | 5.70E-46 | 3.37 |
| 58 | BAALC | 3110217 | 1.01E-45 | 1.31 |
| 59 | TCID2525682 | 2525682 | 3.54E-45 | 1.06 |
| 60 | KCND2 | 3021009 | 2.13E-44 | 2.12 |
| 61 | ADCYAP1 | 3775906 | 2.25E-44 | 1.61 |
| 62 | CACNA2D2 | 2675315 | 3.53E-43 | 1.43 |
| 63 | REST | 2728408 | 4.17E-43 | -1.61 |
| 64 | PCDHB10 | 2832423 | 8.03E-43 | 1.94 |
| 65 | TMEM196 | 3040465 | 8.87E-43 | 2.51 |
| 66 | BMP5 | 2958172 | 1.37E-42 | 3.04 |

Figure 10 Continued

| | | | | |
|---|---|---|---|---|
| 67 | SEMA3E | 3059393 | 1.70E-42 | 3.94 |
| 68 | PPFIA2 | 3463821 | 1.83E-42 | 2.46 |
| 69 | GRIA2 | 2749222 | 7.09E-42 | 2.32 |
| 70 | CACNG2 | 3959787 | 8.76E-42 | 1.90 |
| 71 | PRKAR2B | 3018375 | 1.91E-41 | 2.78 |
| 72 | KCNB2 | 3103062 | 6.57E-41 | 1.26 |
| 73 | PACRG | 2935311 | 8.69E-41 | 1.64 |
| 74 | HMGCLL1 | 2958117 | 1.08E-40 | 1.83 |
| 75 | WASF1 | 2969289 | 2.12E-40 | 1.78 |
| 76 | CNTNAP2 | 3029900 | 5.87E-40 | 1.54 |
| 77 | DDC | 3050388 | 5.92E-40 | 1.24 |
| 78 | FGF14 | 3523499 | 8.04E-40 | 1.77 |
| 79 | NEFL | 3128271 | 9.05E-40 | 1.89 |
| 80 | MAP1B | 2814756 | 6.91E-39 | 2.48 |
| 81 | CPLX2 | 2842255 | 9.32E-39 | 1.03 |
| 82 | FMO5 | 2433232 | 1.57E-38 | 2.36 |
| 83 | CHGA | 3549092 | 2.07E-38 | 1.05 |
| 84 | CEACAM6 | 3834379 | 2.57E-38 | 3.14 |
| 85 | CHST9 | 3802416 | 2.96E-38 | 2.39 |
| 86 | PON3 | 3061964 | 5.03E-38 | 2.97 |
| 87 | TSHR | 3546213 | 5.91E-38 | -4.16 |
| 88 | DNAH5 | 2849056 | 1.67E-37 | 1.66 |
| 89 | GAP43 | 2637112 | 1.91E-37 | 2.66 |
| 90 | GCH1 | 3565524 | 5.81E-37 | 2.77 |
| 91 | KCNH8 | 2613293 | 9.06E-37 | 1.04 |
| 92 | TFF1 | 3933559 | 2.55E-36 | 2.60 |
| 93 | PCDHB4 | 2832315 | 2.72E-36 | 1.74 |
| 94 | KCNJ15 | 3920850 | 3.35E-36 | -2.85 |
| 95 | PON1 | 3061942 | 4.75E-36 | 1.61 |
| 96 | RIMS2 | 3110395 | 8.47E-36 | 3.17 |
| 97 | TXNDC13 | 3896976 | 1.11E-35 | 1.77 |
| 98 | GPX2 | 3568603 | 1.16E-35 | 2.28 |
| 99 | NKAIN2 | 2924081 | 1.40E-35 | 2.01 |
| 100 | TMOD1 | 3181240 | 1.40E-35 | 2.35 |

Figure 10 Continued

| Rank | Gene Symbol | TCID | Ref Seq |
|---|---|---|---|
| 1 | NRCAM | 3067478 | NM_001037132 |
| 2 | DOCK9 | 3522398 | NM_015296 |
| 3 | CAMK2N1 | 2400177 | NM_018584 |
| 4 | C6orf168 | 2966193 | NM_032511 |
| 5 | SCEL | 3494629 | NM_144777 |
| 6 | SIPA1L2 | 2460817 | NM_020808 |
| 7 | IL1RAP | 2657831 | NM_002182 |
| 8 | PPM2C | 3107342 | NM_018444 |
| 9 | RHOBTB3 | 2820925 | NM_014899 |
| 10 | AMOT | 4018454 | NM_133265 |
| 11 | SDC4 | 3907234 | NM_002999 |
| 12 | MET | 3020343 | NM_001127500 |
| 13 | DCBLD2 | 2686023 | NM_080927 |
| 14 | SYTL5 | 3973891 | NM_138780 |
| 15 | AHNAK2 | 3581221 | NM_138420 |
| 16 | MYH10 | 3744463 | NM_005964 |
| 17 | TCID2526806 | 2526806 | unknown |
| 18 | TACSTD2 | 2414958 | NM_002353 |
| 19 | PROS1 | 2685304 | NM_000313 |
| 20 | ERBB3 | 3417249 | NM_001982 |
| 21 | EPS8 | 3445908 | NM_004447 |
| 22 | XPR1 | 2370123 | NM_004736 |
| 23 | KRT19 | 3757108 | NM_002276 |
| 24 | 7A5 | 3040518 | NM_182762 |
| 25 | FN1 | 2598261 | NM_212482 |
| 26 | GABBR2 | 3217242 | NM_005458 |
| 27 | TRAK2 | 2594812 | NM_015049 |
| 28 | GABRB2 | 2884845 | NM_021911 |
| 29 | GALNT7 | 2751936 | NM_017423 |
| 30 | IGFBP6 | 3415744 | NM_002178 |
| 31 | NELL2 | 3451814 | NM_006159 |
| 32 | SGEF | 2648535 | NM_015595 |
| 33 | SLC47A1 | 3713951 | NM_018242 |

Figure 11

| | | | |
|---|---|---|---|
| 34 | PDZRN4 | 3411810 | NM_013377 |
| 35 | MPZL2 | 3393720 | NM_144765 |
| 36 | CMYA5 | 2817464 | NM_153610 |
| 37 | ARMCX6 | 4015838 | NM_019007 |
| 38 | SLC34A2 | 2721959 | NM_006424 |
| 39 | MPPED2 | 3367673 | NM_001584 |
| 40 | TUSC3 | 3087167 | NM_006765 |
| 41 | DTNA | 3784208 | NM_032975 |
| 42 | FAM176A | 2560625 | NM_032181 |
| 43 | C5orf28 | 2855578 | BC013351 |
| 44 | CYSLTR2 | 3489138 | NM_020377 |
| 45 | S100A5 | 4045589 | NM_002962 |
| 46 | PDE5A | 2783596 | NM_001083 |
| 47 | KCNJ2 | 3733275 | NM_000891 |
| 48 | AK1 | 3226138 | NM_000476 |
| 49 | LIPH | 2708855 | NM_139248 |
| 50 | MPP7 | 3282601 | NM_173496 |
| 51 | CSNK1G3 | 2826550 | NM_004384 |
| 52 | ZCCHC16 | 3987607 | NM_001004308 |
| 53 | PSD3 | 3126191 | NM_015310 |
| 54 | BHLHB2 | 2608725 | NM_003670 |
| 55 | EGFR | 3002640 | NM_005228 |
| 56 | SERPINA1 | 3577612 | NM_001002236 |
| 57 | ITGA3 | 3726154 | NM_002204 |
| 58 | CSGALNACT1 | 3126504 | NM_018371 |
| 59 | CHI3L1 | 2451593 | NM_001276 |
| 60 | METTL7B | 3416895 | NM_152637 |
| 61 | TGFA | 2558612 | NM_003236 |
| 62 | NAB2 | 3417809 | NM_005967 |
| 63 | NFATC3 | 3666033 | NM_173163 |
| 64 | NPC2 | 3571904 | NM_006432 |
| 65 | GGCT | 3044129 | ENST00000275428 |
| 66 | TPO | 2466554 | NM_000547 |
| 67 | HGD | 4047070 | NM_000187 |

Figure 11 Continued

| | | | |
|---|---|---|---|
| 68 | GIMAP5 | 3031573 | NM_018384 |
| 69 | PKHD1L1 | 3111561 | NM_177531 |
| 70 | ALDH3A2 | 3714068 | NM_001031806 |
| 71 | PRR15 | 2994981 | NM_175887 |
| 72 | HRASLS3 | 3376529 | NM_007069 |
| 73 | ZCCHC12 | 3988596 | NM_173798 |
| 74 | STK32A | 2834282 | NM_001112724 |
| 75 | ANK2 | 2740067 | NM_001148 |
| 76 | SORBS2 | 2796995 | NM_021069 |
| 77 | ITGA2 | 2809245 | NM_002203 |
| 78 | MYEF2 | 3622934 | NM_016132 |
| 79 | SYNE1 | 2979871 | NM_182961 |
| 80 | PLEKHA4 | 3867458 | NM_020904 |
| 81 | PLCD3 | 3759587 | NM_133373 |
| 82 | LAMB3 | 2453793 | NM_001017402 |
| 83 | FAM43A | 2658785 | NM_153690 |
| 84 | TPD52L1 | 2924330 | NM_001003395 |
| 85 | CLDN1 | 2710599 | NM_021101 |
| 86 | B3GNT3 | 3824596 | NM_014256 |
| 87 | KIAA1217 | 3238962 | NM_019590 |
| 88 | MAP2 | 2525533 | NM_002374 |
| 89 | LRP1B | 2578790 | NM_018557 |
| 90 | ITPR1 | 2608469 | NM_001099952 |
| 91 | CARD8 | 3866958 | NM_014959 |
| 92 | DGKI | 3074912 | NM_004717 |
| 93 | LIFR | 2854092 | NM_002310 |
| 94 | DOCK8 | 3159330 | NM_203447 |
| 95 | C9orf61 | 3173974 | NM_004816 |
| 96 | GPR98 | 2819779 | NM_032119 |
| 97 | TFF3 | 3933536 | NM_003226 |
| 98 | ERO1LB | 2462329 | NM_019891 |
| 99 | ARHGAP24 | 2734421 | NM_001025616 |
| 100 | CDON | 3396770 | NM_016952 |
| 101 | TBC1D4 | 3518086 | NM_014832 |

Figure 11 Continued

| 102 | LRP2 | 2586038 | NM_004525 |

Figure 11 Continued

| Rank | Gene Symbol | TCID |
|---|---|---|
| 1 | TGFA | 2558612 |
| 2 | PROS1 | 2685304 |
| 3 | MET | 3020343 |
| 4 | DPP4 | 2584018 |
| 5 | GALNT7 | 2751936 |
| 6 | TPO | 2466554 |
| 7 | SDC4 | 3907234 |
| 8 | FABP4 | 3142381 |
| 9 | KIT | 2727587 |
| 10 | ELMO1 | 3046197 |
| 11 | CDH3 | 3666366 |
| 12 | CAMK2N1 | 2400177 |
| 13 | KRT19 | 3757108 |
| 14 | SCEL | 3494629 |
| 15 | TFF3 | 3933536 |
| 16 | LRP1B | 2578790 |
| 17 | CITED1 | 4012178 |
| 18 | PLA2R1 | 2583374 |
| 19 | STK32A | 2834282 |
| 20 | IL1RAP | 2657831 |
| 21 | LGALS3 | 3536706 |
| 22 | GPR155 | 2587790 |
| 23 | MPPED2 | 3367673 |
| 24 | C6orf168 | 2966193 |
| 25 | METTL7B | 3416895 |
| 26 | NPC2 | 3571904 |
| 27 | NAB2 | 3417809 |
| 28 | KHDRBS2 | 2959039 |
| 29 | LIPH | 2708855 |
| 30 | CXorf27 | 3973891 |
| 31 | FN1 | 2598261 |
| 32 | EPS8 | 3445908 |
| 33 | ZMAT4 | 3132616 |

Figure 12

| | | |
|---|---|---|
| 34 | SLC26A4 | 3018605 |
| 35 | TNFRSF11B | 3150455 |
| 36 | ANGPTL1 | 2445982 |
| 37 | NFATC3 | 3666033 |
| 38 | ITPR1 | 2608469 |
| 39 | GABRB2 | 2884845 |
| 40 | TBC1D4 | 3518086 |
| 41 | SCG5 | 3587495 |
| 42 | CYP1B1 | 2548699 |
| 43 | HMGA2 | 3420316 |
| 44 | TC2N | 3576704 |
| 45 | ATP10D | 2726072 |
| 46 | RAG2 | 3369931 |
| 47 | DUSP6 | 3464860 |
| 48 | ERO1LB | 2462329 |
| 49 | SCNN1A | 3441885 |
| 50 | ABCC3 | 3726691 |
| 51 | ARHGAP24 | 2734421 |
| 52 | SEMA3D | 3059667 |
| 53 | CHI3L1 | 2451593 |
| 54 | SPOCK1 | 2876897 |
| 55 | PDE5A | 2783596 |
| 56 | MYH10 | 3744463 |
| 57 | SERPINA1 | 3577612 |
| 58 | SIPA1L2 | 2460817 |
| 59 | ITM2A | 4013549 |
| 60 | TNFAIP8 | 2825629 |
| 61 | MYEF2 | 3622934 |
| 62 | KCNJ2 | 3733275 |
| 63 | CRABP1 | 3603295 |
| 64 | MATN2 | 3108526 |
| 65 | CLDN16 | 2657808 |
| 66 | NRCAM | 3067478 |
| 67 | HEY2 | 2924492 |

Figure 12 Continued

| | | |
|---|---|---|
| 68 | PTTG1 | 2838201 |
| 69 | SPINT1 | 3590164 |
| 70 | CDC27 | 3760625 |
| 71 | NOD1 | 3044072 |
| 72 | KPNA5 | 2922840 |
| 73 | DYNLT1 | 2981874 |
| 74 | ODZ1 | 4020655 |
| 75 | GABBR2 | 3217242 |
| 76 | SLC33A1 | 2701927 |
| 77 | UPP1 | 3000953 |
| 78 | AUTS2 | 3006572 |
| 79 | SLC34A2 | 2721959 |
| 80 | MFGE8 | 3638204 |
| 81 | RXRG | 2442008 |
| 82 | KLF8 | 3978943 |
| 83 | ANK2 | 2740067 |
| 84 | TM7SF4 | 3110608 |
| 85 | ZCCHC16 | 3987607 |
| 86 | FNDC4 | 2545953 |
| 87 | GLT8D2 | 3468888 |
| 88 | GDF15 | 3824993 |
| 89 | GIMAP8 | 3031466 |
| 90 | MAP2 | 2525533 |
| 91 | TIMP1 | 3976341 |
| 92 | PGCP | 3108226 |
| 93 | KLK7 | 3868783 |
| 94 | DNASE1L3 | 2678298 |
| 95 | ANKRD12 | 3778252 |
| 96 | CLDN1 | 2710599 |
| 97 | SERINC2 | 2328273 |
| 98 | HSD17B6 | 3417703 |
| 99 | TSC22D1 | 3512294 |
| 100 | TRPC5 | 4018327 |

Figure 12 Continued

| TCID | Gene_Symbol | Subtype 1 | Subtype 2 | Subtype 3 |
|---|---|---|---|---|
| 3132616 | ZMAT4 | FA_FVPTC | FA_PTC | FVPTC_NHP |
| 2809793 | GZMK | FC_LCT | FVPTC_LCT | HC_LCT |
| 3444086 | KLRK1 | FC_LCT | FVPTC_LCT | HC_LCT |
| 2959039 | KHDRBS2 | FA_FC | FA_HC | HC_NHP |
| 2657808 | CLDN16 | FA_FC | FA_PTC | LCT_PTC |
| 4020655 | ODZ1 | FA_FC | FVPTC_LCT | LCT_PTC |
| 3692999 | MT1G | FA_MTC | FA_PTC | MTC_NHP |
| 2710599 | CLDN1 | FA_FC | FA_PTC | NHP_PTC |
| 3536706 | LGALS3 | FA_FVPTC | FA_PTC | NHP_PTC |
| 3577612 | SERPINA1 | FA_FVPTC | FA_PTC | NHP_PTC |
| 2727587 | KIT | FA_FVPTC | FVPTC_NHP | NHP_PTC |
| 3367673 | MPPED2 | FA_PTC | FVPTC_NHP | NHP_PTC |
| 2884845 | GABRB2 | FA_PTC | LCT_PTC | NHP_PTC |
| 2685304 | PROS1 | FA_PTC | LCT_PTC | NHP_PTC |
| 3564210 | PYGL | ATC_FA | ATC_LCT | |
| 3168508 | MELK | ATC_FA | ATC_NHP | |
| 3913483 | TCFL5 | FA_FC | FA_FVPTC | |
| 3726691 | ABCC3 | FA_FC | FA_PTC | |
| 3662201 | MT1H | FA_FC | FA_PTC | |
| 3369931 | RAG2 | FA_FC | FA_PTC | |
| 2573570 | TFCP2L1 | FA_FC | FA_PTC | |
| 2466554 | TPO | FA_FC | FA_PTC | |
| 3944404 | APOL1 | FA_FVPTC | FA_PTC | |
| 3451814 | NELL2 | FA_FVPTC | FA_PTC | |
| 3592214 | DUOX1 | FA_HC | FVPTC_LCT | |
| 2809810 | GZMA | FC_LCT | FVPTC_LCT | |
| 3018605 | SLC26A4 | FA_FC | FVPTC_NHP | |
| 3755862 | IKZF3 | FA_PTC | HC_LCT | |
| 2373842 | PTPRC | FC_LCT | HC_LCT | |
| 3443891 | CLEC2B | FVPTC_LCT | HC_LCT | |
| 3031556 | GIMAP2 | FVPTC_LCT | HC_LCT | |
| 3031517 | GIMAP7 | FVPTC_LCT | HC_LCT | |
| 3160895 | JAK2 | FVPTC_LCT | HC_LCT | |

Figure 13

| | | | |
|---|---|---|---|
| 3666033 | NFATC3 | FVPTC_LCT | HC_LCT |
| 3417703 | HSD17B6 | FA_HC | HC_NHP |
| 3875179 | CHGB | FA_MTC | LCT_MTC |
| 2834282 | STK32A | FA_FC | LCT_PTC |
| 2751936 | GALNT7 | FA_PTC | LCT_PTC |
| 2708855 | LIPH | FA_PTC | LCT_PTC |
| 3393720 | MPZL2 | FA_PTC | LCT_PTC |
| 3464860 | DUSP6 | FVPTC_LCT | LCT_PTC |
| 3416895 | METTL7B | FVPTC_LCT | LCT_PTC |
| 2711225 | ATP13A4 | FVPTC_LCT | MTC_NHP |
| 3364127 | CALCA | LCT_MTC | MTC_NHP |
| 2526806 | 2526806 | FA_PTC | NHP_PTC |
| 3430462 | BTBD11 | FA_PTC | NHP_PTC |
| 3086809 | C8orf79 | FA_PTC | NHP_PTC |
| 3396770 | CDON | FA_PTC | NHP_PTC |
| 2584018 | DPP4 | FA_PTC | NHP_PTC |
| 2598261 | FN1 | FA_PTC | NHP_PTC |
| 2378068 | G0S2 | FA_PTC | NHP_PTC |
| 3925639 | NRIP1 | FA_PTC | NHP_PTC |
| 3270270 | PTPRE | FA_PTC | NHP_PTC |
| 2721959 | SLC34A2 | FA_PTC | NHP_PTC |
| 2730746 | SLC4A4 | FA_PTC | NHP_PTC |
| 2796995 | SORBS2 | FA_PTC | NHP_PTC |
| 3976341 | TIMP1 | FA_PTC | NHP_PTC |
| 2455933 | ESRRG | FVPTC_NHP | NHP_PTC |
| 2819779 | GPR98 | FVPTC_NHP | NHP_PTC |
| 2578790 | LRP1B | FVPTC_NHP | NHP_PTC |
| 2586038 | LRP2 | FVPTC_NHP | NHP_PTC |
| 3108526 | MATN2 | FVPTC_NHP | NHP_PTC |
| 4014029 | RPS6KA6 | FVPTC_NHP | NHP_PTC |
| 2961177 | COL12A1 | ATC_LCT | |
| 3590014 | CASC5 | ATC_NHP | |
| 3258444 | CEP55 | ATC_NHP | |
| 3565663 | DLG7 | ATC_NHP | |

Figure 13 Continued

| | | |
|---|---|---|
| 2838656 | HMMR | ATC_NHP |
| 3258168 | KIF11 | ATC_NHP |
| 3312490 | MKI67 | ATC_NHP |
| 3776139 | NDC80 | ATC_NHP |
| 3590388 | NUSAP1 | ATC_NHP |
| 3881443 | TPX2 | ATC_NHP |
| 2406391 | 2406391 | FA_FC |
| 2445982 | ANGPTL1 | FA_FC |
| 3459722 | AVPR1A | FA_FC |
| 3124344 | C8orf15 | FA_FC |
| 3107234 | C8orf39 | FA_FC |
| 3010503 | CD36 | FA_FC |
| 3580769 | CKB | FA_FC |
| 3603295 | CRABP1 | FA_FC |
| 2336891 | DIO1 | FA_FC |
| 3384704 | DLG2 | FA_FC |
| 2678298 | DNASE1L3 | FA_FC |
| 2981874 | DYNLT1 | FA_FC |
| 3008144 | EIF4H | FA_FC |
| 2462329 | ERO1LB | FA_FC |
| 4027639 | F8 | FA_FC |
| 3142381 | FABP4 | FA_FC |
| 3576749 | FBLN5 | FA_FC |
| 3937967 | FLJ26056 | FA_FC |
| 3393479 | FXYD6 | FA_FC |
| 3197140 | GLIS3 | FA_FC |
| 3250278 | HK1 | FA_FC |
| 2770469 | IGFBP7 | FA_FC |
| 2452440 | KLHDC8A | FA_FC |
| 3067302 | LAMB1 | FA_FC |
| 2854092 | LIFR | FA_FC |
| 3745525 | LOC388335 | FA_FC |
| 3244055 | LOC439911 | FA_FC |
| 3788097 | MAPK4 | FA_FC |

Figure 13 Continued

| | | |
|---|---|---|
| 2581000 | NEB | FA_FC |
| 2980449 | PIP3-E | FA_FC |
| 2955827 | PLA2G7 | FA_FC |
| 3009229 | POR | FA_FC |
| 2349848 | PRMT6 | FA_FC |
| 3555675 | RNASE1 | FA_FC |
| 2984884 | RNASET2 | FA_FC |
| 3363868 | RRAS2 | FA_FC |
| 3899173 | RRBP1 | FA_FC |
| 2387126 | RYR2 | FA_FC |
| 3365136 | SERGEF | FA_FC |
| 2529421 | SGPP2 | FA_FC |
| 3921442 | SH3BGR | FA_FC |
| 2319340 | SLC25A33 | FA_FC |
| 3114832 | SQLE | FA_FC |
| 2932508 | TIAM2 | FA_FC |
| 3943504 | TIMP3 | FA_FC |
| 3388438 | TRPC6 | FA_FC |
| 2538480 | TSSC1 | FA_FC |
| 3441941 | VAMP1 | FA_FC |
| 2331558 | BMP8A | FA_HC |
| 2648991 | KCNAB1 | FA_HC |
| 2931172 | IYD | FA_MTC |
| 3661718 | LPCAT2 | FA_MTC |
| 3889419 | TSHZ2 | FA_MTC |
| 3040518 | 7A5 | FA_PTC |
| 2991233 | AHR | FA_PTC |
| 3244622 | ALOX5 | FA_PTC |
| 3627248 | ANXA2 | FA_PTC |
| 3848039 | C3 | FA_PTC |
| 2739160 | CCDC109B | FA_PTC |
| 2902844 | CFB | FA_PTC |
| 2451593 | CHI3L1 | FA_PTC |
| 3129065 | CLU | FA_PTC |

Figure 13 Continued

| | | |
|---|---|---|
| 3335894 | CST6 | FA_PTC |
| 3385769 | CTSC | FA_PTC |
| 3634811 | CTSH | FA_PTC |
| 2773434 | CXCL2 | FA_PTC |
| 3973891 | CXorf27 | FA_PTC |
| 2548699 | CYP1B1 | FA_PTC |
| 3489138 | CYSLTR2 | FA_PTC |
| 3768535 | FAM20A | FA_PTC |
| 3306984 | GPAM | FA_PTC |
| 3727583 | HLF | FA_PTC |
| 3820443 | ICAM1 | FA_PTC |
| 3415744 | IGFBP6 | FA_PTC |
| 2657831 | IL1RAP | FA_PTC |
| 3787187 | KATNAL2 | FA_PTC |
| 2764192 | KIAA0746 | FA_PTC |
| 3978943 | KLF8 | FA_PTC |
| 3757108 | KRT19 | FA_PTC |
| 2634091 | NFKBIZ | FA_PTC |
| 2639054 | PARP14 | FA_PTC |
| 3111561 | PKHD1L1 | FA_PTC |
| 3977067 | PLP2 | FA_PTC |
| 3426502 | PLXNC1 | FA_PTC |
| 3930360 | RUNX1 | FA_PTC |
| 2908762 | RUNX2 | FA_PTC |
| 3106559 | SLC26A7 | FA_PTC |
| 2827645 | SLC27A6 | FA_PTC |
| 3907190 | SLPI | FA_PTC |
| 2491271 | TMSB10 | FA_PTC |
| 2353669 | CD2 | FC_LCT |
| 2440354 | CD48 | FC_LCT |
| 2326463 | CD52 | FC_LCT |
| 2773947 | CXCL9 | FC_LCT |
| 2854327 | FYB | FC_LCT |
| 2903401 | HLA-DPB1 | FC_LCT |

Figure 13 Continued

| | | |
|---|---|---|
| 3315675 | IFITM1 | FC_LCT |
| 2772566 | IGJ | FC_LCT |
| 2563785 | IGK@ | FC_LCT |
| 3512874 | LCP1 | FC_LCT |
| 3421511 | LYZ | FC_LCT |
| 2519480 | GULP1 | FC_NHP |
| 3110789 | ZFPM2 | FC_NHP |
| 3288518 | C10orf72 | FVPTC_LCT |
| 3410384 | C12orf35 | FVPTC_LCT |
| 3338192 | CCND1 | FVPTC_LCT |
| 3622239 | DUOXA1 | FVPTC_LCT |
| 3217242 | GABBR2 | FVPTC_LCT |
| 2587790 | GPR155 | FVPTC_LCT |
| 3482888 | GTF3A | FVPTC_LCT |
| 3323052 | NAV2 | FVPTC_LCT |
| 2562529 | ST3GAL5 | FVPTC_LCT |
| 2825629 | TNFAIP8 | FVPTC_LCT |
| 2705706 | TNFSF10 | FVPTC_LCT |
| 2448971 | UCHL5 | FVPTC_LCT |
| 2740067 | ANK2 | FVPTC_NHP |
| 3802396 | AQP4 | FVPTC_NHP |
| 2515183 | C2orf37 | FVPTC_NHP |
| 2855578 | C5orf28 | FVPTC_NHP |
| 2742581 | FAT4 | FVPTC_NHP |
| 2726542 | FLJ21511 | FVPTC_NHP |
| 2583374 | PLA2R1 | FVPTC_NHP |
| 2699623 | PLSCR4 | FVPTC_NHP |
| 3513549 | RCBTB2 | FVPTC_NHP |
| 2336539 | ZYG11A | FVPTC_NHP |
| 2439554 | AIM2 | HC_LCT |
| 3945651 | APOBEC3G | HC_LCT |
| 3302187 | ARHGAP19 | HC_LCT |
| 3267314 | BAG3 | HC_LCT |
| 3635198 | BCL2A1 | HC_LCT |

Figure 13 Continued

| | | |
|---|---|---|
| 3866958 | CARD8 | HC_LCT |
| 3389353 | CASP1 | HC_LCT |
| 3393744 | CD3D | HC_LCT |
| 2635741 | CD96 | HC_LCT |
| 3187577 | CEP110 | HC_LCT |
| 3815399 | CNN2 | HC_LCT |
| 3629811 | DENND4A | HC_LCT |
| 3159330 | DOCK8 | HC_LCT |
| 2424524 | DPYD | HC_LCT |
| 2739308 | EGF | HC_LCT |
| 2997907 | EPDR1 | HC_LCT |
| 3397589 | ETS1 | HC_LCT |
| 2422035 | GBP5 | HC_LCT |
| 3031573 | GIMAP5 | HC_LCT |
| 3982612 | GPR174 | HC_LCT |
| 2362394 | IFI16 | HC_LCT |
| 3918447 | IFNAR2 | HC_LCT |
| 2806468 | IL7R | HC_LCT |
| 4013549 | ITM2A | HC_LCT |
| 3404030 | KLRG1 | HC_LCT |
| 2508520 | KYNU | HC_LCT |
| 2531310 | LOC93349 | HC_LCT |
| 4037595 | ND1 | HC_LCT |
| 3256590 | PAPSS2 | HC_LCT |
| 3772525 | PSCD1 | HC_LCT |
| 2362351 | PYHIN1 | HC_LCT |
| 2592356 | STAT4 | HC_LCT |
| 3576704 | TC2N | HC_LCT |
| 3176209 | TLE4 | HC_LCT |
| 2579572 | ZEB2 | HC_LCT |
| 3319898 | ZNF143 | HC_LCT |
| 3197231 | C9orf68 | HC_NHP |
| 2750627 | CPE | HC_NHP |
| 3108226 | PGCP | HC_NHP |

Figure 13 Continued

| | | |
|---|---|---|
| 3301713 | BLNK | LCT_MTC |
| 3110395 | RIMS2 | LCT_MTC |
| 3594003 | SCG3 | LCT_MTC |
| 2966193 | C6orf168 | LCT_PTC |
| 3445908 | EPS8 | LCT_PTC |
| 2708922 | IGF2BP2 | LCT_PTC |
| 3126191 | PSD3 | LCT_PTC |
| 3183757 | RAD23B | LCT_PTC |
| 2711205 | ATP13A4 | MTC_NHP |
| 3486096 | FREM2 | MTC_NHP |
| 2734421 | ARHGAP24 | NHP_PTC |
| 2763278 | GPR125 | NHP_PTC |
| 3625271 | RAB27A | NHP_PTC |
| 3059667 | SEMA3D | NHP_PTC |

Figure 13 Continued

| Sample ID | Sample Type | Subtype Pathology | Simplified Pathology |
|---|---|---|---|
| A0017251 | FNA | FA | B |
| A0017252 | FNA | FA | B |
| A0017255 | FNA | FA | B |
| A0017256 | FNA | FA | B |
| A0017264 | FNA | FA | B |
| A0017267 | FNA | FA | B |
| A0017272 | FNA | FA | B |
| A0017285 | FNA | FA | B |
| A0017289 | FNA | FA | B |
| A0017291 | FNA | FA | B |
| A0017292 | FNA | FA | B |
| A0017298 | FNA | FA | B |
| A0017978 | FNA | FA | B |
| A0017986 | FNA | FA | B |
| A0017987 | FNA | FA | B |
| A0017989 | FNA | FA | B |
| A0017991 | FNA | FA | B |
| A0017995 | FNA | FA | B |
| A0018000 | FNA | FA | B |
| A0018004 | FNA | FA | B |
| A0018006 | FNA | FA | B |
| A0018008 | FNA | FA | B |
| A0018010 | FNA | FA | B |
| A0018011 | FNA | FA | B |
| A0018018 | FNA | FA | B |
| A0017258 | FNA | NHP | B |
| A0017265 | FNA | NHP | B |
| A0017271 | FNA | NHP | B |
| A0017275 | FNA | NHP | B |
| A0017276 | FNA | NHP | B |
| A0017278 | FNA | NHP | B |
| A0017280 | FNA | NHP | B |

Figure 14

| | | | |
|---|---|---|---|
| A0017295 | FNA | NHP | B |
| A0017296 | FNA | NHP | B |
| A0017297 | FNA | NHP | B |
| A0017299 | FNA | NHP | B |
| A0017979 | FNA | NHP | B |
| A0017980 | FNA | NHP | B |
| A0017983 | FNA | NHP | B |
| A0017984 | FNA | NHP | B |
| A0017985 | FNA | NHP | B |
| A0017988 | FNA | NHP | B |
| A0017993 | FNA | NHP | B |
| A0017994 | FNA | NHP | B |
| A0017997 | FNA | NHP | B |
| A0017998 | FNA | NHP | B |
| A0018009 | FNA | NHP | B |
| A0018020 | FNA | NHP | B |
| A0018021 | FNA | NHP | B |
| A0018022 | FNA | NHP | B |
| A0017270 | FNA | FC | M |
| A0017294 | FNA | FC | M |
| A0017981 | FNA | FC | M |
| A0018016 | FNA | FC | M |
| A0018023 | FNA | FC | M |
| A0018025 | FNA | FC | M |
| A0017269 | FNA | FVPTC | M |
| A0017279 | FNA | FVPTC | M |
| A0017982 | FNA | FVPTC | M |
| A0017999 | FNA | FVPTC | M |
| A0017268 | FNA | MTC | M |
| A0017250 | FNA | PTC | M |
| A0017253 | FNA | PTC | M |
| A0017254 | FNA | PTC | M |
| A0017257 | FNA | PTC | M |
| A0017266 | FNA | PTC | M |

Figure 14 Continued

| | | | |
|---|---|---|---|
| A0017273 | FNA | PTC | M |
| A0017274 | FNA | PTC | M |
| A0017281 | FNA | PTC | M |
| A0017282 | FNA | PTC | M |
| A0017284 | FNA | PTC | M |
| A0017286 | FNA | PTC | M |
| A0017290 | FNA | PTC | M |
| A0017293 | FNA | PTC | M |
| A0017990 | FNA | PTC | M |
| A0017992 | FNA | PTC | M |
| A0017996 | FNA | PTC | M |
| A0018001 | FNA | PTC | M |
| A0018002 | FNA | PTC | M |
| A0018003 | FNA | PTC | M |
| A0018005 | FNA | PTC | M |
| A0018007 | FNA | PTC | M |
| A0018012 | FNA | PTC | M |
| A0018014 | FNA | PTC | M |
| A0018015 | FNA | PTC | M |
| A0018017 | FNA | PTC | M |
| A0018019 | FNA | PTC | M |
| A0018024 | FNA | PTC | M |
| A0018027 | FNA | PTC | M |

Figure 14 Continued

| Sample ID | Sample Type | Subtype | Simplified Pathology |
|---|---|---|---|
| miR101 | FNA | PTC | M |
| miR102 | FNA | NHP | B |
| miR103 | FNA | PTC | M |
| miR104 | FNA | BN | B |
| miR105 | FNA | BN | B |
| miR106 | FNA | LCT | B |
| miR107 | FNA | LCT | B |
| miR108 | FNA | BN | B |
| miR109 | FNA | PTC | M |
| miR110 | FNA | FVPTC | M |
| miR111 | FNA | LCT | B |
| miR112 | FNA | PTC | M |
| miR113 | FNA | BN | B |
| miR114 | FNA | NHP | B |
| miR115 | FNA | CN | B |
| miR116 | FNA | B | B |
| miR117 | FNA | NHP | B |
| miR118 | FNA | CN | B |
| miR119 | FNA | PTC | M |
| miR120 | FNA | PTC | M |
| miR121 | FNA | non-diagnostic | non-diagnostic |
| miR122 | FNA | NHP | B |
| miR123 | FNA | NHP | B |
| miR124 | FNA | NHP | B |

Figure 15

| miRNA | CHR | P | DE |
|---|---|---|---|
| hsa-miR-127-5p | 14 | 0.0011 | -1 |
| hsa-miR-154 | 14 | 0.0032 | -1 |
| hsa-miR-29b-1* | 7 | 0.0311 | -1 |
| hsa-miR-220a | X | 0.0347 | -1 |
| hsa-miR-370 | 14 | 0.0779 | -1 |
| hsa-miR-96* | 7 | 0.0843 | -1 |
| hsa-miR-197 | 1 | 0.1004 | 1 |
| hsa-miR-220c | 19 | 0.1137 | -1 |
| hsa-miR-19a | 13 | 0.1159 | 1 |
| hsa-miR-339-3p | 7 | 0.1218 | 1 |
| hsa-miR-146a* | 5 | 0.1388 | 1 |
| hsa-miR-200b* | 1 | 0.1577 | 1 |
| hsa-miR-200b | 1 | 0.1584 | 1 |

Figure 16

| miRNA | PROBE ID | CHR | P | DE | Rep |
|---|---|---|---|---|---|
| hsa-miR-542-5p | ILMN_3167175 | X | 0.0020 | 0.378 | 1 |
| hsa-miR-191* | ILMN_3167124 | 3 | 0.0023 | -0.192 | ND |
| hsa-miR-577 | ILMN_3167406 | 4 | 0.0023 | -0.229 | 1 |
| hsa-miR-542-3p | ILMN_3167074 | X | 0.0040 | 0.284 | 0.55 |
| hsa-miR-604 | ILMN_3167804 | 10 | 0.0041 | -0.376 | 0.95 |
| hsa-miR-125a-5p | ILMN_3167670 | 19 | 0.0041 | 0.099 | 0.95 |
| hsa-miR-27b | ILMN_3168409 | 9 | 0.0045 | 0.134 | 1 |
| hsa-miR-551b | ILMN_3166993 | 3 | 0.0051 | 0.776 | 1 |
| hsa-miR-563 | ILMN_3167408 | 3 | 0.0052 | -0.087 | ND |
| hsa-miR-424 | ILMN_3166938 | X | 0.0054 | 0.138 | 0.59 |
| hsa-miR-135b | ILMN_3167874 | 1 | 0.0057 | 0.261 | 1 |
| hsa-miR-197 | ILMN_3167864 | 1 | 0.0058 | -0.090 | ND |
| hsa-miR-221* | ILMN_3168580 | X | 0.0064 | 0.410 | 1 |
| hsa-miR-221 | ILMN_3167681 | X | 0.0065 | 0.062 | 1 |
| HS_107 | ILMN_3167213 | 0 | 0.0066 | -0.173 | 1 |
| hsa-miR-429 | ILMN_3167806 | 1 | 0.0068 | 0.344 | 0.77 |
| hsa-miR-99a | ILMN_3168213 | 21 | 0.0069 | 0.176 | 0.86 |
| hsa-miR-31 | ILMN_3167837 | 9 | 0.0069 | 0.313 | 1 |
| HS_131 | ILMN_3168028 | 0 | 0.0071 | -0.207 | 0.91 |
| hsa-miR-200b | ILMN_3168294 | 1 | 0.0075 | 0.227 | 0.5 |
| hsa-miR-302c | ILMN_3166944 | 4 | 0.0081 | -0.307 | 1 |
| hsa-miR-181a-2* | ILMN_3168577 | 9 | 0.0082 | 0.186 | 1 |
| hsa-miR-130b* | ILMN_3168588 | 22 | 0.0085 | -0.178 | 1 |
| hsa-let-7e | ILMN_3168463 | 19 | 0.0089 | 0.084 | 0.5 |
| hsa-miR-218 | ILMN_3168380 | 4,5 | 0.0097 | 0.209 | 0.91 |
| hsa-miR-133b | ILMN_3168348 | 6 | 0.0100 | 0.279 | 0.95 |
| hsa-miR-125b | ILMN_3168389 | 21,11 | 0.0102 | 0.080 | ND |
| hsa-miR-1296 | ILMN_3167351 | 10 | 0.0105 | 0.384 | ND |
| hsa-miR-222 | ILMN_3167963 | X | 0.0109 | 0.138 | 1 |
| hsa-miR-222* | ILMN_3168712 | X | 0.0110 | 0.192 | 1 |
| hsa-miR-450a | ILMN_3168187 | X,X | 0.0111 | 0.186 | ND |
| hsa-miR-31* | ILMN_3168847 | 9 | 0.0113 | 0.388 | 1 |
| hsa-let-7i* | ILMN_3168724 | 12 | 0.0113 | 0.225 | 0.77 |

Figure 17

| | | | | | |
|---|---|---|---|---|---|
| HS_73.1 | ILMN_3167416 | 0 | 0.0119 | 0.482 | 1 |
| hsa-miR-200a | ILMN_3167801 | 1 | 0.0121 | 0.416 | ND |
| hsa-miR-922 | ILMN_3168748 | 3 | 0.0123 | -0.074 | ND |
| hsa-miR-136* | ILMN_3168667 | 14 | 0.0131 | 0.224 | ND |
| hsa-miR-1231 | ILMN_3167675 | 1 | 0.0132 | 0.113 | ND |
| hsa-miR-224 | ILMN_3168515 | X | 0.0144 | 0.326 | 0.95 |
| hsa-miR-146b-5p | ILMN_3167894 | 10 | 0.0148 | 0.290 | 1 |
| hsa-miR-141* | ILMN_3168669 | 12 | 0.0148 | 0.368 | ND |
| hsa-miR-708 | ILMN_3168563 | 11 | 0.0150 | 0.348 | ND |
| hsa-miR-296-3p | ILMN_3168049 | 20 | 0.0186 | 0.253 | 0.64 |
| hsa-miR-125b-2* | ILMN_3168804 | 21 | 0.0187 | 0.319 | ND |
| hsa-miR-608 | ILMN_3167500 | 10 | 0.0191 | -0.464 | 1 |
| HS_162 | ILMN_3167742 | 0 | 0.0194 | 0.313 | 1 |
| hsa-miR-200c* | ILMN_3168701 | 12 | 0.0201 | 0.232 | 0.82 |
| hsa-miR-141 | ILMN_3168064 | 12 | 0.0205 | 0.183 | ND |
| HS_151.1 | ILMN_3167470 | 0 | 0.0207 | -0.483 | 1 |
| hsa-miR-451 | ILMN_3167614 | 17 | 0.0209 | -0.027 | ND |
| hsa-miR-424* | ILMN_3168638 | X | 0.0219 | 0.286 | ND |
| hsa-miR-26b | ILMN_3167374 | 2 | 0.0223 | -0.021 | ND |
| hsa-miR-150* | ILMN_3168730 | 19 | 0.0224 | -0.265 | ND |
| hsa-miR-361-3p | ILMN_3168815 | X | 0.0228 | -0.188 | 0.95 |
| HS_120 | ILMN_3166997 | 0 | 0.0229 | -0.183 | ND |
| hsa-miR-495 | ILMN_3167052 | 14 | 0.0241 | 0.096 | ND |
| hsa-miR-519e* | ILMN_3168031 | 19 | 0.0256 | -0.269 | 0.73 |
| HS_101 | ILMN_3167526 | 0 | 0.0256 | -0.175 | ND |
| hsa-miR-1226 | ILMN_3168807 | 3 | 0.0266 | -0.267 | ND |
| hsa-miR-576-3p | ILMN_3168559 | 4 | 0.0272 | -0.188 | 0.77 |
| hsa-miR-146a* | ILMN_3168687 | 5 | 0.0272 | -0.276 | ND |
| hsa-miR-28-3p | ILMN_3168657 | 3 | 0.0273 | -0.121 | ND |
| hsa-miR-1178 | ILMN_3168877 | 12 | 0.0285 | 0.316 | ND |
| hsa-miR-146b-3p | ILMN_3168841 | 10 | 0.0289 | 0.225 | 1 |
| HS_130 | ILMN_3168254 | 0 | 0.0294 | -0.183 | ND |
| hsa-miR-203 | ILMN_3167375 | 14 | 0.0320 | 0.229 | ND |
| hsa-miR-1250 | ILMN_3168585 | 17 | 0.0329 | -0.168 | ND |

Figure 17 Continued

| | | | | | |
|---|---|---|---|---|---|
| hsa-miR-16 | ILMN_3167989 | 3,13 | 0.0334 | -0.032 | ND |
| HS_196.1 | ILMN_3166967 | 0 | 0.0344 | 0.209 | 0.82 |
| HS_266.1 | ILMN_3168251 | 0 | 0.0364 | 0.320 | ND |
| hsa-let-7a* | ILMN_3168708 | 22,9 | 0.0370 | 0.232 | ND |
| HS_48.1 | ILMN_3167790 | 0 | 0.0371 | 0.249 | 1 |
| solexa-7111-119 | ILMN_3168909 | 0 | 0.0378 | 0.151 | ND |
| hsa-miR-766 | ILMN_3167038 | X | 0.0386 | -0.248 | ND |
| hsa-miR-450b-5p | ILMN_3168884 | X | 0.0386 | 0.111 | ND |
| solexa-555-1991 | ILMN_3168904 | 0 | 0.0387 | -0.080 | ND |
| hsa-miR-663 | ILMN_3167088 | 20 | 0.0400 | -0.468 | 0.91 |
| hsa-miR-99b | ILMN_3168262 | 19 | 0.0405 | 0.209 | ND |
| hsa-miR-382 | ILMN_3167239 | 14 | 0.0409 | 0.114 | ND |
| hsa-miR-27b* | ILMN_3168599 | 9 | 0.0422 | 0.140 | 0.86 |
| hsa-miR-566 | ILMN_3167704 | 3 | 0.0424 | -0.194 | ND |
| hsa-miR-452 | ILMN_3167050 | X | 0.0426 | 0.175 | ND |
| hsa-miR-125a-3p | ILMN_3168574 | 19 | 0.0458 | 0.180 | ND |
| hsa-miR-206 | ILMN_3168019 | 6 | 0.0467 | 0.251 | ND |
| hsa-miR-509-3p | ILMN_3168363 | X,X,X | 0.0470 | 0.183 | ND |
| hsa-miR-342-5p | ILMN_3168614 | 14 | 0.0477 | -0.154 | ND |
| hsa-miR-23b | ILMN_3167997 | 9 | 0.0500 | 0.035 | ND |
| hsa-miR-24-1* | ILMN_3168844 | 9 | 0.0504 | 0.289 | ND |
| hsa-miR-200c | ILMN_3167002 | 12 | 0.0524 | 0.092 | ND |
| hsa-miR-1293 | ILMN_3168857 | 12 | 0.0524 | 0.169 | ND |
| HS_231 | ILMN_3167534 | 0 | 0.0525 | 0.251 | ND |
| hsa-miR-372 | ILMN_3167184 | 19 | 0.0533 | -0.087 | ND |
| hsa-miR-335 | ILMN_3167996 | 7 | 0.0535 | 0.077 | ND |
| hsa-miR-193a-3p | ILMN_3168366 | 17 | 0.0548 | 0.113 | 0.86 |
| hsa-miR-200a* | ILMN_3167179 | 1 | 0.0551 | 0.227 | ND |
| hsa-miR-1297 | ILMN_3168867 | 13 | 0.0551 | 0.089 | ND |
| HS_284.1 | ILMN_3168214 | 0 | 0.0558 | -0.156 | ND |
| HS_86 | ILMN_3167504 | 0 | 0.0558 | 0.106 | 0.64 |
| hsa-miR-1180 | ILMN_3168881 | 17 | 0.0567 | -0.097 | ND |
| hsa-miR-187 | ILMN_3168167 | 18 | 0.0575 | 0.164 | ND |
| hsa-miR-135a | ILMN_3167823 | 3,12 | 0.0601 | 0.146 | ND |

Figure 17 Continued

| | | | | | |
|---|---|---|---|---|---|
| hsa-miR-943 | ILMN_3168720 | 4 | 0.0605 | -0.076 | ND |
| hsa-miR-1279 | ILMN_3168811 | 12 | 0.0615 | -0.211 | ND |
| hsa-miR-657 | ILMN_3167034 | 17 | 0.0615 | -0.063 | ND |
| hsa-miR-15a* | ILMN_3168662 | 13 | 0.0617 | 0.218 | ND |
| hsa-miR-449b | ILMN_3168441 | 5 | 0.0634 | -0.076 | ND |
| HS_208 | ILMN_3167907 | 0 | 0.0635 | 0.064 | ND |
| hsa-miR-489 | ILMN_3167272 | 7 | 0.0641 | 0.335 | ND |
| hsa-miR-155* | ILMN_3168715 | 21 | 0.0671 | -0.207 | ND |
| hsa-miR-511 | ILMN_3167598 | 10,10 | 0.0680 | 0.208 | ND |
| HS_116 | ILMN_3167951 | 0 | 0.0682 | -0.235 | ND |
| hsa-miR-34a | ILMN_3168429 | 1 | 0.0695 | 0.189 | ND |
| HS_38.1 | ILMN_3168353 | 0 | 0.0717 | -0.114 | ND |
| hsa-miR-708* | ILMN_3168647 | 11 | 0.0719 | 0.110 | ND |
| HS_35 | ILMN_3167886 | 0 | 0.0732 | 0.153 | ND |
| hsa-miR-515-5p | ILMN_3166959 | 19,19 | 0.0748 | -0.254 | ND |
| HS_3 | ILMN_3168047 | 0 | 0.0755 | 1.395 | ND |
| HS_166.1 | ILMN_3168315 | 0 | 0.0793 | -0.134 | ND |
| HS_156 | ILMN_3168305 | 0 | 0.0794 | 0.250 | ND |
| hsa-miR-376a*:9.1 | ILMN_3167419 | 0 | 0.0798 | 0.218 | ND |
| solexa-5169-164 | ILMN_3168902 | 0 | 0.0822 | 0.167 | ND |
| HS_8 | ILMN_3167836 | 0 | 0.0825 | 0.188 | ND |
| hsa-miR-556-5p | ILMN_3167655 | 1 | 0.0836 | 0.175 | ND |
| hsa-miR-375 | ILMN_3167229 | 2 | 0.0845 | 0.174 | ND |
| hsa-miR-520f | ILMN_3167075 | 19 | 0.0858 | 0.208 | ND |
| hsa-miR-1321 | ILMN_3168663 | X | 0.0859 | -0.122 | ND |
| hsa-miR-548f | ILMN_3168534 | 5,X,2,7,10 | 0.0869 | 0.087 | ND |
| hsa-let-7i | ILMN_3168316 | 12 | 0.0879 | 0.017 | ND |
| hsa-miR-151-3p | ILMN_3168705 | 8 | 0.0888 | 0.065 | ND |
| hsa-miR-561 | ILMN_3167109 | 2 | 0.0890 | -0.157 | ND |
| HS_12 | ILMN_3168104 | 0 | 0.0904 | 0.192 | ND |
| hsa-miR-212 | ILMN_3167761 | 17 | 0.0907 | 0.213 | ND |
| hsa-miR-505 | ILMN_3168412 | X | 0.0913 | -0.203 | ND |
| hsa-miR-524-5p | ILMN_3168284 | 19 | 0.0918 | 0.207 | ND |
| hsa-miR-744* | ILMN_3168733 | 17 | 0.0930 | 0.173 | ND |

Figure 17 Continued

| | | | | | |
|---|---|---|---|---|---|
| hsa-miR-148b* | ILMN_3168567 | 12 | 0.0937 | 0.112 | ND |
| hsa-miR-155 | ILMN_3168170 | 21 | 0.0942 | -0.119 | ND |
| HS_89 | ILMN_3168065 | 0 | 0.0944 | 0.138 | ND |
| HS_267 | ILMN_3167573 | 0 | 0.0948 | -0.094 | ND |
| hsa-miR-630 | ILMN_3167844 | 15 | 0.0959 | -0.282 | ND |
| hsa-miR-33a | ILMN_3167691 | 22 | 0.0969 | 0.237 | ND |
| HS_106 | ILMN_3167464 | 0 | 0.0976 | -0.119 | ND |
| HS_57.1 | ILMN_3167398 | 0 | 0.0992 | -0.212 | ND |
| hsa-miR-658 | ILMN_3168097 | 22 | 0.0999 | 0.244 | ND |
| hsa-miR-101* | ILMN_3168196 | 1 | 0.1001 | 0.119 | ND |

Figure 17 Continued

*Thyroid Clinical Process - Current*
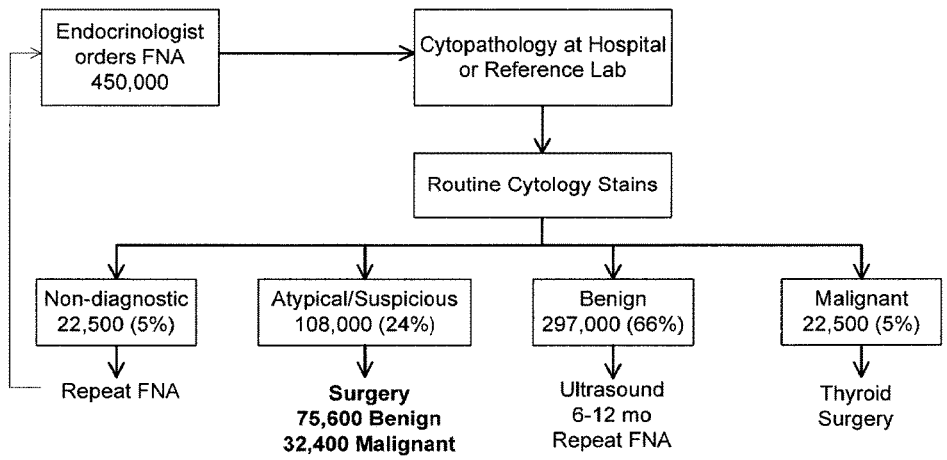
Three quarters of surgeries on nodules with Atypical or Suspicious cytology are potentially avoidable.
*Thyroid Clinical Process - Future*
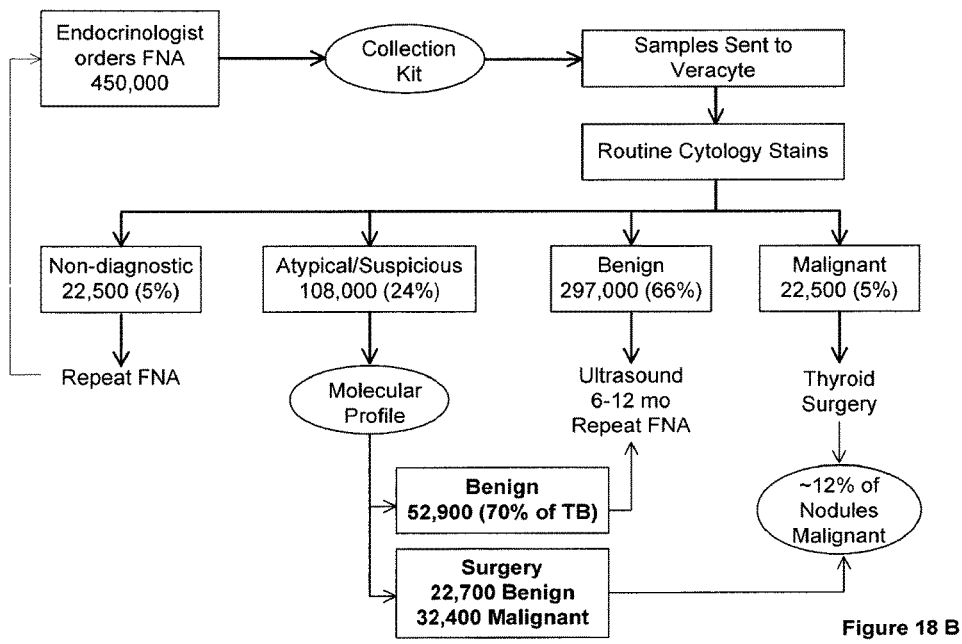
Figure 18 B Molecular Profiling Report Customer: 1234

Tissue Type: thyroid

Preliminary Diagnosis: nodule

Sample Quality: ++

| Nodule ID | Benign | Not Benign | Non Diagnostic |
|---|---|---|---|
| a | + | - | - |
| b | + | - | - |
| c | + | - | - |
| d | + | - | - |

Figure 20

Example of variance decomposition

METHODS FOR PROCESSING OR ANALYZING A SAMPLE OF THYROID TISSUE

CROSS REFERENCE

This application is a continuation-in-part application of U.S. patent application Ser. No. 15/274,492, filed Sep. 23, 2016, which is a continuation application of U.S. patent application Ser. No. 12/964,666, filed Dec. 9, 2010 and now issued as U.S. Pat. No. 9,495,515, which claims the benefit of U.S. Provisional Patent Application No. 61/285,165, filed Dec. 9, 2009, and of U.S. patent application Ser. No. 13/589,022, filed Aug. 17, 2012, which is a continuation application of U.S. patent application Ser. No. 12/592,065, filed Nov. 17, 2009 and now issued as U.S. Pat. No. 8,541,170, which claims the benefit of U.S. Provisional Application No. 61/199,585, filed Nov. 17, 2008, and U.S. Provisional Application No. 61/270,812, filed Jul. 13, 2009, each of which is entirely incorporated herein by reference.

BACKGROUND OF THE INVENTION

Cancer is the second leading cause of death in the United States and one of the leading causes of mortality worldwide. Nearly 25 million people are currently living with cancer, with 11 million new cases diagnosed each year. Furthermore, as the general population continues to age, cancer will become a bigger and bigger problem. The World Health Organization projects that by the year 2020, global cancer rates will increase by 50%.

Successful treatment of cancer starts with early and accurate diagnosis. Current methods of diagnosis include cytological examination of tissue samples taken by biopsy or imaging of tissues and organs for evidence of aberrant cellular proliferation. While these techniques have proven to be both useful and inexpensive, they suffer from a number of drawbacks. First, cytological analysis and imaging techniques for cancer diagnosis often require a subjective assessment to determine the likelihood of malignancy. Second, the increased use of these techniques has lead to a sharp increase in the number of indeterminate results in which no definitive diagnosis can be made. Third, these routine diagnostic methods lack a rigorous method for determining the probability of an accurate diagnosis. Fourth, these techniques may be incapable of detecting a malignant growth at very early stages. Fifth, these techniques do not provide information regarding the basis of the aberrant cellular proliferation.

Many of the newer generation of treatments for cancer, while exhibiting greatly reduced side effects, are specifically targeted to a certain metabolic or signaling pathway, and will only be effective against cancers that are reliant on that pathway. Further, the cost of any treatments can be prohibitive for an individual, insurance provider, or government entity. This cost could be at least partially offset by improved methods that accurately diagnose cancers and the pathways they rely on at early stages. These improved methods would be useful both for preventing unnecessary therapeutic interventions as well as directing treatment.

In the case of thyroid cancer it is estimated that out of the approximately 130,000 thyroid removal surgeries performed each year due to suspected malignancy in the United States, only about 54,000 are necessary. Thus, approximately 76,000 unnecessary surgeries are performed annually. In addition, there are continued treatment costs and complications due to the need for lifelong drug therapy to replace the lost thyroid function. Accordingly, there is a need for improved testing modalities and business practices that improve upon current methods of cancer diagnosis.

The thyroid has at least two kinds of cells that make hormones. Follicular cells make thyroid hormone, which affects heart rate, body temperature, and energy level. C cells make cacitonin, a hormone that helps control the level of calcium in the blood. Abnormal growth in the thyroid can result in the formation of nodules, which can be either benign or malignant. Thyroid cancer includes at least four different kinds of malignant tumors of the thyroid gland: papillary, follicular, medullary and anaplastic.

SUMMARY OF THE INVENTION

In one embodiment, the invention is a method of diagnosing a genetic disorder or cancer comprising the steps of: (a) obtaining a biological sample comprising gene expression products; (b) detecting the gene expression products of the biological sample; (c) comparing to an amount in a control sample, an amount of one or more gene expression products in the biological sample to determine the differential gene expression product level between the biological sample and the control sample; (d) classifying the biological sample by inputting the one or more differential gene expression product levels to a trained algorithm; wherein technical factor variables are removed from data based on differential gene expression product level and normalized prior to and during classification; and (e) identifying the biological sample as positive for a genetic disorder or cancer if the trained algorithm classifies the sample as positive for the genetic disorder or cancer at a specified confidence level.

In another embodiment, the invention is an algorithm for diagnosing a genetic disorder or cancer comprising: (a) determining the level of gene expression products in a biological sample; (b) deriving the composition of cells in the biological sample based on the expression levels of cell-type specific markers in the sample; (c) removing technical variables prior to and during classification of the biological sample; (d) correcting or normalizing the gene product levels determined in step (a) based on the composition of cells determined in step (b); and (e) classifying the biological sample as positive for a genetic disorder or cancer.

The present invention includes a method for diagnosing thyroid disease in a subject, the method comprising (a) providing a nucleic acid sample from a subject; (b) detecting the amount of one or more genes, gene products, or transcripts selected from the group consisting of the genes or transcripts listed in Tables 2 or their complement; and (c) determining whether said subject has or is likely to have a malignant or benign thyroid condition based on the results of step (b).

The present invention also includes a composition comprising one or more binding agents that specifically bind to the one or more polymorphisms selected from the group consisting of the polymorphisms listed in Tables.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is a table listing 75 thyroid samples examined for gene expression analysis using the Affymetrix Human Exon 10ST array to identify genes that are significantly differentially expressed or alternatively spliced between malignant, benign, and normal samples. The name for each sample and the pathological classification is listed.

FIG. 2 is a table listing the top 100 differentially expressed genes at the gene level. Data are from the dataset in which benign malignant and normal thyroid samples were compared at the gene level. Markers were selected based on statistical significance after Benjamini and Hochberg correction for false discover rate (FDR). Positive numbers denote up regulation and negative numbers denote down regulation of expression.

FIG. 3 is a table listing the top 100 alternatively spliced genes. Data are from the dataset in which benign malignant and normal thyroid samples were compared at the gene level. Markers were selected based on statistical significance after Benjamini and Hochberg correction for false discovery rate (FDR).

FIG. 4 is a table listing the top 100 differentially expressed genes at the probe-set level. Data were from the Probe-set dataset. Positive numbers denote up-regulation of gene expression, while negative numbers denote down regulation.

FIG. 5 is a table listing the top 100 significant diagnostic markers determined by gene level analysis. Markers in this list show both differential gene expression and alternative exon splicing. Positive numbers denote up-regulation, while negative numbers denote down regulation. This table lists 3-sets of calculated fold-changes for any given marker to allow comparison between the groups malignant vs. benign, benign, versus normal, and malignant versus normal.

FIG. 6 is a table listing the genes identified as contributing to thyroid cancer diagnosis by molecular profiling of gene expression levels and/or alternative exon splicing. Markers identified from the dataset in which benign, malignant and normal samples were analyzed at the gene level are referred to as BMN in the data source column; and likewise, markers identified from dataset in which the benign and malignant samples were analyzed at the gene level are referred to as BM in the data source column. Similarly, markers identified at the probe-set level from the dataset in which benign, and malignant samples were analyzed are referred to as Probe-set in the data source column.

FIG. 7 is a table listing tissue samples examined for gene expression analysis. The samples were classified by pathological analysis as benign (B) or malignant (M). Benign samples were further classified as follicular adenoma (FA), lymphocytic thyroiditis (LCT), or nodular hyperplasia (NHP). Malignant samples were further classified as Hurthle cell carcinoma (HC), follicular carcinoma (FC), follicular variant of papillary thyroid carcinoma (FVPTC), papillary thyroid carcinoma (PTC), medullary thyroid carcinoma (MTC), or anaplastic carcinoma (ATC).

FIG. 8 is a table listing fine needle aspirate samples examined for gene expression analysis. The samples were classified by pathological analysis as benign (B) or malignant (M). Benign samples were further classified as follicular adenoma (FA), lymphocytic thyroiditis (LCT), Hurthle cell adenoma (HA), or nodular hyperplasia (NHP). Malignant samples were further classified as Hurthle cell carcinoma (HC), follicular carcinoma (FC), follicular variant of papillary thyroid carcinoma (FVPTC), papillary thyroid carcinoma (PTC), medullary thyroid carcinoma (MTC), or anaplastic carcinoma (ATC).

FIG. 9 is a table listing genes identified from expression analysis of the tissue samples listed in FIG. 7 which exhibit significant differences in expression between malignant and benign samples as determined by feature selection using LIMMA (linear models for micro array data) and SVM (support vector machine) for classification of malignant vs. benign samples. Rank denotes the marker significance (lower rank, higher significance) after Benjamini and Hochberg correction for False Discovery Rate (FDR). Gene symbol denotes the name of the gene. TCID denotes the transcript cluster ID of the gene used in the Affymetrix Human Exon 10ST array. Ref Seq denotes the name of the corresponding reference sequence for that gene. The column labeled "Newly Discovered Marker" denotes gene expression markers which have not previously been described as differentially expressed in malignant vs. benign thyroid tissues.

FIG. 10 is a table listing genes identified from expression analysis of the tissue samples listed in FIG. 8 which exhibit significant differences in expression between medullary thyroid carcinoma (MTC) and other pathologies as determined by feature selection using LIMMA (linear models for micro array data) and SVM (support vector machine) for classification of MTC vs. other samples. Rank denotes the marker significance (lower rank, higher significance) after Benjamini and Hochberg correction for False Discovery Rate (FDR). Gene symbol denotes the name of the gene. TCID denotes the transcript cluster ID of the gene used in the Affymetrix Human Exon 10ST array. P value indicates the statistical significance of the differential expression between MTC and non-MTC samples. Fold Change indicates the degree of differential expression between MTC and non-MTC samples. The column labeled "Newly Discovered Marker" denotes gene expression markers which have not previously been described as differentially expressed in malignant vs. benign thyroid tissues.

FIG. 11 is a table listing genes identified from expression analysis of the samples listed in FIGS. 7 and 8 which exhibit significant differences in expression between benign and malignant samples as determined by a repeatability based meta-analysis classification algorithm.

FIG. 12 is a table listing genes identified from expression analysis of the samples listed in FIGS. 7 and 8 which exhibit significant (posterior probability>0.9) differences in expression between benign and malignant samples as determined by Bayesian ranking of the differentially expressed genes. deriving type I and type II error rates from previously published studies to determine prior probabilities, combining these prior probabilities with the output of the dataset derived from expression analysis of the samples listed in FIG. 10 to estimate posterior probabilities of differential gene expression, and then combining the results of the expression analysis of the samples listed in FIG. 11 with the estimated posterior probabilities to calculate final posterior probabilities of differential gene expression. These posterior probabilities were then used to rank the differentially expressed genes.

FIG. 13 is a table listing genes identified from expression analysis of the samples listed in FIG. 7 which exhibit differential expression between samples categorized as FA, LCT, NHP, HC, FC, FVPTC, PTC, MTC, or ATC as determined by feature selection using LIMMA (linear models for micro array data) and SVM (support vector machine) for classification.

FIG. 14 is a table listing fine needle aspirate samples examined for micro RNA (miRNA) expression analysis using an Agilent Human v2 miRNA microarray chip. The samples were classified by pathological analysis as benign (B) or malignant (M). Benign samples were further classified as follicular adenoma (FA), or nodular hyperplasia (NHP). Malignant samples were further classified as follicular carcinoma (FC), follicular variant of papillary thyroid carcinoma (FVPTC), papillary thyroid carcinoma (PTC), or medullary thyroid carcinoma (MTC).

FIG. 15 is a table listing fine needle aspirate samples examined for micro RNA (miRNA) expression analysis using an Illumina Human v2 miRNA array. The samples were classified by pathological analysis as benign (B), non diagnostic, or malignant (M). Benign samples were further classified as benign nodule (BN), follicular neoplasm (FN), (LCT), or (NHP). Malignant samples were further classified as (FVPTC), or (PTC).

FIG. 16 is a table listing micro RNAs (miRNAs) identified from analysis of the samples listed in FIG. 14 which exhibit differential expression between samples categorized as benign or malignant. The miRNA column denotes the name of the miRNA. The CHR column denotes the chromosome the miRNA is located on. The P column denotes the statistical confidence or p-value provided by the analysis. The DE column denotes whether the listed miRNA is upregulated (1) in malignant samples or downregulated (−1) in malignant samples. The patent column denotes any patents or applications that describe these miRNAs.

FIG. 17 is a table listing micro RNAs (miRNAs) identified from analysis of the samples listed in FIG. 15 which exhibit differential expression between samples categorized as benign or malignant. The miRNA column denotes the name of the miRNA. The probe ID column denotes the corresponding probe ID in the Illumina array. The CHR column denotes the chromosome the miRNA is located on. The P column denotes the statistical confidence or p-value provided by the analysis. The DE column denotes whether the listed miRNA is upregulated (no sign) in malignant samples or downregulated (negative sign) in malignant samples. The Rep column denotes the repeatability score provided by a "hot probes" type analysis of the hybridization data. The patent column denotes any patents or applications that describe these miRNAs.

FIG. 18 is a flow chart describing how molecular profiling may be used to improve the accuracy of routine cytological examination. FIG. 18A and FIG. 18B describe alternate embodiments of the molecular profiling business.

FIG. 20 is an illustration of a molecular profiling results report.

DETAILED DESCRIPTION OF THE INVENTION

I. Introduction

Figure 18A:
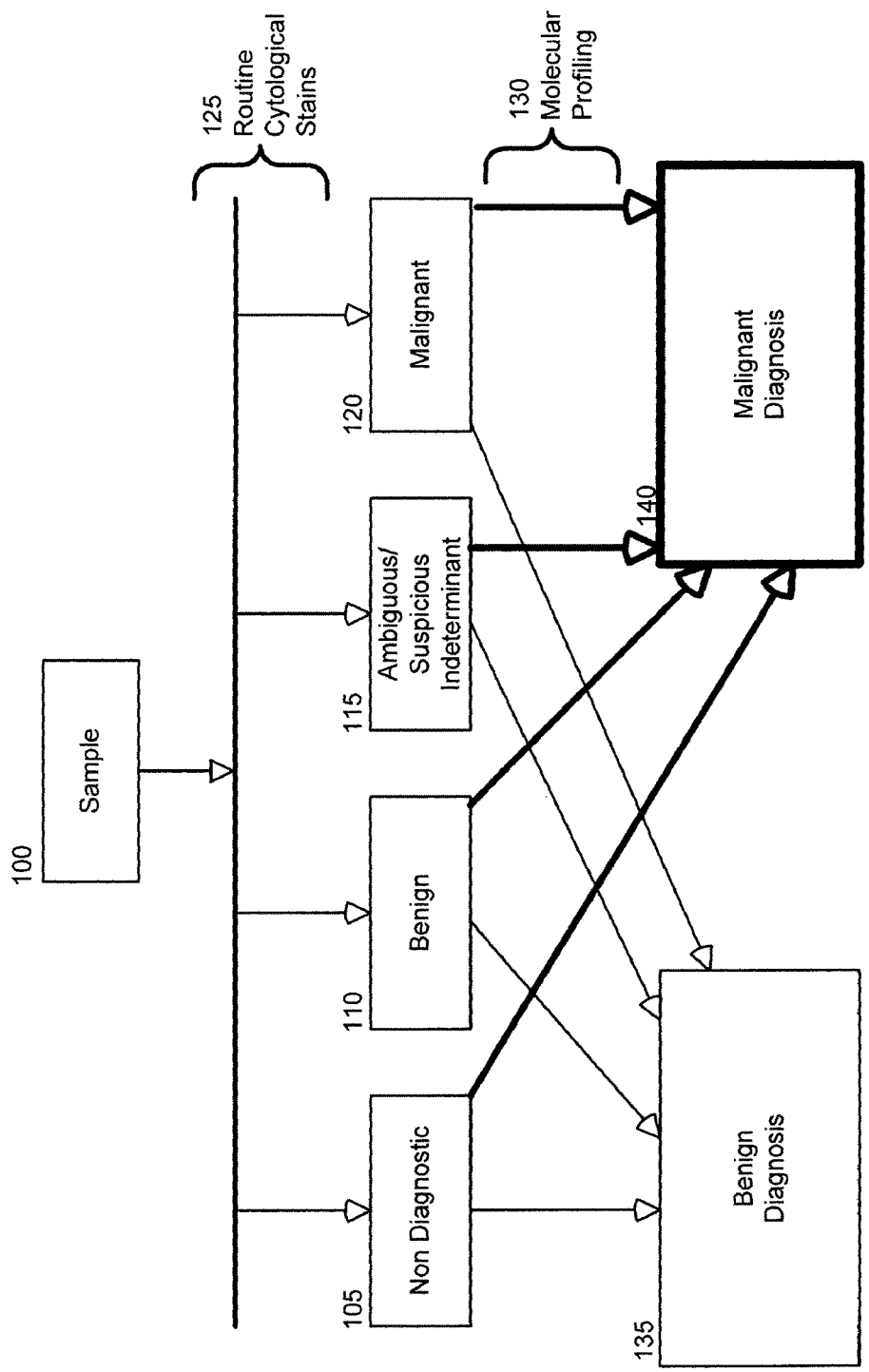

The present disclosure provides novel methods for diagnosing abnormal cellular proliferation from a biological test sample, and related kits and compositions. The present invention also provides methods and compositions for differential diagnosis of types of aberrant cellular proliferation such as carcinomas including follicular carcinomas (FC), follicular variant of papillary thyroid carcinomas (FVPTC), Hurthle cell carcinomas (HC), Hurthle cell adenomas (HA); papillary thyroid carcinomas (PTC), medullary thyroid carcinomas (MTC), and anaplastic carcinomas (ATC); adenomas including follicular adenomas (FA); nodule hyperplasias (NHP); colloid nodules (CN); benign nodules (BN); follicular neoplasms (FN); lymphocytic thyroiditis (LCT), including lymphocytic autoimmune thyroiditis; parathyroid tissue; renal carcinoma metastasis to the thyroid; melanoma metastasis to the thyroid; B-cell lymphoma metastasis to the thyroid; breast carcinoma to the thyroid; benign (B) tumors, malignant (M) tumors, and normal (N) tissues. The present invention further provides novel markers including microRNAs (miRNAs) and gene expression product markers and novel groups of genes and markers useful for the diagnosis, characterization, and treatment of cellular proliferation. Additionally the present invention provides business methods for providing enhanced diagnosis, differential diagnosis, monitoring, and treatment of cellular proliferation.

Cancer is a leading cause of death in the United States. Early and accurate diagnosis of cancer is critical for effective management of this disease. It is therefore important to develop testing modalities and business practices to enable cancer diagnosis that is more accurately and earlier. Expression product profiling, also referred to as molecular profiling, provides a powerful method for early and accurate diagnosis of tumors or other types of cancers from a biological sample.

Typically, screening for the presence of a tumor or other type of cancer, involves analyzing a biological sample taken by various methods such as, for example, a biopsy. The biological sample is then prepared and examined by one skilled in the art. The methods of preparation can include but are not limited to various cytological stains, and immunohistochemical methods. Unfortunately, traditional methods of cancer diagnosis suffer from a number of deficiencies. These deficiencies include: 1) the diagnosis may require a subjective assessment and thus be prone to inaccuracy and lack of reproducibility, 2) the methods may fail to determine the underlying genetic, metabolic or signaling pathways responsible for the resulting pathogenesis, 3) the methods may not provide a quantitative assessment of the test results, and 4) the methods may be unable to provide an unambiguous diagnosis for certain samples.

One hallmark of cancer is dysregulation of normal transcriptional control leading to aberrant expression of genes or other RNA transcripts such as miRNAs. Among the aberrantly expressed transcripts are genes involved in cellular transformation, for example tumor suppressors and oncogenes. Tumor suppressor genes and oncogenes may be up-regulated or down-regulated in tumors when compared to normal tissues. Known tumor suppressors and oncogenes include, but are not limited to brca1, brca2, bcr-abl, bcl-2, HER2, N-myc, C-myc, BRAF, RET, Ras, KIT, Jun, Fos, and p53. This abnormal expression may occur through a variety of different mechanisms. It is not necessary in the present invention to understand the mechanism of aberrant expression, or the mechanism by which carcinogenesis occurs. Nevertheless, finding a marker or set of markers whose expression is up or down regulated in a sample as compared to a normal sample may be indicative of cancer. Furthermore, the particular aberrantly expressed markers or set of markers may be indicative of a particular type of cancer, or even a recommended treatment protocol. Additionally the methods of the present invention are not meant to be limited solely to canonically defined tumor suppressors or oncogenes. Rather, it is understood that any marker, gene or set of genes or markers that is determined to have a statistically significant correlation with respect to expression level or alternative gene splicing to a benign, malignant, or normal diagnosis is encompassed by the present invention.

In one embodiment, the methods of the present invention seek to improve upon the accuracy of current methods of cancer diagnosis. Improved accuracy can result from the measurement of multiple genes and/or expression markers, the identification of gene expression products such as miRNAs, rRNA, tRNA and mRNA gene expression products with high diagnostic power or statistical significance, or the identification of groups of genes and/or expression products with high diagnostic power or statistical significance, or any combination thereof.

For example, increased expression of a number of receptor tyrosine kinases has been implicated in carcinogenesis. Measurement of the gene expression product level of a particular receptor tyrosine kinase known to be differentially expressed in cancer cells may provide incorrect diagnostic results leading to a low accuracy rate. Measurement of a plurality of receptor tyrosine kinases may increase the accuracy level by requiring a combination of alternate expressed genes to occur. In some cases, measurement of a plurality of genes might therefore increase the accuracy of a diagnosis by reducing the likelihood that a sample may exhibit an aberrant gene expression profile by random chance.

Similarly, some gene expression products within a group such as receptor tyrosine kinases may be indicative of a disease or condition when their expression levels are higher or lower than normal. The measurement of expression levels of other gene products within that same group may provide diagnostic utility. Thus, in one embodiment, the invention measures two or more gene expression products that are within a group. For example, in some embodiments, 1, 2, 3, 4, 5, 6, 7, 8, 9, 10, 15, 20, 25, 30, 35, 40, 45 or 50 gene expression products are measured from a group. Various groups are defined within the specification, such as groups useful for diagnosis of subtypes of thyroid cancer or groups of gene expression products that fall within particular ontology groups. In another embodiment, it would be advantageous to measure the expression levels of sets of genes that accurately indicate the presence or absence of cancer from multiple groups. For example, the invention contemplates the use of 1, 2, 3, 4, 5, 6, 7, 8, 9, 10, 15, 20, 25, 30, 35, 40, 45 or 50 gene expression groups, each with 1, 2, 3, 4, 5, 6, 7, 8, 9, 10, 15, 20, 25, 30, 35, 40, 45 or 50 gene expression products measured.

Additionally, increased expression of other oncogenes such as for example Ras in a biological sample may also be indicative of the presence of cancerous cells. In some cases, it may be advantageous to determine the expression level of several different classes of oncogenes such as for example receptor tyrosine kinases, cytoplasmic tyrosine kinases, GTPases, serine/threonine kinases, lipid kinases, mitogens, growth factors, and transcription factors. The determination of expression levels and/or exon usage of different classes or groups of genes involved in cancer progression may in some cases increase the diagnostic power of the present invention.

Groups of expression markers may include markers within a metabolic or signaling pathway, or genetically or functionally homologous markers. For example, one group of markers may include genes involved in the epithelial growth factor signaling pathway. Another group of markers may include mitogen-activated protein kinases. The present invention also provides methods and compositions for detecting (i.e. measuring) measuring gene expression markers from multiple and/or independent metabolic or signaling pathways.

In one embodiment, expression product markers of the present invention may provide increased accuracy of cancer diagnosis through the use of multiple expression product markers and statistical analysis. In particular, the present invention provides, but is not limited to, RNA expression profiles associated with thyroid cancers. The present invention also provides methods of characterizing thyroid tissue samples, and kits and compositions useful for the application of said methods. The disclosure further includes methods for running a molecular profiling business.

The present disclosure provides methods and compositions for improving upon the current state of the art for diagnosing cancer.

In some embodiments, the present invention provides a method of diagnosing cancer comprising the steps of: obtaining a biological sample comprising gene expression products; determining the expression level for one or more gene expression products of the biological sample; and identifying the biological sample as cancerous wherein the gene expression level is indicative of the presence of thyroid cancer in the biological sample. This can be done by correlating the gene expression levels with the presence of thyroid cancer in the biological sample. In one embodiment, the gene expression products are selected from FIG. 6. In some embodiments, the method further comprises the step of comparing the expression level of the one or more gene expression products to a control expression level for each gene expression product in a control sample, wherein the biological sample is identified as cancerous if there is a difference in the gene expression level between a gene expression product in the biological sample and the control sample.

In some embodiments, the present invention provides a method of diagnosing cancer comprising the steps of: obtaining a biological sample comprising alternatively spliced gene expression products; determining the expression level for one or more gene expression products of the biological sample; and identifying the biological sample as cancerous wherein the gene expression level is indicative of the presence of thyroid cancer in the biological sample. This can be done by correlating the gene expression levels with the presence of thyroid cancer in the biological sample. In one embodiment, the alternatively spliced gene expression products are selected from FIG. 6, wherein the differential gene expression product alternative exon usage is compared between the biological sample and a control sample; and identifying the biological sample as cancerous if there is a difference in gene expression product alternative exon usage between the biological sample and the control sample at a specified confidence level. In some embodiments, the genes selected from FIG. 6 are further selected from genes listed in FIG. 2, FIG. 3, FIG. 4, or FIG. 5.

In some embodiments, the present invention provides a method of diagnosing cancer that gives a specificity or sensitivity that is greater than 70% using the subject methods described herein, wherein the gene expression product levels are compared between the biological sample and a control sample; and identifying the biological sample as cancerous if there is a difference in the gene expression levels between the biological sample and the control sample at a specified confidence level. In some embodiments, the specificity and/or sensitivity of the present method is at least 70%, 75%, 80%, 85%, 86%, 87%, 88%, 89%, 90%, 91%, 92%, 93%, 94%, 95%, 96%, 97%, 98%, 99%, or more.

In some embodiments, the nominal specificity is greater than or equal to 70%. The nominal negative predictive value (NPV) is greater than or equal to 95%. In some embodiments, the NPV is at least 95%, 95.5%, 96%, 96.5%, 97%, 97.5%, 98%, 98.5%, 99%, 99.5% or more.

Sensitivity typically refers to TP/(TP+FN), where TP is true positive and FN is false negative. Number of Continued Indeterminate results divided by the total number of malignant results based on adjudicated histopathology diagnosis. Specificity typically refers to TN/(TN+FP), where TN is true negative and FP is false positive. The number of benign results divided by the total number of benign results based on adjudicated histopathology diagnosis. Positive Predictive Value (PPV): TP/(TP+FP); Negative Predictive Value (NPV): TN/(TN+FN).

Figure 22:
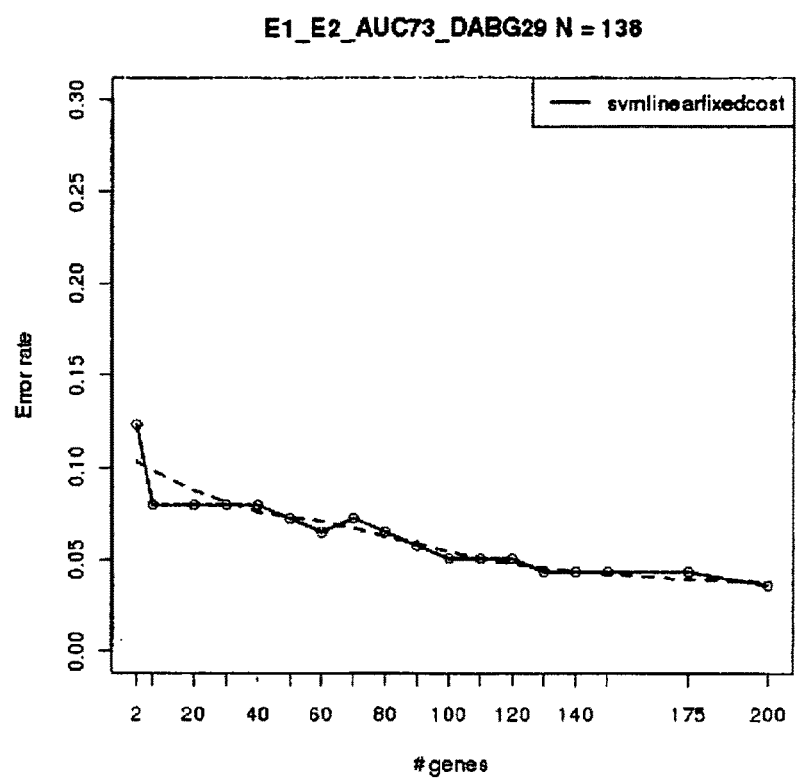
FIG. 22 depicts a titration curve of error rate vs. number of genes using an SVM-based classification algorithm. The titration curve plateaus when the classification algorithm examines 200-250 genes. These data indicate that the overall error rate of the current algorithm was 4% (5/138).

Marker panels are chosen to accommodate adequate separation of benign from non-benign expression profiles. Training of this multi-dimensional classifier, i.e., algorithm, was performed on over 500 thyroid samples, including>300 thyroid FNAs. Many training/test sets were used to develop the preliminary algorithm. An exemplary data set is shown in FIG. 22. First the overall algorithm error rate is shown as a function of gene number for benign vs non-benign samples. All results are obtained using a support vector machine model which is trained and tested in a cross-validated mode (30-fold) on the samples.

In some embodiments, the difference in gene expression level is at least 10%, 15%, 20%, 25%, 30%, 35%, 40%, 45% or 50% or more. In some embodiments, the difference in gene expression level is at least 2, 3, 4, 5, 6, 7, 8, 9, 10 fold or more. In some embodiments, the biological sample is identified as cancerous with an accuracy of greater than 75%, 80%, 85%, 90%, 95%, 99% or more. In some embodiments, the biological sample is identified as cancerous with a sensitivity of greater than 95%. In some embodiments, the biological sample is identified as cancerous with a specificity of greater than 95%. In some embodiments, the biological sample is identified as cancerous with a sensitivity of greater than 95% and a specificity of greater than 95%. In some embodiments, the accuracy is calculated using a trained algorithm.

In some embodiments, the present invention provides gene expression products corresponding to genes selected from Table 3, Table 4 and/or Table 5.

In some embodiments, the present invention provides a method of diagnosing cancer comprising using gene expression products from one or more of the following signaling pathways. The signaling pathways from which the genes can be selected include but are not limited to: acute myeloid leukemia signaling, somatostatin receptor 2 signaling, cAMP-mediated signaling, cell cycle and DNA damage checkpoint signaling, G-protein coupled receptor signaling, integrin signaling, melanoma cell signaling, relaxin signaling, and thyroid cancer signaling. In some embodiments, more than one gene is selected from a single signaling pathway to determine and compare the differential gene expression product level between the biological sample and a control sample. Other signaling pathways include, but are not limited to, an adherens, ECM, thyroid cancer, focal adhesion, apoptosis, p53, tight junction, TGFbeta, ErbB, Wnt, pathways in cancer overview, cell cycle, VEGF, Jak/STAT, MAPK, PPAR, mTOR or autoimmune thyroid pathway. In other embodiments, at least two genes are selected from at least two different signaling pathways to determine and compare the differential gene expression product level between the biological sample and the control sample. Methods and compositions of the invention can have genes selected from 1, 2, 3, 4, 5, 6, 7, 8, 9, 10, 15, 20, 25, 30, 35, 40, 45, 50 or more signaling pathways and can have from 1, 2, 3, 4, 5, 6, 7, 8, 9, 10, 15, 20, 25, 30, 35, 40, 45, 50 or more gene expression products from each signaling pathway, in any combination. In some embodiments, the set of genes combined give a specificity or sensitivity of greater than 70%, 75%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 95%, 95.5%, 96%, 96.5%, 97%, 97.5%, 98%, 98.5%, 99%, 99.5% or more.

In some embodiments, the present invention provides a method of diagnosing cancer comprising genes selected from at least two different ontology groups. In some embodiments, the ontology groups from which the genes can be selected include but are not limited to: cell aging, cell cortex, cell cycle, cell death/apoptosis, cell differentiation, cell division, cell junction, cell migration, cell morphogenesis, cell motion, cell projection, cell proliferation, cell recognition, cell soma, cell surface, cell surface linked receptor signal transduction, cell adhesion, transcription, immune response, or inflammation. In some embodiments, more than one gene is selected from a single ontology group to determine and compare the differential gene expression product level between the biological sample and a control sample. In other embodiments, at least two genes are selected from at least two different ontology groups to determine and compare the differential gene expression product level between the biological sample and the control sample. Methods and compositions of the invention can have genes selected from 1, 2, 3, 4, 5, 6, 7, 8, 9, 10, 15, 20, 25, 30, 35, 40, 45, 50 or more gene ontology groups and can have from 1, 2, 3, 4, 5, 6, 7, 8, 9, 10, 15, 20, 25, 30, 35, 40, 45, 50 or more gene expression products from each gene ontology group, in any combination. In some embodiments, the set of genes combined give a specificity or sensitivity of greater than 70%, 75%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 95%, 95.5%, 96%, 96.5%, 97%, 97.5%, 98%, 98.5%, 99%, 99.5% or more.

In some embodiments, the present invention provides a method of classifying cancer comprising the steps of: obtaining a biological sample comprising gene expression products; determining the expression level for one or more gene expression products of the biological sample that are differentially expressed in different subtypes of a cancer; and identifying the biological sample as cancerous wherein the gene expression level is indicative for a subtype of cancer. In some embodiments, the method further comprises the step of comparing the expression level of the one or more gene expression products to a control expression level for each gene expression product in a control sample, wherein the biological sample is identified as cancerous if there is a difference in the gene expression level between a gene expression product in the biological sample and the control sample. In some embodiments, the subject methods distinguish follicular carcinoma from medullary carcinoma. In some embodiments, the subject methods distinguish a benign thyroid disease from a malignant thyroid tumor/carcinoma.

In some embodiments, the gene expression product of the subject methods is a protein, and the amount of protein is compared. The amount of protein can be determined by one or more of the following: ELISA, mass spectrometry, blotting, or immunohistochemistry. RNA can be measured by one or more of the following: microarray, SAGE, blotting, RT-PCR, or quantitative PCR.

In some embodiments, the difference in gene expression level, for example, mRNA, protein, or alternatively spliced gene product, between a biological sample and a control sample that can be used to diagnose cancer is at least 1.5, 2, 2.5, 3, 3.5, 4, 4.5, 5, 5.5, 6, 6.5, 7, 7.5, 8, 8.5, 9, 9.5, 10 fold or more.

In some embodiments, the biological sample is classified as cancerous or positive for a subtype of cancer with an accuracy of greater than 75%, 80%, 85%, 86%, 87%, 88%, 89%, 90%, 91%, 92%, 93%, 94%, 95%, 96%, 97%, 98%, 99%, or 99.5%. The diagnosis accuracy as used herein includes specificity, sensitivity, positive predictive value, negative predictive value, and/or false discovery rate.

When classifying a biological sample for diagnosis of cancer, there are typically four possible outcomes from a binary classifier. If the outcome from a prediction is p and the actual value is also p, then it is called a true positive (TP); however if the actual value is n then it is said to be a false positive (FP). Conversely, a true negative has occurred when both the prediction outcome and the actual value are n, and false negative is when the prediction outcome is n while the actual value is p. In one embodiment, consider a diagnostic test that seeks to determine whether a person has a certain disease. A false positive in this case occurs when the person tests positive, but actually does not have the disease. A false negative, on the other hand, occurs when the person tests negative, suggesting they are healthy, when they actually do have the disease. In some embodiments, ROC curve assuming real-world prevalence of subtypes can be generated by re-sampling errors achieved on available samples in relevant proportions.

The positive predictive value (PPV), or precision rate, or post-test probability of disease, is the proportion of patients with positive test results who are correctly diagnosed. It is the most important measure of a diagnostic method as it reflects the probability that a positive test reflects the underlying condition being tested for. Its value does however depend on the prevalence of the disease, which may vary. In one example, FP (false positive); TN (true negative); TP (true positive); FN (false negative).

False positive rate ($\alpha$)=FP/(FP+TN)−specificity

False negative rate ($\beta$)=FN/(TP+FN)−sensitivity

Power=sensitivity=1−$\beta$

Likelihood-ratio positive=sensitivity/(1−specificity)

Likelihood-ratio negative=(1−sensitivity)/specificity

The negative predictive value is the proportion of patients with negative test results who are correctly diagnosed. PPV and NPV measurements can be derived using appropriate disease subtype prevalence estimates. An estimate of the pooled malignant disease prevalence can be calculated from the pool of indeterminates which roughly classify into B vs M by surgery. For subtype specific estimates, in some embodiments, disease prevalence may sometimes be incalculable because there are not any available samples. In these cases, the subtype disease prevalence can be substituted by the pooled disease prevalence estimate.

In some embodiments, the level of expression products or alternative exon usage is indicative of one of the following: follicular cell carcinoma, anaplastic carcinoma, medullary carcinoma, or sarcoma. In some embodiments, the one or more genes selected using the methods of the present invention for diagnosing cancer contain representative sequences corresponding to a set of metabolic or signaling pathways indicative of cancer.

In some embodiments, the results of the expression analysis of the subject methods provide a statistical confidence level that a given diagnosis is correct. In some embodiments, such statistical confidence level is above 85%, 90%, 91%, 92%, 93%, 94%, 95%, 96%, 97%, 98%, 99% or 99.5%.

In another aspect, the present invention provides a composition for diagnosing cancer comprising oligonucleotides comprising a portion of one or more of the genes listed in FIG. 6 or their complement, and a substrate upon which the oligonucleotides are covalently attached. The composition of the present invention is suitable for use in diagnosing cancer at a specified confidence level using a trained algorithm. In one example, the composition of the present invention is used to diagnose thyroid cancer.

In one aspect of the present disclosure, samples that have been processed by a cytological company, subjected to routine methods and stains, diagnosed and categorized, are then subjected to molecular profiling as a second diagnostic screen. This second diagnostic screen enables: 1) a significant reduction of false positives and false negatives, 2) a determination of the underlying genetic, metabolic, or signaling pathways responsible for the resulting pathology, 3) the ability to assign a statistical probability to the accuracy of the diagnosis, 4) the ability to resolve ambiguous results, and 5) the ability to distinguish between sub-types of cancer.

For example, in the specific case of thyroid cancer, molecular profiling of the present invention may further provide a diagnosis for the specific type of thyroid cancer (e.g. papillary, follicular, medullary, or anaplastic). The results of the molecular profiling may further allow one skilled in the art, such as a scientist or medical professional to suggest or prescribe a specific therapeutic intervention. Molecular profiling of biological samples may also be used to monitor the efficacy of a particular treatment after the initial diagnosis. It is further understood that in some cases, molecular profiling may be used in place of, rather than in addition to, established methods of cancer diagnosis.

In one aspect, the present invention provides algorithms and methods that can be used for diagnosis and monitoring of a genetic disorder. A genetic disorder is an illness caused by abnormalities in genes or chromosomes. While some diseases, such as cancer, are due in part to genetic disorders, they can also be caused by environmental factors. In some embodiments, the algorithms and the methods disclosed herein are used for diagnosis and monitoring of a cancer such as thyroid cancer.

Genetic disorders can be typically grouped into two categories: single gene disorders and multifactorial and polygenic (complex) disorders. A single gene disorder is the result of a single mutated gene. There are estimated to be over 4000 human diseases caused by single gene defects. Single gene disorders can be passed on to subsequent generations in several ways. There are several types of inheriting a single gene disorder including but not limited to autosomal dominant, autosomal recessive, X-linked dominant, X-linked recessive, P-linked and mitochondrial inheritance. Only one mutated copy of the gene will be necessary for a person to be affected by an autosomal dominant disorder. Examples of autosomal dominant type of disorder include but are not limited to Huntington's disease, Neurofibromatosis 1, Marfan Syndrome, Hereditary nonpolyposis colorectal cancer, and Hereditary multiple exostoses. In autosomal recessive disorder, two copies of the gene must be mutated for a person to be affected by an autosomal recessive disorder. Examples of this type of disorder include but are not limited to cystic fibrosis, sickle-cell disease (also partial sickle-cell disease), Tay-Sachs disease, Niemann-Pick disease, spinal muscular atrophy, and dry earwax. X-linked dominant disorders are caused by mutations in genes on the X chromosome. Only a few disorders have this inheritance pattern, with a prime example being X-linked hypophosphatemic rickets. Males and females are both affected in these disorders, with males typically being more severely affected than females. Some X-linked dominant conditions such as Rett syndrome, Incontinentia Pigmenti type 2 and Aicardi Syndrome are usually fatal in males either in utero or shortly after birth, and are therefore predominantly seen in females. X-linked recessive disorders are also caused by mutations in genes on the X chromosome. Examples of this type of disorder include but are not limited to Hemophilia A, Duchenne muscular dystrophy, red-green color blindness, muscular dystrophy and Androgenetic alopecia. Y-linked disorders are caused by mutations on the Y chromosome. Examples include but are not limited to Male Infertility and hypertrichosis pinnae. Mitochondrial inheritance, also known as maternal inheritance, applies to genes in mitochondrial DNA. An example of this type of disorder is Leber's Hereditary Optic Neuropathy.

Genetic disorders may also be complex, multifactorial or polygenic, this means that they are likely associated with the effects of multiple genes in combination with lifestyle and environmental factors. Although complex disorders often cluster in families, they do not have a clear-cut pattern of inheritance. This makes it difficult to determine a person's risk of inheriting or passing on these disorders. Complex disorders are also difficult to study and treat because the specific factors that cause most of these disorders have not yet been identified. Multifactoral or polygenic disorders that can be diagnosed, characterized and/or monitored using the algorithms and methods of the present invention include but are not limited to heart disease, diabetes, asthma, autism, autoimmune diseases such as multiple sclerosis, cancers, ciliopathies, cleft palate, hypertension, inflammatory bowel disease, mental retardation and obesity.

Other genetic disorders that can be diagnosed, characterized and/or monitored using the algorithms and methods of the present invention include but are not limited to 1p36 deletion syndrome, 21-hydroxylase deficiency, 22q11.2 deletion syndrome, 47,XYY syndrome, 48, XXXX, 49, XXXXX, aceruloplasminemia, achondrogenesis, type II, achondroplasia, acute intermittent porphyria, adenylosuccinate lyase deficiency, Adrenoleukodystrophy, ALA deficiency porphyria, ALA dehydratase deficiency, Alexander disease, alkaptonuria, alpha-1 antitrypsin deficiency, Alstrom syndrome, Alzheimer's disease (type 1, 2, 3, and 4), Amelogenesis Imperfecta, amyotrophic lateral sclerosis, Amyotrophic lateral sclerosis type 2, Amyotrophic lateral sclerosis type 4, amyotrophic lateral sclerosis type 4, androgen insensitivity syndrome, Anemia, Angelman syndrome, Apert syndrome, ataxia-telangiectasia, Beare-Stevenson cutis gyrata syndrome, Benjamin syndrome, beta thalassemia, biotinidase deficiency, Birt-Hogg-Dubé syndrome, bladder cancer, Bloom syndrome, Bone diseases, breast cancer, CADASIL, Camptomelic dysplasia, Canavan disease, Cancer, Celiac Disease, CGD Chronic Granulomatous Disorder, Charcot-Marie-Tooth disease, Charcot-Marie-Tooth disease Type 1, Charcot-Marie-Tooth disease Type 4, Charcot-Marie-Tooth disease, type 2, Charcot-Marie-Tooth disease, type 4, Cockayne syndrome, Coffin-Lowry syndrome, collagenopathy, types II and XI, Colorectal Cancer, Congenital absence of the vas deferens, congenital bilateral absence of vas deferens, congenital diabetes, congenital erythropoietic porphyria, Congenital heart disease, congenital hypothyroidism, Connective tissue disease, Cowden syndrome, Cri du chat, Crohn's disease, fibrostenosing, Crouzon syndrome, Crouzonodermoskeletal syndrome, cystic fibrosis, De Grouchy Syndrome, Degenerative nerve diseases, Dent's disease, developmental disabilities, DiGeorge syndrome, Distal spinal muscular atrophy type V, Down syndrome, Dwarfism, Ehlers-Danlos syndrome, Ehlers-Danlos syndrome arthrochalasia type, Ehlers-Danlos syndrome classical type, Ehlers-Danlos syndrome dermatosparaxis type, Ehlers-Danlos syndrome kyphoscoliosis type, vascular type, erythropoietic protoporphyria, Fabry's disease, Facial injuries and disorders, factor V Leiden thrombophilia, familial adenomatous polyposis, familial dysautonomia, fanconi anemia, FG syndrome, fragile X syndrome, Friedreich ataxia, Friedreich's ataxia, G6PD deficiency, galactosemia, Gaucher's disease (type 1, 2, and 3), Genetic brain disorders, Glycine encephalopathy, Haemochromatosis type 2, Haemochromatosis type 4, Harlequin Ichthyosis, Head and brain malformations, Hearing disorders and deafness, Hearing problems in children, hemochromatosis (neonatal, type 2 and type 3), hemophilia, hepatoerythropoietic porphyria, hereditary coproporphyria, Hereditary Multiple Exostoses, hereditary neuropathy with liability to pressure palsies, hereditary nonpolyposis colorectal cancer, homocystinuria, Huntington's disease, Hutchinson Gilford Progeria Syndrome, hyperoxaluria, primary, hyperphenylalaninemia, hypochondrogenesis, hypochondroplasia, idic15, incontinentia pigmenti, Infantile Gaucher disease, infantile-onset ascending hereditary spastic paralysis, Infertility, Jackson-Weiss syndrome, Joubert syndrome, Juvenile Primary Lateral Sclerosis, Kennedy disease, Klinefelter syndrome, Kniest dysplasia, Krabbe disease, Learning disability, Lesch-Nyhan syndrome, Leukodystrophies, Li-Fraumeni syndrome, lipoprotein lipase deficiency, familial, Male genital disorders, Marfan syndrome, McCune-Albright syndrome, McLeod syndrome, Mediterranean fever, familial, MEDNIK, Menkes disease, Menkes syndrome, Metabolic disorders, methemoglobinemia beta-globin type, Methemoglobinemia congenital methaemoglobinaemia, methylmalonic acidemia, Micro syndrome, Microcephaly, Movement disorders, Mowat-Wilson syndrome, Mucopolysaccharidosis (MPS I), Muenke syndrome, Muscular dystrophy, Muscular dystrophy, Duchenne and Becker type, muscular dystrophy, Duchenne and Becker types, myotonic dystrophy, Myotonic dystrophy type 1 and type 2, Neonatal hemochromatosis, neurofibromatosis, neurofibromatosis 1, neurofibromatosis 2, Neurofibromatosis type I, neurofibromatosis type II, Neurologic diseases, Neuromuscular disorders, Niemann-Pick disease, Nonketotic hyperglycinemia, non-syndromic deafness, Nonsyndromic deafness autosomal recessive, Noonan syndrome, osteogenesis imperfecta (type I and type III), otospondylomegaepiphyseal dysplasia, pantothenate kinase-associated neurodegeneration, Patau Syndrome (Trisomy 13), Pendred syndrome, Peutz-Jeghers syndrome, Pfeiffer syndrome, phenylketonuria, porphyria, porphyria cutanea tarda, Prader-Willi syndrome, primary pulmonary hypertension, prion disease, Progeria, propionic acidemia, protein C deficiency, protein S deficiency, pseudo-Gaucher disease, pseudoxanthoma elasticum, Retinal disorders, retinoblastoma, retinoblastoma FA—Friedreich ataxia, Rett syndrome, Rubinstein-Taybi syndrome, SADDAN, Sandhoff disease, sensory and autonomic neuropathy type III, sickle cell anemia, skeletal muscle regeneration, Skin pigmentation disorders, Smith Lemli Opitz Syndrome, Speech and communication disorders, spinal muscular atrophy, spinal-bulbar muscular atrophy, spinocerebellar ataxia, spondyloepimetaphyseal dysplasia, Strudwick type, spondyloepiphyseal dysplasia congenita, Stickler syndrome, Stickler syndrome COL2A1, Tay-Sachs disease, tetrahydrobiopterin deficiency, thanatophoric dysplasia, thiamine-responsive megaloblastic anemia with diabetes mellitus and sensorineural deafness, Thyroid disease, Tourette's Syndrome, Treacher Collins syndrome, triple X syndrome, tuberous sclerosis, Turner syndrome, Usher syndrome, variegate porphyria, von Hippel-Lindau disease, Waardenburg syndrome, Weissenbacher-Zweymüller syndrome, Wilson disease, Wolf-Hirschhorn syndrome, Xeroderma Pigmentosum, X-linked severe combined immunodeficiency, X-linked sideroblastic anemia, and X-linked spinal-bulbar muscle atrophy.

In one embodiment, the subject methods and algorithm are used to diagnose, characterize, and monitor thyroid cancer. Other types of cancer that can be diagnosed, characterized and/or monitored using the algorithms and methods of the present invention include but are not limited to adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's disease, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, uterine cancer (e.g. uterine sarcoma), vaginal cancer, vulvar cancer, and Waldenstrom's macroglobulinemia.

In some embodiments, gene expression product markers of the present invention may provide increased accuracy of genetic disorder or cancer diagnosis through the use of multiple gene expression product markers in low quantity and quality, and statistical analysis using the algorithms of the present invention. In particular, the present invention provides, but is not limited to, methods of diagnosing, characterizing and classifying gene expression profiles associated with thyroid cancers. The present invention also provides algorithms for characterizing and classifying thyroid tissue samples, and kits and compositions useful for the application of said methods. The disclosure further includes methods for running a molecular profiling business.

In one embodiment of the invention, markers and genes can be identified to have differential expression in thyroid cancer samples compared to thyroid benign samples. Illustrative examples having a benign pathology include follicular adenoma, Hurthle cell adenoma, lymphocytic thyroiditis, and nodular hyperplasia. Illustrative examples having a malignant pathology include follicular carcinoma, follicular variant of papillary thyroid carcinoma, medullary carcinoma, and papillary thyroid carcinoma.

Biological samples may be treated to extract nucleic acid such as DNA or RNA. The nucleic acid may be contacted with an array of probes of the present invention under conditions to allow hybridization. The degree of hybridization may be assayed in a quantitative matter using a number of methods known in the art. In some cases, the degree of hybridization at a probe position may be related to the intensity of signal provided by the assay, which therefore is related to the amount of complementary nucleic acid sequence present in the sample. Software can be used to extract, normalize, summarize, and analyze array intensity data from probes across the human genome or transcriptome including expressed genes, exons, introns, and miRNAs. In some embodiments, the intensity of a given probe in either the benign or malignant samples can be compared against a reference set to determine whether differential expression is occurring in a sample. An increase or decrease in relative intensity at a marker position on an array corresponding to an expressed sequence is indicative of an increase or decrease respectively of expression of the corresponding expressed sequence. Alternatively, a decrease in relative intensity may be indicative of a mutation in the expressed sequence.

The resulting intensity values for each sample can be analyzed using feature selection techniques including filter techniques which assess the relevance of features by looking at the intrinsic properties of the data, wrapper methods which embed the model hypothesis within a feature subset search, and embedded techniques in which the search for an optimal set of features is built into a classifier algorithm.

Filter techniques useful in the methods of the present invention include (1) parametric methods such as the use of two sample t-tests, ANOVA analyses, Bayesian frameworks, and Gamma distribution models (2) model free methods such as the use of Wilcoxon rank sum tests, between-within class sum of squares tests, rank products methods, random permutation methods, or TNoM which involves setting a threshold point for fold-change differences in expression between two datasets and then detecting the threshold point in each gene that minimizes the number of missclassifications (3) and multivariate methods such as bivariate methods, correlation based feature selection methods (CFS), minimum redundancy maximum relevance methods (MRMR), Markov blanket filter methods, and uncorrelated shrunken centroid methods. Wrapper methods useful in the methods of the present invention include sequential search methods, genetic algorithms, and estimation of distribution algorithms. Embedded methods useful in the methods of the present invention include random forest algorithms, weight vector of support vector machine algorithms, and weights of logistic regression algorithms. Bioinformatics. 2007 Oct. 1; 23(19):2507-17 provides an overview of the relative merits of the filter techniques provided above for the analysis of intensity data.

Selected features may then be classified using a classifier algorithm. Illustrative algorithms include but are not limited to methods that reduce the number of variables such as principal component analysis algorithms, partial least squares methods, and independent component analysis algorithms. Illustrative algorithms further include but are not limited to methods that handle large numbers of variables directly such as statistical methods and methods based on machine learning techniques. Statistical methods include penalized logistic regression, prediction analysis of microarrays (PAM), methods based on shrunken centroids, support vector machine analysis, and regularized linear discriminant analysis. Machine learning techniques include bagging procedures, boosting procedures, random forest algorithms, and combinations thereof. Cancer Inform. 2008; 6: 77-97 provides an overview of the classification techniques provided above for the analysis of microarray intensity data.

The markers and genes of the present invention can be utilized to characterize the cancerous or non-cancerous status of cells or tissues. The present invention includes a method for diagnosing benign tissues or cells from malignant tissues or cells comprising determining the differential expression of a marker or gene in a thyroid sample of a subject wherein said marker or gene is a marker or gene listed in FIG. 2-6, 9-13, 16 or 17. The present invention also includes methods for diagnosing medullary thyroid carcinoma comprising determining the differential expression of a marker or gene in a thyroid sample of a subject wherein said marker or gene is a marker or gene listed in FIG. 10. The present invention also includes methods for diagnosing thyroid pathology subtypes comprising determining the differential expression of a marker or gene in a thyroid sample of a subject wherein said marker or gene is a marker or gene listed in FIG. 13. The present invention also includes methods for diagnosing benign tissues or cells from malignant tissues or cells comprising determining the differential expression of an miRNA in a thyroid sample of a subject wherein said miRNA is an miRNA listed in FIG. 16 or 17.

In accordance with the foregoing, the differential expression of a gene, genes, markers, miRNAs, or a combination thereof as disclosed herein may be determined using northern blotting and employing the sequences as identified in herein to develop probes for this purpose. Such probes may be composed of DNA or RNA or synthetic nucleotides or a combination of the above and may advantageously be comprised of a contiguous stretch of nucleotide residues matching, or complementary to, a sequence as identified in FIG. 2-6, 9-13, 16 or 17. Such probes will most usefully comprise a contiguous stretch of at least 15-200 residues or more including 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, 100, 110, 120, 130, 140, 150, 160, 175, or 200 nucleotides or more, derived from one or more of the sequences as identified in FIG. 2-6, 9-13, 16 or 17. Thus, where a single probe binds multiple times to the transcriptome of a sample of cells that are cancerous, or are suspected of being cancerous, or predisposed to become cancerous, whereas binding of the same probe to a similar amount of transcriptome derived from the genome of otherwise non-cancerous cells of the same organ or tissue results in observably more or less binding, this is indicative of differential expression of a gene, multiple genes, markers, or miRNAs comprising, or corresponding to, the sequences identified in FIG. 2-6, 9-13, 16 or 17 from which the probe sequenced was derived.

In one such embodiment, the elevated expression, as compared to normal cells and/or tissues of the same organ, is determined by measuring the relative rates of transcription of RNA, such as by production of corresponding cDNAs and then analyzing the resulting DNA using probes developed from the gene sequences as identified in FIG. 2-6, 9-13, 16 or 17. Thus, the levels of cDNA produced by use of reverse transcriptase with the full RNA complement of a cell suspected of being cancerous produces a corresponding amount of cDNA that can then be amplified using polymerase chain reaction, or some other means, such as linear amplification, isothermal amplification, NASB, or rolling circle amplification, to determine the relative levels of resulting cDNA and, thereby, the relative levels of gene expression.

Increased expression may also be determined using agents that selectively bind to, and thereby detect, the presence of expression products of the genes disclosed herein. For example, an antibody, possibly a suitably labeled antibody, such as where the antibody is bound to a fluorescent or radiolabel, may be generated against one of the polypeptides comprising a sequence as identified in FIGS. 2-6, and 9-13, and said antibody will then react with, binding either selectively or specifically, to a polypeptide encoded by one of the genes that corresponds to a sequence disclosed herein. Such antibody binding, especially relative extent of such binding in samples derived from suspected cancerous, as opposed to otherwise non-cancerous, cells and tissues, can then be used as a measure of the extent of expression, or over-expression, of the cancer-related genes identified herein. Thus, the genes identified herein as being over-expressed in cancerous cells and tissues may be over-expressed due to increased copy number, or due to over-transcription, such as where the over-expression is due to over-production of a transcription factor that activates the gene and leads to repeated binding of RNA polymerase, thereby generating large than normal amounts of RNA transcripts, which are subsequently translated into polypeptides, such as the polypeptides comprising amino acid sequences as identified in FIGS. 2-6, and 9-13. Such analysis provides an additional means of ascertaining the expression of the genes identified according to the invention and thereby determining the presence of a cancerous state in a sample derived from a patient to be tested, of the predisposition to develop cancer at a subsequent time in said patient.

In employing the methods of the invention, it should be borne in mind that gene or marker expression indicative of a cancerous state need not be characteristic of every cell found to be cancerous. Thus, the methods disclosed herein are useful for detecting the presence of a cancerous condition within a tissue where less than all cells exhibit the complete pattern of over-expression. For example, a set of selected genes or markers, comprising sequences homologous under stringent conditions, or at least 90%, preferably 95%, identical to at least one of the sequences as identified in FIG. 2-6, 9-13, 16 or 17, may be found, using appropriate probes, either DNA or RNA, to be present in as little as 60% of cells derived from a sample of tumorous, or malignant, tissue while being absent from as much as 60% of cells derived from corresponding non-cancerous, or otherwise normal, tissue (and thus being present in as much as 40% of such normal tissue cells). In one embodiment, such expression pattern is found to be present in at least 70% of cells drawn from a cancerous tissue and absent from at least 70% of a corresponding normal, non-cancerous, tissue sample. In another embodiment, such expression pattern is found to be present in at least 80% of cells drawn from a cancerous tissue and absent from at least 80% of a corresponding normal, non-cancerous, tissue sample. In another embodiment, such expression pattern is found to be present in at least 90% of cells drawn from a cancerous tissue and absent from at least 90% of a corresponding normal, non-cancerous, tissue sample. In another embodiment, such expression pattern is found to be present in at least 100% of cells drawn from a cancerous tissue and absent from at least 100% of a corresponding normal, non-cancerous, tissue sample, although the latter embodiment may represent a rare occurrence.

In some embodiments molecular profiling includes detection, analysis, or quantification of nucleic acid (DNA, or RNA), protein, or a combination thereof. The diseases or conditions to be diagnosed by the methods of the present invention include for example conditions of abnormal growth in one or more tissues of a subject including but not limited to skin, heart, lung, kidney, breast, pancreas, liver, muscle, smooth muscle, bladder, gall bladder, colon, intestine, brain, esophagus, or prostate. In some embodiments, the tissues analyzed by the methods of the present invention include thyroid tissues.

In some embodiments, the diseases or conditions diagnosed by the methods of the present invention include benign and malignant hyperproliferative disorders including but not limited to cancers, hyperplasias, or neoplasias. In some cases, the hyperproliferative disorders diagnosed by the methods of the present invention include but are not limited to breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer. In some cases, the diseases or conditions diagnosed by the methods of the present invention include but are not limited to thyroid disorders such as for example benign thyroid disorders including but not limited to follicular adenomas, Hurthle cell adenomas, lymphocytic thyroiditis, and thyroid hyperplasia. In some cases, the diseases or conditions diagnosed by the methods of the present invention include but are not limited to malignant thyroid disorders such as for example follicular carcinomas, follicular variant of papillary thyroid carcinomas, medullary carcinomas, and papillary carcinomas. In some cases, the methods of the present invention provide for a diagnosis of a tissue as diseased or normal. In other cases, the methods of the present invention provide for a diagnosis of normal, benign, or malignant. In some cases, the methods of the present invention provide for a diagnosis of benign/normal, or malignant. In some cases, the methods of the present invention provide for a diagnosis of one or more of the specific diseases or conditions provided herein.

II. Obtaining a Biological Sample

In some embodiments, the methods of the present invention provide for obtaining a sample from a subject. As used herein, the term subject refers to any animal (e g a mammal), including but not limited to humans, non-human primates, rodents, dogs, pigs, and the like. The methods of obtaining provided herein include methods of biopsy including fine needle aspiration, core needle biopsy, vacuum assisted biopsy, incisional biopsy, excisional biopsy, punch biopsy, shave biopsy or skin biopsy. The sample may be obtained from any of the tissues provided herein including but not limited to skin, heart, lung, kidney, breast, pancreas, liver, muscle, smooth muscle, bladder, gall bladder, colon, intestine, brain, prostate, esophagus, or thyroid. Alternatively, the sample may be obtained from any other source including but not limited to blood, sweat, hair follicle, buccal tissue, tears, menses, feces, or saliva. In some embodiments of the present invention, a medical professional may obtain a biological sample for testing. In some cases the medical professional may refer the subject to a testing center or laboratory for submission of the biological sample. In other cases, the subject may provide the sample. In some cases, a molecular profiling business of the present invention may obtain the sample.

The sample may be obtained by methods known in the art such as the biopsy methods provided herein, swabbing, scraping, phlebotomy, or any other methods known in the art. In some cases, the sample may be obtained, stored, or transported using components of a kit of the present invention. In some cases, multiple samples, such as multiple thyroid samples may be obtained for diagnosis by the methods of the present invention. In some cases, multiple samples, such as one or more samples from one tissue type (e.g. thyroid) and one or more samples from another tissue (e.g. buccal) may be obtained for diagnosis by the methods of the present invention. In some cases, multiple samples such as one or more samples from one tissue type (e.g. thyroid) and one or more samples from another tissue (e.g. buccal) may be obtained at the same or different times. In some cases, the samples obtained at different times are stored and/or analyzed by different methods. For example, a sample may be obtained and analyzed by cytological analysis (routine staining). In some cases, further sample may be obtained from a subject based on the results of a cytological analysis. The diagnosis of cancer may include an examination of a subject by a physician, nurse or other medical professional. The examination may be part of a routine examination, or the examination may be due to a specific complaint including but not limited to one of the following: pain, illness, anticipation of illness, presence of a suspicious lump or mass, a disease, or a condition. The subject may or may not be aware of the disease or condition. The medical professional may obtain a biological sample for testing. In some cases the medical professional may refer the subject to a testing center or laboratory for submission of the biological sample.

In some cases, the subject may be referred to a specialist such as an oncologist, surgeon, or endocrinologist for further diagnosis. The specialist may likewise obtain a biological sample for testing or refer the individual to a testing center or laboratory for submission of the biological sample. In any case, the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample, or the molecular profiling business of the present disclosure may consult on which assays or tests are most appropriately indicated. The molecular profiling business may bill the individual or medical or insurance provider thereof for consulting work, for sample acquisition and or storage, for materials, or for all products and services rendered.

In some embodiments of the present invention, a medical professional need not be involved in the initial diagnosis or sample acquisition. An individual may alternatively obtain a sample through the use of an over the counter kit. Said kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately.

A sample suitable for use by the molecular profiling business may be any material containing tissues, cells, nucleic acids, genes, gene fragments, expression products, gene expression products, or gene expression product fragments of an individual to be tested. Methods for determining sample suitability and/or adequacy are provided. A sample may include but is not limited to, tissue, cells, or biological material from cells or derived from cells of an individual. The sample may be a heterogeneous or homogeneous population of cells or tissues. The biological sample may be obtained using any method known to the art that can provide a sample suitable for the analytical methods described herein.

The sample may be obtained by non-invasive methods including but not limited to: scraping of the skin or cervix, swabbing of the cheek, saliva collection, urine collection, feces collection, collection of menses, tears, or semen. In other cases, the sample is obtained by an invasive procedure including but not limited to: biopsy, alveolar or pulmonary lavage, needle aspiration, or phlebotomy. The method of biopsy may further include incisional biopsy, excisional biopsy, punch biopsy, shave biopsy, or skin biopsy. The method of needle aspiration may further include fine needle aspiration, core needle biopsy, vacuum assisted biopsy, or large core biopsy. In some embodiments, multiple samples may be obtained by the methods herein to ensure a sufficient amount of biological material. Methods of obtaining suitable samples of thyroid are known in the art and are further described in the ATA Guidelines for thyroid nodule management (Cooper et al. *Thyroid* Vol. 16 No. 2 2006), herein incorporated by reference in its entirety. Generic methods for obtaining biological samples are also known in the art and further described in for example Ramzy, Ibrahim *Clinical Cytopathology and Aspiration Biopsy* 2001 which is herein incorporated by reference in its entirety. In one embodiment, the sample is a fine needle aspirate of a thyroid nodule or a suspected thyroid tumor. In some cases, the fine needle aspirate sampling procedure may be guided by the use of an ultrasound, X-ray, or other imaging device.

In some embodiments of the present invention, the molecular profiling business may obtain the biological sample from a subject directly, from a medical professional, from a third party, or from a kit provided by the molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

III. Storing the Sample

In some embodiments, the methods of the present invention provide for storing the sample for a time such as seconds, minutes, hours, days, weeks, months, years or longer after the sample is obtained and before the sample is analyzed by one or more methods of the invention. In some cases, the sample obtained from a subject is subdivided prior to the step of storage or further analysis such that different portions of the sample are subject to different downstream methods or processes including but not limited to storage, cytological analysis, adequacy tests, nucleic acid extraction, molecular profiling or a combination thereof.

In some cases, a portion of the sample may be stored while another portion of said sample is further manipulated. Such manipulations may include but are not limited to molecular profiling; cytological staining; nucleic acid (RNA or DNA) extraction, detection, or quantification; gene expression product (RNA or Protein) extraction, detection, or quantification; fixation; and examination. The sample may be fixed prior to or during storage by any method known to the art such as using glutaraldehyde, formaldehyde, or methanol. In other cases, the sample is obtained and stored and subdivided after the step of storage for further analysis such that different portions of the sample are subject to different downstream methods or processes including but not limited to storage, cytological analysis, adequacy tests, nucleic acid extraction, molecular profiling or a combination thereof. In some cases, samples are obtained and analyzed by for example cytological analysis, and the resulting sample material is further analyzed by one or more molecular profiling methods of the present invention. In such cases, the samples may be stored between the steps of cytological analysis and the steps of molecular profiling. Samples may be stored upon acquisition to facilitate transport, or to wait for the results of other analyses. In another embodiment, samples may be stored while awaiting instructions from a physician or other medical professional.

The acquired sample may be placed in a suitable medium, excipient, solution, or container for short term or long term storage. Said storage may require keeping the sample in a refrigerated, or frozen environment. The sample may be quickly frozen prior to storage in a frozen environment. The frozen sample may be contacted with a suitable cryopreservation medium or compound including but not limited to: glycerol, ethylene glycol, sucrose, or glucose. A suitable medium, excipient, or solution may include but is not limited to: hanks salt solution, saline, cellular growth medium, an ammonium salt solution such as ammonium sulphate or ammonium phosphate, or water. Suitable concentrations of ammonium salts include solutions of about 0.1 g/ml, 0.2 g/ml, 0.3 g/ml, 0.4 g/ml, 0.5 g/ml, 0.6 g/ml, 0.7 g/ml, 0.8 g/ml, 0.9 g/ml, 1.0 g/ml, 1.1 g/ml, 1.2 g/ml, 1.3 g/ml, 1.4 g/ml, 1.5 g/ml, 1.6 g/ml, 1.7 g/ml, 1.8 g/ml, 1.9 g/ml, 2.0 g/ml, 2.2 g/ml, 2.3 g/ml, 2.5 g/ml or higher. The medium, excipient, or solution may or may not be sterile.

The sample may be stored at room temperature or at reduced temperatures such as cold temperatures (e.g. between about 20° C. and about 0° C.), or freezing temperatures, including for example 0 C, −1 C, −2 C, −3 C, −4 C, −5 C, −6 C, −7 C, −8 C, −9 C, −10 C, −12 C, −14 C, −15 C, −16 C, −20 C, −22 C, −25 C, −28 C, −30 C, −35 C, −40 C, −45 C, −50 C, −60 C, −70 C, −80 C, −100 C, −120 C, −140 C, −180 C, −190 C, or about −200 C. In some cases, the samples may be stored in a refrigerator, on ice or a frozen gel pack, in a freezer, in a cryogenic freezer, on dry ice, in liquid nitrogen, or in a vapor phase equilibrated with liquid nitrogen.

The medium, excipient, or solution may contain preservative agents to maintain the sample in an adequate state for subsequent diagnostics or manipulation, or to prevent coagulation. Said preservatives may include citrate, ethylene diamine tetraacetic acid, sodium azide, or thimersol. The medium, excipient or solution may contain suitable buffers or salts such as Tris buffers or phosphate buffers, sodium salts (e.g. NaCl), calcium salts, magnesium salts, and the like. In some cases, the sample may be stored in a commercial preparation suitable for storage of cells for subsequent cytological analysis such as but not limited to Cytyc Thin-Prep, SurePath, or Monoprep.

The sample container may be any container suitable for storage and or transport of the biological sample including but not limited to: a cup, a cup with a lid, a tube, a sterile tube, a vacuum tube, a syringe, a bottle, a microscope slide, or any other suitable container. The container may or may not be sterile.

IV. Transportation of the Sample

The methods of the present invention provide for transport of the sample. In some cases, the sample is transported from a clinic, hospital, doctor's office, or other location to a second location whereupon the sample may be stored and/or analyzed by for example, cytological analysis or molecular profiling. In some cases, the sample may be transported to a molecular profiling company in order to perform the analyses described herein. In other cases, the sample may be transported to a laboratory such as a laboratory authorized or otherwise capable of performing the methods of the present invention such as a Clinical Laboratory Improvement Amendments (CLIA) laboratory. The sample may be transported by the individual from whom the sample derives. Said transportation by the individual may include the individual appearing at a molecular profiling business or a designated sample receiving point and providing a sample. Said providing of the sample may involve any of the techniques of sample acquisition described herein, or the sample may have already have been acquired and stored in a suitable container as described herein. In other cases the sample may be transported to a molecular profiling business using a courier service, the postal service, a shipping service, or any method capable of transporting the sample in a suitable manner. In some cases, the sample may be provided to a molecular profiling business by a third party testing laboratory (e.g. a cytology lab). In other cases, the sample may be provided to a molecular profiling business by the subject's primary care physician, endocrinologist or other medical professional. The cost of transport may be billed to the individual, medical provider, or insurance provider. The molecular profiling business may begin analysis of the sample immediately upon receipt, or may store the sample in any manner described herein. The method of storage may or may not be the same as chosen prior to receipt of the sample by the molecular profiling business.

The sample may be transported in any medium or excipient including any medium or excipient provided herein suitable for storing the sample such as a cryopreservation medium or a liquid based cytology preparation. In some cases, the sample may be transported frozen or refrigerated such as at any of the suitable sample storage temperatures provided herein.

Upon receipt of the sample by the molecular profiling business, a representative or licensee thereof, a medical professional, researcher, or a third party laboratory or testing center (e.g. a cytology laboratory) the sample may be assayed using a variety of routine analyses known to the art such as cytological assays, and genomic analysis. Such tests may be indicative of cancer, the type of cancer, any other disease or condition, the presence of disease markers, or the absence of cancer, diseases, conditions, or disease markers. The tests may take the form of cytological examination including microscopic examination as described below. The tests may involve the use of one or more cytological stains. The biological material may be manipulated or prepared for the test prior to administration of the test by any suitable method known to the art for biological sample preparation. The specific assay performed may be determined by the molecular profiling company, the physician who ordered the test, or a third party such as a consulting medical professional, cytology laboratory, the subject from whom the sample derives, or an insurance provider. The specific assay may be chosen based on the likelihood of obtaining a definite diagnosis, the cost of the assay, the speed of the assay, or the suitability of the assay to the type of material provided.

V. Test for Adequacy

Subsequent to or during sample acquisition, including before or after a step of storing the sample, the biological material may be collected and assessed for adequacy, for example, to asses the suitability of the sample for use in the methods and compositions of the present invention. The assessment may be performed by the individual who obtains the sample, the molecular profiling business, the individual using a kit, or a third party such as a cytological lab, pathologist, endocrinologist, or a researcher. The sample may be determined to be adequate or inadequate for further analysis due to many factors including but not limited to: insufficient cells, insufficient genetic material, insufficient protein, DNA, or RNA, inappropriate cells for the indicated test, or inappropriate material for the indicated test, age of the sample, manner in which the sample was obtained, or manner in which the sample was stored or transported. Adequacy may be determined using a variety of methods known in the art such as a cell staining procedure, measurement of the number of cells or amount of tissue, measurement of total protein, measurement of nucleic acid, visual examination, microscopic examination, or temperature or pH determination. In one embodiment, sample adequacy will be determined from the results of performing a gene expression product level analysis experiment. In another embodiment sample adequacy will be determined by measuring the content of a marker of sample adequacy. Such markers include elements such as iodine, calcium, magnesium, phosphorous, carbon, nitrogen, sulfur, iron etc.; proteins such as but not limited to thyroglobulin; cellular mass; and cellular components such as protein, nucleic acid, lipid, or carbohydrate.

In some cases, iodine may be measured by a chemical method such as described in U.S. Pat. No. 3,645,691 which is incorporated herein by reference in its entirety or other chemical methods known in the art for measuring iodine content. Chemical methods for iodine measurement include but are not limited to methods based on the Sandell and Kolthoff reaction. Said reaction proceeds according to the following equation:

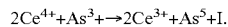

$$2Ce^{4+}+As^{3+}\rightarrow 2Ce^{3+}+As^{5+}+I.$$

Iodine has a catalytic effect upon the course of the reaction, i.e., the more iodine present in the preparation to be analyzed, the more rapidly the reaction proceeds. The speed of reaction is proportional to the iodine concentration. In some cases, this analytical method may carried out in the following manner:

A predetermined amount of a solution of arsenous oxide $As_2O_3$ in concentrated sulfuric or nitric acid is added to the biological sample and the temperature of the mixture is adjusted to reaction temperature, i.e., usually to a temperature between 20° C. and 60° C. A predetermined amount of a cerium (IV) sulfate solution in sulfuric or nitric acid is added thereto. Thereupon, the mixture is allowed to react at the predetermined temperature for a definite period of time. Said reaction time is selected in accordance with the order of magnitude of the amount of iodine to be determined and with the respective selected reaction temperature. The reaction time is usually between about 1 minute and about 40 minutes. Thereafter, the content of the test solution of cerium (IV) ions is determined photometrically. The lower the photometrically determined cerium (IV) ion concentration is, the higher is the speed of reaction and, consequently, the amount of catalytic agent, i.e., of iodine. In this manner the iodine of the sample can directly and quantitatively be determined.

In other cases, iodine content of a sample of thyroid tissue may be measured by detecting a specific isotope of iodine such as for example $^{123}I$, $^{124}I$, $^{125}I$, and $^{131}I$. In still other cases, the marker may be another radioisotope such as an isotope of carbon, nitrogen, sulfur, oxygen, iron, phosphorous, or hydrogen. The radioisotope in some instances may be administered prior to sample collection. Methods of radioisotope administration suitable for adequacy testing are well known in the art and include injection into a vein or artery, or by ingestion. A suitable period of time between administration of the isotope and acquisition of thyroid nodule sample so as to effect absorption of a portion of the isotope into the thyroid tissue may include any period of time between about a minute and a few days or about one week including about 1 minute, 2 minutes, 5 minutes, 10 minutes, 15 minutes, ½ an hour, an hour, 8 hours, 12 hours, 24 hours, 48 hours, 72 hours, or about one, one and a half, or two weeks, and may readily be determined by one skilled in the art. Alternatively, samples may be measured for natural levels of isotopes such as radioisotopes of iodine, calcium, magnesium, carbon, nitrogen, sulfur, oxygen, iron, phosphorous, or hydrogen.

(i) Cell and/or Tissue Content Adequacy Test

Methods for determining the amount of a tissue include but are not limited to weighing the sample or measuring the volume of sample. Methods for determining the amount of cells include but are not limited to counting cells which may in some cases be performed after dis-aggregation with for example an enzyme such as trypsin or collagenase or by physical means such as using a tissue homogenizer for example. Alternative methods for determining the amount of cells recovered include but are not limited to quantification of dyes that bind to cellular material, or measurement of the volume of cell pellet obtained following centrifugation. Methods for determining that an adequate number of a specific type of cell is present include PCR, Q-PCR, RT-PCR, immuno-histochemical analysis, cytological analysis, microscopic, and or visual analysis.

(ii) Nucleic Acid Content Adequacy Test

Samples may be analyzed by determining nucleic acid content after extraction from the biological sample using a variety of methods known to the art. In some cases, nucleic acids such as RNA or mRNA is extracted from other nucleic acids prior to nucleic acid content analysis. Nucleic acid content may be extracted, purified, and measured by ultraviolet absorbance, including but not limited to absorbance at 260 nanometers using a spectrophotometer. In other cases nucleic acid content or adequacy may be measured by fluorometer after contacting the sample with a stain. In still other cases, nucleic acid content or adequacy may be measured after electrophoresis, or using an instrument such as an agilent bioanalyzer for example. It is understood that the methods of the present invention are not limited to a specific method for measuring nucleic acid content and or integrity.

In some embodiments, the RNA quantity or yield from a given sample is measured shortly after purification using a NanoDrop spectrophotometer in a range of nano- to micrograms. In some embodiments, RNA quality is measured using an Agilent 2100 Bioanalyzer instrument, and is characterized by a calculated RNA Integrity Number (RIN, 1-10). The NanoDrop is a cuvette-free spectrophotometer. It uses 1 microleter to measure from 5 ng/µl to 3,000 ng/µl of sample. The key features of NanoDrop include low volume of sample and no cuvette; large dynamic range 5 ng/µl to 3,000 ng/µl; and it allows quantitation of DNA, RNA and proteins. NanoDrop™ 2000c allows for the analysis of 0.5 µl-2.0 µl samples, without the need for cuvettes or capillaries.

RNA quality can be measured by a calculated RNA Integrity Number (RIN). The RNA integrity number (RIN) is an algorithm for assigning integrity values to RNA measurements. The integrity of RNA is a major concern for gene expression studies and traditionally has been evaluated using the 28S to 18S rRNA ratio, a method that has been shown to be inconsistent. The RIN algorithm is applied to electrophoretic RNA measurements and based on a combination of different features that contribute information about the RNA integrity to provide a more robust universal measure. In some embodiments, RNA quality is measured using an Agilent 2100 Bioanalyzer instrument. The protocols for measuring RNA quality are known and available commercially, for example, at Agilent website. Briefly, in the first step, researchers deposit total RNA sample into an RNA Nano LabChip. In the second step, the LabChip is inserted into the Agilent bioanalyzer and let the analysis run, generating a digital electropherogram. In the third step, the new RIN algorithm then analyzes the entire electrophoretic trace of the RNA sample, including the presence or absence of degradation products, to determine sample integrity. Then, The algorithm assigns a 1 to 10 RIN score, where level 10 RNA is completely intact. Because interpretation of the electropherogram is automatic and not subject to individual interpretation, universal and unbiased comparison of samples is enabled and repeatability of experiments is improved. The RIN algorithm was developed using neural networks and adaptive learning in conjunction with a large database of eukaryote total RNA samples, which were obtained mainly from human, rat, and mouse tissues. Advantages of RIN include obtain a numerical assessment of the integrity of RNA; directly comparing RNA samples, e.g. before and after archival, compare integrity of same tissue across different labs; and ensuring repeatability of experiments, e.g. if RIN shows a given value and is suitable for microarray experiments, then the RIN of the same value can always be used for similar experiments given that the same organism/tissue/extraction method is used (Schroeder A, et al. BMC Molecular Biology 2006, 7:3 (2006)).

In some embodiments, RNA quality is measured on a scale of RIN 1 to 10, 10 being highest quality. In one aspect, the present invention provides a method of analyzing gene expression from a sample with an RNA RIN value equal or less than 6.0. In some embodiments, a sample containing RNA with an RIN number of 1.0, 2.0, 3.0, 4.0, 5.0 or 6.0 is analyzed for microarray gene expression using the subject methods and algorithms of the present invention. In some embodiments, the sample is a fine needle aspirate of thyroid tissue. The sample can be degraded with an RIN as low as 2.0.

Determination of gene expression in a given sample is a complex, dynamic, and expensive process. RNA samples with RIN≤5.0 are typically not used for multi-gene microarray analysis, and may instead be used only for single-gene RT-PCR and/or TaqMan assays. This dichotomy in the usefulness of RNA according to quality has thus far limited the usefulness of samples and hampered research efforts. The present invention provides methods via which low quality RNA can be used to obtain meaningful multi-gene expression results from samples containing low concentrations of RNA, for example, thyroid FNA samples.

In addition, samples having a low and/or un-measurable RNA concentration by NanoDrop normally deemed inadequate for multi-gene expression profiling can be measured and analyzed using the subject methods and algorithms of the present invention. The most sensitive and "state of the art" apparatus used to measure nucleic acid yield in the laboratory today is the NanoDrop spectrophotometer. Like many quantitative instruments of its kind, the accuracy of a NanoDrop measurement decreases significantly with very low RNA concentration. The minimum amount of RNA necessary for input into a microarray experiment also limits the usefulness of a given sample. In the present invention, a sample containing a very low amount of nucleic acid can be estimated using a combination of the measurements from both the NanoDrop and the Bioanalyzer instruments, thereby optimizing the sample for multi-gene expression assays and analysis.

(iii) Protein Content Adequacy Test

In some cases, protein content in the biological sample may be measured using a variety of methods known to the art, including but not limited to: ultraviolet absorbance at 280 nanometers, cell staining as described herein, or protein staining with for example coomassie blue, or bichichonic acid. In some cases, protein is extracted from the biological sample prior to measurement of the sample. In some cases, multiple tests for adequacy of the sample may be performed in parallel, or one at a time. In some cases, the sample may be divided into aliquots for the purpose of performing multiple diagnostic tests prior to, during, or after assessing adequacy. In some cases, the adequacy test is performed on a small amount of the sample which may or may not be suitable for further diagnostic testing. In other cases, the entire sample is assessed for adequacy. In any case, the test for adequacy may be billed to the subject, medical provider, insurance provider, or government entity.

In some embodiments of the present invention, the sample may be tested for adequacy soon or immediately after collection. In some cases, when the sample adequacy test does not indicate a sufficient amount sample or sample of sufficient quality, additional samples may be taken.

VI. Analysis of Sample

In one aspect, the present invention provides methods for performing microarray gene expression analysis with low quantity and quality of polynucleotide, such as DNA or RNA. In some embodiments, the present disclosure describes methods of diagnosing, characterizing and/or monitoring a cancer by analyzing gene expression with low quantity and quality of RNA. In one embodiment, the cancer is thyroid cancer. Thyroid RNA can be obtained from fine needle aspirates (FNA). In some embodiments, gene expression profile is obtained from degraded samples with an RNA RIN value of 9.0, 8.0, 7.0, 6.0, 5.0, 4.0, 3.0, 2.0, 1.0 or less. In particular embodiments, gene expression profile is obtained from a sample with an RIN of equal or less than 6, i.e. 6.0, 5.0, 4.0, 3.0, 2.0, 1.0 or less. Provided by the present invention are methods by which low quality RNA can be used to obtain meaningful gene expression results from samples containing low concentrations of nucleic acid, such as thyroid FNA samples.

Another estimate of sample usefulness is RNA yield, typically measured in nanogram to microgram amounts for gene expression assays. The most sensitive and "state of the art" apparatus used to measure nucleic acid yield in the laboratory today is the NanoDrop spectrophotometer. Like many quantitative instruments of its kind, the accuracy of a NanoDrop measurement decreases significantly with very low RNA concentration. The minimum amount of RNA necessary for input into a microarray experiment also limits the usefulness of a given sample. In some aspects, the present invention solves the low RNA concentration problem by estimating sample input using a combination of the measurements from both the NanoDrop and the Bioanalyzer instruments. Since the quality of data obtained from a gene expression study is dependent on RNA quantity, meaningful gene expression data can be generated from samples having a low or un-measurable RNA concentration as measured by NanoDrop.

The subject methods and algorithms enable: 1) gene expression analysis of samples containing low amount and/or low quality of nucleic acid; 2) a significant reduction of false positives and false negatives, 3) a determination of the underlying genetic, metabolic, or signaling pathways responsible for the resulting pathology, 4) the ability to assign a statistical probability to the accuracy of the diagnosis of genetic disorders, 5) the ability to resolve ambiguous results, and 6) the ability to distinguish between subtypes of cancer.

Cytological Analysis

Samples may be analyzed by cell staining combined with microscopic examination of the cells in the biological sample. Cell staining, or cytological examination, may be performed by a number of methods and suitable reagents known to the art including but not limited to: EA stains, hematoxylin stains, cytostain, papanicolaou stain, eosin, nissl stain, toluidine blue, silver stain, azocarmine stain, neutral red, or janus green. In some cases the cells are fixed and/or permeablized with for example methanol, ethanol, glutaraldehyde or formaldehyde prior to or during the staining procedure. In some cases, the cells are not fixed. In some cases, more than one stain is used in combination. In other cases no stain is used at all. In some cases measurement of nucleic acid content is performed using a staining procedure, for example with ethidium bromide, hematoxylin, nissl stain or any nucleic acid stain known to the art.

In some embodiments of the present invention, cells may be smeared onto a slide by standard methods well known in the art for cytological examination. In other cases, liquid based cytology (LBC) methods may be utilized. In some cases, LBC methods provide for an improved means of cytology slide preparation, more homogenous samples, increased sensitivity and specificity, and improved efficiency of handling of samples. In liquid based cytology methods, biological samples are transferred from the subject to a container or vial containing a liquid cytology preparation solution such as for example Cytyc ThinPrep, SurePath, or Monoprep or any other liquid based cytology preparation solution known in the art. Additionally, the sample may be rinsed from the collection device with liquid cytology preparation solution into the container or vial to ensure substantially quantitative transfer of the sample. The solution containing the biological sample in liquid based cytology preparation solution may then be stored and/or processed by a machine or by one skilled in the art to produce a layer of cells on a glass slide. The sample may further be stained and examined under the microscope in the same way as a conventional cytological preparation.

In some embodiments of the present invention, samples may be analyzed by immuno-histochemical staining Immuno-histochemical staining provides for the analysis of the presence, location, and distribution of specific molecules or antigens by use of antibodies in a biological sample (e.g. cells or tissues). Antigens may be small molecules, proteins, peptides, nucleic acids or any other molecule capable of being specifically recognized by an antibody. Samples may be analyzed by immuno-histochemical methods with or without a prior fixing and/or permeabilization step. In some cases, the antigen of interest may be detected by contacting the sample with an antibody specific for the antigen and then non-specific binding may be removed by one or more washes. The specifically bound antibodies may then be detected by an antibody detection reagent such as for example a labeled secondary antibody, or a labeled avidin/streptavidin. In some cases, the antigen specific antibody may be labeled directly instead. Suitable labels for immuno-histochemistry include but are not limited to fluorophores such as fluoroscein and rhodamine, enzymes such as alkaline phosphatase and horse radish peroxidase, and radionuclides such as $^{32}P$ and $^{125}I$. Gene product markers that may be detected by immuno-histochemical staining include but are not limited to Her2/Neu, Ras, Rho, EGFR, VEGFR, UbcH10, RET/PTC1, cytokeratin 20, calcitonin, GAL-3, thyroid peroxidase, and thyroglobulin.

VII. Assay Results

The results of routine cytological or other assays may indicate a sample as negative (cancer, disease or condition free), ambiguous or suspicious (suggestive of the presence of a cancer, disease or condition), diagnostic (positive diagnosis for a cancer, disease or condition), or non diagnostic (providing inadequate information concerning the presence or absence of cancer, disease, or condition). The diagnostic results may be further classified as malignant or benign. The diagnostic results may also provide a score indicating for example, the severity or grade of a cancer, or the likelihood of an accurate diagnosis, such as via a p-value, a corrected p-value, or a statistical confidence indicator. In some cases, the diagnostic results may be indicative of a particular type of a cancer, disease, or condition, such as for example follicular adenoma, Hurthle cell adenoma, lymphocytic thyroiditis, hyperplasia, follicular carcinoma, follicular variant of papillary thyroid carcinoma, papillary carcinoma, or any of the diseases or conditions provided herein. In some cases, the diagnostic results may be indicative of a particular stage of a cancer, disease, or condition. The diagnostic results may inform a particular treatment or therapeutic intervention for the type or stage of the specific cancer disease or condition diagnosed. In some embodiments, the results of the assays performed may be entered into a database. The molecular profiling company may bill the individual, insurance provider, medical provider, or government entity for one or more of the following: assays performed, consulting services, reporting of results, database access, or data analysis. In some cases all or some steps other than molecular profiling are performed by a cytological laboratory or a medical professional.

VIII. Molecular Profiling

Cytological assays mark the current diagnostic standard for many types of suspected tumors including for example thyroid tumors or nodules. In some embodiments of the present invention, samples that assay as negative, indeterminate, diagnostic, or non diagnostic may be subjected to subsequent assays to obtain more information. In the present invention, these subsequent assays comprise the steps of molecular profiling of genomic DNA, RNA, mRNA expression product levels, miRNA levels, gene expression product levels or gene expression product alternative splicing. In some embodiments of the present invention, molecular profiling means the determination of the number (e.g. copy number) and/or type of genomic DNA in a biological sample. In some cases, the number and/or type may further be compared to a control sample or a sample considered normal. In some embodiment, genomic DNA can be analyzed for copy number variation, such as an increase (amplification) or decrease in copy number, or variants, such as insertions, deletions, truncations and the like. Molecular profiling may be performed on the same sample, a portion of the same sample, or a new sample may be acquired using any of the methods described herein. The molecular profiling company may request additional sample by directly contacting the individual or through an intermediary such as a physician, third party testing center or laboratory, or a medical professional. In some cases, samples are assayed using methods and compositions of the molecular profiling business in combination with some or all cytological staining or other diagnostic methods. In other cases, samples are directly assayed using the methods and compositions of the molecular profiling business without the previous use of routine cytological staining or other diagnostic methods. In some cases the results of molecular profiling alone or in combination with cytology or other assays may enable those skilled in the art to diagnose or suggest treatment for the subject. In some cases, molecular profiling may be used alone or in combination with cytology to monitor tumors or suspected tumors over time for malignant changes.

The molecular profiling methods of the present invention provide for extracting and analyzing protein or nucleic acid (RNA or DNA) from one or more biological samples from a subject. In some cases, nucleic acid is extracted from the entire sample obtained. In other cases, nucleic acid is extracted from a portion of the sample obtained. In some cases, the portion of the sample not subjected to nucleic acid extraction may be analyzed by cytological examination or immuno-histochemistry. Methods for RNA or DNA extraction from biological samples are well known in the art and include for example the use of a commercial kit, such as the Qiagen DNeasy Blood and Tissue Kit, or the Qiagen EZ1 RNA Universal Tissue Kit.

(i) Tissue-Type Fingerprinting

In many cases, biological samples such as those provided by the methods of the present invention of may contain several cell types or tissues, including but not limited to thyroid follicular cells, thyroid medullary cells, blood cells (RBCs, WBCs, platelets), smooth muscle cells, ducts, duct cells, basement membrane, lumen, lobules, fatty tissue, skin cells, epithelial cells, and infiltrating macrophages and lymphocytes. In the case of thyroid samples, diagnostic classification of the biological samples may involve for example primarily follicular cells (for cancers derived from the follicular cell such as papillary carcinoma, follicular carcinoma, and anaplastic thyroid carcinoma) and medullary cells (for medullary cancer). The diagnosis of indeterminate biological samples from thyroid biopsies in some cases concerns the distinction of follicular adenoma vs. follicular carcinoma. The molecular profiling signal of a follicular cell for example may thus be diluted out and possibly confounded by other cell types present in the sample. Similarly diagnosis of biological samples from other tissues or organs often involves diagnosing one or more cell types among the many that may be present in the sample.

In some embodiments, the methods of the present invention provide for an upfront method of determining the cellular make-up of a particular biological sample so that the resulting molecular profiling signatures can be calibrated against the dilution effect due to the presence of other cell and/or tissue types. In one aspect, this upfront method is an algorithm that uses a combination of known cell and/or tissue specific gene expression patterns as an upfront mini-classifier for each component of the sample. This algorithm utilizes this molecular fingerprint to pre-classify the samples according to their composition and then apply a correction/normalization factor. This data may in some cases then feed in to a final classification algorithm which would incorporate that information to aid in the final diagnosis.

(ii) Genomic Analysis

In some embodiments, genomic sequence analysis, or genotyping, may be performed on the sample. This genotyping may take the form of mutational analysis such as single nucleotide polymorphism (SNP) analysis, insertion deletion polymorphism (InDel) analysis, variable number of tandem repeat (VNTR) analysis, copy number variation (CNV) analysis or partial or whole genome sequencing. Methods for performing genomic analyses are known to the art and may include high throughput sequencing such as but not limited to those methods described in U.S. Pat. Nos. 7,335,762; 7,323,305; 7,264,929; 7,244,559; 7,211,390; 7,361,488; 7,300,788; and 7,280,922. Methods for performing genomic analyses may also include microarray methods as described hereinafter. In some cases, genomic analysis may be performed in combination with any of the other methods herein. For example, a sample may be obtained, tested for adequacy, and divided into aliquots. One or more aliquots may then be used for cytological analysis of the present invention, one or more may be used for RNA expression profiling methods of the present invention, and one or more can be used for genomic analysis. It is further understood the present invention anticipates that one skilled in the art may wish to perform other analyses on the biological sample that are not explicitly provided herein.

(iii) Expression Product Profiling

Gene expression profiling is the measurement of the activity (the expression) of thousands of genes at once, to create a global picture of cellular function. These profiles can, for example, distinguish between cells that are actively dividing, or show how the cells react to a particular treatment. Many experiments of this sort measure an entire genome simultaneously, that is, every gene present in a particular cell. Microarray technology measures the relative activity of previously identified target genes. Sequence based techniques, like serial analysis of gene expression (SAGE, SuperSAGE) are also used for gene expression profiling. SuperSAGE is especially accurate and can measure any active gene, not just a predefined set. In an RNA, mRNA or gene expression profiling microarray, the expression levels of thousands of genes are simultaneously monitored to study the effects of certain treatments, diseases, and developmental stages on gene expression. For example, microarray-based gene expression profiling can be used to characterize gene signatures of a genetic disorder disclosed herein, or different cancer types, subtypes of a cancer, and/or cancer stages.

Expression profiling experiments often involve measuring the relative amount of gene expression products, such as mRNA, expressed in two or more experimental conditions. This is because altered levels of a specific sequence of a gene expression product suggest a changed need for the protein coded for by the gene expression product, perhaps indicating a homeostatic response or a pathological condition. For example, if breast cancer cells express higher levels of mRNA associated with a particular transmembrane receptor than normal cells do, it might be that this receptor plays a role in breast cancer. One aspect of the present invention encompasses gene expression profiling as part of an important diagnostic test for genetic disorders and cancers, particularly, thyroid cancer.

In some embodiments, RNA samples with RIN≤5.0 are typically not used for multi-gene microarray analysis, and may instead be used only for single-gene RT-PCR and/or TaqMan assays. Microarray, RT-PCR and TaqMan assays are standard molecular techniques well known in the relevant art. TaqMan probe-based assays are widely used in real-time PCR including gene expression assays, DNA quantification and SNP genotyping.

In one embodiment, gene expression products related to cancer that are known to the art are profiled. Such gene expression products have been described and include but are not limited to the gene expression products detailed in U.S. Pat. Nos. 7,358,061; 7,319,011; 5,965,360; 6,436,642; and US patent applications 2003/0186248, 2005/0042222, 2003/0190602, 2005/0048533, 2005/0266443, 2006/0035244, 2006/083744, 2006/0088851, 2006/0105360, 2006/0127907, 2007/0020657, 2007/0037186, 2007/0065833, 2007/0161004, 2007/0238119, and 2008/0044824.

It is further anticipated that other gene expression products related to cancer may become known, and that the methods and compositions described herein may include such newly discovered gene expression products.

In some embodiments of the present invention gene expression products are analyzed alternatively or additionally for characteristics other than expression level. For example, gene products may be analyzed for alternative splicing. Alternative splicing, also referred to as alternative exon usage, is the RNA splicing variation mechanism wherein the exons of a primary gene transcript, the pre-mRNA, are separated and reconnected (i.e. spliced) so as to produce alternative mRNA molecules from the same gene. In some cases, these linear combinations then undergo the process of translation where a specific and unique sequence of amino acids is specified by each of the alternative mRNA molecules from the same gene resulting in protein isoforms. Alternative splicing may include incorporating different exons or different sets of exons, retaining certain introns, or using utilizing alternate splice donor and acceptor sites.

In some cases, markers or sets of markers may be identified that exhibit alternative splicing that is diagnostic for benign, malignant or normal samples. Additionally, alternative splicing markers may further provide a diagnosis for the specific type of thyroid cancer (e.g. papillary, follicular, medullary, or anaplastic). Alternative splicing markers diagnostic for malignancy known to the art include those listed in U.S. Pat. No. 6,436,642.

In some cases expression of RNA expression products that do not encode for proteins such as miRNAs, and siRNAs may be assayed by the methods of the present invention. Differential expression of these RNA expression products may be indicative of benign, malignant or normal samples. Differential expression of these RNA expression products may further be indicative of the subtype of the benign sample (e.g. FA, NHP, LCT, BN, CN, HA) or malignant sample (e.g. FC, PTC, FVPTC, ATC, MTC). In some cases, differential expression of miRNAs, siRNAs, alternative splice RNA isoforms, mRNAs or any combination thereof may be assayed by the methods of the present invention.

In some embodiments, the current invention provides 16 panels of biomarkers, each panel being required to characterize, rule out, and diagnose pathology within the thyroid. The sixteen panels are:

1 Normal Thyroid (NML)
2 Lymphocytic, Autoimmune Thyroiditis (LCT)
3 Nodular Hyperplasia (NHP)
4 Follicular Thyroid Adenoma (FA)
5 Hurthle Cell Thyroid Adenoma (HC)
6 Parathyroid (non thyroid tissue)
7 Anaplastic Thyroid Carcinoma (ATC)
8 Follicular Thyroid Carcinoma (FC)
9 Hurthle Cell Thyroid Carcinoma (HC)
10 Papillary Thyroid Carcinoma (PTC)
11 Follicular Variant of Papillary Carcinoma (FVPTC)
12 Medullary Thyroid Carcinoma (MTC)
13 Renal Carcinoma metastasis to the Thyroid
14 Melanoma metastasis to the Thyroid
15 B cell Lymphoma metastasis to the Thyroid
16 Breast Carcinoma metastasis to the Thyroid Each panel includes a set of biomarkers required to characterize, rule out, and diagnose a given pathology within the thyroid. Panels 1-6 describe benign pathology. Panels 7-16 describe malignant pathology.

The biological nature of the thyroid and each pathology found within it, suggests that there is redundancy between the plurality of biomarkers in one panel versus the plurality of biomarkers in another panel. Mirroring each pathology subtype, each diagnostic panel is heterogeneous and semi-redundant with the biomarkers in another panel. Heterogeneity and redundancy reflect the biology of the tissues sampled in a given FNA and the differences in gene expression that characterize each pathology subtype from one another.

In one aspect, the diagnostic value of the present invention lies in the comparison of i) one or more markers in one panel, versus ii) one or more markers in each additional panel. The utility of the invention is its higher diagnostic accuracy in FNA than presently possible by any other means.

In some embodiments, the biomarkers within each panel are interchangeable (modular). The plurality of biomarkers in all panels can be substituted, increased, reduced, or improved to accommodate the definition of new pathologic subtypes (e.g. new case reports of metastasis to the thyroid from other organs). The current invention describes the plurality of markers that define each of sixteen heterogeneous, semi-redundant, and distinct pathologies found in the thyroid. All sixteen panels are required to arrive at an accurate diagnosis, and any given panel alone does not have sufficient power to make a true diagnostic determination. In some embodiments, the biomarkers in each panel are interchanged with a suitable combination of biomarkers, such that the plurality of biomarkers in each panel still defines a given pathology subtype within the context of examining the plurality of biomarkers that define all other pathology subtypes.

Methods and compositions of the invention can have genes selected from 1, 2, 3, 4, 5, 6, 7, 8, 9, 10, 11, 12, 13, 14, 15 or 16 or more biomarker panels and can have from 1, 2, 3, 4, 5, 6, 7, 8, 9, 10, 15, 20, 25, 30, 35, 40, 45, 50 or more gene expression products from each biomarker panel, in any combination. In some embodiments, the set of genes combined give a specificity or sensitivity of greater than 70%, 75%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 95%, 95.5%, 96%, 96.5%, 97%, 97.5%, 98%, 98.5%, 99%, 99.5% or more.

(1) In Vitro Methods of Determining Expression Product Levels

The general methods for determining gene expression product levels are known to the art and may include but are not limited to one or more of the following: additional cytological assays, assays for specific proteins or enzyme activities, assays for specific expression products including protein or RNA or specific RNA splice variants, in situ hybridization, whole or partial genome expression analysis, microarray hybridization assays, SAGE, enzyme linked immuno-absorbance assays, mass-spectrometry, immunohistochemistry, or blotting. Gene expression product levels may be normalized to an internal standard such as total mRNA or the expression level of a particular gene including but not limited to glyceraldehyde 3 phosphate dehydrogenase, or tublin.

In some embodiments of the present invention, gene expression product markers and alternative splicing markers may be determined by microarray analysis using, for example, Affymetrix arrays, cDNA microarrays, oligonucleotide microarrays, spotted microarrays, or other microarray products from Biorad, Agilent, or Eppendorf. Microarrays provide particular advantages because they may contain a large number of genes or alternative splice variants that may be assayed in a single experiment. In some cases, the microarray device may contain the entire human genome or transcriptome or a substantial fraction thereof allowing a comprehensive evaluation of gene expression patterns, genomic sequence, or alternative splicing. Markers may be found using standard molecular biology and microarray analysis techniques as described in Sambrook *Molecular Cloning a Laboratory Manual* 2001 and Baldi, P., and Hatfield, W. G., *DNA Microarrays and Gene Expression* 2002.

Microarray analysis begins with extracting and purifying nucleic acid from a biological sample, (e.g. a biopsy or fine needle aspirate) using methods known to the art. For expression and alternative splicing analysis it may be advantageous to extract and/or purify RNA from DNA. It may further be advantageous to extract and/or purify mRNA from other forms of RNA such as tRNA and rRNA.

Purified nucleic acid may further be labeled with a fluorescent, radionuclide, or chemical label such as biotin or digoxin for example by reverse transcription, PCR, ligation, chemical reaction or other techniques. The labeling can be direct or indirect which may further require a coupling stage. The coupling stage can occur before hybridization, for example, using aminoallyl-UTP and NHS amino-reactive dyes (like cyanine dyes) or after, for example, using biotin and labelled streptavidin. The modified nucleotides (e.g. at a 1 aaUTP: 4 TTP ratio) are added enzymatically at a lower rate compared to normal nucleotides, typically resulting in 1 every 60 bases (measured with a spectrophotometer). The aaDNA may then be purified with, for example, a column or a diafiltration device. The aminoallyl group is an amine group on a long linker attached to the nucleobase, which reacts with a reactive label (e.g. a fluorescent dye).

The labeled samples may then be mixed with a hybridization solution which may contain SDS, SSC, dextran sulfate, a blocking agent (such as COT1 DNA, salmon sperm DNA, calf thymum DNA, PolyA or PolyT), Denhardt's solution, formamine, or a combination thereof.

A hybridization probe is a fragment of DNA or RNA of variable length, which is used to detect in DNA or RNA samples the presence of nucleotide sequences (the DNA target) that are complementary to the sequence in the probe. The probe thereby hybridizes to single-stranded nucleic acid (DNA or RNA) whose base sequence allows probe-target base pairing due to complementarity between the probe and target. The labeled probe is first denatured (by heating or under alkaline conditions) into single DNA strands and then hybridized to the target DNA.

To detect hybridization of the probe to its target sequence, the probe is tagged (or labeled) with a molecular marker; commonly used markers are $^{32}P$ or Digoxigenin, which is non-radioactive antibody-based marker. DNA sequences or RNA transcripts that have moderate to high sequence similarity to the probe are then detected by visualizing the hybridized probe via autoradiography or other imaging techniques. Detection of sequences with moderate or high similarity depends on how stringent the hybridization conditions were applied—high stringency, such as high hybridization temperature and low salt in hybridization buffers, permits only hybridization between nucleic acid sequences that are highly similar, whereas low stringency, such as lower temperature and high salt, allows hybridization when the sequences are less similar Hybridization probes used in DNA microarrays refer to DNA covalently attached to an inert surface, such as coated glass slides or gene chips, and to which a mobile cDNA target is hybridized.

This mix may then be denatured by heat or chemical means and added to a port in a microarray. The holes may then be sealed and the microarray hybridized, for example, in a hybridization oven, where the microarray is mixed by rotation, or in a mixer. After an overnight hybridization, non specific binding may be washed off (e.g. with SDS and SSC). The microarray may then be dried and scanned in a special machine where a laser excites the dye and a detector measures its emission. The image may be overlaid with a template grid and the intensities of the features (several pixels make a feature) may be quantified.

Various kits can be used for the amplification of nucleic acid and probe generation of the subject methods. Examples of kit that can be used in the present invention include but are not limited to Nugen WT-Ovation FFPE kit, cDNA amplification kit with Nugen Exon Module and Frag/Label module. The NuGEN WT-Ovation™ FFPE System V2 is a whole transcriptome amplification system that enables conducting global gene expression analysis on the vast archives of small and degraded RNA derived from FFPE samples. The system is comprised of reagents and a protocol required for amplification of as little as 50 ng of total FFPE RNA. The protocol can be used for qPCR, sample archiving, fragmentation, and labeling. The amplified cDNA can be fragmented and labeled in less than two hours for GeneChip® 3' expression array analysis using NuGEN's FL-Ovation™ cDNA Biotin Module V2. For analysis using Affymetrix GeneChip® Exon and Gene ST arrays, the amplified cDNA can be used with the WT-Ovation Exon Module, then fragmented and labeled using the FL-Ovation™ cDNA Biotin Module V2. For analysis on Agilent arrays, the amplified cDNA can be fragmented and labeled using NuGEN's FL-Ovation™ cDNA Fluorescent Module.

In some embodiments, Ambion WT-expression kit can be used. Ambion WT-expression kit allows amplification of total RNA directly without a separate ribosomal RNA (rRNA) depletion step. With the Ambion® WT Expression Kit, samples as small as 50 ng of total RNA can be analyzed on Affymetrix® GeneChip® Human, Mouse, and Rat Exon and Gene 1.0 ST Arrays. In addition to the lower input RNA requirement and high concordance between the Affymetrix® method and TaqMan@ real-time PCR data, the Ambion® WT Expression Kit provides a significant increase in sensitivity. For example, a greater number of probe sets detected above background can be obtained at the exon level with the Ambion® WT Expression Kit as a result of an increased signal-to-noise ratio. Ambion WT-expression kit may be used in combination with additional Affymetrix labeling kit.

In some embodiments, AmpTec Trinucleotide Nano mRNA Amplification kit (6299-A15) can be used in the subject methods. The ExpressArt® TRinucleotide mRNA amplification Nano kit is suitable for a wide range, from 1 ng to 700 ng of input total RNA. According to the amount of input total RNA and the required yields of aRNA, it can be used for 1-round (input>300 ng total RNA) or 2-rounds (minimal input amount 1 ng total RNA), with aRNA yields in the range of >10 µg. AmpTec's proprietary TRinucleotide priming technology results in preferential amplification of mRNAs (independent of the universal eukaryotic 3'-poly (A)-sequence), combined with selection against rRNAs. This kit can be used in combination with cDNA conversion kit and Affymetrix labeling kit.

The raw data may then be normalized, for example, by subtracting the background intensity and then dividing the intensities making either the total intensity of the features on each channel equal or the intensities of a reference gene and then the t-value for all the intensities may be calculated. More sophisticated methods, include z-ratio, loess and lowess regression and RMA (robust multichip analysis) for Affymetrix chips.

(2) In Vivo methods of Determining Gene Expression Product Levels

It is further anticipated that the methods and compositions of the present invention may be used to determine gene expression product levels in an individual without first obtaining a sample. For example, gene expression product levels may be determined in vivo, that is in the individual. Methods for determining gene expression product levels in vivo are known to the art and include imaging techniques such as CAT, MRI; NMR; PET; and optical, fluorescence, or biophotonic imaging of protein or RNA levels using antibodies or molecular beacons. Such methods are described in US 2008/0044824, US 2008/0131892, herein incorporated by reference. Additional methods for in vivo molecular profiling are contemplated to be within the scope of the present invention.

In some embodiments of the present invention, molecular profiling includes the step of binding the sample or a portion of the sample to one or more probes of the present invention. Suitable probes bind to components of the sample, i.e. gene products, that are to be measured and include but are not limited to antibodies or antibody fragments, aptamers, nucleic acids, and oligonucleotides. The binding of the sample to the probes of the present invention represents a transformation of matter from sample to sample bound to one or more probes. The method of diagnosing cancer based on molecular profiling further comprises the steps of detecting gene expression products (i.e. mRNA or protein) and levels of the sample, comparing it to an amount in a normal control sample to determine the differential gene expression product level between the sample and the control; and classifying the test sample by inputting one or more differential gene expression product levels to a trained algorithm of the present invention; validating the sample classification using the selection and classification algorithms of the present invention; and identifying the sample as positive for a genetic disorder or a type of cancer.

(i) Comparison of Sample to Normal

The results of the molecular profiling performed on the sample provided by the individual (test sample) may be compared to a biological sample that is known or suspected to be normal. A normal sample is that which is or is expected to be free of any cancer, disease, or condition, or a sample that would test negative for any cancer disease or condition in the molecular profiling assay. The normal sample may be from a different individual from the individual being tested, or from the same individual. In some cases, the normal sample is a sample obtained from a buccal swab of an individual such as the individual being tested for example. The normal sample may be assayed at the same time, or at a different time from the test sample.

The results of an assay on the test sample may be compared to the results of the same assay on a normal sample. In some cases the results of the assay on the normal sample are from a database, or a reference. In some cases, the results of the assay on the normal sample are a known or generally accepted value by those skilled in the art. In some cases the comparison is qualitative. In other cases the comparison is quantitative. In some cases, qualitative or quantitative comparisons may involve but are not limited to one or more of the following: comparing fluorescence values, spot intensities, absorbance values, chemiluminescent signals, histograms, critical threshold values, statistical significance values, gene product expression levels, gene product expression level changes, alternative exon usage, changes in alternative exon usage, protein levels, DNA polymorphisms, coy number variations, indications of the presence or absence of one or more DNA markers or regions, or nucleic acid sequences.

(ii) Evaluation of Results

In some embodiments, the molecular profiling results are evaluated using methods known to the art for correlating gene product expression levels or alternative exon usage with specific phenotypes such as malignancy, the type of malignancy (e.g. follicular carcinoma), benignancy, or normalcy (e.g. disease or condition free). In some cases, a specified statistical confidence level may be determined in order to provide a diagnostic confidence level. For example, it may be determined that a confidence level of greater than 90% may be a useful predictor of malignancy, type of malignancy, or benignancy. In other embodiments, more or less stringent confidence levels may be chosen. For example, a confidence level of approximately 70%, 75%, 80%, 85%, 90%, 95%, 97.5%, 99%, 99.5%, or 99.9% may be chosen as a useful phenotypic predictor. The confidence level provided may in some cases be related to the quality of the sample, the quality of the data, the quality of the analysis, the specific methods used, and the number of gene expression products analyzed. The specified confidence level for providing a diagnosis may be chosen on the basis of the expected number of false positives or false negatives and/or cost. Methods for choosing parameters for achieving a specified confidence level or for identifying markers with diagnostic power include but are not limited to Receiver Operator Curve analysis (ROC), binormal ROC, principal component analysis, partial least squares analysis, singular value decomposition, least absolute shrinkage and selection operator analysis, least angle regression, and the threshold gradient directed regularization method.

(iii) Data Analysis

Raw gene expression level and alternative splicing data may in some cases be improved through the application of algorithms designed to normalize and or improve the reliability of the data. In some embodiments of the present invention the data analysis requires a computer or other device, machine or apparatus for application of the various algorithms described herein due to the large number of individual data points that are processed. A "machine learning algorithm" refers to a computational-based prediction methodology, also known to persons skilled in the art as a "classifier", employed for characterizing a gene expression profile. The signals corresponding to certain expression levels, which are obtained by, e.g., microarray-based hybridization assays, are typically subjected to the algorithm in order to classify the expression profile. Supervised learning generally involves "training" a classifier to recognize the distinctions among classes and then "testing" the accuracy of the classifier on an independent test set. For new, unknown samples the classifier can be used to predict the class in which the samples belong.

In some cases, the robust multi-array Average (RMA) method may be used to normalize the raw data. The RMA method begins by computing background-corrected intensities for each matched cell on a number of microarrays. The background corrected values are restricted to positive values as described by Irizarry et al. *Biostatistics* 2003 Apr. 4 (2): 249-64. After background correction, the base-2 logarithm of each background corrected matched-cell intensity is then obtained. The back-ground corrected, log-transformed, matched intensity on each microarray is then normalized using the quantile normalization method in which for each input array and each probe expression value, the array percentile probe value is replaced with the average of all array percentile points, this method is more completely described by Bolstad et al. *Bioinformatics* 2003. Following quantile normalization, the normalized data may then be fit to a linear model to obtain an expression measure for each probe on each microarray. Tukey's median polish algorithm (Tukey, J. W., *Exploratory Data Analysis.* 1977) may then be used to determine the log-scale expression level for the normalized probe set data.

Data may further be filtered to remove data that may be considered suspect. In some embodiments, data deriving from microarray probes that have fewer than about 4, 5, 6, 7 or 8 guanosine+cytosine nucleotides may be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine+cytosine nucleotides may be considered unreliable due to their aberrant hybridization propensity or secondary structure issues.

In some cases, unreliable probe sets may be selected for exclusion from data analysis by ranking probe-set reliability against a series of reference datasets. For example, RefSeq or Ensembl (EMBL) are considered very high quality reference datasets. Data from probe sets matching RefSeq or Ensembl sequences may in some cases be specifically included in microarray analysis experiments due to their expected high reliability. Similarly data from probe-sets matching less reliable reference datasets may be excluded from further analysis, or considered on a case by case basis for inclusion. In some cases, the Ensembl high throughput cDNA (HTC) and/or mRNA reference datasets may be used to determine the probe-set reliability separately or together. In other cases, probe-set reliability may be ranked. For example, probes and/or probe-sets that match perfectly to all reference datasets such as for example RefSeq, HTC, and mRNA, may be ranked as most reliable (1). Furthermore, probes and/or probe-sets that match two out of three reference datasets may be ranked as next most reliable (2), probes and/or probe-sets that match one out of three reference datasets may be ranked next (3) and probes and/or probe sets that match no reference datasets may be ranked last (4). Probes and or probe-sets may then be included or excluded from analysis based on their ranking. For example, one may choose to include data from category 1, 2, 3, and 4 probe-sets; category 1, 2, and 3 probe-sets; category 1 and 2 probe-sets; or category 1 probe-sets for further analysis. In another example, probe-sets may be ranked by the number of base pair mismatches to reference dataset entries. It is understood that there are many methods understood in the art for assessing the reliability of a given probe and/or probe-set for molecular profiling and the methods of the present invention encompass any of these methods and combinations thereof.

In some embodiments of the present invention, data from probe-sets may be excluded from analysis if they are not expressed or expressed at an undetectable level (not above background). A probe-set is judged to be expressed above background if for any group:

Integral from T0 to Infinity of the standard normal distribution<Significance (0.01)

Where:

T0=Sqr(GroupSize) (T−P)/Sqr(Pvar),

GroupSize=Number of CEL files in the group,

T=Average of probe scores in probe-set,

P=Average of Background probes averages of GC content, and

Pvar=Sum of Background probe variances/(Number of probes in probe-set)^2,

This allows including probe-sets in which the average of probe-sets in a group is greater than the average expression of background probes of similar GC content as the probe-set probes as the center of background for the probe-set and enables one to derive the probe-set dispersion from the background probe-set variance.

In some embodiments of the present invention, probe-sets that exhibit no, or low variance may be excluded from further analysis. Low-variance probe-sets are excluded from the analysis via a Chi-Square test. A probe-set is considered to be low-variance if its transformed variance is to the left of the 99 percent confidence interval of the Chi-Squared distribution with (N−1) degrees of freedom.

$$(N-1)*\text{Probe-set Variance}/(\text{Gene Probe-set Variance}) \sim \text{Chi-Sq}(N-1)$$

where N is the number of input CEL files, (N−1) is the degrees of freedom for the Chi-Squared distribution, and the 'probe-set variance for the gene' is the average of probe-set variances across the gene.

In some embodiments of the present invention, probe-sets for a given gene or transcript cluster may be excluded from further analysis if they contain less than a minimum number of probes that pass through the previously described filter steps for GC content, reliability, variance and the like. For example in some embodiments, probe-sets for a given gene or transcript cluster may be excluded from further analysis if they contain less than about 1, 2, 3, 4, 5, 6, 7, 8, 9, 10, 11, 12, 13, 14, 15, or less than about 20 probes.

Methods of data analysis of gene expression levels or of alternative splicing may further include the use of a feature selection algorithm as provided herein. In some embodiments of the present invention, feature selection is provided by use of the LIMMA software package (Smyth, G. K. (2005). Limma: linear models for microarray data. In: *Bioinformatics and Computational Biology Solutions using R and Bioconductor,* R. Gentleman, V. Carey, S. Dudoit, R. Irizarry, W. Huber (eds.), Springer, N.Y., pages 397-420).

Methods of data analysis of gene expression levels and or of alternative splicing may further include the use of a pre-classifier algorithm. For example, an algorithm may use a cell-specific molecular fingerprint to pre-classify the samples according to their composition and then apply a correction/normalization factor. This data/information may then be fed in to a final classification algorithm which would incorporate that information to aid in the final diagnosis.

Methods of data analysis of gene expression levels and or of alternative splicing may further include the use of a classifier algorithm as provided herein. In some embodiments of the present invention a support vector machine (SVM) algorithm, a random forest algorithm, or a combination thereof is provided for classification of microarray data. In some embodiments, identified markers that distinguish samples (e.g. benign vs. malignant, normal vs. malignant) or distinguish subtypes (e.g. PTC vs. FVPTC) are selected based on statistical significance. In some cases, the statistical significance selection is performed after applying a Benjamini Hochberg correction for false discovery rate (FDR).

In some cases, the classifier algorithm may be supplemented with a meta-analysis approach such as that described by Fishel and Kaufman et al. 2007 *Bioinformatics* 23(13): 1599-606. In some cases, the classifier algorithm may be supplemented with a meta-analysis approach such as a repeatability analysis. In some cases, the repeatability analysis selects markers that appear in at least one predictive expression product marker set.

In some cases, the results of feature selection and classification may be ranked using a Bayesian post-analysis method. For example, microarray data may be extracted, normalized, and summarized using methods known in the art such as the methods provided herein. The data may then be subjected to a feature selection step such as any feature selection methods known in the art such as the methods provided herein including but not limited to the feature selection methods provided in LIMMA. The data may then be subjected to a classification step such as any of the classification methods known in the art such as the use of any of the algorithms or methods provided herein including but not limited to the use of SVM or random forest algorithms. The results of the classifier algorithm may then be ranked by according to a posterior probability function. For example, the posterior probability function may be derived from examining known molecular profiling results, such as published results, to derive prior probabilities from type I and type II error rates of assigning a marker to a category (e.g. benign, malignant, normal, ATC, PTC, MTC, FC, FN, FA, FVPTC CN, HA, HC, LCT, NHP etc.). These error rates may be calculated based on reported sample size for each study using an estimated fold change value (e.g. 1.1, 1.2., 1.3, 1.4, 1.5, 1.6, 1.7, 1.8, 1.9, 2, 2.2, 2.4, 2.5, 3, 4, 5, 6, 7, 8, 9, 10 or more). These prior probabilities may then be combined with a molecular profiling dataset of the present invention to estimate the posterior probability of differential gene expression. Finally, the posterior probability estimates may be combined with a second dataset of the present invention to formulate the final posterior probabilities of differential expression. Additional methods for deriving and applying posterior probabilities to the analysis of microarray data are known in the art and have been described for example in Smyth, G. K. 2004 *Stat. Appl. Genet. Mol. Biol.* 3: Article 3. In some cases, the posterior probabilities may be used to rank the markers provided by the classifier algorithm. In some cases, markers may be ranked according to their posterior probabilities and those that pass a chosen threshold may be chosen as markers whose differential expression is indicative of or diagnostic for samples that are for example benign, malignant, normal, ATC, PTC, MTC, FC, FN, FA, FVPTC CN, HA, HC, LCT, or NHP. Illustrative threshold values include prior probabilities of 0.7, 0.75, 0.8, 0.85, 0.9, 0.925, 0.95, 0.975, 0.98, 0.985, 0.99, 0.995 or higher.

A statistical evaluation of the results of the molecular profiling may provide a quantitative value or values indicative of one or more of the following: the likelihood of diagnostic accuracy, the likelihood of cancer, disease or condition, the likelihood of a particular cancer, disease or condition, the likelihood of the success of a particular therapeutic intervention. Thus a physician, who is not likely to be trained in genetics or molecular biology, need not understand the raw data. Rather, the data is presented directly to the physician in its most useful form to guide patient care. The results of the molecular profiling can be statistically evaluated using a number of methods known to the art including, but not limited to: the students T test, the two sided T test, pearson rank sum analysis, hidden markov model analysis, analysis of q-q plots, principal component analysis, one way ANOVA, two way ANOVA, LIMMA and the like.

In some embodiments of the present invention, the use of molecular profiling alone or in combination with cytological analysis may provide a diagnosis that is between about 85% accurate and about 99% or about 100% accurate. In some cases, the molecular profiling business may through the use of molecular profiling and/or cytology provide a diagnosis of malignant, benign, or normal that is about 85%, 86%, 87%, 88%, 90%, 91%, 92%, 93%, 94%, 95%, 96%, 97%, 97.5%, 98%, 98.5%, 99%, 99.5%, 99.75%, 99.8%, 99.85%, or 99.9% accurate.

In some cases, accuracy may be determined by tracking the subject over time to determine the accuracy of the original diagnosis. In other cases, accuracy may be established in a deterministic manner or using statistical methods. For example, receiver operator characteristic (ROC) analysis may be used to determine the optimal assay parameters to achieve a specific level of accuracy, specificity, positive predictive value, negative predictive value, and/or false discovery rate. Methods for using ROC analysis in cancer diagnosis are known in the art and have been described for example in US Patent Application No. 2006/019615 herein incorporated by reference in its entirety.

In some embodiments of the present invention, gene expression products and compositions of nucleotides encoding for such products which are determined to exhibit the greatest difference in expression level or the greatest difference in alternative splicing between benign and normal, benign and malignant, or malignant and normal may be chosen for use as molecular profiling reagents of the present invention. Such gene expression products may be particularly useful by providing a wider dynamic range, greater signal to noise, improved diagnostic power, lower likelihood of false positives or false negative, or a greater statistical confidence level than other methods known or used in the art.

In other embodiments of the present invention, the use of molecular profiling alone or in combination with cytological analysis may reduce the number of samples scored as non-diagnostic by about 100%, 99%, 95%, 90%, 80%, 75%, 70%, 65%, or about 60% when compared to the use of standard cytological techniques known to the art. In some cases, the methods of the present invention may reduce the number of samples scored as intermediate or suspicious by about 100%, 99%, 98%, 97%, 95%, 90%, 85%, 80%, 75%, 70%, 65%, or about 60%, when compared to the standard cytological methods used in the art.

In some cases the results of the molecular profiling assays, are entered into a database for access by representatives or agents of the molecular profiling business, the individual, a medical provider, or insurance provider. In some cases assay results include interpretation or diagnosis by a representative, agent or consultant of the business, such as a medical professional. In other cases, a computer or algorithmic analysis of the data is provided automatically. In some cases the molecular profiling business may bill the individual, insurance provider, medical provider, researcher, or government entity for one or more of the following: molecular profiling assays performed, consulting services, data analysis, reporting of results, or database access.

In some embodiments of the present invention, the results of the molecular profiling are presented as a report on a computer screen or as a paper record. In some cases, the report may include, but is not limited to, such information as one or more of the following: the number of genes differentially expressed, the suitability of the original sample, the number of genes showing differential alternative splicing, a diagnosis, a statistical confidence for the diagnosis, the likelihood of cancer or malignancy, and indicated therapies.

(iv) Categorization of Samples Based on Molecular Profiling Results

The results of the molecular profiling may be classified into one of the following: benign (free of a cancer, disease, or condition), malignant (positive diagnosis for a cancer, disease, or condition), or non diagnostic (providing inadequate information concerning the presence or absence of a cancer, disease, or condition). In some cases, a diagnostic result may further classify the type of cancer, disease or condition. In other cases, a diagnostic result may indicate a certain molecular pathway involved in the cancer disease or condition, or a certain grade or stage of a particular cancer disease or condition. In still other cases a diagnostic result may inform an appropriate therapeutic intervention, such as a specific drug regimen like a kinase inhibitor such as Gleevec or any drug known to the art, or a surgical intervention like a thyroidectomy or a hemithyroidectomy.

In some embodiments of the present invention, results are classified using a trained algorithm. Trained algorithms of the present invention include algorithms that have been developed using a reference set of known malignant, benign, and normal samples including but not limited to the samples listed in FIG. 1. Algorithms suitable for categorization of samples include but are not limited to k-nearest neighbor algorithms, concept vector algorithms, naive bayesian algorithms, neural network algorithms, hidden markov model algorithms, genetic algorithms, and mutual information feature selection algorithms or any combination thereof. In some cases, trained algorithms of the present invention may incorporate data other than gene expression or alternative splicing data such as but not limited to DNA polymorphism data, sequencing data, scoring or diagnosis by cytologists or pathologists of the present invention, information provided by the pre-classifier algorithm of the present invention, or information about the medical history of the subject of the present invention.

(v) Monitoring of Subjects or Therapeutic Interventions via Molecular Profiling

In some embodiments, a subject may be monitored using methods and compositions of the present invention. For example, a subject may be diagnosed with cancer or a genetic disorder. This initial diagnosis may or may not involve the use of molecular profiling. The subject may be prescribed a therapeutic intervention such as a thyroidectomy for a subject suspected of having thyroid cancer. The results of the therapeutic intervention may be monitored on an ongoing basis by molecular profiling to detect the efficacy of the therapeutic intervention. In another example, a subject may be diagnosed with a benign tumor or a precancerous lesion or nodule, and the tumor, nodule, or lesion may be monitored on an ongoing basis by molecular profiling to detect any changes in the state of the tumor or lesion.

Molecular profiling may also be used to ascertain the potential efficacy of a specific therapeutic intervention prior to administering to a subject. For example, a subject may be diagnosed with cancer. Molecular profiling may indicate the upregulation of a gene expression product known to be involved in cancer malignancy, such as for example the RAS oncogene. A tumor sample may be obtained and cultured in vitro using methods known to the art. The application of various inhibitors of the aberrantly activated or dysregulated pathway, or drugs known to inhibit the activity of the pathway may then be tested against the tumor cell line for growth inhibition. Molecular profiling may also be used to monitor the effect of these inhibitors on for example downstream targets of the implicated pathway.

(vi) Molecular Profiling as a Research Tool

In some embodiments, molecular profiling may be used as a research tool to identify new markers for diagnosis of suspected tumors; to monitor the effect of drugs or candidate drugs on biological samples such as tumor cells, cell lines, tissues, or organisms; or to uncover new pathways for oncogenesis and/or tumor suppression.

(vii) Biomarker Groupings Based on Molecular Profiling

Thyroid genes are described according to the groups 1) Benign vs. Malignant, 2) alternative gene splicing, 3) KEGG Pathways, 4) Normal Thyroid, 5) Thyroid pathology subtype, 6) Gene Ontology, and 7) Biomarkers of metastasis to the thyroid from non-thyroid organs. Methods and compositions of the invention can have genes selected from one or more of the groups listed above and/or 1, 2, 3, 4, 5, 6, 7, 8, 9, 10, 15, 20, 25, 30, 35, 40, 45, 50 or more subgroups from any of the groups listed above (e.g. one or more different KEGG pathway) and can have from 1, 2, 3, 4, 5, 6, 7, 8, 9, 10, 15, 20, 25, 30, 35, 40, 45, 50 or more gene expression products from each group, in any combination. In some embodiments, the set of genes combined give a specificity or sensitivity of greater than 70%, 75%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 95%, 95.5%, 96%, 96.5%, 97%, 97.5%, 98%, 98.5%, 99%, 99.5% or more.

In some embodiments, the extracellular matrix, adherens, focal adhesion, and tight junction genes are used as biomarkers of thyroid cancer. In some embodiments, the signaling pathway is selected from one of the following three pathways: adherens pathway, focal adhesion pathway, and tight junction pathway. In some embodiments, at least one gene is selected from one of the 3 pathways. In some embodiments, at least one gene is selected from each one of the three pathways. In some embodiments, at least one gene is selected from two of the three pathways. In some embodiments, at least one gene that is involved in all three pathways is selected. In one example, a set of genes that is involved in adherens pathway, focal adhesion pathway, and tight junction pathway is selected as the markers for diagnosis of a cancer such as thyroid cancer.

The follicular cells that line thyroid follicles are highly polarized and organized in structure, requiring distinct roles of their luminal and apical cell membranes. In some embodiments, cytoskeleton, plasma membrane, and extracellular space genes are used as biomarkers of thyroid cancer. In some embodiments, genes that overlap all four pathways, i.e. ECM, focal adhesion, adherens, and tight junction pathways, are used as biomarkers of thyroid cancer. In one example, the present invention provides the Benign vs malignant group (n=948) as a thyroid classification gene list. This list has been grouped according to alternative splicing, KEGG pathways, and gene ontology. KEGG pathways are further described in Table 1.

In some embodiments, the present invention provides a method of diagnosing cancer comprising gene expression products from one or more signaling pathways that include but are not limited to the following: acute myeloid leukemia signaling, somatostatin receptor 2 signaling, cAMP-mediated signaling, cell cycle and DNA damage checkpoint signaling, G-protein coupled receptor signaling, integrin signaling, melanoma cell signaling, relaxin signaling, and thyroid cancer signaling. Methods and compositions of the invention can have genes selected from 1, 2, 3, 4, 5, 6, 7, 8, 9, 10, 15, 20, 25, 30, 35, 40, 45, 50 or more signaling pathways and can have from 1, 2, 3, 4, 5, 6, 7, 8, 9, 10, 15, 20, 25, 30, 35, 40, 45, 50 or more gene expression products from each signaling pathway, in any combination. In some embodiments, the set of genes combined give a specificity or sensitivity of greater than 70%, 75%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 95%, 95.5%, 96%, 96.5%, 97%, 97.5%, 98%, 98.5%, 99%, 99.5% or more.

In some embodiments, the present invention provides a method of diagnosing cancer comprising gene expression products from one or more ontology groups that include but are not limited to the following: cell aging, cell cortex, cell cycle, cell death/apoptosis, cell differentiation, cell division, cell junction, cell migration, cell morphogenesis, cell motion, cell projection, cell proliferation, cell recognition, cell soma, cell surface, cell surface linked receptor signal transduction, cell adhesion, transcription, immune response, or inflammation. Methods and compositions of the invention can have genes selected from 1, 2, 3, 4, 5, 6, 7, 8, 9, 10, 15, 20, 25, 30, 35, 40, 45, 50 or more ontology groups and can have from 1, 2, 3, 4, 5, 6, 7, 8, 9, 10, 15, 20, 25, 30, 35, 40, 45, 50 or more gene expression products from each ontology group, in any combination. In some embodiments, the set of genes combined give a specificity or sensitivity of greater than 70%, 75%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 95%, 95.5%, 96%, 96.5%, 97%, 97.5%, 98%, 98.5%, 99%, 99.5% or more.

TABLE 1

Genes involved in the KEGG Pathways

| KEGG Pathway | % in Top 948 B vs. M list | Genes in Top 948 B vs. M list | Total Genes in Pathway |
| --- | --- | --- | --- |
| ECM | 23 | 18 | 84 |
| p53 | 14 | 10 | 69 |
| PPAR | 14 | 10 | 69 |
| Thyroid Cancer | 14 | 4 | 29 |
| Focal Adhesion | 13 | 26 | 201 |
| Adherens | 12 | 9 | 77 |
| Tight Junction | 11 | 14 | 134 |
| Pathways in Cancer Overview | 10 | 33 | 332 |
| Jak/STAT | 10 | 14 | 155 |
| Cell Cycle | 7 | 9 | 129 |
| TGFbeta | 7 | 6 | 87 |
| Wnt | 7 | 10 | 151 |
| ErbB | 6 | 5 | 87 |
| Apoptosis | 6 | 5 | 88 |
| MAPK | 5 | 14 | 269 |
| Autoimmune Thyroid | 4 | 2 | 53 |
| mTOR | 2 | 1 | 53 |
| VEGF | 1 | 1 | 76 |

Top Biomarkers of benign vs. malignant thyroid, n=948, are listed below in List 1:

List 1

TCID-2406391, TCID-3153400, TCID-3749600, ABCC3, ABCD2, ABTB2, ACBD7, ACSL1, ACTA2, ADAMTS5, ADAMTS9, ADK, ADORA1, AEBP1, AFAP1, AGR2, AHNAK2, AHR, AIDA, AIM2, AK1, AKR1C3, ALAS2, ALDH1A3, ALDH1B1, ALDH6A1, ALOX5, AMIGO2, AMOT, ANGPTL1, ANK2, ANKS6, ANO5, ANXA1, ANXA2, ANXA2P1, ANXA3, ANXA6, AOAH, AP3S1, APOBEC3F, APOBEC3G, APOL1, APOO, AQP4, AQP9, ARHGAP19, ARHGAP24, ARL13B, ARL4A, ARMCX3, ARMCX6, ARNTL, ARSG, ASAP2, ATIC, ATM, ATP13A4, ATP6VOD2, ATP8A1, AUTS2, AVPR1A, B3GNT3, BAG3, BCL2, BCL2A1, BCL9, BHLHE40, BHLHE41, BIRC5, BLNK, BMP1, BMP8A, BTBD11, BTG3, C10orf13l, C10orf72, C11orf72, C11orf74, C11orf80, C12orf35, C12orf49, C14orf45, C16orf45, C17orf87, C19orf33, C1orf115, C1orf116, C2, C22orf9, C2orf40, C3, C4A, C4B, C4orf34, C4orf7, C5orf28, C6orf168, C6orf174, C7orf62, C8orf16, C8orf39, C8orf4, C8orf79, C9orf68, CA11, CADM1, CALCA, CAMK2N1, CAMK4, CAND1, CARD16, CARD17, CARD8, CASC5, CASP1, CAV1, CAV2, CCDC109B, CCDC121, CCDC146, CCDC148, CCDC152, CCDC80, CCL13, CCL19, CCND1, CCND2, CD151, CD180, CD2, CD200, CD36, CD3D, CD48, CD52, CD69, CD79A, CD96, CDCP1, CDH11, CDH3, CDH6, CDK2, CDKL2, CDO1, CDON, CDR1, CEP110, CEP55, CERKL, CFB, CFH, CFHR1, CFI, CHAF1B, CHD4, CHGB, CHI3L1, CITED1, CKB, CKS2, CLC, CLDN1, CLDN10, CLDN16, CLDN4, CLDN7, CLEC2B, CLEC4E, CLIP3, CLU, CMAH, CNN2, CNN3, COL12A1, COL1A1, COPZ2, CP, CPE, CPNE3, CR2, CRABP1, CRABP2, CSF3R, CSGALNACT1, CST6, CTNNAL1, CTNNB1, CTSC, CTSH, CTTN, CWH43, CXCL1, CXCL11, CXCL13, CXCL14, CXCL17, CXCL2, CXCL3, CXCL9, CXorf18, CXorf27, CYP1B1, CYP24A1, CYP27A1, CYP4B1, CYSLTR1, CYSLTR2, CYTH1, DAPK2, DCAF17, DCBLD2, DCUN1D3, DDAH1, DDB2, DDX52, DENND4A, DGKH, DGKI, DHRS1, DHRS3, DIOL, DIRAS3, DLC1, DLG2, DLG4, DLGAP5, DNAJB14, DNASE1L3, DOCK8, DOCK8, DOK4, DPH3B, DPP4, DPYD, DPYSL3, DSG2, DSP, DST, DUOX1, DUOX2, DUOXA1, DUOXA2, DUSP4, DUSP5, DUSP6, DYNC1I2, DYNLT1, DZIP1, ECE1, EDNRB, EFEMP1, EGF, EGFR, EHBP1, EHD2, EHF, EIF2B2, EIF4H, ELK3, ELMO1, EMP2, EMR3, ENAH, ENDOD1, ENTPD1, EPB41, EPDR1, EPHA4, EPHX4, EPR1, EPS8, ERBB2, ERBB3, ERI2, ERO1LB, ERP27, ESRRG, ETNK2, ETS1, ETV1, ETV4, ETV5, F2RL2, F8, FAAH2, FABP4, FAM111A, FAM111B, FAM164A, FAM176A, FAM20A, FAM55C, FAM82B, FAM84B, FAT4, FBLN5, FBXO2, FBXO21, FCN1, FCN2, FGF2, FGFR1OP2, FIBIN, FLJ20184, FLJ26056, FLJ32810, FLJ42258, FLRT3, FN1, FPR1, FPR2, FREM2, FRMD3, FXYD6, FYB, FZD4, FZD6, FZD7, G0S2, GABBR2, GABRB2, GADD45A, GALE, GALNT12, GALNT3, GALNT7, GBE1, GBP1, GBP3, GBP5, GGCT, GIMAP2, GIMAP5, GIMAP7, GJA4, GLA, GLDC, GLDN, GLIS3, GNG12, GOLT1A, GPAM, GPR110, GPR125, GPR155, GPR174, GPR98, GPRC5B, GRAMD3, GSN, GTF3A, GULP1, GYPB, GYPC, GYPE, GZMA, GZMK, HEMGN, HEY2, HIGD1A, HIPK2, HIST1H1A, HIST1H3B, HIST1H4L, HK1, HLA-DPB1, HLA-DQB2, HLF, HMGA2, HMMR, HNRNPM, HPN, HPS3, HRASLS, HSD17B6, HSPH1, ICAM1, ID3, IFI16, IFITM1, IFNAR2, IGF2BP2, IGFBP5, IGFBP6, IGFBP7, IGJ, IGK, IGKC, IGKV1-5, IGKV3-15, IGKV3-20, IGKV3D-11, IGKV3D-15, IGSF1, IKZF2, IKZF3, IKZF4, IL1RAP, IL1RL1, IL2RA, IL7R, IL8, IL8RA, IL8RB, IL8RBP, IMPDH2, INPP5F, IPCEF1, IQGAP2, ISYNA1, ITGA2, ITGA3, ITGA4, ITGA9, ITGB1, ITGB4, ITGB6, ITGB8, ITM2A, ITPR1, IYD, JAK2, JUB, KAL1, KATNAL2, KBTBD8, KCNA3, KCNAB1, KCNK5, KCNQ3, KCTD14, KDELC1, KDELR3, KHDRBS2, KIAA0284, KIAA0408, KIAA1217, KIAA1305, KIF11, KIT, KLF8, KLHDC8A, KLHL6, KLK10, KLK7, KLRB1, KLRC4, KLRG1, KLRK1, KRT18, KRT19, KYNU, LAMB1, LAMB3, LAMC1, LAMC2, LCA5, LCMT1, LCN2, LCP1, LDOC1, LEMD1, LGALS2, LGALS3, LIFR, LILRA1, LILRB1, LIMA1, LINGO2, LIPH, LMO3, LMO4, LOC100124692, LOC100127974, LOC100129112, LOC100129115, LOC100129171, LOC100129961, LOC100130100, LOC100130248, LOC100131102, LOC100131490, LOC100131869, LOC100131938, LOC100131993, LOC100132338, LOC100132764, LOC26080, LOC283508, LOC284861, LOC439911, LOC440434, LOC440871, L00554202, LOC643454, LOC646358, LOC648149, LOC650405, LOC652493, LOC652694, LOC653264, LOC653354, LOC653498, LOC728212, LOC729461, LOC730031, LONRF2, LOX, LPAR1, LPAR5, LPCAT2, LPL, LRP1B, LRP2, LRRC69, LRRN1, LRRN3, LTBP2, LTBP3, LUM, LYPLA1, LYRM1, LYZ, MACC1, MAFG, MAGOH2, MAMLD1, MAP2, MAPK4, MAPK6, MATN2, MBOAT2, MCM4, MCMI, MDK, ME1, MED13, MED13L, MELK, MET, METTL7B, MEX3C, MFGE8, MGAM, MGAT1, MGAT4C, MGC2889, MGST1, MIS12, MKI67, MLLT3, MLLT4, MMP16, MNDA, MORC4, MPPED2, MPZL2, MRC2, MRPL14, MT1F, MT1G, MT1H, MT1M, MT1P2, MT1P3, MTHFD1L, MTIF3, MUC1, MUC15, MVP, MXRA5, MYEF2, MYH10, MYO1B, MYO1D, MYO5A, MYO6, NAB2, NAE1, NAG20, NAV2, NCAM1, NCKAP1, ND1, NDC80, NDFIP2, NEB, NEDD4L, NELL2, NEXN, NFATC3, NFE2, NFIB, NFKBIZ, NIPAL3, NIPSNAP3A, NIPSNAP3B, NOD1, NPAS3, NPAT, NPC2, NPEPPS, NPL, NPY1R, NRCAM, NRIP1, NRP2, NT5E, NTAN1, NUCB2, NUDT6, NUPR1, NUSAP1, OCIAD2, OCR1, ODZ1, ORAOV1, OSBPL1A, OSGEP, OSMR, P2RY13, P4HA2, PAM, PAPSS2, PARD6B, PARP14, PARP4, PARVA, PBX1, PCDH1, PCMTD1, PCNXL2, PDE5A, PDE9A, PDGFRL, PDK4, PDLIM1, PDLIM4, PDZRN4, PEG10, PERP, PGCP, PHEX, PHF16, PHLDB2, PHYHIP, PIAS3, PIGN, PKHD1L1, PKP2, PKP4, PLA2G16, PLA2G7, PLA2R1, PLAGI, PLAU, PLCD3, PLCL1, PLEK, PLEKHA4, PLEKHA5, PLEKHF2, PLK2, PLP2, PLS3, PLSCR4, PLXNC1, PMEPA1, POLR2J4, PON2, POR, POU2F3, PPAP2C, PPARGC1A, PPBP, PPL, PPP1R14C, PRCP, PRICKLE1, PRINS, PRMT6, PROK2, PROS1, PRR15, PRRG1, PRSS23, PSAT1, PSD3, PTK7, PTPN14, PTPN22, PTPRC, PTPRE, PTPRF, PTPRG, PTPRK, PTPRU, PTRF, PXDNL, PYGL, PYHIN1, QTRT1, RAB25, RAB27A, RAB32, RAB34, RAD23B, RAG2, RAI2, RAPGEF5, RARG, RASA1, RASD2, RBBP7, RBBP8, RBMS2, RCBTB2, RCE1, RDH5, RG9MTD2, RGS13, RGS18, RGS2, RHOBTB3, RHOH, RHOU, RICH2, RIMS2, RNASE1, RNASET2, RND3, ROS1, RPL39L, RPL9P11, RPRD1A, RPS6KA6, RRAS, RRAS2, RRBP1, RRM2, RUNX1, RUNX2, RXRG, RYR2, S100A12, S100A14, S100A16, S100A8, S100A9, SALL1, SAV1, SC4MOL, SCARA3, SCARNA11, SCEL, SCG3, SCG5, SCNN1A, SCP2, SCRN1, SDC4, SDK1, SEH1L, SEL1L3, SELL, SEMA3C, SEMA3D, SEMA4C, SEPP1, SEPT11, SERGEF, SERINC2, SERPINA1, SERPINA2, SERPINE2, SERPING1, SFN, SFTPB, SGCB, SGCE, SGEF, SGMS2, SGPP2, SH2D4A, SH3BGR, SH3PXD2A, SIPA1L2, SIRPA, SIRPB1, SLA, SLC12A2, SLC16A4, SLC16A6, SLC17A5, SLC24A5, SLC25A33, SLC26A4, SLC26A7, SLC27A2, SLC27A6, SLC34A2, SLC35D2, SLC35F2, SLC39A6, SLC4A4, SLC5A8, SLC7A11, SLC7A2, SLIT1, SLIT2, SLPI, SMAD9, SMOC2, SMURF2, SNCA, SNX1, SNX22, SNX7, SOAT1, SORBS2, SP140, SP140L, SPATS2, SPATS2L, SPC25, SPINT1, SPOCK1, SPP1, SPRED2, SPRY1, SPRY2, SQLE, SRL, SSPN, ST20, ST3GAL5, STAT4, STEAP2, STK17B, STK32A, STXBP6, SULF1, SYNE1, SYT14, SYTL5, TACSTD2, TASP1, TBC1D3F, TC2N, TCERG1L, TCF7L2, TCFL5, TDRKH, TEAD1, TFCP2L1, TFF3, TFPI, TGFA, TGFB2, TGFBR1, THSD4, TIAM2, TIMP1, TIMP3, TIPARP, TJP1, TJP2, TLCD1, TLE4, TLR10, TLR8, TM4SF1, TM4SF4, TM7SF4, TMEM100, TMEM117, TMEM133, TMEM156, TMEM163, TMEM171, TMEM215, TMEM220, TMEM90A, TMEM98, TMPRSS4, TMSB10, TMSB15A, TMSB15B, TNC, TNFAIP8, TNFRSF11B, TNFRSF12A, TNFRSF17, TNFSF10, TNFSF15, TOMM34, TOX, TPD52L1, TPO, TPX2, TRIP10, TRPC5, TRPC6, TSC22D1, TSHZ2, TSPAN13, TSPAN6, TSPAN8, TSSC1, TTC39A, TUBB1, TUBB6, TULP3, TUSC3, TXNL1, TXNRD1, TYMS, UCHL5, VAMP1, VNN1, VNN2, VNN3, WDR40A, WDR54, WDR72, WIPI1, WNT5A, XKRX, XPR1, YIF1B, YIPF1, YTHDC2, ZBTB33, ZCCHC12, ZCCHC16, ZEB2, ZFP36L1, ZFPM2, ZMAT3, ZMAT4, ZNF143, ZNF208, ZNF487, ZNF643, ZNF804B, ZYG11A.

Alternative spliced genes, n=283, are listed below in List 2:

List 2

ABCC3, ADAMTS5, ADAMTS9, AIDA, AK1, AKR1C3, ALDH1A3, ALDH6A1, AMIGO2, AMOT, ANGPTL1, ANKS6, ANO5, ANXA1, ANXA2, ANXA2P1, ANXA3, AQP4, ARHGAP24, ARL4A, ARMCX3, ARMCX6, ARSG, ATIC, ATP13A4, ATP8A1, AUTS2, BAG3, BCL2, BCL9, BHLHE41, C10orf131, C11orf74, C14orf45, C16orf45, C19orf33, C2orf40, C3, C5orf28, C8orf79, CA11, CALCA, CAV1, CCND1, CCND2, CD36, CD36, CDH3, CDH6, CDON, CFH, CFHR1, CHD4, CITED1, CLDN16, CLU, COPZ2, CP, CRABP1, CSGALNACT1, CTSC, CTSH, CTTN, CWH43, CYSLTR2, DCBLD2, DCUN1D3, DDB2, DGKH, DGKI, DIO1, DLG2, DOCK9, DPH3B, DPP4, DSP, DST, DUSP6, EFEMP1, EIF2B2, ELMO1, EMP2, ENAH, ENTPD1, EPHX4, ERBB3, ERI2, ERO1LB, ETNK2, ETV1, ETV5, F8, FABP4, FAM111B, FAM20A, FAM55C, FAT4, FBLN5, FGFR1OP2, FLJ42258, FLRT3, FN1, FREM2, FXYD6, GABBR2, GABRB2, GALNT7, GBE1, GBP1, GBP3, GGCT, GIMAP7, GPAM, GPR125, GPR155, GRAMD3, GSN, HLF, HMGA2, HSPH1, IMPDH2, IQGAP2, ITGA2, ITGA3, ITGA9, ITGB6, ITGB8, ITM2A, ITPR1, IYD, KATNAL2, KCNA3, KCNQ3, KDELC1, KHDRBS2, KIAA0284, KIAA1217, KIT, KLF8, KLK10, KRT19, LAMB3, LAMC2, LEMD1, LIFR, LINGO2, LMO3, LOC100127974, LOC100129112, LOC100131490, LOC100131869, LOC283508, LOC648149, LOC653354, LONRF2, LPCAT2, LPL, LRP1B, LRP2, LRRC69, LRRN1, LRRN3, LYRM1, MACC1, MAFG, MAP2, MAPK4, MAPK6, MATN2, MED13, MET, METTL7B, MFGE8, MLLT3, MPPED2, MPZL2, MRPL14, MT1F, MT1G, MT1H, MT1P2, MTHFD1L, MUC1, MVP, MYEF2, MYH10, MYO1D, NAG20, NAV2, NEB, NEDD4L, NELL2, NFATC3, NFKBIZ, NPC2, NRCAM, NUCB2, ORAOV1, P4HA2, PAM, PAPSS2, PARVA, PDLIM4, PEG10, PGCP, PIGN, PKHD1L1, PLA2G16, PLA2G7, PLA2R1, PLAU, PLEKHA4, PLP2, PLSCR4, PLXNC1, PMEPA1, PON2, PPARGC1A, PRINS, PROS1, PSD3, PTPRK, PYHIN1, QTRT1, RAB27A, RAB34, RAD23B, RASA1, RHOBTB3, RNASET2, RPS6KA6, RUNX1, SCARNA11, SCG5, SDC4, SERPINA1, SERPINA2, SGEF, SH2D4A, SLA, SLC12A2, SLC24A5, SLC26A4, SLC26A7, SLC27A2, SLC27A6, SLC35F2, SLC4A4, SLC5A8, SLC7A2, SOAT1, SPATS2, SPATS2L, SPINT1, SPP1, SSPN, STK32A, SULF1, SYNE1, TCFL5, TFPI, TGFBR1, TIPARP, TJP1, TLE4, TM7SF4, TMEM171, TMEM90A, TNFAIP8, TNFRSF11B, TOMM34, TPD52L1, TPO, TSC22D1, TUSC3, TYMS, WDR54, WDR72, WIPI1, XPR1, YIF1B, ZFPM2, ZMAT4.

Genes involved in the KEGG pathways are listed below in Table 6: there are 18 pathways with a total of n=109 unique genes.

TABLE 6

| Signaling Pathway | Number of Genes | Genes |
|---|---|---|
| ECM Pathway | 19 | CD36, COL1A1, FN1, HMMR, ITGA2, ITGA3, ITGA4, ITGA9, ITGB1, ITGB4, ITGB6, ITGB8, LAMB1, LAMB3, LAMC1, LAMC2, SDC4, SPP1, TNC |
| p53 Pathway | 10 | ATM, CCND1, CCND2, CDK2, DDB2, GADD45A, PERP, RRM2, SFN, ZMAT3 |
| PPAR Pathway | 10 | ACSL1, CD36, CYP27A1, FABP4, LPL, ME1, RXRG, SCP2, SLC27A2, SLC27A6 |
| Thyroid Cancer Pathway | 4 | CCND1, CTNNB1, RXRG, TCF7L2 |
| Focal Adhesion Pathway | 26 | BCL2, CAV1, CAV2, CCND1, CCND2, COL1A1, CTNNB1, EGF, EGFR, ERBB2, FN1, ITGA2, ITGA3, ITGA4, ITGA9, ITGB1, ITGB6, ITGB8, LAMB1, LAMB3, LAMC1, LAMC2, MET, PARVA, SPP1, TNC |
| Adherens Pathway | 9 | CTNNB1, EGFR, ERBB2, MET, MLLT4, PTPRF, TCF7L2, TGFBR1, TJP1 |
| Tight Junctions Pathway | 15 | CLDN1, CLDN10, CLDN16, CLDN4, CLDN7, CTNNB1, CTTN, EPB41, MLLT4, MYH10, PARD6B, RRAS, RRAS2, TJP1, TJP2 |
| Pathways in Cancer Overview | 34 | BCL2, BIRC5, CCND1, CDK2, CSF3R, CTNNB1, DAPK2, EGF, EGFR, ERBB2, ETS1, FGF2, FN1, FZD4, FZD6, FZD7, IL8, ITGA2, ITGA3, ITGB1, KIT, LAMB1, LAMB3, LAMC1, LAMC2, MET, PIAS3, RUNX1, RXRG, TCF7L2, TGFA, TGFB2, TGFBR1, WNT5A |
| Jak/STAT Pathway | 16 | CCND1, CCND2, CSF3R, IFNAR2, IL2RA, IL7R, ITGB4, JAK2, LIFR, OSMR, PIAS3, SPRED2, SPRY1, SPRY2, STAT4, TPO |
| Cell Cycle Pathway | 9 | ATM, CCND1, CCND2, CDK2, GADD45A, MCM4, MCM7, SFN, TGFB2 |
| TGFbeta Pathway | 6 | BMP8A, ID3, SMAD9, SMURF2, TGFB2, TGFBR1 |
| Wnt Pathway | 10 | CCND1, CCND2, CTNNB1, FZD4, FZD6, FZD7, NFATC3, PRICKLE1, TCF7L2, WNT5A |
| Erb Pathway | 5 | EGF, EGFR, ERBB2, ERBB3, TGFA |
| Apoptosis Pathway | 5 | ATM, BCL2, ENDOD1, IL1RAP, TNFSF10 |
| MAPK Pathway | 14 | DUSP4, DUSP5, DUSP6, EGF, EGFR, FGF2, GADD45A, GNG12, RASA1, RPS6KA6, RRAS, RRAS2, TGFB2, TGFBR1 |
| Autoimmune Thyroid pathway | 2 | HLA-DPB1, TPO |
| mTOR Pathway | 1 | RPS6KA6 |
| VEGF Pathway | 1 | NFATC3 |

Top genes separating benign and malignant thyroid (combined) from normal thyroid, n=55, are listed below in List 3:

List 3

ANGPTL1, ANXA3, C10orf131, C2orf40, C7orf62, CAV1, CCDC80, CDR1, CFH, CFHR1, CLDN16, CP, CRABP1, EFEMP1, ENTPD1, FABP4, FBLN5, FN1, GBP1, GBP3, GULP1, HSD17B6, IPCEF1, KIT, LRP1B, LRRC69, LUM, MAPK6, MATN2, MPPED2, MT1F, MT1G, MT1H, MT1M, MT1P2, MT1P3, MYEF2, NRCAM, ODZ1, PAPSS2, PKHD1L1, PLA2R1, RYR2, SEMA3D, SLC24A5, SLC26A4, SLC26A7, SLIT2, TFPI, TMEM171, TPO, TSPAN8, YTHDC2, ZFPM2, ZNF804B.

Thyroid surgical pathology subtypes, n=873, are listed below:

(i) List 4: FA subtype, n=243:

TCID-3124344, AHR, ALOX5, ANGPTL1, ANXA2, ANXA2P1, APOL1, AVPR1A, BMP8A, BTBD11, C2, C3, C8orf39, CCDC109B, CD36, CDON, CFB, CHGB, CHI3L1, CKB, CLDN1, CP, CRABP1, CTSC, CTSH, CXCL1, CXCL2, CXCL3, CXorf27, CYP1B1, DLG2, DNASE1L3, DPP4, DUOX1, DUOX2, DYNLT1, EIF4H, F8, FABP4, FAM20A, FAM55C, FBLN5, FLJ26056, FXYD6, GOS2, GALNT7, GLIS3, GPAM, HIGD1A, HK1, HLF, HSD17B6, ICAM1, IGFBP7, IL1RAP, IPCEF1, IYD, KATNAL2, KCNAB1, KHDRBS2, KLF8, KLHDC8A, LAMB1, LGALS3, LOC100131869, LOC26080, LOC284861, LOC439911, LOC653264, LOC728212, LOC729461, LPCAT2, LRRC69, MAGOH2, MAPK4, MAPK6, MELK, MPPED2, MT1G, NEB, NFKBIZ, NRIP1, PARP14, PKHD1L1, PLA2G7, PLP2, PLXNC1, POR, PRMT6, PROS1, PSMB2, PTPRE, PYGL, RNASE1, RNASET2, RPL9P11, RRAS2, RRBP1, RUNX1, RUNX2, RYR2, SCP2, SEL1L3, SERGEF, SGPP2, SH3BGR, SLC25A33, SLC26A4, SLC26A7, SLC27A6, SLC4A4, SLPI, SORBS2, SQLE, STK32A, SYTL5, TFCP2L1, TIAM2, TIMP3, TMEM220, TMSB10, TRPC6, TSHZ2, TSSC1, VAMP1, ZNF487, ABCC3, C11orf72, C8orf79, CLDN16, CLU, CST6, CYSLTR2, DIO1, DPH3B, ERO1LB, FN1, GABRB2, IGFBP6, IKZF3, KIT, KRT19, LIFR, LIPH, MACC1, MAFG, MPZL2, MT1F, MT1H, MT1P2, NELL2, ODZ1, RAG2, ROS1, SERPINA1, SERPINA2, SLC34A2, TCFL5, TIMP1, TPO, ZMAT4, ADAMTS9, ALDH1B1, ALDH6A1, ANO5, APOO, C10orf72, C11orf74, C14orf45, C2orf40, C4A, C4B, C5orf28, C6orf174, CAMK2N1, CCDC121, CCND1, CDH3, CITED1, COPZ2, CPNE3, CRABP2, CSGALNACT1, DAPK2, DLC1, ECE1, EIF2B2, EMP2, ERBB2, FAM82B, FIBIN, FLJ42258, FRMD3, HEY2, HRASLS, ID3, IGF2BP2, IGSF1, IKZF2, ITGA9, KIAA0408, KIAA1305, LMO3, MATN2, MDK, MET, METTL7B, MFGE8, MGC2889, MIS12, NAV2, NCAM1, NIPSNAP3A, NIPSNAP3B, NOD1, NTAN1, NUCB2, NUPR1, PCMTD1, PIGN, PLAG1, PSAT1, PXDNL, QTRT1, RG9MTD2, RXRG, SDC4, SLC35D2, SLC7A11, SMAD9, SPRY1, STEAP2, TASP1, TCF7L2, TMEM171, TNFRSF11B, TNFRSF12A, TRPC5, TXNL1, WDR72, YIPF1, ZCCHC12, ZCCHC16.

(ii) List 5: FC subtype, n=102:

TCID-3124344, ABCC3, ANGPTL1, AVPR1A, C8orf39, CD2, CD36, CD48, CD52, CKB, CLDN1, CLDN16, CRABP1, CXCL9, DIO1, DLG2, DNASE1L3, DPH3B, DYNLT1, EIF4H, ERO1LB, F8, FABP4, FBLN5, FLJ26056, FXYD6, FYB, GLIS3, GULP1, GZMA, GZMK, HK1, HLA-DPB1, IFITM1, IGFBP7, IGJ, IGK@, IGKC, IGKV1-5, IGKV3-15, IGKV3-20, IGKV3D-11, IGKV3D-15, IPCEF1, KHDRBS2, KLHDC8A, KLRC4, KLRK1, LAMB1, LCP1, LIFR, LOC100130100, LOC100131869, LOC26080, LOC284861, LOC439911, LOC440871, LOC650405, LOC652493, LOC652694, LOC653264, LOC728212, LOC729461, LYZ, MAGOH2, MAPK4, MT1F, MT1H, MT1P2, NEB, ODZ1, PLA2G7, POR, PRMT6, PSMB2, PTPRC, RAG2, RNASE1, RNASET2, RPL9P11, RRAS2, RRBP1, RYR2, SCP2, SERGEF, SGPP2, SH3BGR, SLC25A33, SLC26A4, SQLE, STK32A, TCFL5, TFCP2L1, TIAM2, TIMP3, TMEM220, TPO, TRPC6, TSSC1, VAMP1, ZFPM2, ZNF487.

(iii) List 6: LCT subtype, n=140:

ADAMTS9, AIM2, APOBEC3F, APOBEC3G, ARHGAP19, ATP13A4, BAG3, BCL2A1, BIRC5, BLNK, C10orf72, C11orf72, C12orf35, C4orf7, C6orf168, CALCA, CARD17, CARD8, CASP1, CCL19, CCND1, CD180, CD2, CD3D, CD48, CD52, CD79A, CD96, CEP110, CHGB, CLDN16, CLEC2B, CNN2, COL12A1, CR2, CXCL13, CXCL9, CYTH1, DENND4A, DNAJB14, DOCK8, DPYD, DUOX1, DUOX2, DUOXA1, DUOXA2, DUSP6, DYNC1I2, EGF, EPDR1, EPR1, EPS8, ETS1, FLJ42258, FYB, GABBR2, GABRB2, GALNT7, GBP5, GIMAP2, GIMAP5, GIMAP7, GPR155, GPR174, GTF3A, GZMA, GZMK, HIST1H3B, HIST1H4L, HLA-DPB1, HNRNPM, IFI16, IFITM1, IFNAR2, IGF2BP2, IGJ, IGK@, IGKC, IGKV1-5, IGKV3-15, IGKV3-20, IGKV3D-11, IGKV3D-15, IKZF3, IL7R, ITM2A, JAK2, KBTBD8, KLHL6, KLRC4, KLRG1, KLRK1, KYNU, LCP1, LIPH, LOC100130100, LOC100131490, LOC440871, LOC646358, LOC650405, LOC652493, LOC652694, LONRF2, LYZ, MED13L, METTL7B, MPZL2, MTIF3, NAV2, ND1, NFATC3, ODZ1, PAPSS2, PROS1, PSD3, PTPRC, PYGL, PYHIN1, RAD23B, RGS13, RIMS2, RRM2, SCG3, SLIT1, SP140, SP140L, SPC25, ST20, ST3GAL5, STAT4, STK32A, TC2N, TLE4, TNFAIP8, TNFRSF17, TNFSF10, TOX, UCHL5, ZEB2, ZNF143.

(iv) List 7: FVPTC subtype, n=182:

ABCC3, ADAMTS9, AIDA, ALDH1B1, ALDH6A1, ANK2, ANO5, APOL1, APOO, AQP4, ATP13A4, BMP8A, C10orf72, C11orf72, C11orf74, C12orf35, C14orf45, C2orf40, C4A, C4B, C5orf28, C6orf174, C8orf79, CAMK2N1, CCDC121, CCND1, CCND2, CD36, CDH3, CITED1, CLDN1, CLDN16, CLDN4, CLEC2B, CLU, COPZ2, CPNE3, CRABP2, CSGALNACT1, CST6, CWH43, CYSLTR2, DAPK2, DCAF17, DIO1, DIRAS3, DLC1, DOCK9, DPH3B, DUOX1, DUOX2, DUOXA1, DUOXA2, DUSP6, ECE1, EIF2B2, EMP2, ERBB2, ERO1LB, ESRRG, FABP4, FAM82B, FAT4, FIBIN, FLJ42258, FN1, FRMD3, GABBR2, GABRB2, GIMAP2, GIMAP7, GPR155, GPR98, GTF3A, GZMA, GZMK, HEY2, HRASLS, ID3, IGF2BP2, IGFBP6, IGSF1, IKZF2, IKZF3, ITGA9, JAK2, KIAA0284, KIAA0408, KIAA1217, KIAA1305, KIT, KLRC4, KLRK1, KRT19, LGALS3, LIFR, LIPH, LMO3, LOC100131490, LOC100131993, LRP1B, LRP2, MACC1, MAFG, MAPK6, MATN2, MDK, MET, METTL7B, MFGE8, MGC2889, MIS12, MPPED2, MPZL2, MT1F, MT1G, MT1H, MT1P2, MTIF3, NAV2, NCAM1, NELL2, NFATC3, NIPSNAP3A, NIPSNAP3B, NOD1, NRCAM, NTAN1, NUCB2, NUPR1, ODZ1, PCMTD1, PDE5A, PIGN, PKHD1L1, PLA2R1, PLAG1, PLSCR4, PRINS, PSAT1, PXDNL, QTRT1, RAG2, RCBTB2, RG9MTD2, ROS1, RPS6KA6, RXRG, SALL1, SCG5, SDC4, SERPINA1, SERPINA2, SLC26A4, SLC34A2, SLC35D2, SLC7A11, SMAD9, SPRY1, ST3GAL5, STEAP2, STK32A, TASP1, TCF7L2, TCFL5, TIMP1, TMEM171, TMEM215, TNFAIP8, TNFRSF11B, TNFRSF12A, TNFSF10, TPO, TRPC5, TXNL1, UCHL5, WDR72, YIPF1, ZCCHC12, ZCCHC16, ZMAT4, ZYG11A.

(v) List 8: PTC subtype, n=604:

TCID-3153400, TCID-3749600, ABCC3, ABTB2, ACBD7, ACSL1, ACTA2, ADAMTS5, ADAMTS9, ADK, AGR2, AHNAK2, AHR, AIDA, AK1, ALAS2, ALDH1A3, ALOX5, AMIGO2, AMOT, ANK2, ANXA1, ANXA2, ANXA2P1, ANXA3, AOAH, AP3S1, APOL1, AQP9, ARHGAP24, ARL13B, ARL4A, ARMCX3, ARMCX6, ARNTL, ASAP2, ATIC, ATP13A4, ATP13A4, B3GNT3, BCL9, BHLHE40, BHLHE41, BMP8A, BTBD11, BTG3, C11orf72, C11orf80, C12orf49, C16orf45, C19orf33, C1orf115, C1orf116, C2, C2orf40, C3, C4A, C4B, C4orf34, C6orf168, C6orf174, C7orf62, C8orf4, C8orf79, CA11, CADM1, CAMK2N1, CAND1, CAV1, CAV2, CCDC109B, CCDC121, CCDC148, CCDC80, CCL13, CCND1, CCND2, CD151, CD200, CD36, CDCP1, CDH11, CDH3, CDH6, CDK2, CDKL2, CDO1, CDON, CDR1, CFB, CFH, CFHR1, CFI, CHAF1B, CHD4, CHI3L1, CITED1, CKS2, CLC, CLDN1, CLDN10, CLDN16, CLDN4, CLDN7, CLEC4E, CLU, CNN3, COL1A1, CP, CRABP1, CRABP2, CSF3R, CST6, CTNNAL1, CTNNB1, CTSC, CTSH, CTTN, CXCL1, CXCL14, CXCL17, CXCL2, CXCL3, CXorf18, CXorf27, CYP1B1, CYSLTR2, DAPK2, DCBLD2, DCUN1D3, DDAH1, DDB2, DDX52, DGKH, DGKI, DHRS1, DHRS3, DIO1, DIRAS3, DLC1, DOCK9, DPP4, DPYSL3, DSG2, DSP, DST, DUSP4, DUSP5, DUSP6, DZIP1, ECE1, EDNRB, EGFR, EHBP1, EHD2, EHF, ELK3, ELMO1, EMP2, EMR3, ENAH, ENDOD1, EPB41, EPHA4, EPHX4, EPS8, ERBB3, ERI2, ERP27, ESRRG, ETNK2, ETV1, ETV5, F2RL2, FAAH2, FABP4, FAM111A, FAM111B, FAM164A, FAM176A, FAM20A, FAM55C, FAM84B, FBXO2, FBXO21, FCN1, FCN2, FGF2, FGFR1OP2, FLJ20184, FLJ32810, FLJ42258, FLRT3, FN1, FPR1, FPR2, FRMD3, FZD4, FZD6, FZD7, G0S2, GABBR2, GABRB2, GADD45A, GALE, GALNT12, GALNT3, GALNT7, GBP1, GBP3, GGCT, GLDN, GNG12, GOLT1A, GPAM, GPR110, GPR110, GPR125, GPR98, GPRC5B, GRAMD3, GSN, GYPB, GYPC, GYPE, HEMGN, HEY2, HIGD1A, HIST1H1A, HLA-DQB2, HLF, HMGA2, HPN, HSPH1, ICAM1, IGF2BP2, IGFBP5, IGFBP6, IGSF1, IKZF3, IL1RAP, IL1RL1, IL8RA, IL8RB, IL8RB, IL8RBP, IL8RBP, IMPDH2, INPP5F, IPCEF1, IQGAP2, ITGA2, ITGA3, ITGA9, ITGB1, ITGB6, ITGB8, ITPR1, JUB, KAL1, KATNAL2, KCNK5, KCNQ3, KCTD14, KDELC1, KDELR3, KHDRBS2, KIAA0284, KIAA0408, KIAA1217, KIT, KLF8, KLK10, KLK7, KRT18, KRT19, LAMB3, LAMC1, LAMC2, LCA5, LCMT1, LCN2, LDOC1, LEMD1, LGALS3, LILRA1, LILRB1, LIMA1, LINGO2, LIPH, LMO3, LMO4, LOC100124692, LOC100127974, LOC100129112, LOC100129115, LOC100129171, LOC100129961, LOC100130248, LOC100131102, LOC100131490, LOC100131938, LOC100132338, LOC100132764, LOC283508, LOC440434, L00554202, LOC643454, LOC648149, LOC653354, LOC653498, LOC730031, LONRF2, LOX, LPAR5, LPL, LRP1B, LRP2, LRRC69, LRRN1, LUM, LYRM1, MACC1, MAFG, MAMLD1, MAP2, MAPK6, MATN2, MBOAT2, MCM4, MCM7, MDK, MED13, MET, METTL7B, MEX3C, MFGE8, MGAM, MGAT4C, MGST1, MLLT4, MMP16, MMP16, MNDA, MORC4, MPPED2, MPZL2, MRPL14, MT1F, MT1G, MT1H, MT1M, MT1P2, MT1P3, MTHFD1L, MUC1, MUC15, MVP, MXRA5, MYEF2, MYH10, MYO1B, MYO1D, MYO6, NAB2, NAE1, NAG20, NCKAP1, NDFIP2, NEDD4L, NELL2, NEXN, NFE2, NFIB, NFKBIZ, NIPAL3, NOD1, NPC2, NPEPPS, NPY1R, NRCAM, NRIP1, NRP2, NT5E, NUDT6, OCIAD2, OCR1, ODZ1, OSGEP, OSMR, P2RY13, P4HA2, PAM, PARP14, PARP4, PARVA, PBX1, PDE5A, PDE9A, PDGFRL, PDLIM1, PDLIM4, PDZRN4, PEG10, PERP, PHEX, PHF16, PHLDB2, PHYHIP, PKHD1L1, PKP4, PLA2G16, PLA2R1, PLAG1, PLAU, PLCD3, PLEKHA4, PLEKHA5, PLK2, PLP2, PLS3, PLXNC1, PMEPA1, PON2, PPARGC1A, PPBP, PPL, PPP1R14C, PRICKLE1, PRINS, PROK2, PROS1, PRR15, PRRG1, PRSS23, PSD3, PTPN14, PTPRE, PTPRF, PTPRG, PTPRK, PTRF, QTRT1, RAB25, RAB27A, RAB34, RAD23B, RAG2, RAI2, RAPGEF5, RARG, RASA1, RASD2, RBBP7, RBBP8, RBMS2, RCE1, RDH5, RGS18, RGS2, RHOU, RND3, ROS1, RPL39L, RPRD1A, RPS6KA6, RRAS, RUNX1, RUNX2, RXRG, S100A12, S100A14, S100A16, S100A8, S100A9, SALL1, SAV1, SC4MOL, SCARA3, SCARNA11, SCEL, SCG5, SCNN1A, SCRN1, SDC4, SEH1L, SEL1L3, SELL, SEMA3D, SEPT11, SERINC2, SERPINA1, SERPINA2, SERPINE2, SERPING1, SFN, SFTPB, SGCB, SGCE, SGEF, SGMS2, SH2D4A, SH3PXD2A, SIRPA, SIRPB1, SLA, SLC12A2, SLC16A4, SLC17A5, SLC24A5, SLC26A4, SLC26A7, SLC27A2, SLC27A6, SLC34A2, SLC35F2, SLC39A6, SLC4A4, SLC5A8, SLC7A2, SLIT2, SLPI, SMOC2, SMURF2, SNCA, SNX1, SNX22, SNX7, SORBS2, SPATS2, SPATS2L, SPINT1, SPRED2, SPRY1, SPRY2, SRL, SSPN, ST3GAL5, STK32A, SULF1, SYNE1, SYT14, SYTL5, TACSTD2, TBC1D3F, TDRKH, TEAD1, TEAD1, TFCP2L1, TFF3, TGFA, TGFB2, TGFBR1, TIMP1, TIPARP, TJP1, TJP2, TLCD1, TLR8, TM4SF1, TM4SF4, TM7SF4, TMEM100, TMEM117, TMEM133, TMEM163, TMEM215, TMEM90A, TMEM98, TMPRSS4, TMSB10, TNC, TNFRSF12A, TNFSF15, TOMM34, TPD52L1, TPO, TRIP10, TRPC5, TSC22D1, TSPAN13, TSPAN6, TUBB1, TUBB6, TULP3, TUSC3, TYMS, VNN2, VNN3, WDR40A, WDR54, WNT5A, XKRX, XPR1, YIF1B, YTHDC2, ZBTB33, ZCCHC12, ZCCHC16, ZFP36L1, ZMAT3, ZMAT4, ZNF643, ZNF804B.

(vi) List 9: NHP subtype, n=653:

TCID-3153400, TCID-3749600, ABTB2, ACBD7, ACSL1, ACTA2, ADAMTS5, ADAMTS9, ADK, AGR2, AHNAK2, AHR, AIDA, AK1, AKR1C3, ALAS2, ALDH1A3, AMIGO2, AMOT, ANK2, ANO5, ANXA1, ANXA3, ANXA6, AOAH, AP3S1, APOO, AQP4, AQP9, ARHGAP24, ARL13B, ARL4A, ARMCX3, ARMCX6, ARNTL, ARSG, ASAP2, ATIC, ATP13A4, ATP6V0D2, B3GNT3, BCL9, BHLHE40, BHLHE41, BMP8A, BTBD11, BTG3, C10orf72, C11orf72, C11orf74, C11orf80, C12orf49, C16orf45, C19orf33, C1orf115, C1orf116, C2, C22orf9, C2orf40, C3, C4A, C4B, C4orf34, C5orf28, C6orf168, C6orf174, C7orf62, C8orf4, C8orf79, C9orf68, CA11, CADM1, CALCA, CAMK2N1, CAND1, CASC5, CAV1, CAV2, CCDC121, CCDC148, CCDC80, CCL13, CCND1, CCND1, CCND2, CD151, CD200, CD36, CDCP1, CDH11, CDH3, CDH6, CDK2, CDKL2, CDO1, CDON, CDR1, CEP55, CFB, CFH, CFHR1, CFI, CHAF1B, CHD4, CITED1, CKS2, CLC, CLDN1, CLDN10, CLDN16, CLDN4, CLDN7, CLEC4E, CLU, CNN3, COL1A1, COPZ2, CP, CPE, CRABP1, CRABP2, CSF3R, CST6, CTNNAL1, CTNNB1, CTSH, CTTN, CWH43, CXCL1, CXCL14, CXCL17, CXCL2, CXCL3, CXorf18, CXorf27, CYP24A1, CYP27A1, CYSLTR2, DAPK2, DCAF17, DCBLD2, DCUN1D3, DDAH1, DDB2, DDX52, DGKH, DGKI, DHRS1, DHRS3, DIOL, DIRAS3, DLC1, DLGAP5, DOCK8, DPP4, DPYSL3, DSG2, DSP, DST, DUOX1, DUOX2, DUOXA1, DUOXA2, DUSP4, DUSP5, DUSP6, DZIP1, ECE1, EDNRB, EGFR, EHBP1, EHD2, EHF, ELK3, ELMO1, EMP2, EMR3, ENAH, ENDOD1, EPB41, EPHA4, EPHX4, EPS8, ERBB3, ERI2, ERP27, ESRRG, ETNK2, ETV1, ETV5, F2RL2, FAAH2, FABP4, FAM111A, FAM111B, FAM164A, FAM176A, FAM20A, FAM84B, FAT4, FBXO2, FBXO21, FCN1, FCN2, FGF2, FGFR1OP2, FLJ20184, FLJ32810, FLJ42258, FLJ42258, FLRT3, FN1, FPR1, FPR2, FREM2, FRMD3, FXYD6, FZD4, FZD6, FZD7, G0S2, GABBR2, GABRB2, GADD45A, GALE, GALNT12, GALNT3, GALNT7, GBE1, GBP1, GBP3, GGCT, GLA, GLDN, GNG12, GOLT1A, GPR110, GPR110, GPR125, GPR98, GPRC5B, GRAMD3, GSN, GYPB, GYPC, GYPE, HEMGN, HEY2, HIST1H1A, HLA-DQB2, HMGA2, HMMR, HPN, HSD17B6, HSPH1, ICAM1, IGFBP5, IGFBP6, IGSF1, IKZF2, IL1RL1, IL2RA, IL8, IL8RA, IL8RB, IL8RB, IL8RBP, IL8RBP, IMPDH2, INPP5F, IPCEF1, IQGAP2, ITGA2, ITGA3, ITGA9, ITGB1, ITGB6, ITGB8, ITPR1, JUB, KAL1, KCNK5, KCNQ3, KCTD14, KDELC1, KDELR3, KHDRBS2, KIAA0284, KIAA0408, KIAA1217, KIF11, KIT, KLF8, KLK10, KLK7, KRT18, KRT19, LAMB3, LAMC1, LAMC2, LCA5, LCMT1, LCN2, LDOC1, LEMD1, LGALS3, LILRA1, LILRB1, LIMA1, LINGO2, LIPH, LMO3, LMO4, LOC100124692, LOC100127974, LOC100129112, LOC100129115, LOC100129171, LOC100129961, LOC100130248, LOC100131102, LOC100131490, LOC100131938, LOC100131993, LOC100132338, LOC100132764, LOC283508, LOC440434, L00554202, LOC643454, LOC648149, LOC653354, LOC653498, LOC730031, LONRF2, LOX, LPAR1, LPAR5, LPL, LRP1B, LRP2, LRRC69, LRRN1, LUM, LYRM1, MACC1, MAFG, MAMLD1, MAP2, MAPK6, MATN2, MBOAT2, MCM4, MCMI, MDK, ME1, MED13, MELK, MET, METTL7B, MEX3C, MFGE8, MGAM, MGAT1, MGAT4C, MGST1, MKI67, MLLT4, MMP16, MMP16, MNDA, MORC4, MPPED2, MPZL2, MRPL14, MT1F, MT1G, MT1H, MT1M, MT1P2, MT1P3, MTHFD1L, MUC1, MUC15, MVP, MXRA5, MYEF2, MYH10, MYO1B, MYO1D, MYO5A, MYO6, NAB2, NAE1, NAG20, NAV2, NCKAP1, NDC80, NDFIP2, NEDD4L, NELL2, NEXN, NFE2, NFIB, NIPAL3, NOD1, NPC2, NPEPPS, NPL, NPY1R, NRCAM, NRIP1, NRP2, NT5E, NUCB2, NUDT6, NUSAP1, OCIAD2, OCR1, ODZ1, ORAOV1, OSBPL1A, OSGEP, OSMR, P2RY13, P4HA2, PAM, PAPSS2, PARP4, PARVA, PBX1, PDE5A, PDE9A, PDGFRL, PDLIM1, PDLIM4, PDZRN4, PEG10, PERP, PGCP, PHEX, PHF16, PHLDB2, PHYHIP, PKHD1L1, PKP4, PLA2G16, PLA2G7, PLA2R1, PLAG1, PLAU, PLCD3, PLCL1, PLEKHA4, PLEKHA5, PLK2, PLS3, PLSCR4, PMEPA1, PON2, PPARGC1A, PPBP, PPL, PPP1R14C, PRCP, PRICKLE1, PRINS, PROK2, PROS1, PRR15, PRRG1, PRSS23, PSD3, PSD3, PTPN14, PTPRE, PTPRF, PTPRG, PTPRK, PTRF, QTRT1, RAB25, RAB27A, RAB32, RAB34, RAD23B, RAG2, RAI2, RAPGEF5, RARG, RASA1, RASD2, RBBP7, RBBP8, RBMS2, RCBTB2, RCE1, RDH5, RGS18, RGS2, RHOU, RND3, ROS1, RPL39L, RPRD1A, RPS6KA6, RRAS, RXRG, S100A12, S100A14, S100A16, S100A8, S100A9, SALL1, SAV1, SC4MOL, SCARA3, SCARNA11, SCEL, SCG5, SCNN1A, SCRN1, SDC4, SEH1L, SELL, SEMA3C, SEMA3D, SEPT11, SERINC2, SERPINA1, SERPINA2, SERPINE2, SERPING1, SFN, SFTPB, SGCB, SGCE, SGEF, SGMS2, SH2D4A, SH3PXD2A, SIRPA, SIRPB1, SLA, SLC12A2, SLC16A4, SLC16A6, SLC17A5, SLC24A5, SLC26A4, SLC26A7, SLC27A2, SLC27A6, SLC34A2, SLC35F2, SLC39A6, SLC4A4, SLC5A8, SLC7A11, SLC7A2, SLIT2, SLPI, SMOC2, SMURF2, SNCA, SNX1, SNX22, SNX7, SOAT1, SORBS2, SPATS2, SPATS2L, SPINT1, SPRED2, SPRY1, SPRY2, SRL, SSPN, ST3GAL5, STK32A, STXBP6, SULF1, SYNE1, SYT14, SYTL5, TACSTD2, TBC1D3F, TDRKH, TEAD1, TEAD1, TFCP2L1, TFF3, TFPI, TGFA, TGFB2, TGFBR1, TIMP1, TIPARP, TJP1, TJP2, TLCD1, TLR8, TM4SF1, TM4SF4, TM7SF4, TMEM100, TMEM117, TMEM133, TMEM163, TMEM171, TMEM215, TMEM90A, TMEM98, TMPRSS4, TNC, TNFRSF12A, TNFSF15, TOMM34, TPD52L1, TPO, TPX2, TRIP10, TRPC5, TSC22D1, TSPAN13, TSPAN6, TUBB1, TUBB6, TULP3, TUSC3, TXNRD1, TYMS, UCHL5, VNN1, VNN2, VNN3, WDR40A, WDR54, WIPI1, WNT5A, XKRX, XPR1, YIF1B, YTHDC2, ZBTB33, ZCCHC12, ZCCHC16, ZFP36L1, ZMAT3, ZMAT4, ZNF643, ZNF804B, ZYG11A.

(vii) List 10: MTC subtype, n=48:
ANXA3, ATP13A4, BLNK, C10orf131, C6orf174, C8orf79, CALCA, CHGB, CP, CPE, DSG2, FREM2, GPR98, IGJ, IYD, KIAA0408, LOC100129171, LPCAT2, LRRC69, MACC1, MAPK6, MGAT4C, MGST1, MMP16, MT1G, MT1H, MT1M, MT1P2, MT1P3, MUC15, MYEF2, NT5E, PKHD1L1, PLS3, RBMS2, RIMS2, SCG3, SEMA3D, SLA, SLC24A5, SMOC2, SULF1, TOX, TSHZ2, TSPAN6, WDR72, ZFP36L1, ZNF208.

(viii) List 11: HC subtype, n=65:
AIM2, APOBEC3F, APOBEC3G, ARHGAP19, BAG3, BCL2A1, BMP8A, C9orf68, CARD17, CARD8, CASP1, CD3D, CD96, CEP110, CLEC2B, CNN2, CPE, CYTH1, DENND4A, DNAJB14, DOCK8, DPYD, DUOX1, DUOX2, DYNC1I2, EGF, EPDR1, ETS1, GBP5, GIMAP2, GIMAP5, GIMAP7, GPR174, GZMK, HNRNPM, HSD17B6, IFI16, IFNAR2, IKZF3, IL7R, ITM2A, JAK2, KCNAB1, KHDRBS2, KLRC4, KLRG1, KLRK1, KYNU, LOC646358, MED13L, ND1, NFATC3, PAPSS2, PGCP, PTPRC, PYHIN1, SLIT1, SP140, SP140L, ST20, STAT4, TC2N, TLE4, ZEB2, ZNF143.

(ix) List 12: HA subtype, n=24:
BCL2, CADM1, CAV1, CRABP1, CTNNB1, CYTH1, DIRAS3, IFITM1, IGFBP5, IGFBP6, LOX, MAP2, MATN2, MET, MKI67, MYO1B, ND1, NUCB2, SCG5, SCNN1A, SEL1L3, SGCE, TNFSF10, TRPC6.

(x) List 13: ATC subtype, n=12:
CASC5, CEP55, COL12A1, DLGAP5, HMMR, KIF11, MELK, MKI67, NDC80, NUSAP1, PYGL, TPX2.

Dominant gene ontology of top 948 thyroid biomarkers are listed below:

List 14: Angiogenesis, n=23
ACTA2, ANXA2, ARHGAP24, CALCA, CAV1, CITED1, COL1A1, CXCL17, EGF, ELK3, IL8, LOX, PLCD3, PROK2, RASA1, SEMA3C, TCF7L2, TGFA, TGFB2, TIPARP, TNFRSF12A, ZFP36L1, ZFPM2.

List 15: Apoptosis, n=43
AHR, ANXA1, BAG3, BCL2, BCL2A1, BIRC5, C8orf4, CADM1, CD2, CLU, CTNNB1, DAPK2, DLC1, DNASE1L3, ECE1, ELMO1, FAM176A, FGF2, GADD45A, GULP1, GZMA, HIPK2, IL2RA, IL8RB, JAK2, NCKAP1, NOD1, NUPR1, PEG10, PERP, PROK2, RYR2, SLC5A8, STK17B, SULF1, TCF7L2, TGFB2, TNFAIP8, TNFRSF11B, TNFRSF12A, TNFSF10, VNN1, ZMAT3.

List 16: Cell Cycle, Transcription Factors, n=184
AEBP1, AHR, AK1, ANXA1, APOBEC3F, APOBEC3G, ARHGAP24, ARNTL, ATM, BCL2, BHLHE40, BHLHE41, BIRC5, BMP1, BMP8A, CADM1, CAND1, CARD8, CASP1, CCND1, CCND2, CDK2, CEP110, CEP55, CHAF1B, CHD4, CITED1, CKS2, CLU, CRABP2, CSGALNACT1, CTNNB1, CXCL1, CXCL17, DENND4A, DLGAP5, DST, DZIP1, EGF, EHF, EIF2B2, EIF4H, ELK3, EMP2, EPS8, ERBB2, ERBB3, ESRRG, ETS1, ETV1, ETV4, ETV5, FABP4, FGF2, GOS2, GADD45A, GLDN, GLIS3, GTF3A, HEMGN, HEY2, HIPK2, HLF, HMGA2, HPN, ID3, IFI16, IFNAR2, IGSF1, IKZF2, IKZF3, IKZF4, IL2RA, IL8, ITPR1, JAK2, JUB, KHDRBS2, KIF11, KLF8, KLK10, KRT18, LGALS3, LIFR, LMO3, LMO4, LRP2, LTBP2, LTBP3, MACC1, MAFG, MAMLD1, MAPK4, MAPK6, MCM4, MCM1, MDK, MED13, MED13L, MIS12, MKI67, MLLT3, MNDA, MTIF3, MYH10, NAB2, NAE1, NDC80, NFATC3, NFE2, NFIB, NFKBIZ, NOD1, NPAS3, NPAT, NRIP1, NRP2, NUDT6, NUPR1, NUSAP1, OSMR, PARD6B, PARP14, PARP4, PBX1, PDLIM1, PEG10, PIAS3, PLAG1, POU2F3, PPARGC1A, PPBP, PRMT6, PROK2, PTRF, PYHIN1, RARG, RBBP7, RBBP8, RGS2, RHOH, RRM2, RUNX1, RUNX2, RXRG, SALL1, SEMA3D, SERPINE2, SLIT1, SLIT2, SMAD9, SMURF2, SP140, SPC25, SPOCK1, STAT4, SYNE1, TACSTD2, TCF7L2, TCFL5, TEAD1, TFCP2L1, TGFA, TGFB2, TGFBR1, TLE4, TNFAIP8, TNFRSF12A, TNFRSF17, TPX2, TSC22D1, TSHZ2, TULP3, TYMS, WNT5A, ZBTB33, ZCCHC12, ZEB2, ZFP36L1, ZFPM2, ZNF143, ZNF208, ZNF487, ZNF643.

List 17: Cell Membrane, n=410
ABCC3, ABCD2, ACSL1, ADAMTS5, ADAMTS9, ADORA1, AFAP1, AK1, ALOX5, AMIGO2, ANK2, ANO5, AP3S1, APOL1, APOO, AQP4, AQP9, ARMCX3, ARMCX6, ASAP2, ATP13A4, ATP6VOD2, ATP8A1, AVPR1A, B3GNT3, BCL2, BLNK, BTBD11, C10orf72, C17orf87, C1orf115, C4orf34, C5orf28, C6orf174, CADM1, CAMK2N1, CAV1, CAV2, CCDC109B, CD151, CD180, CD2, CD200, CD36, CD3D, CD48, CD48, CD52, CD69, CD79A, CD96, CDCP1, CDH11, CDH3, CDH6, CDON, CFB, CFI, CHI3L1, CLDN1, CLDN10, CLDN16, CLDN4, CLDN7, CLEC2B, CLEC4E, COL12A1, COL1A1, COPZ2, CP, CPE, CR2, CSF3R, CSGALNACT1, CTNNAL1, CTNNB1, CWH43, CYP1B1, CYP27A1, CYP4B1, CYSLTR1, CYSLTR2, CYTH1, DCAF17, DCBLD2, DHRS3, DIOL, DIRAS3, DLG2, DLG4, DNAJB14, DOCK9, DPP4, DPYSL3, DSG2, DUOX1, DUOX2, DUOXA1, DUOXA2, ECE1, EDNRB, EFEMP1, EGF, EGFR, EHBP1, EHD2, ELMO1, EMP2, EMR3, ENTPD1, EPB41, EPHA4, EPHX4, ERBB2, ERBB3, ERO1LB, F2RL2, F8, FAAH2, FAM176A, FAM84B, FAT4, FBLN5, FLRT3, FN1, FPR1, FPR2, FREM2, FRMD3, FXYD6, FZD4, FZD6, FZD7, GABBR2, GABRB2, GALNT12, GALNT3, GALNT7, GBP1, GBP3, GBP5, GIMAP2, GIMAP5, GJA4, GLDN, GNG12, GOLT1A, GPAM, GPR110, GPR125, GPR155, GPR174, GPR98, GPRC5B, GYPB, GYPC, GYPE, HIGD1A, HK1, HLA-DPB1, HNRNPM, HPN, HSD17B6, ICAM1, IFITM1, IFNAR2, IGSF1, IL1RAP, IL1RL1, IL2RA, IL7R, IL8RA, IL8RB, IPCEF1, ITGA2, ITGA3, ITGA4, ITGA9, ITGB1, ITGB4, ITGB6, ITGB8, ITM2A, ITPR1, IYD, JAK2, JUB, KAL1, KCNA3, KCNAB1, KCNK5, KCNQ3, KCTD14, KDELR3, KIAA1305, KIT, KLRB1, KLRC4, KLRG1, KLRK1, LAMB1, LAMC1, LEMD1, LGALS3, LIFR, LILRA1, LILRB1, LINGO2, LIPH, LPAR1, LPAR5, LPCAT2, LPL, LRP1B, LRP2, LRRN1, LRRN3, LUM, MATN2, MBOAT2, MET, MFGE8, MGAM, MGAT1, MGAT4C, MGST1, MMP16, MPZL2, MRC2, MUC1, MUC15, MYH10, MYO6, NAE1, NCAM1, NCKAP1, ND1, NDFIP2, NIPAL3, NPY1R, NRCAM, NRP2, NT5E, NUCB2, ODZ1, OSMR, P2RY13, PAM, PARD6B, PARP14, PARVA, PCDH1, PCNXL2, PERP, PHEX, PHLDB2, PIGN, PKHD1L1, PKP2, PLA2G16, PLA2R1, PLAU, PLCD3, PLEK, PLEKHA4, PLP2, PLSCR4, PLXNC1, PMEPA1, PON2, POR, PPAP2C, PPL, PPP1R14C, PRICKLE1, PRRG1, PSD3, PTK7, PTPRC, PTPRE, PTPRF, PTPRG, PTPRK, PTPRU, PTRF, RAB25, RAB27A, RARG, RASA1, RASD2, RCE1, RDH5, RGS13, RHOH, RHOU, RIMS2, RND3, ROS1, RRAS, RRAS2, RRBP1, RYR2, S100A12, SC4MOL, SCARA3, SCEL, SCNN1A, SDC4, SDK1, SEL1L3, SELL, SEMA3C, SEMA3D, SEMA4C, SERINC2, SERPINA1, SGCB, SGCE, SGMS2, SGPP2, SIRPA, SIRPB1, SLC12A2, SLC16A4, SLC16A6, SLC17A5, SLC24A5, SLC25A33, SLC26A4, SLC26A7, SLC27A2, SLC27A6, SLC34A2, SLC35D2, SLC35F2, SLC39A6, SLC4A4, SLC5A8, SLC7A11, SLC7A2, SMURF2, SNCA, SNX1, SOAT1, SPINT1, SPOCK1, SPRED2, SPRY1, SPRY2, SQLE, SSPN, ST3GAL5, STEAP2, STXBP6, SYNE1, SYT14, SYTL5, TACSTD2, TFCP2L1, TFF3, TFPI, TGFA, TGFB2, TGFBR1, TIMP1, TJP1, TJP2, TLCD1, TLR10, TLR8, TM4SF1, TM4SF4, TM7SF4, TMEM100, TMEM117, TMEM133, TMEM156, TMEM163, TMEM171, TMEM215, TMEM220, TMEM90A, TMEM98, TMPRSS4, TNC, TNFRSF11B, TNFRSF12A, TNFRSF17, TNFSF10, TNFSF15, TOMM34, TPO, TRIP10, TRPC5, TRPC6, TSPAN13, TSPAN6, TSPAN8, TULP3, TUSC3, VAMP1, VNN1, VNN2, VNN3, WNT5A, XKRX, XPR1, YIF1B, YIPF1, ZBTB33.

List 18: Rare Membrane Components, n=55

AMOT, ANXA1, ANXA2, CALCA, CAMK2N1, CAV1, CAV2, CCDC80, CLU, CST6, CTNNB1, CTTN, DLC1, DPP4, DSG2, DSP, DST, ENAH, GJA4, HIPK2, ITGB1, ITGB4, JAK2, JUB, KRT19, LCP1, LRP2, MYH10, MYO5A, MYO6, NEB, PARVA, PCDH1, PERP, PKP2, PKP4, PLEK, PPL, PTRF, RAB34, RASA1, RYR2, SCEL, SGCB, SGCE, SLC27A6, SLIT1, SPRY1, SRL, SSPN, SYNE1, TGFB2, TIAM2, TJP1, TNFRSF12A.

List 19: Cell-cell adhesion, n=85

AEBP1, AFAP1, AMIGO2, ARHGAP24, BCL2, CADM1, CALCA, CD151, CD2, CD36, CD96, CDH3, CDH6, CDON, CLDN1, CLDN10, COL12A1, CSF3R, CTNNAL1, CTNNB1, DCBLD2, DLC1, DSG2, DST, EGFR, ENAH, ENTPD1, EPDR1, F8, FAT4, FBLN5, FLRT3, FN1, FPR2, FREM2, GPR98, ICAM1, IGFBP7, IL1RL1, ITGA2, ITGA3, ITGA4, ITGA9, ITGB1, ITGB4, ITGB6, ITGB8, JUB, KAL1, LAMB1, LAMB3, LAMC1, LAMC2, LIMA1, MFGE8, MLLT4, MPZL2, NCAM1, NELL2, NRCAM, NRP2, PARVA, PCDH1, PERP, PKP2, PKP4, PLXNC1, PTK7, PTPRC, PTPRF, PTPRK, PTPRU, RHOU, RND3, SDK1, SELL, SGCE, SIRPA, SPOCK1, SPP1, SSPN, TJP1, TNC, TNFRSF12A, VNN1.

List 20: Apical cell membrane, n=15

ANK2, ATP6VOD2, CTNNB1, CTNNB1, DPP4, DUOX1, ERBB2, ERBB3, F2RL2, FZD6, LRP2, SCNN1A, SLC26A4, SLC34A2, TFF3.

List 21: Basolateral, Lateral cell membrane, n=28

ANK2, ANXA1, ANXA2, CADM1, CCDC80, CTNNB1, CTTN, DSP, DST, EGFR, EPB41, ERBB2, ERBB3, FREM2, LAMB1, LAMB3, LAMC1, LAMC2, MET, MYH10, MYO6, PTPRK, SLC26A7, SMOC2, SNCA, TIMP3, TJP1, TRIP10.

List 22: Integrins, n=14

ADAMTS5, DST, FBLN5, ICAM1, ITGA2, ITGA3, ITGA4, ITGA9, ITGB1, ITGB4, ITGB6, ITGB8, MFGE8, PLEK.

List 23: Cell Junction, n=40

AMOT, ARHGAP24, ARHGAP24, CADM1, CAMK2N1, CLDN1, CLDN10, CLDN16, CLDN4, CLDN7, CNN2, DLG2, DLG4, DPYSL3, DSP, ENAH, GABBR2, GABRB2, GJA4, JUB, LIMA1, MLLT4, NCKAP1, NEXN, PARD6B, PARVA, PCDH1, PERP, PPL, PSD3, PTPRK, PTPRU, RHOU, RIMS2, SH3PXD2A, SSPN, TGFB2, TJP1, TJP2, VAMP1.

List 24: Cell surface, n=17

CD36, DCBLD2, DPP4, GPR98, HMMR, IL1RL1, IL8RB, ITGA4, ITGB1, KAL1, MMP16, PTPRK, SDC4, SULF1, TGFA, TM7SF4, TNFRSF12A.

List 25: Extracellular space, n=156

ADAMTS5, ADAMTS9, AEBP1, AGR2, ANGPTL1, ANXA2, APOL1, APOO, BMP1, BMP8A, C12orf49, C2, C2orf40, C3, C4A, C4B, C4orf7, CA11, CALCA, CCDC80, CCL13, CCL19, CDCP1, CFB, CFH, CFHR1, CFI, CHGB, CHI3L1, CLU, COL12A1, COL1A1, CP, CPE, CSF3R, CST6, CXCL1, CXCL11, CXCL13, CXCL14, CXCL17, CXCL2, CXCL3, CXCL9, DPP4, EFEMP1, EGF, EGFR, EMR3, ENDOD1, EPDR1, ERBB3, F8, FAM20A, FAM55C, FBLN5, FCN1, FCN2, FGF2, FIBIN, FN1, FXYD6, GLA, GSN, GZMA, GZMK, ICAM1, IFNAR2, IGFBP5, IGFBP6, IGFBP7, IGJ, IGKC, IGKV1-5, IGKV3-20, IGKV3D-11, IGSF1, IL1RAP, IL1RL1, IL7R, IL8, KAL1, KIT, KLK10, KLK7, LAMB1, LAMB3, LAMC1, LAMC2, LCN2, LIFR, LIPH, LOC652694, LOX, LPL, LTBP2, LTBP3, LUM, LYZ, MATN2, MDK, MFGE8, MMP16, MUC1, MUC15, MXRA5, NCAM1, NELL2, NPC2, NUCB2, ODZ1, PAM, PDGFRL, PGCP, PLA2G7, PLA2R1, PLAU, PON2, PPBP, PROK2, PROS1, PRRG1, PRSS23, PXDNL, RNASE1, RNASET2, SCG3, SCG5, SEMA3C, SEMA3D, SEPP1, SERPINA1, SERPINE2, SERPING1, SFN, SFTPB, SLIT1, SLIT2, SLPI, SMOC2, SPINT1, SPOCK1, SPP1, SULF1, TFF3, TFPI, TGFA, TGFB2, THSD4, TIMP1, TIMP3, TNC, TNFRSF11B, TNFSF10, TNFSF15, WNT5A.

List 26: Cytoskeleton, n=94

ACTA2, ADORA1, AFAP1, AMOT, ANK2, ANXA2, AP3S1, ARHGAP24, ATM, ATP8A1, BCL2, BIRC5, C2orf40, CASC5, CLU, CNN2, CNN3, COL12A1, COL1A1, COPZ2, CTNNAL1, CTNNB1, CTTN, CXCL1, DLG4, DLGAP5, DPYSL3, DST, DYNC1I2, DYNLT1, EGFR, ELMO1, ENAH, EPB41, EPS8, FAM82B, FRMD3, GPRC5B, GSN, GYPC, IGF2BP2, IQGAP2, JAK2, JUB, KATNAL2, KIAA0284, KIF11, KRT18, LCA5, LCP1, LIMA1, LOX, LUM, MAP2, MPZL2, MYH10, MYO1B, MYO1D, MYO5A, MYO6, NEB, NEXN, NFE2, NUSAP1, PARVA, PDLIM1, PKP2, PLEK, PLS3, PPL, PTPN14, RHOU, RND3, S100A9, SCNN1A, SDC4, SGCB, SGCE, SNCA, SORBS2, SPRED2, SPRY2, STK17B, SYNE1, TGFB2, TGFBR1, TMSB10, TMSB15A, TPX2, TRIP10, TUBB1, TUBB6, VAMP1, WIPI1.

In some embodiments, the present invention provides a method of classifying cancer comprising the steps of: obtaining a biological sample comprising gene expression products; determining the expression level for one or more gene expression products of the biological sample; and identifying the biological sample as cancerous wherein the gene expression level is indicative of the presence of thyroid cancer in the biological sample. This can be done by correlating the gene expression levels with the presence of thyroid cancer in the biological sample. In one embodiment, the gene expression products are selected from one or more genes listed in Table 2. In some embodiments, the method further includes identifying the biological sample as positive for a cancer that has metastasized to thyroid from a non-thyroid organ if there is a difference in the gene expression levels between the biological sample and a control sample at a specified confidence level.

Biomarkers involved in metastasis to thyroid from a non-thyroid organ are provided. Such metastatic cancers that metastasize to thyroid and can be diagnosed using the subject methods of the present invention include but are not limited to metastatic parathyroid cancer, metastatic melanoma, metastatic renal carcinoma, metastatic breast carcinoma, and metastatic B cell lymphoma. Exemplary biomarkers that can be used by the subject methods to diagnose metastasis to thyroid are listed in Table 2.

TABLE 2

Biomarkers involved in metastasis to thyroid

| Type of metastasis | Number of genes | Genes |
|---|---|---|
| Top Biomarkers of Non-thyroid Metastases to the Thyroid | 73 | ACADL, ATP13A4, BIRC5, BTG3, C2orf40, C7orf62, CD24, CHEK1, CP, CRABP1, CXADR, CXADRP2, DIO1, DIO2, EPCAM, EPR1, GPX3, HSD17B6, IQCA1, IYD, KCNJ15, KCNJ16, KRT7, LMO3, LOC100129258, LOC100130518, LPCAT2, LRRC2, LRRC69, MAL2, MAPK6, MGAT4C, MGC9913, MT1F, MT1G, MT1H, MT1P2, MUC15, NEBL, NPNT, NTRK2, PAR1, PCP4, PDE1A, PDE8B, PKHD1L1, PLS3, PVRL2, PVRL3, RGN, RPL3, RRM2, SCD, SEMA3D, SH3BGRL2, SLC26A4, SLC26A7, SNRPN, SPC25, SYT14, TBCKL, TCEAL2, TCEAL4, TG, TPO, TSHR, WDR72, ZBED2, ZNF208, ZNF43, ZNF676, ZNF728, ZNF99 |
| Parathyroid Metastasis to Thyroid | 101 | TCID-2688277, ACSL3, ACTR3B, ADAM23, ADH5, ARP11, AS3MT, BANK1, C10orf32, C11orf41, C2orf67, C7orf62, C8orf34, CA8, CASR, CD109, CD226, CD24, CD44, CDCA7L, CHEK1, CLDN1, CP, DIO2, DMRT2, DNAH11, DPP4, ELOVL2, ENPEP, EPHA7, ESRRG, EYA1, FMN2, GCM2, GPR160, GPR64, HSD17B6, ID2, ID2B, IYD, KIDINS220, KIF13B, KL, LGI2, LMO3, LOC100131599, LOC150786, LPL, LRRC69, MAPK6, MGST1, MT1F, MT1G, MT1H, MT1P2, MUC15, NAALADL2, NPNT, OGN, PDE8B, PEX5L, PKHD1L1, PLA2G4A, PLCB1, PRLR, PTH, PTN, PTPRD, PTTG1, PTTG2, PVALB, PVRL2, RAB6A, RAB6C, RAPGEF5, RARRES2, RGN, RNF217, RPE, SACS, SEMA3D, SGK1, SLA, SLC15A1, SLC26A4, SLC26A7, SLC7A8, SPOCK3, ST3GAL5, STXBP5, SYCP2L, TBCKL, TG, TINF2, TMEM167A, TPO, TSHR, TTR, WDR72, YAP1, ZBED2 |
| Melanoma Metastasis to Thyroid | 190 | TCID-2840750, ABCB5, AHNAK2, ALX1, ANLN, AP1S2, APOD, ASB11, ATP13A4, ATP1B1, ATRNL1, AZGP1, BACE2, BAMBI, BCHE, BIRC5, BRIP1, BZW1, BZW1L1, C2orf40, C6orf218, C7orf62, CA14, CASC1, CCNB2, CD24, CDH19, CDK2, CDKN3, CENPF, CHRNA5, CP, CRABP1, DCT, DEPDC1, DIO1, DIO2, DLGAP5, DSCC1, DSP, EDNRB, EIF1AY, EIF4A1, ENPP1, EPCAM, EPR1, ESRP1, FABP7, FANCI, GAS2L3, GGH, GPM6B, GPNMB, GPR19, GPX3, GULP1, GYG2, HAS2, HEATR5A, HMCN1, HTN1, IL13RA2, IQCA1, IYD, KCNJ15, KCNJ16, KIAA0894, KIF23, KRT7, KRTAP19-1, LGALS1, LMO3, LOC100129171, LOC100129258, LOC100130275, LOC100130357, LOC100130518, LOC100131821, LOC145694, LOC653653, LRP2, LRRC69, LSAMP, LUM, MAL2, MAPK6, MGC87042, MITF, MLANA, MME, MND1, MOXD1, MSMB, MUC15, NDC80, NEBL, NLGN1, NOX4, NPNT, NTRK2, NUDT10, NUDT11, PAX3, PBK, PCP4, PDE3B, PDE8B, PI15, PICA, PIR, PKHD1L1, PLP1, PLXNC1, POLG, POMGNT1, POPDC3, POSTN, PRAME, PRAMEL, PTPRZ1, PVRL2, PYGL, QPCT, RGN, RNF128, ROPN1, ROPN1B, RPL3, RPSA, RPSAP15, RPSAP58, S100B, SACS, SAMD12, SCD, SEMA3C, SERPINA3, SERPINE2, SERPINF1, SHC4, SILV, SLA, SLC16A1, SLC26A4, SLC26A7, SLC39A6, SLC45A2, SLC5A8, |

TABLE 2-continued

Biomarkers involved in metastasis to thyroid

| Type of metastasis | Number of genes | Genes |
|---|---|---|
| | | SLC6A15, SNAI2, SNCA, SNORA48, SNORA67, SORBS1, SPC25, SPP1, SPRY2, SRPX, ST3GAL6, STEAP1, STK33, TBC1D7, TBCKL, TCEAL2, TCEAL4, TCN1, TF, TFAP2A, TG, TMP2, TMSB15A, TMSB15B, TNFRSF11B, TOP2A, TPO, TPX2, TRPM1, TSHR, TSPAN1, TUBB4, TYR, TYRL, TYRP1, WDR72, ZBED2, ZNF208, ZNF43, ZNF676, ZNF728, ZNF99 |
| Renal Carcinoma Metastasis to Thyroid | 130 | TCID-2763154, ADFP, AKR1C3, ALPK2, APOL1, ASPA, ATP13A4, ATP8A1, BHMT, BHMT2, BICC1, BIRC3, C12orf75, C1S, C2orf40, C3, C7orf62, CA12, CDH6, CLRN3, CP, CYB5A, DAB2, DEFB1, DIO2, EFNA5, EGLN3, EIF1AY, ENPEP, ENPP1, ENPP3, EPCAM, ESRP1, FABP6, FABP7, FAM133B, FCGR3A, FCGR3B, FXYD2, GAS2L3, GLYAT, GSTA1, GSTA2, GSTA5, HAVCR1, HLA-DQA1, HPS3, IGFBP3, IL20RB, IYD, KMO, LEPREL1, LMO3, LOC100101266, LOC100129233, LOC100129518, LOC100130232, LOC100130518, LOC100133763, LOC728640, LOX, LRRC69, MAPK6, MGC9913, MME, MMP7, MT1G, MUC15, NEBL, NLGN1, NNMT, NPNT, NR1H4, OPN3, OSMR, PCOLCE2, PCP4, PDE8B, PDZK1IP1, PIGA, PKHD1L1, POSTN, PREPL, PTHLH, RPS6KA6, S100A10, SAA1, SAA2, SCD, SLC16A1, SLC16A4, SLC17A3, SLC26A4, SLC26A7, SLC3A1, SLCO4C1, SNX10, SOD2, SPINK1, SPP1, SYT14, TBCKL, TCEAL2, TCEAL4, TG, TMEM161B, TMEM176A, TMEM45A, TNFAIP6, TNFSF10, TPO, TSHR, UGT1A1, UGT1A10, UGT1A3, UGT1A4, UGT1A5, UGT1A6, UGT1A7, UGT1A8, UGT1A9, UGT2A3, UGT2B7, VCAM1, VCAN, ZNF208, ZNF43, ZNF676, ZNF728, ZNF99 |
| Breast Carcinoma Metastasis to Thyroid | 117 | TCID-3777770, ACADL, AGR2, AGR3, ALDH1A1, ANLN, ASPM, ATP13A4, AZGP1, BIRC5, BRIP1, C10orf81, C7orf62, C8orf79, CA2, CCNB2, CCNE2, CDC2, CDC6, CDKN3, CENPF, CHEK1, CP, CSNK1G1, DEPDC1, DIO1, DIO2, DLGAP5, DTL, EHF, EPR1, EZH2, FAM111B, FANCI, GALNT5, GPX3, HHEX, HPS3, IQCA1, ITGB3, IYD, KCNJ15, KCNJ16, KIAA0101, KIF23, LMO3, LOC100129258, LOC100130518, LOC100131821, LOC145694, LRP2, LRRC2, LRRC69, MAPK6, MELK, MGAT4C, MKI67, MND1, MUC15, MYB, NDC80, NPY1R, NUF2, NUSAP1, PAR1, PARP8, PBK, PCP4, PDE1A, PDE8B, PI15, PIP, PKHD1L1, POLG, PPARGC1A, PRC1, PVRL2, PVRL3, RAD51AP1, RGN, RPL3, RRM2, SAA1, SAA2, SCD, SCGB1D2, SCGB2A2, SEMA3C, SERPINA3, SLA, SLC26A4, SLC26A7, SNRPN, SPC25, ST3GAL5, STK33, SULT1C2, SYCP2, SYT14, TFF1, TG, THBS1, TOP2A, TPO, TPX2, TRPS1, TSHR, TTK, UNQ353, VTCN1, WDR72, ZBED2, ZNF208, ZNF43, ZNF676, ZNF728, ZNF99 |
| B cell Lymphoma Metastasis to Thyroid | 160 | ACADL, AIM2, ALDH1A1, ALG9, APP, ARHGAP29, ATP13A4, ATP1B1, BCL2A1, BIRC3, BIRC5, BTG3, C11orf74, C2orf40, C7orf62, CALCRL, CALD1, CD180, CD24, CD48, CD52, CD53, CDH1, CNN3, COX11, CP, CPE, CR2, CRYAB, CXADR, CXADRP2, CXorf65, DCBLD2, DIO2, DLGAP5, DSP, EAF2, EFCAB2, ENPP1, EPCAM, EPR1, ESRP1, FABP4, FDXACB1, FNBP1L, GJA1, GNAI1, GNG12, GPR174, GPX3, GTSF1, HCG11, IKZF3, IL2RG, IQCA1, IYD, KCNJ16, KLHL6, LAPTM5, LCP1, LIFR, LMO3, LOC100128219, LOC100129258, LOC100130518, LOC100131821, LOC100131938, LOC647979, LOC729828, LPCAT2, LPHN2, LRIG3, LRMP, LRP2, LRRC6, LRRC69, MAL2, MAOA, MAPK6, MATN2, MCOLN2, MGC9913, MGP, MKI67, MS4A1, MT1F, MT1G, MT1H, MT1L, MT1P2, MUC15, NCKAP1, NCKAP1L, NEBL, NME5, NPNT, NUDT12, PAR1, PBX1, PCP4, PDE8B, PDK4, PERP, PFN2, PKHD1L1, PLOD2, PLS3, POMGNT1, PPARGC1A, PPIC, PTPRC, PTPRM, PVRL3, RASEF, RGN, RGS13, RGS5, RHOH, RPL3, RPL37AP8, RRM2, S100A1, S100A13, SDC2, SELL, SEMA3D, SH3BGRL2, SLC26A4, SLC26A7, SMARCA1, SNRPN, SP140, SP140L, SPARCL1, SPC25, SPTLC3, ST20, STK17B, SYT14, TBCKL, TCEAL2, TCEAL4, TEAD1, TG, TJP1, TLR10, TOM1L1, TOP2A, TSHR, TSPAN1, TSPAN6, UACA, VNN2, WBP5, WDR72, ZNF208, ZNF43, ZNF676, ZNF728, ZNF99 |

(viii) Classification Error Rates

In some embodiments, top thyroid biomarkers (948 genes) are subdivided into bins (50 TCIDs per bin) to demonstrate the minimum number of genes required to achieve an overall classification error rate of less than 4% (FIG. 1). The original TCIDs used for classification correspond to the Affymetrix Human Exon 1.0ST microarray chip and each may map to more than one gene or no genes at all (Affymetrix annotation file: HuEx-1_0-st-v2.na29.hg18.transcript.csv). When no genes map to a TCID the biomarker is denoted as TCID-######.

List 27: Error Rate Bin 1 (TCID 1-50 (n=50), gene symbols, n=58)

AMIGO2, C11orf72, C11orf80, C6orf174, CAMK2N1, CDH3, CITED1, CLDN1, CLDN16, CST6, CXorf27, DLC1, EMP2, ERBB3, FZD4, GABRB2, GOLT1A, HEY2, HMGA2, IGFBP6, ITGA2, KCNQ3, KIAA0408, KRT19, LIPH, LOC100129115, MACC1, MDK, MET, METTL7B, MFGE8, MPZL2, NAB2, NOD1, NRCAM, PDE5A, PDLIM4, PHYHIP, PLAG1, PLCD3, PRICKLE1, PROS1, PRR15, PRSS23, PTPRF, QTRT1, RCE1, RDH5, ROS1, RXRG, SDC4, SLC27A6, SLC34A2, SYTL5, TNFRSF12A, TRPC5, TUSC3, ZCCHC12.

List 28: Error Rate Bin 2 (TCID 51-100 (n=50), gene symbols, n=59)

AHNAK2, AIDA, AMOT, ARMCX3, BCL9, C1orf115, C1orf116, C4A, C4B, C6orf168, CCDC121, CCND1, CDH6, CFI, CLDN10, CLU, CRABP2, CXCL14, DOCK9, DZIP1, EDNRB, EHD2, ENDOD1, EPHA4, EPS8, ETNK2, FAM176A, FLJ42258, HPN, ITGA3, ITGB8, KCNK5, KLK10, LAMB3, LEMD1, LOC100129112, LOC100132338, L00554202, MAFG, MAMLD1, MED13, MYH10, NELL2, PCNXL2, PDE9A, PLEKHA4, RAB34, RARG, SCG5, SFTPB, SLC35F2, SLIT2, TACSTD2, TGFA, TIMP1, TMEM100, TMPRSS4, TNC, ZCCHC16.

List 29: Error Rate Bin 3 (TCID 101-150 (n=50), gene symbols, n=52)

ABTB2, ADAMTS9, ADORA1, B3GNT3, BMP1, C19orf33, C3, CDH11, CLIP3, COL1A1, CXCL17, CYSLTR2, DAPK2, DHRS3, DIRAS3, DPYSL3, DUSP4, ECE1, FBXO2, FGF2, FN1, GALE, GPRC5B, GSN, IKZF4, IQGAP2, ITGB4, KIAA0284, KLF8, KLK7, LONRF2, LPAR5, MPPED2, MUC1, NRIP1, NUDT6, ODZ1, PAM, POU2F3, PPL, PTRF, RAPGEF5, RASD2, SCARA3, SCEL, SEMA4C, SNX22, SPRY1, SSPN, TM4SF4, XPR1, YIF1B.

List 30: Error Rate Bin 4 (TCID 151-200 (n=50), gene symbols, n=58)

AFAP1, ARMCX6, ARNTL, ASAP2, C2, C8orf4, CCDC148, CFB, CHAF1B, CLDN4, DLG4, DUSP6, ELMO1, FAAH2, FAM20A, FLRT3, FRMD3, GALNT12, GALNT7, IGFBP5, IKZF2, ISYNA1, LOC100131490, LOC648149, LOC653354, LRP1B, MAP2, MRC2, MT1F, MT1G, MT1H, MT1P2, MYEF2, NPAS3, PARD6B, PCDH1, PMEPA1, PPAP2C, PSD3, PTPRK, PTPRU, RAI2, RRAS, SDK1, SERPINA1, SERPINA2, SGMS2, SLC24A5, SMURF2, SPATS2L, SPINT1, TDRKH, TIPARP, TM4SF1, TMEM98, WNT5A, XKRX, ZMAT4.

List 31: Error Rate Bin 5 (TCID 201-250 (n=50), gene symbols, n=53)

ABCC3, AEBP1, C16orf45, C19orf33, CA11, CCND2, CDO1, CYP4B1, DOK4, DUSP5, ETV4, FAM111A, FN1, GABBR2, GGCT, GJA4, GPR110, HIPK2, ITGA9, JUB, KDELR3, KIAA1217, LAMC2, LCA5, LTBP2, LTBP3, MAPK6, NAV2, NIPAL3, OSMR, PDZRN4, PHLDB2, PIAS3, PKHD1L1, PKP2, PKP4, PRINS, PTK7, PTPRG, RAB27A, RAD23B, RASA1, RICH2, SCRN1, SFN, ST3GAL5, STK32A, TCERG1L, THSD4, TJP2, TM7SF4, TPO, YIF1B.

IX. Compositions (i) Gene Expression Products and Splice Variants of the Present Invention Molecular profiling may also include but is not limited to assays of the present disclosure including assays for one or more of the following: proteins, protein expression products, DNA, DNA polymorphisms, RNA, RNA expression products, RNA expression product levels, or RNA expression product splice variants of the genes provided in FIG. 2-6, 9-13, 16 or 17. In some cases, the methods of the present invention provide for improved cancer diagnostics by molecular profiling of about 1, 2, 3, 4, 5, 6, 7, 8, 9, 10, 15, 20, 25, 30, 35, 40, 45, 50, 60, 70, 80, 90, 100, 120, 140, 160, 180, 200, 240, 280, 300, 350, 400, 450, 500, 600, 700, 800, 1000, 1500, 2000, 2500, 3000, 3500, 4000, 5000 or more DNA polymorphisms, expression product markers, and/or alternative splice variant markers.

In one embodiment, molecular profiling involves microarray hybridization that is performed to determine gene expression product levels for one or more genes selected from: FIG. 2-6, 9-13, 16 or 17. In some cases, gene expression product levels of one or more genes from one group are compared to gene expression product levels of one or more genes in another group or groups. As an example only and without limitation, the expression level of gene TPO may be compared to the expression level of gene GAPDH. In another embodiment, gene expression levels are determined for one or more genes involved in one or more of the following metabolic or signaling pathways: thyroid hormone production and/or release, protein kinase signaling pathways, lipid kinase signaling pathways, and cyclins. In some cases, the methods of the present invention provide for analysis of gene expression product levels and or alternative exon usage of at least one gene of 1, 2, 3, 4, 5, 6, 7, 9, 10, 11, 12, 13, 14, or 15 or more different metabolic or signaling pathways.

(ii) Compositions of the Present Invention

Compositions of the present disclosure are also provided which composition comprises one or more of the following: nucleotides (e.g. DNA or RNA) corresponding to the genes or a portion of the genes provided in FIG. 2-6, 9-13, 16 or 17, and nucleotides (e.g. DNA or RNA) corresponding to the complement of the genes or a portion of the complement of the genes provided in FIG. 2-6, 9-13, 16 or 17. The nucleotides of the present invention can be at least about 10, 15, 20, 25, 30, 35, 40, 45, 50, 55, 60, 65, 70, 75, 100, 150, 200, 250, 300, 350, or about 400 or 500 nucleotides in length. In some embodiments of the present invention, the nucleotides can be natural or man-made derivatives of ribonucleic acid or deoxyribonucleic acid including but not limited to peptide nucleic acids, pyranosyl RNA, nucleosides, methylated nucleic acid, pegylated nucleic acid, cyclic nucleotides, and chemically modified nucleotides. In some of the compositions of the present invention, nucleotides of the present invention have been chemically modified to include a detectable label. In some embodiments of the present invention the biological sample has been chemically modified to include a label.

A further composition of the present disclosure comprises oligonucleotides for detecting (i.e. measuring) the expression products of the genes provided in FIG. 2-6, 9-13, 16 or 17 and their complement. A further composition of the present disclosure comprises oligonucleotides for detecting (i.e. measuring) the expression products of polymorphic alleles of the genes provided in FIG. 2-6, 9-13, 16 or 17 and their complement. Such polymorphic alleles include but are not limited to splice site variants, single nucleotide polymorphisms, variable number repeat polymorphisms, insertions, deletions, and homologues. In some cases, the variant alleles are between about 99.9% and about 70% identical to the genes listed in FIG. 6, including about 99.75%, 99.5%, 99.25%, 99%, 97.5%, 95%, 92.5%, 90%, 85%, 80%, 75%, and about 70% identical. In some cases, the variant alleles differ by between about 1 nucleotide and about 500 nucleotides from the genes provided in FIG. 2-6, 9-13, 16 or 17, including about 1, 2, 3, 5, 7, 10, 15, 20, 25, 30, 35, 50, 75, 100, 150, 200, 250, 300, and about 400 nucleotides.

In some embodiments, the composition of the present invention may be specifically selected from the top differentially expressed gene products between benign and malignant samples, or the top differentially spliced gene products between benign and malignant samples, or the top differentially expressed gene products between normal and benign or malignant samples, or the top differentially spliced gene products between normal and benign or malignant samples. In some cases the top differentially expressed gene products may be selected from FIG. 2 and/or FIG. 4. In some cases, the top differentially spliced gene products may be selected from FIG. 3 and/or FIG. 5.

IX. Business Methods

As described herein, the term customer or potential customer refers to individuals or entities that may utilize methods or services of the molecular profiling business. Potential customers for the molecular profiling methods and services described herein include for example, patients, subjects, physicians, cytological labs, health care providers, researchers, insurance companies, government entities such as Medicaid, employers, or any other entity interested in achieving more economical or effective system for diagnosing, monitoring and treating cancer.

Such parties can utilize the molecular profiling results, for example, to selectively indicate expensive drugs or therapeutic interventions to patients likely to benefit the most from said drugs or interventions, or to identify individuals who would not benefit or may be harmed by the unnecessary use of drugs or other therapeutic interventions.

(i) Methods of Marketing

The services of the molecular profiling business of the present invention may be marketed to individuals concerned about their health, physicians or other medical professionals, for example as a method of enhancing diagnosis and care; cytological labs, for example as a service for providing enhanced diagnosis to a client; health care providers, insurance companies, and government entities, for example as a method for reducing costs by eliminating unwarranted therapeutic interventions. Methods of marketing to potential clients, further includes marketing of database access for researchers and physicians seeking to find new correlations between gene expression products and diseases or conditions.

The methods of marketing may include the use of print, radio, television, or internet based advertisement to potential customers. Potential customers may be marketed to through specific media, for example, endocrinologists may be marketed to by placing advertisements in trade magazines and medical journals including but not limited to *The Journal of the American Medical Association, Physicians Practice, American Medical News, Consultant, Medical Economics, Physician's Money Digest, American Family Physician, Monthly Prescribing Reference, Physicians' Travel and Meeting Guide, Patient Care, Cortlandt Forum, Internal Medicine News, Hospital Physician, Family Practice Management, Internal Medicine World Report, Women's Health in Primary Care, Family Practice News, Physician's Weekly, Health Monitor, The Endocrinologist, Journal of Endocrinology, The Open Endocrinology Journal,* and *The Journal of Molecular Endocrinology*. Marketing may also take the form of collaborating with a medical professional to perform experiments using the methods and services of the present invention and in some cases publish the results or seek funding for further research. In some cases, methods of marketing may include the use of physician or medical professional databases such as, for example, the American Medical Association (AMA) database, to determine contact information.

In one embodiment methods of marketing comprises collaborating with cytological testing laboratories to offer a molecular profiling service to customers whose samples cannot be unambiguously diagnosed using routine methods.

(ii) Business Methods Utilizing a Computer

The molecular profiling business may utilize one or more computers in the methods of the present invention such as a computer 800 as illustrated in FIG. 22. The computer 800 may be used for managing customer and sample information such as sample or customer tracking, database management, analyzing molecular profiling data, analyzing cytological data, storing data, billing, marketing, reporting results, or storing results. The computer may include a monitor 807 or other graphical interface for displaying data, results, billing information, marketing information (e.g. demographics), customer information, or sample information. The computer may also include means for data or information input 816, 815. The computer may include a processing unit 801 and fixed 803 or removable 811 media or a combination thereof. The computer may be accessed by a user in physical proximity to the computer, for example via a keyboard and/or mouse, or by a user 822 that does not necessarily have access to the physical computer through a communication medium 805 such as a modem, an internet connection, a telephone connection, or a wired or wireless communication signal carrier wave. In some cases, the computer may be connected to a server 809 or other communication device for relaying information from a user to the computer or from the computer to a user. In some cases, the user may store data or information obtained from the computer through a communication medium 805 on media, such as removable media 812. It is envisioned that data relating to the present invention can be transmitted over such networks or connections for reception and/or review by a party. The receiving party can be but is not limited to an individual, a health care provider or a health care manager. In one embodiment, a computer-readable medium includes a medium suitable for transmission of a result of an analysis of a biological sample, such as exosome bio-signatures. The medium can include a result regarding an exosome bio-signature of a subject, wherein such a result is derived using the methods described herein.

The molecular profiling business may enter sample information into a database for the purpose of one or more of the following: inventory tracking, assay result tracking, order tracking, customer management, customer service, billing, and sales. Sample information may include, but is not limited to: customer name, unique customer identification, customer associated medical professional, indicated assay or assays, assay results, adequacy status, indicated adequacy tests, medical history of the individual, preliminary diagnosis, suspected diagnosis, sample history, insurance provider, medical provider, third party testing center or any information suitable for storage in a database. Sample history may include but is not limited to: age of the sample, type of sample, method of acquisition, method of storage, or method of transport.

The database may be accessible by a customer, medical professional, insurance provider, third party, or any individual or entity which the molecular profiling business grants access. Database access may take the form of electronic communication such as a computer or telephone. The database may be accessed through an intermediary such as a customer service representative, business representative, consultant, independent testing center, or medical professional. The availability or degree of database access or sample information, such as assay results, may change upon payment of a fee for products and services rendered or to be rendered. The degree of database access or sample information may be restricted to comply with generally accepted or legal requirements for patient or customer confidentiality. The molecular profiling company may bill the individual, insurance provider, medical provider, or government entity for one or more of the following: sample receipt, sample storage, sample preparation, cytological testing, molecular profiling, input and update of sample information into the database, or database access.

(iii) Business Flow

Figure 21:
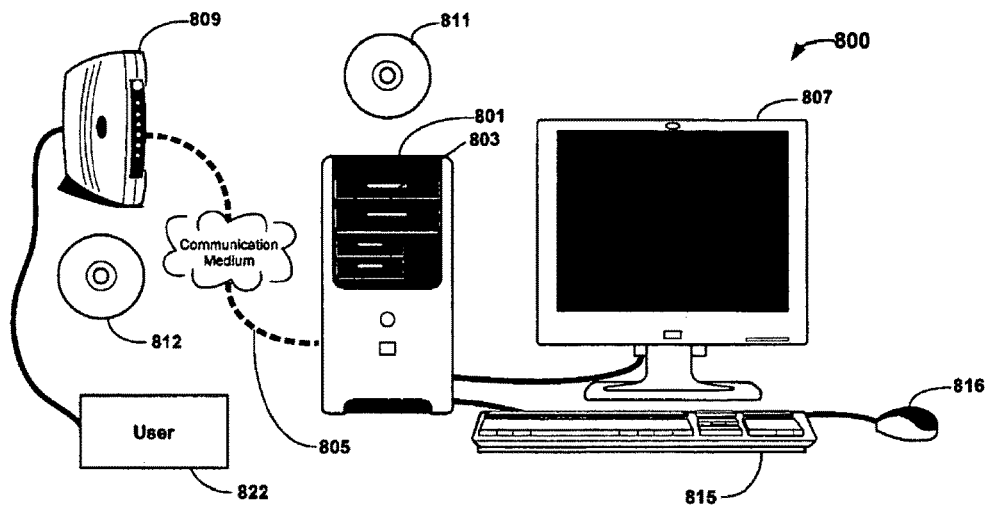
FIG. 21 depicts a computer useful for displaying, storing, retrieving, or calculating diagnostic results from the molecular profiling; displaying, storing, retrieving, or calculating raw data from genomic or nucleic acid expression analysis; or displaying, storing, retrieving, or calculating any sample or customer information useful in the methods of the present invention.

FIG. 18a is a flow chart illustrating one way in which samples might be processed by the molecular profiling business. Samples of thyroid cells, for example, may be obtained by an endocrinologist perhaps via fine needle aspiration 100. Samples are subjected to routine cytological staining procedures 125. Said routine cytological staining provides four different possible preliminary diagnoses non-diagnostic 105, benign 110, ambiguous or suspicious 115, or malignant 120. The molecular profiling business may then analyze gene expression product levels as described herein 130. Said analysis of gene expression product levels, molecular profiling, may lead to a definitive diagnosis of malignant 140 or benign 135. In some cases only a subset of samples are analyzed by molecular profiling such as those that provide ambiguous and non-diagnostic results during routine cytological examination. Alternative embodiments by which samples may be processed by the methods of the present invention are provided in FIGS. 18b and 21.

In some cases the molecular profiling results confirms the routine cytological test results. In other cases, the molecular profiling results differ. In such cases, samples may be further tested, data may be reexamined, or the molecular profiling results or cytological assay results may be taken as the correct diagnosis. Benign diagnoses may also include diseases or conditions that, while not malignant cancer, may indicate further monitoring or treatment. Similarly, malignant diagnoses may further include diagnosis of the specific type of cancer or a specific metabolic or signaling pathway involved in the disease or condition. Said diagnoses, may indicate a treatment or therapeutic intervention such as radioactive iodine ablation, surgery, thyroidectomy; or further monitoring.

XI. Kits

Figure 19:
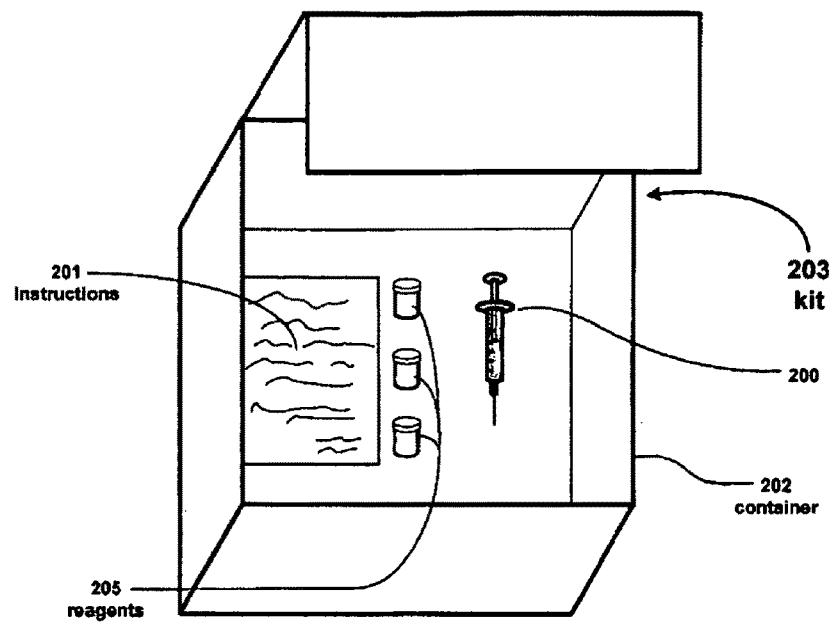
FIG. 19 is an illustration of a kit provided by the molecular profiling business.

The molecular profiling business may provide a kit for obtaining a suitable sample. Said kit 203 as depicted in FIG. 19 may comprise a container 202, a means for obtaining a sample 200, reagents for storing the sample 205, and instructions for use of said kit. In another embodiment, the kit further comprises reagents and materials for performing the molecular profiling analysis. In some cases, the reagents and materials include a computer program for analyzing the data generated by the molecular profiling methods. In still other cases, the kit contains a means by which the biological sample is stored and transported to a testing facility such as the molecular profiling business or a third party testing center.

The molecular profiling business may also provide a kit for performing molecular profiling. Said kit may comprise a means for extracting protein or nucleic acids including all necessary buffers and reagents; and, a means for analyzing levels of protein or nucleic acids including controls, and reagents. The kit may further comprise software or a license to obtain and use software for analysis of the data provided using the methods and compositions of the present invention.

EXAMPLES

Example 1: Gene Expression Product Analysis of Thyroid Samples 75 thyroid samples were examined for gene expression analysis using the Affymetrix Human Exon 10ST array according to manufacturer's instructions to identify genes that showed significantly differential expression and/or alternative splicing between malignant, benign, and normal samples. Three groups were compared and classified according to pathological surgical diagnosis of the tissue: benign (n=29), malignant (n=37), and normal (n=9). The samples were prepared from surgical thyroid tissue, snap frozen and then the RNA was prepared by standard methods. The names and pathological classification of the 75 samples are depicted in FIG. 1.

Microarray analysis was run with XRAY version 2.69 (Biotique Systems Inc.). Input files were normalized with full quantile normalization (Irizarry et al. *Biostatistics* 2003 Apr. 4 (2): 249-64). For each input array and each probe expression value, the array -ith percentile probe value was replaced with the average of all array -ith percentile points. A total of 6,553,590 probes were manipulated in the analysis. Probes with GC count less than 6 and greater than 17 were excluded from the analysis. The expression score for each probe-set was derived via application of median-polish (exon RMA) to the probe scores across all input hybridizations and probe-sets with fewer than 3 probes (that pass all of the tests defined above) were excluded from further analysis. Only 'Core' probe-sets, corresponding to probe-sets matching entries in the high quality databases RefSeq and Ensembl, were analyzed. Non-expressed probes and invariant probes were also removed from analysis for both gene level and probe set level analyses. One-way ANOVA analysis was used to examine gene expression at the probe set level between groups malignant and benign.

The top 100 differentially expressed genes by gene level analysis (i.e. those genes which showed the greatest differential expression) were obtained from the dataset in which benign malignant and normal thyroid samples were compared. Markers were selected based on statistical significance after Benjamini and Hochberg correction for false discover rate (FDR). An FDR filter value of $p<0.01$ was used, followed by ranking with absolute fold change $(>1.9)$ calculated per maker as the highest differential gene expression value in any group (benign malignant or normal) divided by the lowest differential expression in the remaining two groups. The results of this analysis are shown in FIG. 2. This table lists three sets of calculated fold changes for any given marker to allow comparison between the groups. The fold changes malignant/benign, malignant/normal, and benign/normal were all calculated by dividing the expression of one group by the expression of another.

The top 100 alternatively spliced genes were obtained from the dataset in which benign malignant and normal thyroid samples were compared. Markers were selected based on statistical significance after Benjamini and Hochberg correction for false discovery rate (FDR). An FDR filter value of p<0.01 was used, and markers were ranked starting with lowest p-value. The threshold for listing a numerical value with the software used was p<1.0E-301, any numbers having a smaller p-value were automatically assigned a value of 0.00E+00. The results of this analysis are shown in FIG. 3. All the markers depicted are highly significant for alternative exon splicing.

The top 100 differentially expressed genes in the thyroid samples from FIG. 1 by probe-set level analysis were obtained from the dataset in which benign and malignant samples were analyzed. Markers were selected based on significance after Benjamini and Hochberg correction for false discovery rate (FDR). Markers were selected based on significance after Benjamini and Hochberg correction for false discovery rate (FDR). An FDR filter value of p<0.01 was used, followed by ranking with absolute fold-change (>2.0) calculated per marker as Malignant expression divided by Benign expression. The results of this analysis are shown in FIG. 4.

The top 100 statistically significant diagnostic markers determined by gene level analysis of the thyroid samples shown in FIG. 1 were also compiled. Data from the comparison between benign, malignant, and normal and from comparison between benign and malignant datasets were used. Markers were selected based on significance after Benjamini and Hochberg correction for false discovery rate (FDR). An FDR filter value of p<0.01 was used, followed by ranking with absolute fold-change (>1.6) calculated per marker as the highest differential expression value in any group (benign, malignant or normal) divided by the lowest differential expression in the remaining two groups. The fold-changes for Malignant/Benign, Malignant/Normal, and Benign/Normal were all calculated in similar fashion by dividing the expression of one group by the expression of another. The results of this analysis are shown in FIG. 5.

The full list of 4918 genes identified as statistically significantly differentially expressed, differentially spliced or both between benign and malignant, benign and normal, or malignant and normal samples at either the probe-set or gene level was also compiled. Markers were selected based on statistical significance after Benjamini and Hochberg correction for false discovery rate (FDR), and an FDR filter value of p<0.01 was used. The results are depicted in FIG. 6.

Example 2: Gene Expression Product Analysis of Thyroid Tissue Samples

A total of 205 thyroid tissue samples (FIG. 7) are examined with an Affymetrix HumanExon10ST array chip to identify genes that differ significantly in RNA expression levels between benign and malignant samples. Samples are classified according to post-surgical thyroid pathology: samples exhibiting follicular adenoma (FA), lymphocytic thyroiditis (LCT), or nodular hyperplasia (NHP) are classified as benign; samples exhibiting Hurthle cell carcinoma (HC), follicular carcinoma (FC), follicular variant of papillary thyroid carcinoma (FVPTC), papillary thyroid carcinoma (PTC), medullary thyroid carcinoma (MTC), or anaplastic carcinoma (ATC) are classified as malignant.

Affymetrix software is used to extract, normalize, and summarize intensity data from roughly 6.5 million probes. Approximately 280,000 core probe sets are subsequently used in feature selection and classification. The models used are LIMMA for feature selection and random forest and support vector machine (SVM) for classification. Iterative rounds of training, classification, and cross validation are performed using random subsets of data. Top features are identified in two separate analyses (malignant vs. benign and MTC vs. rest) using the classification engine described above.

Markers are selected based on significance after Benjamini and Hochberg correction for false data discovery rate (FDR). An FDR filter of p<0.05 is used.

A malignant vs. benign comparison of thyroid tissue samples finds 413 markers that are diagnostic for thyroid diseases or conditions. The top 100 markers are listed in FIG. 9.

An MTC vs. the rest (i.e. non-MTC) comparison of thyroid tissue samples finds 671 markers that are diagnostic for thyroid diseases or conditions. The top 100 markers are listed in FIG. 10.

Example 3: Meta-analysis of Gene Expression Product Data from Thyroid Samples

Surgical thyroid tissue samples (FIG. 7) and thyroid samples obtained via fine needle aspiration (FIG. 8) are identified as benign or malignant by pathological examination and then examined by hybridization to an Affymetrix HumanExon10ST array. A meta-analysis approach is utilized which allows the identification of genes with repeatable features in each classification. Affymetrix software is used to extract, normalize, and summarize intensity data from approximately 6.5 million probes. Roughly 280,000 probe sets are used for feature selection and classification. LIMMA is used for feature selection. Classification is performed with random forest and SVM methods. Markers that repeatedly appear in multiple iterative rounds of training, classification, and cross validation of the surgical and fine needle aspirate samples are identified and ranked. A joint set of core features are created using the top ranked features that appear for both the surgical and fine needle aspirate data. Markers with a non-zero repeatability score are selected as significant. A total of 102 markers are found to be significant and are listed in FIG. 11.

Example 4: Bayesian Analysis of Gene Expression Product Data from Thyroid Samples Two groups of well-characterized samples are compared in order to identify genes that distinguish benign from malignant nodules in the human thyroid. Samples are derived from surgical thyroid tissue (tissue; n=205, FIG. 7) or from fine needle aspirates (FNA; n=74, FIG. 8) and are examined by hybridization to the HumanExon10ST microarray. Pathology labels for each distinct thyroid subtype are coded as either benign (B) or malignant (M). A total of 499 markers that show distinct differential expression between benign and malignant samples are identified.

Affymetrix software is used to extract, normalize, and summarize intensity data from approximately 6.5 million probes. Roughly 280,000 core probe sets are subsequently used in feature selection and classification of ~22,000 genes. The models used are LIMMA (for feature selection) and SVM (for classification) respectively.

Next, we previously published molecular profile studies are examined in order to derive the type I and type II error rates of assigning a gene into the "benign" or "malignant" category. The error rates are calculated based on the sample size reported in each particular published study with an estimated fold-change value of two. Lastly, these prior probabilities are combined with the output of the Tissue dataset to estimate the posterior probability of differential gene expression, and then combined with the FNA dataset to formulate the final posterior probabilities of differential expression (Smyth 2004). These posterior probabilities are used to rank the genes and those that exceed a posterior probability threshold of 0.9 are selected. A total of 499 markers are identified as significant and the top 100 are listed in FIG. 12.

Example 5: Subtype Analysis of Gene Expression Product Data from Thyroid Samples Well-characterized samples are examined in order to distinguish benign nodules from those with distinct pathology in the human thyroid. 205 hybridizations to the HumanExon10ST microarray are examined. Pathology labels for each distinct thyroid subtype are used to systematically compare one group versus another. A total of 250 mRNA markers that separate thyroid into a wide range of pathology subtypes are identified.

A total of 205 thyroid tissue samples are examined with the Affymetrix HumanExon10ST array chip to identify genes that differ significantly in mRNA expression between distinct thyroid pathology subtypes (FIG. 7). Samples classified according to post-surgical thyroid pathology as: follicular adenoma (FA, n=22), lymphocytic thyroiditis (LCT, n=39), nodular hyperplasia (NHP, n=24)), are all collectively classified as benign (n=85). In contrast, samples classified as Hurthle cell carcinoma (HC, n=27), follicular carcinoma (FC, n=19), follicular variant of papillary thyroid carcinoma (FVPTC, n=21), papillary thyroid carcinoma (PTC, n=26), medullary thyroid carcinoma (MTC, n=22), and anaplastic carcinoma (ATC, n=5) are all collectively classified as malignant (n=120).

Affymetrix software is used to extract, normalize, and summarize intensity data from roughly 6.5 million probes. Approximately 280,000 core probe sets are subsequently used in feature selection and classification. A given benign subtype (e.g., NHP) set is compared against a pool of all other malignant subtypes (e.g., NHP vs. M) next the benign subset is compared again against each set of malignant subtypes (NHP vs. FC, NHP vs. PTC, etc). The models used in the classification engine are LIMMA (for feature selection), and random forest and SVM are used for classification. Iterative rounds of training, classification, and cross-validation are performed using random subsets of data. A joint core-set of genes that separate distinct thyroid subtypes is created.

Markers are selected based on the set of genes that optimizes the classifier after pair-wise classification. A total of 251 markers mapping to 250 distinct genes allow the separation of 1-3 distinct thyroid subtypes (FIG. 13).

Example 6: Differentially Expressed miRNAs Identified Via the Agilent Vs microRNA Array Thyroid samples are hybridized to the Agilent Human v2 microRNA (miRNA) array. This array contains probes to 723 human and 76 viral miRNAs, and these are targeted using ~15,000 probesets. A comparison between benign (B) and malignant (M) thyroid samples is performed to identify significant differentially expressed miRNAs. All samples are derived from clinical fine needle aspirates (n=89, FIG. 14).

Array intensity data is extracted, normalized, and summarized, followed by modeling using classification engine. Briefly, the models used are LIMMA (for feature selection), and random forest and support vector machine (SVM) are used for classification. Iterative rounds of training, classification, and cross-validation are performed using random subsets of data. Although several miRNAs are differentially expressed in malignant as compared to benign (FIG. 16), no stand-alone classifiers were identified with this approach.

Example 7 Differentially Expressed miRNAs that are Diagnostic for Thyroid Diseases Thyroid nodule samples are hybridized to the Illumina Human v2 miRNA array. This array contains probes to 1146 human miRNAs. A comparison between benign and malignant thyroid samples is performed to identify significant differentially expressed miRNAs. All samples are derived from clinical FNAs (n=24, FIG. 15).

Array intensity data is extracted, normalized, and summarized, followed by modeling using a classification engine. Briefly, the models used are LIMMA (for feature selection), and random forest, and support vector machine (SVM) for classification. An additional "hot probes" method is added to the classification engine, which in part incorporates a meta-analysis approach to the algorithm. Iterative rounds of training, classification, and cross-validation are performed using random subsets of data. The "hot probes" method identifies probes that appear in every loop of cross-validation, thereby creating a set of robust, repeatable features. Markers are selected based on the p-value (P) of a comparison between malignant and benign samples. A total of 145 miRNAs are identified whose differential expression is identified as diagnostic for benign or malignant thyroid conditions (FIG. 17).

Example 8: An Exemplary Device for Molecular Profiling

The molecular profiling business of the present invention compiles the list of 4918 genes of FIG. 6 that are differentially expressed, differentially spliced or both between benign and malignant, benign and normal, or malignant and normal samples at either the probe-set or the gene level. A subset of the 4918 genes are chosen for use in the diagnosis of biological samples by the molecular profiling business. Compositions of short (i.e. 12-25 nucleotide long) oligonucleotides complimentary to the subset of 4918 genes chose for use by the molecular profiling business are synthesized by standard methods known in the art and immobilized on a solid support such as nitrocellulose, glass, a polymer, or a chip at known positions on the solid support.

Example 9: Molecular Profiling of a Biological Sample

A biological sample is obtained by fine needle aspiration and stored in two aliquots, one for molecular profiling and one for cytological analysis. The aliquot of biological sample for molecular profiling is added to lysis buffer and triturated which results in lysing of the cells of the biological sample. Lysis buffer is prepared as follows: For 1 ml of cDNA lysis buffer, the following were mixed together on ice: 0.2 ml of Moloney murine leukemia virus (MMLV)

reverse transcriptase, 5× (Gibco-BRL), 0.76 ml of H20 (RNAse, DNAse free, Specialty Media), 5 µl of Nonidet P40 (USB), 10 µl of PrimeRNase inhibitor (3'5' Incorporated), 10 µl of RNAguard (Pharmacia), and 20 µl of freshly made, 1/24 dilution of stock primer mix. The stock primer mix, kept aliquoted at −20° C., includes 10 µl each of 100 mM dATP, dCTP, dGTP, dTTP solutions (12.5 mM final)(Boehringer); 10 µl of 50 OD/ml pd(T)19-24 (Pharmacia); and 30 µl H20.

Cell RNA is then primed with an oligo dT primer. Reverse transcription with reverse transcriptase is then performed in limiting conditions of time and reagents to facilitate incomplete extension and to prepare short cDNA of between about 500 bp to about 1000 bp. The cDNA is then tailed at the 5' end with multiple dATP using polyA (dATP) and terminal transferase.

The cDNA is then amplified with PCR reagents using a 60mer primer having 24(dT) at the 3' end. PCR cycling is performed at 94° C. for 1 minute, then 42° C. for 2 minutes and then 72° C. for 6 minutes with 10 second extension times at each cycle. 10 cycles are performed. Then additional Taq polymerase is added and an additional 25 cycles are performed.

cDNA is extracted in phenol-chloroform, precipitated with ethanol and then half of the sample is frozen at −80° C. as a stock to avoid thawing and freezing the entire amount of cDNA while analyzing it.

5 µg of PCR product is combined with 15.5µ 1 EF sln (Tris in Qiagen kit PCR purification), 4µ 1 of lox One-Phor-All buffer from Promega, and 0.5 units of DNase I. The total volume is then held at 37° C. for 14 minutes, then held at 99° C. for 15 minutes and then put on ice for 5 minutes to fragment the PCR product into segments about 50 bp to about 100 bp in length. The fragments are then end-labeled by combining the total volume with 1 µl of Biotin-N6-ddATP ("NEN") and 1.5 µl of TdT (terminal transferase) (15 unit/µl). The total volume is then held at 37° C. for 1 hour, then held at 99° C. for 15 minutes and then held on ice for 5 minutes.

The labeled and fragmented cDNA is hybridized with the probeset of the present invention in 200 microliters of hybridization solution containing 5-10 microgram labeled target in 1×MES buffer (0.1 M MES, 1.0 M NaCl, 0.01% Triton X-100, pH 6.7) and 0.1 mg/ml herring sperm DNA. The arrays used are Affymetrix Human Exon 10ST arrays. The arrays are placed on a rotisserie and rotated at 60 rpm for 16 hours at 45° C. Following hybridization, the arrays are washed with 6×SSPE-T (0.9 M NaCl, 60 mM NaH2P04, 6 mM EDTA, 0.005% Triton X-100, pH 7.6) at 22° C. on a fluidics station (Affymetrix) for 10×2 cycles, and then washed with 0.1 MES at 45° C. for 30 min. The arrays are then stained with a streptavidin-phycoerythrin conjugate (Molecular Probes), followed by 6×SSPE-T wash on the fluidics station for 10×2 cycles again. To enhance the signals, the arrays are further stained with Anti-streptavidin antibody for 30 min followed by a 15 min staining with a streptavidin-phycoerythrin conjugate again. After 6×SSPE-T wash on the fluidics station for 10×2 cycles, the arrays are scanned at a resolution of 3 microns using a modified confocal scanner to determine raw fluorescence intensity values at each position in the array, corresponding to gene expression levels for the sequence at that array position.

The raw fluorescence intensity values are converted to gene expression product levels, normalized via the RMA method, filtered to remove data that may be considered suspect, and input to a pre-classifier algorithm which corrects the gene expression product levels for the cell-type composition of the biological sample. The corrected gene expression product levels are input to a trained algorithm for classifying the biological sample as benign, malignant, or normal. The trained algorithm provides a record of its output including a diagnosis, and a confidence level.

Example 10: Molecular Profiling of Thyroid Nodule

An individual notices a lump on his thyroid. The individual consults his family physician. The family physician decides to obtain a sample from the lump and subject it to molecular profiling analysis. Said physician uses a kit from the molecular profiling business to obtain the sample via fine needle aspiration, perform an adequacy test, store the sample in a liquid based cytology solution, and send it to the molecular profiling business. The molecular profiling business divides the sample for cytological analysis of one part and for the remainder of the sample extracts mRNA from the sample, analyzes the quality and suitability of the mRNA sample extracted, and analyses the expression levels and alternative exon usage of a subset of the genes listed in FIG. 5. In this case, the particular gene expression products profiled is determined by the sample type, by the preliminary diagnosis of the physician, and by the molecular profiling company.

The molecular profiling business analyses the data and provides a resulting diagnosis to the individual's physician as illustrated in FIG. 20. The results provide 1) a list of gene expression products profiled, 2) the results of the profiling (e.g. the expression level normalized to an internal standard such as total mRNA or the expression of a well characterized gene product such as tubulin, 3) the gene product expression level expected for normal tissue of matching type, and 4) a diagnosis and recommended treatment for Bob based on the gene product expression levels. The molecular profiling business bills the individual's insurance provider for products and services rendered.

Example 11: Molecular Profiling as an Adjunct to Cytological Examination

An individual notices a suspicious lump on her thyroid. The individual consults her primary care physician who examines the individual and refers her to an endocrinologist. The endocrinologist obtains a sample via fine needle aspiration, and sends the sample to a cytological testing laboratory. The cytological testing laboratory performs routine cytological testing on a portion of the fine needle aspirate, the results of which are ambiguous (i.e. indeterminate). The cytological testing laboratory suggests to the endocrinologist that the remaining sample may be suitable for molecular profiling, and the endocrinologist agrees.

The remaining sample is analyzed using the methods and compositions herein. The results of the molecular profiling analysis suggest a high probability of early stage follicular cell carcinoma. The results further suggest that molecular profiling analysis combined with patient data including patient age, and lump or nodule size indicates thyroidectomy followed by radioactive iodine ablation. The endocrinologist reviews the results and prescribes the recommended therapy.

The cytological testing laboratory bills the endocrinologist for routine cytological tests and for the molecular profiling. The endocrinologist remits payment to the cytological testing laboratory and bills the individual's insurance provider for all products and services rendered. The cytological testing laboratory passes on payment for molecular profiling to the molecular profiling business and withholds a small differential.

Example 12: Molecular Profiling Performed by a Third Party

An individual complains to her physician about a suspicious lump on her neck. The physician examines the individual, and prescribes a molecular profiling test and a follow up examination pending the results. The individual visits a clinical testing laboratory also known as a CLIA lab. The CLIA lab is licensed to perform molecular profiling of the current invention. The individual provides a sample at the CLIA lab via fine needle aspiration, and the sample is analyzed using the molecular profiling methods and compositions herein. The results of the molecular profiling are electronically communicated to the individual's physician, and the individual is contacted to schedule a follow up examination. The physician presents the results of the molecular profiling to the individual and prescribes a therapy.

Example 13: Overlapping Genes Using Different Analysis Methods

The results described in Example 2 were obtained by examining surgical thyroid nodule tissue samples and comparing gene expression in malignant versus benign ("malignant vs. benign" data set). This analysis identified 412 genes that are differentially expressed (FDR p<0.05). In a previous study described in Example 1, using i) a different cohort of samples and ii) a different analysis method, we describe 4918 genes that can distinguish between malignant and benign thyroid nodules ("4918"). The "malignant vs. benign" tissue discovery dataset shares 231/412 genes with the "4918" discovery dataset, while 181/412 genes have been newly discovered.

A similar comparison between medullary thyroid cancer (MTC) and the "Rest" of the thyroid subtypes using the tissue cohort pointed to 668 significant genes that are differentially expressed between these two groups (FIG. 10). When cross-checked against our previous "4918" gene list, we note that 305/668 genes had been previously described, while 363/668 genes have been newly discovered.

We next combined the surgical tissue dataset with a fine needle aspirate (FNA) dataset and once again compared malignant versus benign using i) a "hot probes" and ii) a "Bayes" approach. Each analysis identified 102 and 498 significant genes, respectively (Tables 11 and 12).

Up until this point a total of 1343 significant genes were identified. However, a subsequent subset analysis aimed at identifying those genes that separate distinct pathology subtypes from one another was also performed. This analysis used the surgical tissue cohort and resulted in 250 significant genes (FIG. 13).

In sum, the five comparisons described here give rise to 1437 significant genes. Of these, 636/1437 genes are described for the first time as distinguishing malignant versus benign thyroid pathology. As of today, 568/636 have not yet been described in published scientific literature or patent applications as diagnostic markers of thyroid cancer.

Example 14: Clinical Thyroid FNA

Methods

Prospective clinical thyroid FNA samples were examined with the Affymetrix Human Exon 1.0ST microarray in order to identify genes that differ significantly in mRNA expression between benign and malignant samples.

Affymetrix software was used to extract, normalize, and summarize intensity data from roughly 6.5 million probes. Approximately 280,000 core probe sets were subsequently used in feature selection and classification. The models used were LIMMA (for feature selection), random forest and SVM were used for classification (Smyth 2004; Diaz-Uriarte and Alvarez de Andres 2006). Iterative rounds of training, classification, and cross-validation were performed using random subsets of data. Top features were identified in three separate analyses using the classification engine described above.

While the annotation and mapping of genes to transcript cluster indentifiers (TCID) is constantly evolving, the nucleotide sequences in the probesets that make up a TCID do not change. Furthermore, a number of significant TCIDs do not map any known genes, yet these are equally important biomarkers in the classification of thyroid malignancy. Results are described using both the TCID and the genes currently mapped to each (Affymetrix annotation file: HuEx-1_0-st-v2.na29.hg18.transcript.csv).

Results

The study of differential gene expression in prospectively collected, clinical thyroid FNA required a number of statistical sub-analyses. These sub-analyses alone resulted in the discovery of genes that are valuable in the classification of thyroid nodules of unknown pathology. However, the joining of the datasets has resulted in the novel characterization of thyroid gene panels, which can correctly classify thyroid FNA with improved accuracy over current cytopathology, and molecular profiling methods.

TABLE 3

Top Benign vs. Malignant Analysis.
This analysis resulted in 175 unique
TCIDs, currently mapping to 198 genes.

| TCID | Gene Symbol (Affy v.na29) | FDR LIMMA p-value | Fold Change |
|---|---|---|---|
| 2884845 | GABRB2 | 2.85E−35 | 3.22 |
| 2400177 | CAMK2N1 | 8.23E−30 | 2.50 |
| 3638204 | MFGE8 | 2.16E−29 | 1.75 |
| 3638204 | QTRT1 | 2.16E−29 | 1.75 |
| 2708855 | C11orf72 | 4.11E−27 | 2.27 |
| 2708855 | LIPH | 4.11E−27 | 2.27 |
| 3415744 | IGFBP6 | 5.44E−27 | 1.81 |
| 3136178 | PLAG1 | 1.64E−26 | 1.76 |
| 2657808 | CLDN16 | 3.63E−26 | 3.01 |
| 3451375 | PRICKLE1 | 3.63E−26 | 1.78 |
| 2442008 | RXRG | 7.62E−26 | 2.17 |
| 3329343 | MDK | 3.60E−24 | 1.34 |
| 3666366 | CDH3 | 3.60E−24 | 1.25 |
| 3757108 | KRT19 | 1.06E−23 | 1.44 |
| 3040518 | MACC1 | 1.14E−23 | 1.73 |
| 3988596 | ZCCHC12 | 2.14E−23 | 2.22 |
| 3416895 | METTL7B | 2.90E−23 | 1.33 |
| 2721959 | ROS1 | 6.26E−23 | 3.05 |
| 2721959 | SLC34A2 | 6.26E−23 | 3.05 |
| 3125116 | DLC1 | 9.12E−23 | 0.82 |
| 2828441 | PDLIM4 | 9.51E−23 | 0.81 |
| 2783596 | PDE5A | 1.60E−22 | 1.93 |
| 3645555 | TNFRSF12A | 1.71E−22 | 1.25 |
| 3973891 | CXorf27 | 1.75E−22 | 1.38 |
| 3973891 | SYTL5 | 1.75E−22 | 1.38 |
| 2827645 | SLC27A6 | 2.02E−22 | 2.28 |
| 3020343 | MET | 2.02E−22 | 2.25 |
| 3452478 | AMIGO2 | 2.03E−22 | 1.17 |
| 2451931 | GOLT1A | 2.15E−22 | 0.84 |

TABLE 3-continued

Top Benign vs. Malignant Analysis. This analysis resulted in 175 unique TCIDs, currently mapping to 198 genes.

| TCID | Gene Symbol (Affy v.na29) | FDR LIMMA p-value | Fold Change |
|---|---|---|---|
| 3679959 | EMP2 | 3.81E-22 | 1.51 |
| 3417249 | ERBB3 | 1.11E-21 | 1.05 |
| 3087167 | TUSC3 | 1.16E-21 | 1.90 |
| 2924492 | HEY2 | 1.38E-21 | 1.38 |
| 2685304 | PROS1 | 1.48E-21 | 2.15 |
| 3335894 | CST6 | 1.50E-21 | 2.50 |
| 3393720 | MPZL2 | 1.52E-21 | 1.86 |
| 3907234 | SDC4 | 1.60E-21 | 1.64 |
| 4012178 | CITED1 | 4.03E-21 | 2.42 |
| 2994981 | PRR15 | 5.89E-21 | 0.94 |
| 2973232 | C6orf174 | 6.09E-21 | 1.07 |
| 2973232 | KIAA0408 | 6.09E-21 | 1.07 |
| 2809245 | ITGA2 | 6.13E-21 | 1.84 |
| 3067478 | NRCAM | 9.01E-21 | 1.70 |
| 3420316 | HMGA2 | 1.13E-20 | 0.94 |
| 4018327 | TRPC5 | 1.14E-20 | 1.78 |
| 3416921 | RDH5 | 1.24E-20 | 0.55 |
| 2333318 | PTPRF | 1.42E-20 | 0.78 |
| 3336486 | C11orf80 | 1.71E-20 | 0.58 |
| 3336486 | RCE1 | 1.71E-20 | 0.58 |
| 3044072 | NOD1 | 3.06E-20 | 1.01 |
| 3417809 | NAB2 | 3.40E-20 | 0.57 |
| 2710599 | CLDN1 | 4.47E-20 | 2.53 |
| 3343452 | FZD4 | 4.93E-20 | 1.49 |
| 3343452 | PRSS23 | 4.93E-20 | 1.49 |
| 2720584 | SLIT2 | 6.84E-20 | 1.45 |
| 3389976 | SLC35F2 | 1.16E-19 | 0.94 |
| 3587495 | SCG5 | 1.45E-19 | 1.60 |
| 3744463 | MYH10 | 1.58E-19 | 1.40 |
| 3987607 | CCDC121 | 1.87E-19 | 1.56 |
| 3987607 | ZCCHC16 | 1.87E-19 | 1.56 |
| 3984945 | ARMCX3 | 3.69E-19 | 1.11 |
| 2558612 | TGFA | 9.18E-19 | 0.89 |
| 3522398 | AIDA | 1.02E-18 | 1.33 |
| 3522398 | DOCK9 | 1.02E-18 | 1.33 |
| 2781736 | CFI | 1.04E-18 | 1.91 |
| 3338192 | CCND1 | 1.09E-18 | 1.25 |
| 3338192 | FLJ42258 | 1.09E-18 | 1.25 |
| 2414958 | TACSTD2 | 1.12E-18 | 0.91 |
| 2991860 | ITGB8 | 1.51E-18 | 1.30 |
| 2805078 | CDH6 | 1.64E-18 | 1.58 |
| 3976341 | TIMP1 | 1.98E-18 | 1.68 |
| 2562435 | EDNRB | 1.98E-18 | 1.61 |
| 2562435 | SFTPB | 1.98E-18 | 1.61 |
| 3726154 | ITGA3 | 2.04E-18 | 1.17 |
| 2381249 | C1orf115 | 4.38E-18 | 0.92 |
| 2356818 | BCL9 | 6.05E-18 | 0.63 |
| 3451814 | MAFG | 7.13E-18 | 1.92 |
| 3451814 | NELL2 | 7.13E-18 | 1.92 |
| 3445908 | EPS8 | 7.19E-18 | 1.60 |
| 2451870 | ETNK2 | 8.68E-18 | 1.00 |
| 3201345 | LOC554202 | 1.08E-17 | 1.05 |
| 3581221 | AHNAK2 | 1.14E-17 | 1.28 |
| 2966193 | C6orf168 | 1.23E-17 | 0.85 |
| 2876608 | CXCL14 | 1.85E-17 | 1.76 |
| 3129065 | CLU | 1.85E-17 | 1.37 |
| 3222170 | TNC | 1.94E-17 | 1.24 |
| 2438458 | CRABP2 | 2.16E-17 | 1.24 |
| 2600689 | EPHA4 | 2.17E-17 | 1.51 |
| 3763390 | TMEM100 | 2.61E-17 | 1.34 |
| 2902958 | C4A | 3.56E-17 | 1.36 |
| 2902958 | C4B | 3.56E-17 | 1.36 |
| 2952834 | KCNK5 | 6.07E-17 | 0.51 |
| 2452478 | LEMD1 | 9.66E-17 | 1.27 |
| 3751002 | RAB34 | 1.14E-16 | 0.83 |
| 3489138 | CYSLTR2 | 1.72E-16 | 1.61 |
| 2417362 | DIRAS3 | 1.72E-16 | 1.15 |
| 2370123 | XPR1 | 1.81E-16 | 0.89 |
| 2680046 | ADAMTS9 | 1.83E-16 | 1.40 |
| 3494629 | SCEL | 2.04E-16 | 1.61 |
| 3040967 | RAPGEF5 | 2.04E-16 | 0.92 |
| 3554452 | KIAA0284 | 2.33E-16 | 0.59 |
| 4020655 | ODZ1 | 2.44E-16 | 1.97 |
| 2400518 | ECE1 | 3.31E-16 | 0.98 |
| 2598261 | FN1 | 3.58E-16 | 2.41 |
| 3187686 | GSN | 4.03E-16 | 0.78 |
| 2742224 | SPRY1 | 3.51E-15 | 1.18 |
| 3628832 | DAPK2 | 4.59E-15 | 1.17 |
| 3408831 | SSPN | 4.69E-15 | 0.99 |
| 3925639 | NRIP1 | 5.01E-15 | 1.02 |
| 3683377 | GPRC5B | 5.39E-15 | 1.10 |
| 2397025 | DHRS3 | 5.83E-15 | 1.14 |
| 2816298 | IQGAP2 | 6.56E-15 | -1.04 |
| 3848039 | C3 | 7.85E-15 | 1.62 |
| 3367673 | MPPED2 | 7.93E-15 | -1.71 |
| 2822215 | PAM | 8.70E-15 | 1.08 |
| 2567167 | LONRF2 | 1.12E-14 | 1.40 |
| 2522094 | SPATS2L | 2.21E-14 | 0.96 |
| 3898355 | FLRT3 | 2.70E-14 | 1.96 |
| 3717870 | TMEM98 | 2.72E-14 | 1.51 |
| 3212008 | FRMD3 | 3.50E-14 | 1.43 |
| 2597867 | IKZF2 | 3.58E-14 | 0.91 |
| 3007960 | CLDN4 | 6.44E-14 | 1.27 |
| 2468811 | ASAP2 | 7.11E-14 | 0.89 |
| 3046197 | ELMO1 | 8.04E-14 | -1.10 |
| 3132616 | ZMAT4 | 8.04E-14 | -1.29 |
| 3181600 | GALNT12 | 8.25E-14 | 0.74 |
| 3095313 | C8orf4 | 8.38E-14 | 1.28 |
| 2525533 | LOC648149 | 8.38E-14 | 1.01 |
| 2525533 | MAP2 | 8.38E-14 | 1.01 |
| 3464860 | DUSP6 | 9.39E-14 | 1.10 |
| 3464860 | LOC100131490 | 9.39E-14 | 1.10 |
| 2751936 | GALNT7 | 1.52E-13 | 0.93 |
| 2578790 | LRP1B | 1.65E-13 | -1.33 |
| 2700365 | TM4SF1 | 2.19E-13 | 1.60 |
| 2598828 | IGFBP5 | 2.87E-13 | 1.67 |
| 3126191 | PSD3 | 3.12E-13 | 1.34 |
| 3979101 | FAAH2 | 3.88E-13 | 0.68 |
| 3577612 | SERPINA1 | 3.99E-13 | 1.12 |
| 3577612 | SERPINA2 | 3.99E-13 | 1.12 |
| 3622934 | MYEF2 | 4.25E-13 | 0.92 |
| 3622934 | SLC24A5 | 4.25E-13 | 0.92 |
| 2738664 | SGMS2 | 4.47E-13 | 1.13 |
| 3692999 | MT1G | 4.65E-13 | -2.43 |
| 2902844 | C2 | 7.40E-13 | 1.36 |
| 2902844 | CFB | 7.40E-13 | 1.36 |
| 3662201 | MT1F | 8.84E-13 | -1.87 |
| 3662201 | MT1H | 8.84E-13 | -1.87 |
| 3662201 | MT1P2 | 8.84E-13 | -1.87 |
| 2617188 | ITGA9 | 1.07E-12 | 1.05 |
| 3401704 | CCND2 | 1.09E-12 | 0.86 |
| 2562529 | ST3GAL5 | 1.34E-12 | 0.88 |
| 2371139 | LAMC2 | 1.53E-12 | 0.99 |
| 2626802 | PTPRG | 1.83E-12 | 1.06 |
| 2834282 | STK32A | 2.53E-12 | 1.23 |
| 2526806 | FN1 | 3.12E-12 | 1.84 |
| 3111561 | MAPK6 | 3.66E-12 | -2.04 |
| 3111561 | PKHD1L1 | 3.66E-12 | -2.04 |
| 3238962 | KIAA1217 | 7.24E-12 | 1.21 |
| 3238962 | PRINS | 7.24E-12 | 1.21 |
| 3110608 | TM7SF4 | 7.72E-12 | 1.92 |
| 2466554 | TPO | 1.14E-11 | -1.78 |
| 3126368 | PSD3 | 2.30E-11 | 1.39 |
| 3558418 | STXBP6 | 3.35E-11 | 0.94 |
| 2980449 | IPCEF1 | 3.42E-11 | -1.05 |
| 3907190 | SLPI | 4.25E-11 | 1.61 |
| 2955932 | GPR110 | 5.17E-11 | 1.29 |
| 2976360 | PERP | 7.31E-11 | 1.31 |
| 2686023 | DCBLD2 | 8.03E-11 | 0.98 |
| 2915828 | NT5E | 9.40E-11 | 1.19 |
| 3219621 | CTNNAL1 | 1.17E-10 | 1.01 |
| 3971451 | PHEX | 1.39E-10 | 1.53 |
| 3417583 | RBMS2 | 1.39E-10 | 1.09 |
| 2424102 | CNN3 | 1.58E-10 | 1.07 |
| 3369931 | RAG2 | 2.12E-10 | -1.41 |
| 2730746 | SLC4A4 | 2.24E-10 | -1.21 |

TABLE 3-continued

Top Benign vs. Malignant Analysis.
This analysis resulted in 175 unique
TCIDs, currently mapping to 198 genes.

| TCID | Gene Symbol (Affy v.na29) | FDR LIMMA p-value | Fold Change |
|---|---|---|---|
| 3010503 | CD36 | 2.91E−10 | −1.42 |
| 3446137 | LMO3 | 3.09E−10 | 1.44 |
| 3933536 | TFF3 | 3.09E−10 | −1.10 |
| 4021777 | IGSF1 | 3.11E−10 | 1.55 |
| 3467949 | SLC5A8 | 4.08E−10 | −1.34 |
| 3288518 | C10orf72 | 4.26E−10 | 1.18 |
| 2336891 | DIO1 | 4.31E−10 | −1.73 |
| 2498274 | C2orf40 | 4.39E−10 | 1.71 |
| 2740067 | ANK2 | 5.52E−10 | −0.90 |
| 2924330 | TPD52L1 | 6.04E−10 | 1.09 |
| 2427469 | SLC16A4 | 6.71E−10 | 1.37 |
| 2727587 | KIT | 1.23E−09 | −1.24 |
| 3464417 | MGAT4C | 1.45E−09 | 1.26 |
| 2331558 | BMP8A | 3.61E−09 | −1.55 |
| 2711205 | ATP13A4 | 6.51E−09 | 1.15 |
| 3142381 | FABP4 | 7.25E−09 | −1.59 |
| 3743551 | CLDN7 | 8.01E−09 | 1.13 |
| 3662150 | MT1M | 8.06E−09 | −1.47 |
| 3662150 | MT1P3 | 8.06E−09 | −1.47 |
| 3166644 | TMEM215 | 9.05E−09 | 1.51 |
| 3087659 | SLC7A2 | 1.32E−08 | 1.28 |
| 3321055 | TEAD1 | 1.37E−07 | 1.10 |
| 3059667 | SEMA3D | 1.43E−07 | −1.83 |

TABLE 4

Top Subtype Analysis
This analysis resulted in 599 unique TCIDs, currently mapping to 681 genes.

| TCID | Gene Symbol (Affy vna29) | Subtype 1 | Subtype 2 | Subtype 3 | Subtype 4 |
|---|---|---|---|---|---|
| 3153400 | 3153400 | NHP_PTC | | | |
| 3749600 | 3749600 | NHP_PTC | | | |
| 3726691 | ABCC3 | | | FA_FVPTC | |
| 3368940 | ABTB2 | NHP_PTC | | | |
| 3279058 | ACBD7 | NHP_PTC | | | |
| 2796553 | ACSL1 | NHP_PTC | | | |
| 3299504 | ACTA2 | NHP_PTC | | | |
| 3927480 | ADAMTS5 | NHP_PTC | | | |
| 2680046 | ADAMTS9 | NHP_PTC | FA_FVPTC | NHP_FVPTC | LCT_REST |
| 3252170 | ADK | NHP_PTC | | | |
| 3039791 | AGR2 | NHP_PTC | | | |
| 3581221 | AHNAK2 | NHP_PTC | | | |
| 2991233 | AHR | NHP_PTC | | | |
| 3522398 | AIDA | NHP_PTC | | NHP_FVPTC | |
| 3226138 | AK1 | NHP_PTC | | | |
| 3233049 | AKR1C3 | | | NHP_FVPTC | |
| 4009849 | ALAS2 | NHP_PTC | | | |
| 3611625 | ALDH1A3 | NHP_PTC | | | |
| 3169331 | ALDH1B1 | | FA_FVPTC | | |
| 3571727 | ALDH6A1 | | FA_FVPTC | | |
| 3452478 | AMIGO2 | NHP_PTC | | | |
| 4018454 | AMOT | NHP_PTC | | | |
| 2740067 | ANK2 | NHP_PTC | | NHP_FVPTC | |
| 3323748 | ANO5 | | FA_FVPTC | NHP_FVPTC | |
| 3174816 | ANXA1 | NHP_PTC | | | |
| 2732844 | ANXA3 | NHP_PTC | | | |
| 2881747 | ANXA6 | | | NHP_FVPTC | |
| 3046062 | AOAH | NHP_PTC | | | |
| 2455418 | AP3S1 | NHP_PTC | | | |
| 4002809 | APOO | | FA_FVPTC | NHP_FVPTC | |
| 3595594 | AQP9 | NHP_PTC | | | |
| 2734421 | ARHGAP24 | NHP_PTC | | | |
| 2632453 | ARL13B | NHP_PTC | | | |
| 2931391 | ARL4A | NHP_PTC | | | |
| 3984945 | ARMCX3 | NHP_PTC | | | |
| 4015838 | ARMCX6 | NHP_PTC | | | |
| 3321150 | ARNTL | NHP_PTC | | | |
| 3768474 | ARSG | | | NHP_FVPTC | |
| 2468811 | ASAP2 | NHP_PTC | | | |
| 2526759 | ATIC | NHP_PTC | | | |
| 2711225 | ATP13A4 | NHP_PTC | | | |
| 2711205 | ATP13A4 | NHP_PTC | | | |
| 3105749 | ATP6V0D2 | | | NHP_FVPTC | |
| 3824596 | B3GNT3 | NHP_PTC | | | |
| 2356818 | BCL9 | NHP_PTC | | | |
| 2608725 | BHLHE40 | NHP_PTC | | | |
| 3448088 | BHLHE41 | NHP_PTC | | | |
| 3772187 | BIRC5 | | | | LCT_REST |
| 2331558 | BMP8A | NHP_PTC | | NHP_FVPTC | |
| 3926080 | BTG3 | NHP_PTC | | | |

TABLE 4-continued

Top Subtype Analysis
This analysis resulted in 599 unique TCIDs, currently mapping to 681 genes.

| TCID | Gene Symbol (Affy vna29) | Subtype 1 | Subtype 2 | Subtype 3 | Subtype 4 |
|---|---|---|---|---|---|
| 3288518 | C10orf72 |  | FA_FVPTC | NHP_FVPTC |  |
| 2708855 | C11orf72 | NHP_PTC | FA_FVPTC | NHP_FVPTC |  |
| 3327166 | C11orf74 |  | FA_FVPTC | NHP_FVPTC |  |
| 3336486 | C11orf80 | NHP_PTC |  |  |  |
| 3473331 | C12orf49 | NHP_PTC |  |  |  |
| 3571727 | C14orf45 |  | FA_FVPTC |  |  |
| 3649714 | C16orf45 | NHP_PTC |  |  |  |
| 3832280 | C19orf33 | NHP_PTC |  |  |  |
| 2381249 | C1orf115 | NHP_PTC |  |  |  |
| 2453065 | C1orf116 | NHP_PTC |  |  |  |
| 2902844 | C2 | NHP_PTC |  |  |  |
| 3963676 | C22orf9 |  |  | NHP_FVPTC |  |
| 2498274 | C2orf40 | NHP_PTC | FA_FVPTC | NHP_FVPTC |  |
| 3848039 | C3 | NHP_PTC |  |  |  |
| 2902958 | C4A | NHP_PTC | FA_FVPTC | NHP_FVPTC |  |
| 2902958 | C4B | NHP_PTC | FA_FVPTC | NHP_FVPTC |  |
| 2766492 | C4orf34 | NHP_PTC |  |  |  |
| 2730303 | C4orf7 |  |  |  | LCT_REST |
| 2855578 | C5orf28 |  | FA_FVPTC |  |  |
| 2966193 | C6orf168 | NHP_PTC |  |  |  |
| 2973232 | C6orf174 | NHP_PTC | FA_FVPTC |  |  |
| 3060450 | C7orf62 | NHP_PTC |  |  |  |
| 3095313 | C8orf4 | NHP_PTC |  |  |  |
| 3086809 | C8orf79 |  | FA_FVPTC |  |  |
| 3867264 | CA11 | NHP_PTC |  |  |  |
| 3392332 | CADM1 | NHP_PTC |  |  |  |
| 2400177 | CAMK2N1 | NHP_PTC | FA_FVPTC | NHP_FVPTC |  |
| 3420713 | CAND1 | NHP_PTC |  |  |  |
| 3020302 | CAV1 | NHP_PTC |  |  |  |
| 3020273 | CAV2 | NHP_PTC |  |  |  |
| 3987607 | CCDC121 | NHP_PTC | FA_FVPTC | NHP_FVPTC |  |
| 2582701 | CCDC148 | NHP_PTC |  |  |  |
| 2688813 | CCDC80 | NHP_PTC |  |  |  |
| 3718204 | CCL13 | NHP_PTC |  |  |  |
| 3204285 | CCL19 |  |  |  | LCT_REST |
| 3338192 | CCND1 | NHP_PTC | FA_FVPTC | NHP_FVPTC |  |
| 3380065 | CCND1 |  |  | NHP_FVPTC |  |
| 3401704 | CCND2 | NHP_PTC |  | NHP_FVPTC |  |
| 3316344 | CD151 | NHP_PTC |  |  |  |
| 2860178 | CD180 |  |  |  | LCT_REST |
| 2636125 | CD200 | NHP_PTC |  |  |  |
| 3010503 | CD36 | NHP_PTC |  | NHP_FVPTC |  |
| 3834502 | CD79A |  |  |  | LCT_REST |
| 2671728 | CDCP1 | NHP_PTC |  |  |  |
| 3694657 | CDH11 | NHP_PTC |  |  |  |
| 3666366 | CDH3 | NHP_PTC | FA_FVPTC |  |  |
| 2805078 | CDH6 | NHP_PTC |  |  |  |
| 3417146 | CDK2 | NHP_PTC |  |  |  |
| 2773719 | CDKL2 | NHP_PTC |  |  |  |
| 2871896 | CDO1 | NHP_PTC |  |  |  |
| 4024373 | CDR1 | NHP_PTC |  |  |  |
| 2902844 | CFB | NHP_PTC |  |  |  |
| 2373336 | CFH | NHP_PTC |  |  |  |
| 2373336 | CFHR1 | NHP_PTC |  |  |  |
| 2781736 | CFI | NHP_PTC |  |  |  |
| 3920003 | CHAF1B | NHP_PTC |  |  |  |
| 3442054 | CHD4 | NHP_PTC |  |  |  |
| 4012178 | CITED1 | NHP_PTC | FA_FVPTC | NHP_FVPTC |  |
| 3178583 | CKS2 | NHP_PTC |  |  |  |
| 3862108 | CLC | NHP_PTC |  |  |  |
| 2710599 | CLDN1 | NHP_PTC |  | NHP_FVPTC |  |
| 3497195 | CLDN10 | NHP_PTC |  |  |  |
| 2657808 | CLDN16 | NHP_PTC | FA_FVPTC | NHP_FVPTC |  |
| 3007960 | CLDN4 | NHP_PTC |  | NHP_FVPTC |  |
| 3743551 | CLDN7 | NHP_PTC |  |  |  |
| 3443183 | CLEC4E | NHP_PTC |  |  |  |
| 3129065 | CLU | NHP_PTC | FA_FVPTC |  |  |
| 2424102 | CNN3 | NHP_PTC |  |  |  |
| 3762198 | COL1A1 | NHP_PTC |  |  |  |
| 3761054 | COPZ2 |  | FA_FVPTC | NHP_FVPTC |  |
| 3106559 | CP | NHP_PTC |  |  |  |
| 3105904 | CPNE3 |  | FA_FVPTC |  |  |
| 2377283 | CR2 |  |  |  | LCT_REST |
| 3603295 | CRABP1 | NHP_PTC |  |  |  |

TABLE 4-continued

Top Subtype Analysis
This analysis resulted in 599 unique TCIDs, currently mapping to 681 genes.

| TCID | Gene Symbol (Affy vna29) | Subtype 1 | Subtype 2 | Subtype 3 | Subtype 4 |
|---|---|---|---|---|---|
| 2438458 | CRABP2 | NHP_PTC | FA_FVPTC | | |
| 2406783 | CSF3R | NHP_PTC | | | |
| 3126504 | CSGALNACT1 | | FA_FVPTC | | |
| 3335894 | CST6 | NHP_PTC | FA_FVPTC | NHP_FVPTC | |
| 3219621 | CTNNAL1 | NHP_PTC | | | |
| 2618940 | CTNNB1 | NHP_PTC | | | |
| 3634811 | CTSH | NHP_PTC | | | |
| 3338552 | CTTN | NHP_PTC | | | |
| 2773434 | CXCL1 | NHP_PTC | | | |
| 2732508 | CXCL13 | | | | LCT_REST |
| 2876608 | CXCL14 | NHP_PTC | | | |
| 3863640 | CXCL17 | NHP_PTC | | | |
| 2773434 | CXCL2 | NHP_PTC | | | |
| 2773434 | CXCL3 | NHP_PTC | | | |
| 4024420 | CXorf18 | NHP_PTC | | | |
| 3973891 | CXorf27 | NHP_PTC | | | |
| 3910429 | CYP24A1 | | | NHP_FVPTC | |
| 2528093 | CYP27A1 | | | NHP_FVPTC | |
| 3489138 | CYSLTR2 | NHP_PTC | FA_FVPTC | NHP_FVPTC | |
| 3628832 | DAPK2 | NHP_PTC | FA_FVPTC | NHP_FVPTC | |
| 2686023 | DCBLD2 | NHP_PTC | | | |
| 3683845 | DCUN1D3 | NHP_PTC | | | |
| 2420832 | DDAH1 | NHP_PTC | | | |
| 3329649 | DDB2 | NHP_PTC | | | |
| 3754736 | DDX52 | NHP_PTC | | | |
| 3487095 | DGKH | NHP_PTC | | | |
| 3074912 | DGKI | NHP_PTC | | | |
| 3558118 | DHRS1 | NHP_PTC | | | |
| 2397025 | DHRS3 | NHP_PTC | | | |
| 2336891 | DIO1 | NHP_PTC | FA_FVPTC | NHP_FVPTC | |
| 2417362 | DIRAS3 | NHP_PTC | | NHP_FVPTC | |
| 3125116 | DLC1 | NHP_PTC | FA_FVPTC | | |
| 3522398 | DOCK9 | NHP_PTC | | NHP_FVPTC | |
| 3913483 | DPH3B | | FA_FVPTC | | |
| 2584018 | DPP4 | NHP_PTC | | | |
| 2880292 | DPYSL3 | NHP_PTC | | | |
| 3783529 | DSG2 | NHP_PTC | | | |
| 2893794 | DSP | NHP_PTC | | | |
| 2958325 | DST | NHP_PTC | | | |
| 3622176 | DUOX1 | | | NHP_FVPTC | |
| 3622176 | DUOX2 | | | NHP_FVPTC | |
| 3622239 | DUOXA1 | | | NHP_FVPTC | |
| 3622239 | DUOXA2 | | | NHP_FVPTC | |
| 3129731 | DUSP4 | NHP_PTC | | | |
| 3263743 | DUSP5 | NHP_PTC | | | |
| 3464860 | DUSP6 | NHP_PTC | | | |
| 3497195 | DZIP1 | NHP_PTC | | | |
| 2400518 | ECE1 | NHP_PTC | FA_FVPTC | NHP_FVPTC | |
| 2562435 | EDNRB | NHP_PTC | | | |
| 3002640 | EGFR | NHP_PTC | | | |
| 2484970 | EHBP1 | NHP_PTC | | | |
| 3837431 | EHD2 | NHP_PTC | | | |
| 3326461 | EHF | NHP_PTC | | | |
| 3544387 | EIF2B2 | | FA_FVPTC | | |
| 3427098 | ELK3 | NHP_PTC | | | |
| 3046197 | ELMO1 | NHP_PTC | | | |
| 3679959 | EMP2 | NHP_PTC | FA_FVPTC | NHP_FVPTC | |
| 3852832 | EMR3 | NHP_PTC | | | |
| 2458338 | ENAH | NHP_PTC | | | |
| 3345427 | ENDOD1 | NHP_PTC | | | |
| 2327677 | EPB41 | NHP_PTC | | | |
| 2600689 | EPHA4 | NHP_PTC | | | |
| 2346625 | EPHX4 | NHP_PTC | | | |
| 3772187 | EPR1 | | | | LCT_REST |
| 3445908 | EPS8 | NHP_PTC | | | |
| 3720402 | ERBB2 | | FA_FVPTC | | |
| 3417249 | ERBB3 | NHP_PTC | | | |
| 3683845 | ERI2 | NHP_PTC | | | |
| 2462329 | ERO1LB | | FA_FVPTC | | |
| 3445768 | ERP27 | NHP_PTC | | | |
| 2451870 | ETNK2 | NHP_PTC | | | |
| 3039177 | ETV1 | NHP_PTC | | | |
| 2709132 | ETV5 | NHP_PTC | | | |
| 2863363 | F2RL2 | NHP_PTC | | | |

TABLE 4-continued

Top Subtype Analysis
This analysis resulted in 599 unique TCIDs, currently mapping to 681 genes.

| TCID | Gene Symbol (Affy vna29) | Subtype 1 | Subtype 2 | Subtype 3 | Subtype 4 |
|---|---|---|---|---|---|
| 3979101 | FAAH2 | NHP_PTC | | | |
| 3142381 | FABP4 | NHP_PTC | | NHP_FVPTC | |
| 3331926 | FAM111A | NHP_PTC | | | |
| 3331903 | FAM111B | NHP_PTC | | | |
| 3104323 | FAM164A | NHP_PTC | | | |
| 2560625 | FAM176A | NHP_PTC | | | |
| 3768535 | FAM20A | NHP_PTC | | | |
| 3143330 | FAM82B | | FA_FVPTC | | |
| 3152558 | FAM84B | NHP_PTC | | | |
| 2396750 | FBXO2 | NHP_PTC | | | |
| 3473480 | FBXO21 | NHP_PTC | | | |
| 3229338 | FCN1 | NHP_PTC | | | |
| 3229338 | FCN2 | NHP_PTC | | | |
| 2742109 | FGF2 | NHP_PTC | | | |
| 3413950 | FGFR1OP2 | NHP_PTC | | | |
| 3324447 | FIBIN | | FA_FVPTC | | |
| 2738244 | FLJ20184 | NHP_PTC | | | |
| 3346147 | FLJ32810 | NHP_PTC | | | |
| 3338192 | FLJ42258 | NHP_PTC | FA_FVPTC | NHP_FVPTC | |
| 3380065 | FLJ42258 | | | NHP_FVPTC | |
| 3898355 | FLRT3 | NHP_PTC | | | |
| 2526806 | FN1 | NHP_PTC | | | |
| 2598261 | FN1 | NHP_PTC | FA_FVPTC | | |
| 3869237 | FPR1 | NHP_PTC | | | |
| 3839910 | FPR2 | NHP_PTC | | | |
| 3212008 | FRMD3 | NHP_PTC | FA_FVPTC | NHP_FVPTC | |
| 3393479 | FXYD6 | | | NHP_FVPTC | |
| 3343452 | FZD4 | NHP_PTC | | | |
| 3110272 | FZD6 | NHP_PTC | | | |
| 2523045 | FZD7 | NHP_PTC | | | |
| 3217242 | GABBR2 | NHP_PTC | | | |
| 2884845 | GABRB2 | NHP_PTC | FA_FVPTC | NHP_FVPTC | |
| 2341083 | GADD45A | NHP_PTC | | | |
| 2401581 | GALE | NHP_PTC | | | |
| 3181600 | GALNT12 | NHP_PTC | | | |
| 2585129 | GALNT3 | NHP_PTC | | | |
| 2751936 | GALNT7 | NHP_PTC | | | |
| 2684187 | GBE1 | | | NHP_FVPTC | |
| 2421843 | GBP1 | NHP_PTC | | | |
| 2421843 | GBP3 | NHP_PTC | | | |
| 3044129 | GGCT | NHP_PTC | | | |
| 4015763 | GLA | | | NHP_FVPTC | |
| 3593931 | GLDN | NHP_PTC | | | |
| 2417272 | GNG12 | NHP_PTC | | | |
| 2451931 | GOLT1A | NHP_PTC | | | |
| 2955932 | GPR110 | NHP_PTC | | | |
| 2955999 | GPR110 | NHP_PTC | | | |
| 2819779 | GPR98 | NHP_PTC | | NHP_FVPTC | |
| 3683377 | GPRC5B | NHP_PTC | | | |
| 2827057 | GRAMD3 | NHP_PTC | | | |
| 3187686 | GSN | NHP_PTC | | | |
| 2787958 | GYPB | NHP_PTC | | | |
| 2504328 | GYPC | NHP_PTC | | | |
| 2787958 | GYPE | NHP_PTC | | | |
| 2809793 | GZMK | | | | LCT_REST |
| 3217077 | HEMGN | NHP_PTC | | | |
| 2924492 | HEY2 | NHP_PTC | FA_FVPTC | NHP_FVPTC | |
| 2946194 | HIST1H1A | NHP_PTC | | | |
| 2946215 | HIST1H3B | | | | LCT_REST |
| 2947081 | HIST1H4L | | | | LCT_REST |
| 2950125 | HLA-DQB2 | NHP_PTC | | | |
| 3420316 | HMGA2 | NHP_PTC | | | |
| 3830065 | HPN | NHP_PTC | | | |
| 2658275 | HRASLS | | FA_FVPTC | | |
| 3508330 | HSPH1 | NHP_PTC | | | |
| 3820443 | ICAM1 | NHP_PTC | | | |
| 2401493 | ID3 | | FA_FVPTC | | |
| 2708922 | IGF2BP2 | | FA_FVPTC | | |
| 2598828 | IGFBP5 | NHP_PTC | | | |
| 3415744 | IGFBP6 | NHP_PTC | FA_FVPTC | NHP_FVPTC | |
| 4021777 | IGSF1 | NHP_PTC | FA_FVPTC | | |
| 2597867 | IKZF2 | | FA_FVPTC | NHP_FVPTC | |
| 3755862 | IKZF3 | | FA_FVPTC | | |
| 2497082 | IL1RL1 | NHP_PTC | | | |

TABLE 4-continued

Top Subtype Analysis
This analysis resulted in 599 unique TCIDs, currently mapping to 681 genes.

| TCID | Gene Symbol (Affy vna29) | Subtype 1 | Subtype 2 | Subtype 3 | Subtype 4 |
|---|---|---|---|---|---|
| 3275729 | IL2RA | | | NHP_FVPTC | |
| 2731332 | IL8 | | | NHP_FVPTC | |
| 2599303 | IL8RA | NHP_PTC | | | |
| 2599303 | IL8RB | NHP_PTC | | | |
| 2527580 | IL8RB | NHP_PTC | | | |
| 2599303 | IL8RBP | NHP_PTC | | | |
| 2527580 | IL8RBP | NHP_PTC | | | |
| 2673873 | IMPDH2 | NHP_PTC | | | |
| 3267382 | INPP5F | NHP_PTC | | | |
| 2980449 | IPCEF1 | NHP_PTC | | | |
| 2816298 | IQGAP2 | NHP_PTC | | | |
| 2809245 | ITGA2 | NHP_PTC | | | |
| 3726154 | ITGA3 | NHP_PTC | | | |
| 2617188 | ITGA9 | NHP_PTC | FA_FVPTC | | |
| 3852832 | ITGB1 | NHP_PTC | | | |
| 2583465 | ITGB6 | NHP_PTC | | | |
| 2991860 | ITGB8 | NHP_PTC | | | |
| 4013549 | ITM2A | | | | LCT_REST |
| 2608469 | ITPR1 | NHP_PTC | | | |
| 3556990 | JUB | NHP_PTC | | | |
| 3998766 | KAL1 | NHP_PTC | | | |
| 2628260 | KBTBD8 | | | | LCT_REST |
| 2952834 | KCNK5 | NHP_PTC | | | |
| 3154002 | KCNQ3 | NHP_PTC | | | |
| 3383130 | KCTD14 | NHP_PTC | | | |
| 2827525 | KDELC1 | NHP_PTC | | | |
| 3945314 | KDELR3 | NHP_PTC | | | |
| 2959039 | KHDRBS2 | NHP_PTC | | | |
| 3554452 | KIAA0284 | NHP_PTC | | NHP_FVPTC | |
| 2973232 | KIAA0408 | NHP_PTC | FA_FVPTC | | |
| 3238962 | KIAA1217 | NHP_PTC | | NHP_FVPTC | |
| 3529951 | KIAA1305 | | FA_FVPTC | | |
| 2727587 | KIT | NHP_PTC | FA_FVPTC | NHP_FVPTC | |
| 3978943 | KLF8 | NHP_PTC | | | |
| 2708066 | KLHL6 | | | | LCT_REST |
| 3868828 | KLK10 | NHP_PTC | | | |
| 3868783 | KLK7 | NHP_PTC | | | |
| 3415576 | KRT18 | NHP_PTC | | | |
| 3757108 | KRT19 | NHP_PTC | FA_FVPTC | | |
| 2453793 | LAMB3 | NHP_PTC | | | |
| 2371065 | LAMC1 | NHP_PTC | | | |
| 2371139 | LAMC2 | NHP_PTC | | | |
| 2962026 | LCA5 | NHP_PTC | | | |
| 3653619 | LCMT1 | NHP_PTC | | | |
| 3190190 | LCN2 | NHP_PTC | | | |
| 4024420 | LDOC1 | NHP_PTC | | | |
| 2452478 | LEMD1 | NHP_PTC | | | |
| 2854092 | LIFR | | FA_FVPTC | | |
| 3841545 | LILRA1 | NHP_PTC | | | |
| 3841545 | LILRB1 | NHP_PTC | | | |
| 3454331 | LIMA1 | NHP_PTC | | | |
| 3202528 | LINGO2 | NHP_PTC | | | |
| 2708855 | LIPH | NHP_PTC | FA_FVPTC | NHP_FVPTC | |
| 3446137 | LMO3 | NHP_PTC | FA_FVPTC | NHP_FVPTC | |
| 2345286 | LMO4 | NHP_PTC | | | |
| 3028011 | LOC100124692 | NHP_PTC | | | |
| 3442054 | LOC100127974 | NHP_PTC | | | |
| 3765689 | LOC100129112 | NHP_PTC | | | |
| 3759587 | LOC100129115 | NHP_PTC | | | |
| 2601414 | LOC100129171 | NHP_PTC | | | |
| 2577482 | LOC100129961 | NHP_PTC | | | |
| 2504328 | LOC100130248 | NHP_PTC | | | |
| 3110272 | LOC100131102 | NHP_PTC | | | |
| 3464860 | LOC100131490 | NHP_PTC | | | |
| 2364677 | LOC100131938 | NHP_PTC | | | |
| 3922793 | LOC100132338 | NHP_PTC | | | |
| 3392332 | LOC100132764 | NHP_PTC | | | |
| 3487095 | LOC283508 | NHP_PTC | | | |
| 3724698 | LOC440434 | NHP_PTC | | | |
| 3201345 | LOC554202 | NHP_PTC | | | |
| 2455418 | LOC643454 | NHP_PTC | | | |
| 2525533 | LOC648149 | NHP_PTC | | | |
| 4015838 | LOC653354 | NHP_PTC | | | |
| 3724698 | LOC653498 | NHP_PTC | | | |

TABLE 4-continued

Top Subtype Analysis
This analysis resulted in 599 unique TCIDs, currently mapping to 681 genes.

| TCID | Gene Symbol (Affy vna29) | Subtype 1 | Subtype 2 | Subtype 3 | Subtype 4 |
|---|---|---|---|---|---|
| 2936857 | LOC730031 | NHP_PTC | | | |
| 2567167 | LONRF2 | NHP_PTC | | | LCT_REST |
| 2872848 | LOX | NHP_PTC | | | |
| 3220384 | LPAR1 | | | NHP_FVPTC | |
| 3442137 | LPAR5 | NHP_PTC | | | |
| 3088486 | LPL | NHP_PTC | | | |
| 2578790 | LRP1B | NHP_PTC | | NHP_FVPTC | |
| 3106559 | LRRC69 | NHP_PTC | | | |
| 2608309 | LRRN1 | NHP_PTC | | | |
| 3465248 | LUM | NHP_PTC | | | |
| 3683845 | LYRM1 | NHP_PTC | | | |
| 3040518 | MACC1 | NHP_PTC | FA_FVPTC | | |
| 3451814 | MAFG | NHP_PTC | FA_FVPTC | | |
| 3994710 | MAMLD1 | NHP_PTC | | | |
| 2525533 | MAP2 | NHP_PTC | | | |
| 3111561 | MAPK6 | NHP_PTC | | NHP_FVPTC | |
| 3108526 | MATN2 | | FA_FVPTC | | |
| 2539607 | MBOAT2 | NHP_PTC | | | |
| 3097152 | MCM4 | NHP_PTC | | | |
| 3063685 | MCM7 | NHP_PTC | | | |
| 3329343 | MDK | NHP_PTC | FA_FVPTC | | |
| 2962820 | ME1 | | | NHP_FVPTC | |
| 3765689 | MED13 | NHP_PTC | | | |
| 3020343 | MET | NHP_PTC | FA_FVPTC | NHP_FVPTC | |
| 3416895 | METTL7B | NHP_PTC | FA_FVPTC | NHP_FVPTC | |
| 3808096 | MEX3C | NHP_PTC | | | |
| 3638204 | MFGE8 | NHP_PTC | FA_FVPTC | NHP_FVPTC | |
| 3028011 | MGAM | NHP_PTC | | | |
| 2890859 | MGAT1 | | | NHP_FVPTC | |
| 3464417 | MGAT4C | NHP_PTC | | | |
| 2658275 | MGC2889 | | FA_FVPTC | | |
| 3406589 | MGST1 | NHP_PTC | | | |
| 3707759 | MIS12 | | FA_FVPTC | | |
| 2936857 | MLLT4 | NHP_PTC | | | |
| 3143660 | MMP16 | NHP_PTC | | | |
| 3143643 | MMP16 | NHP_PTC | | | |
| 2362333 | MNDA | NHP_PTC | | | |
| 4017212 | MORC4 | NHP_PTC | | | |
| 3367673 | MPPED2 | NHP_PTC | | | |
| 3393720 | MPZL2 | NHP_PTC | FA_FVPTC | NHP_FVPTC | |
| 2955025 | MRPL14 | NHP_PTC | | | |
| 3662201 | MT1F | NHP_PTC | FA_FVPTC | | |
| 3692999 | MT1G | NHP_PTC | | NHP_FVPTC | |
| 3662201 | MT1H | NHP_PTC | FA_FVPTC | | |
| 3662150 | MT1M | NHP_PTC | | | |
| 3662201 | MT1P2 | NHP_PTC | FA_FVPTC | | |
| 3662150 | MT1P3 | NHP_PTC | | | |
| 2931391 | MTHFD1L | NHP_PTC | | | |
| 2437118 | MUC1 | NHP_PTC | | | |
| 3366903 | MUC15 | NHP_PTC | | | |
| 3655723 | MVP | NHP_PTC | | | |
| 3997825 | MXRA5 | NHP_PTC | | | |
| 3622934 | MYEF2 | NHP_PTC | | | |
| 3744463 | MYH10 | NHP_PTC | | | |
| 2520429 | MYO1B | NHP_PTC | | | |
| 3752709 | MYO1D | NHP_PTC | | | |
| 3624607 | MYO5A | | | NHP_FVPTC | |
| 2914070 | MYO6 | NHP_PTC | | | |
| 3417809 | NAB2 | NHP_PTC | | | |
| 3695268 | NAE1 | NHP_PTC | | | |
| 3074912 | NAG20 | NHP_PTC | | | |
| 3323052 | NAV2 | | FA_FVPTC | NHP_FVPTC | |
| 3349293 | NCAM1 | | FA_FVPTC | | |
| 2590736 | NCKAP1 | NHP_PTC | | | |
| 3495076 | NDFIP2 | NHP_PTC | | | |
| 3789947 | NEDD4L | NHP_PTC | | | |
| 3451814 | NELL2 | NHP_PTC | FA_FVPTC | | |
| 2343231 | NEXN | NHP_PTC | | | |
| 3456666 | NFE2 | NHP_PTC | | | |
| 3199207 | NFIB | NHP_PTC | | | |
| 2325410 | NIPAL3 | NHP_PTC | | | |
| 3182957 | NIPSNAP3A | | FA_FVPTC | | |
| 3182957 | NIPSNAP3B | | FA_FVPTC | | |
| 3044072 | NOD1 | NHP_PTC | FA_FVPTC | | |

TABLE 4-continued

Top Subtype Analysis
This analysis resulted in 599 unique TCIDs, currently mapping to 681 genes.

| TCID | Gene Symbol (Affy vna29) | Subtype 1 | Subtype 2 | Subtype 3 | Subtype 4 |
|---|---|---|---|---|---|
| 3571904 | NPC2 | NHP_PTC | | | |
| 3724698 | NPEPPS | NHP_PTC | | | |
| 2370926 | NPL | | | NHP_FVPTC | |
| 2792127 | NPY1R | NHP_PTC | | | |
| 3067478 | NRCAM | NHP_PTC | | NHP_FVPTC | |
| 3925639 | NRIP1 | NHP_PTC | | | |
| 2524301 | NRP2 | NHP_PTC | | | |
| 2915828 | NT5E | NHP_PTC | | | |
| 3143330 | NTAN1 | | FA_FVPTC | | |
| 3322251 | NUCB2 | | FA_FVPTC | NHP_FVPTC | |
| 2742109 | NUDT6 | NHP_PTC | | | |
| 3654699 | NUPR1 | | FA_FVPTC | | |
| 2768654 | OCIAD2 | NHP_PTC | | | |
| 2375338 | OCR1 | NHP_PTC | | | |
| 4020655 | ODZ1 | NHP_PTC | FA_FVPTC | NHP_FVPTC | |
| 3380065 | ORAOV1 | | | NHP_FVPTC | |
| 3801621 | OSBPL1A | | | NHP_FVPTC | |
| 3555461 | OSGEP | NHP_PTC | | | |
| 2807359 | OSMR | NHP_PTC | | | |
| 2701071 | P2RY13 | NHP_PTC | | | |
| 2875193 | P4HA2 | NHP_PTC | | | |
| 2822215 | PAM | NHP_PTC | | | |
| 3256590 | PAPSS2 | | | NHP_FVPTC | |
| 3505781 | PARP4 | NHP_PTC | | | |
| 3320865 | PARVA | NHP_PTC | | | |
| 2364677 | PBX1 | NHP_PTC | | | |
| 3134922 | PCMTD1 | | FA_FVPTC | | |
| 2783596 | PDE5A | NHP_PTC | | NHP_FVPTC | |
| 3922793 | PDE9A | NHP_PTC | | | |
| 3087703 | PDGFRL | NHP_PTC | | | |
| 3301218 | PDLIM1 | NHP_PTC | | | |
| 2828441 | PDLIM4 | NHP_PTC | | | |
| 3411810 | PDZRN4 | NHP_PTC | | | |
| 3013255 | PEG10 | NHP_PTC | | | |
| 2976360 | PERP | NHP_PTC | | | |
| 3971451 | PHEX | NHP_PTC | | | |
| 3975893 | PHF16 | NHP_PTC | | | |
| 2635906 | PHLDB2 | NHP_PTC | | | |
| 3127385 | PHYHIP | NHP_PTC | | | |
| 3811086 | PIGN | | FA_FVPTC | | |
| 3111561 | PKHD1L1 | NHP_PTC | | NHP_FVPTC | |
| 2511820 | PKP4 | NHP_PTC | | | |
| 3376529 | PLA2G16 | NHP_PTC | | | |
| 2955827 | PLA2G7 | | | NHP_FVPTC | |
| 2583374 | PLA2R1 | NHP_PTC | | | |
| 3136178 | PLAG1 | NHP_PTC | FA_FVPTC | NHP_FVPTC | |
| 3252036 | PLAU | NHP_PTC | | | |
| 3759587 | PLCD3 | NHP_PTC | | | |
| 2521574 | PLCL1 | | | NHP_FVPTC | |
| 3867458 | PLEKHA4 | NHP_PTC | | | |
| 3407096 | PLEKHA5 | NHP_PTC | | | |
| 2858023 | PLK2 | NHP_PTC | | | |
| 3987996 | PLS3 | NHP_PTC | | | |
| 3911217 | PMEPA1 | NHP_PTC | | | |
| 3061997 | PON2 | NHP_PTC | | | |
| 2763550 | PPARGC1A | NHP_PTC | | | |
| 2773358 | PPBP | NHP_PTC | | | |
| 3678462 | PPL | NHP_PTC | | | |
| 2931090 | PPP1R14C | NHP_PTC | | | |
| 3384270 | PRCP | | | NHP_FVPTC | |
| 3451375 | PRICKLE1 | NHP_PTC | | | |
| 3238962 | PRINS | NHP_PTC | | NHP_FVPTC | |
| 2682271 | PROK2 | NHP_PTC | | | |
| 2685304 | PROS1 | NHP_PTC | | | |
| 2994981 | PRR15 | NHP_PTC | | | |
| 3973692 | PRRG1 | NHP_PTC | | | |
| 3343452 | PRSS23 | NHP_PTC | | | |
| 3175971 | PSAT1 | | FA_FVPTC | | |
| 3126368 | PSD3 | NHP_PTC | | | |
| 3126191 | PSD3 | NHP_PTC | | | |
| 2455418 | PTPN14 | NHP_PTC | | | |
| 2333318 | PTPRF | NHP_PTC | | | |
| 2626802 | PTPRG | NHP_PTC | | | |
| 2973376 | PTPRK | NHP_PTC | | | |

TABLE 4-continued

Top Subtype Analysis
This analysis resulted in 599 unique TCIDs, currently mapping to 681 genes.

| TCID | Gene Symbol (Affy vna29) | Subtype 1 | Subtype 2 | Subtype 3 | Subtype 4 |
|---|---|---|---|---|---|
| 3757917 | PTRF | NHP_PTC | | | |
| 3134922 | PXDNL | | FA_FVPTC | | |
| 3638204 | QTRT1 | NHP_PTC | FA_FVPTC | NHP_FVPTC | |
| 2361257 | RAB25 | NHP_PTC | | | |
| 3625271 | RAB27A | NHP_PTC | | | |
| 2929699 | RAB32 | | | NHP_FVPTC | |
| 3751002 | RAB34 | NHP_PTC | | | |
| 3183757 | RAD23B | NHP_PTC | | | |
| 3369931 | RAG2 | NHP_PTC | FA_FVPTC | | |
| 4001223 | RAI2 | NHP_PTC | | | |
| 3040967 | RAPGEF5 | NHP_PTC | | | |
| 3456081 | RARG | NHP_PTC | | | |
| 2819044 | RASA1 | NHP_PTC | | | |
| 3944210 | RASD2 | NHP_PTC | | | |
| 4000944 | RBBP7 | NHP_PTC | | | |
| 3781429 | RBBP8 | NHP_PTC | | | |
| 3417583 | RBMS2 | NHP_PTC | | | |
| 3336486 | RCE1 | NHP_PTC | | | |
| 3416921 | RDH5 | NHP_PTC | | | |
| 2779335 | RG9MTD2 | | FA_FVPTC | | |
| 2372812 | RGS13 | | | | LCT_REST |
| 2372719 | RGS18 | NHP_PTC | | | |
| 2372858 | RGS2 | NHP_PTC | | | |
| 2384401 | RHOU | NHP_PTC | | | |
| 2580802 | RND3 | NHP_PTC | | | |
| 2721959 | ROS1 | NHP_PTC | FA_FVPTC | NHP_FVPTC | |
| 2709606 | RPL39L | NHP_PTC | | | |
| 3804143 | RPRD1A | NHP_PTC | | | |
| 3867965 | RRAS | NHP_PTC | | | |
| 2469252 | RRM2 | | | | LCT_REST |
| 2442008 | RXRG | NHP_PTC | FA_FVPTC | NHP_FVPTC | |
| 2435981 | S100A12 | NHP_PTC | | | |
| 4045665 | S100A14 | NHP_PTC | | | |
| 4045643 | S100A16 | NHP_PTC | | | |
| 2435989 | S100A8 | NHP_PTC | | | |
| 2359664 | S100A9 | NHP_PTC | | | |
| 3691326 | SALL1 | NHP_PTC | | NHP_FVPTC | |
| 3564027 | SAV1 | NHP_PTC | | | |
| 2750594 | SC4MOL | NHP_PTC | | | |
| 3091475 | SCARA3 | NHP_PTC | | | |
| 3442054 | SCARNA11 | NHP_PTC | | | |
| 3494629 | SCEL | NHP_PTC | | | |
| 3587495 | SCG5 | NHP_PTC | | NHP_FVPTC | |
| 3441885 | SCNN1A | NHP_PTC | | | |
| 3043895 | SCRN1 | NHP_PTC | | | |
| 3907234 | SDC4 | NHP_PTC | FA_FVPTC | NHP_FVPTC | |
| 3779756 | SEH1L | NHP_PTC | | | |
| 2443450 | SELL | NHP_PTC | | | |
| 3058759 | SEMA3C | | | NHP_FVPTC | |
| 3059667 | SEMA3D | NHP_PTC | | | |
| 2732273 | SEPT11 | NHP_PTC | | | |
| 2328273 | SERINC2 | NHP_PTC | | | |
| 3577612 | SERPINA1 | NHP_PTC | FA_FVPTC | | |
| 3577612 | SERPINA2 | NHP_PTC | FA_FVPTC | | |
| 2601414 | SERPINE2 | NHP_PTC | | | |
| 3331355 | SERPING1 | NHP_PTC | | | |
| 2326774 | SFN | NHP_PTC | | | |
| 2562435 | SFTPB | NHP_PTC | | | |
| 2768981 | SGCB | NHP_PTC | | | |
| 3061805 | SGCE | NHP_PTC | | | |
| 2648535 | SGEF | NHP_PTC | | | |
| 2738664 | SGMS2 | NHP_PTC | | | |
| 3088213 | SH2D4A | NHP_PTC | | | |
| 3304970 | SH3PXD2A | NHP_PTC | | | |
| 3894727 | SIRPA | NHP_PTC | | | |
| 3894727 | SIRPB1 | NHP_PTC | | | |
| 3154263 | SLA | NHP_PTC | | | |
| 2827525 | SLC12A2 | NHP_PTC | | | |
| 2427469 | SLC16A4 | NHP_PTC | | | |
| 3768412 | SLC16A6 | | | NHP_FVPTC | |
| 2960955 | SLC17A5 | NHP_PTC | | | |
| 3622934 | SLC24A5 | NHP_PTC | | | |
| 3018605 | SLC26A4 | NHP_PTC | | | |
| 3106559 | SLC26A7 | NHP_PTC | | | |

TABLE 4-continued

Top Subtype Analysis
This analysis resulted in 599 unique TCIDs, currently mapping to 681 genes.

| TCID | Gene Symbol (Affy vna29) | Subtype 1 | Subtype 2 | Subtype 3 | Subtype 4 |
|---|---|---|---|---|---|
| 3593575 | SLC27A2 | NHP_PTC | | | |
| 2827645 | SLC27A6 | NHP_PTC | | | |
| 2721959 | SLC34A2 | NHP_PTC | FA_FVPTC | NHP_FVPTC | |
| 3216276 | SLC35D2 | | FA_FVPTC | | |
| 3389976 | SLC35F2 | NHP_PTC | | | |
| 3804195 | SLC39A6 | NHP_PTC | | | |
| 2730746 | SLC4A4 | NHP_PTC | | | |
| 3467949 | SLC5A8 | NHP_PTC | | | |
| 2786322 | SLC7A11 | | FA_FVPTC | NHP_FVPTC | |
| 3087659 | SLC7A2 | NHP_PTC | | | |
| 2720584 | SLIT2 | NHP_PTC | | | |
| 3907190 | SLPI | NHP_PTC | | | |
| 3509842 | SMAD9 | | FA_FVPTC | | |
| 2937144 | SMOC2 | NHP_PTC | | | |
| 3766960 | SMURF2 | NHP_PTC | | | |
| 2777714 | SNCA | NHP_PTC | | | |
| 3597857 | SNX1 | NHP_PTC | | | |
| 3597914 | SNX22 | NHP_PTC | | | |
| 2348437 | SNX7 | NHP_PTC | | | |
| 2369557 | SOAT1 | | | NHP_FVPTC | |
| 2797202 | SORBS2 | NHP_PTC | | | |
| 3413950 | SPATS2 | NHP_PTC | | | |
| 2522094 | SPATS2L | NHP_PTC | | | |
| 2585933 | SPC25 | | | | LCT_REST |
| 3590164 | SPINT1 | NHP_PTC | | | |
| 2556752 | SPRED2 | NHP_PTC | | | |
| 2742224 | SPRY1 | NHP_PTC | FA_FVPTC | | |
| 3519309 | SPRY2 | NHP_PTC | | | |
| 3677969 | SRL | NHP_PTC | | | |
| 3408831 | SSPN | NHP_PTC | | | |
| 2562529 | ST3GAL5 | NHP_PTC | | | |
| 3011861 | STEAP2 | | FA_FVPTC | | |
| 2834282 | STK32A | NHP_PTC | | NHP_FVPTC | |
| 3558418 | STXBP6 | | | NHP_FVPTC | |
| 3102372 | SULF1 | NHP_PTC | | | |
| 2979871 | SYNE1 | NHP_PTC | | | |
| 2378256 | SYT14 | NHP_PTC | | | |
| 3973891 | SYTL5 | NHP_PTC | | | |
| 2414958 | TACSTD2 | NHP_PTC | | | |
| 3898126 | TASP1 | | FA_FVPTC | | |
| 3724698 | TBC1D3F | NHP_PTC | | | |
| 3264621 | TCF7L2 | | FA_FVPTC | | |
| 3913483 | TCFL5 | | FA_FVPTC | | |
| 2435218 | TDRKH | NHP_PTC | | | |
| 3320944 | TEAD1 | NHP_PTC | | | |
| 3321055 | TEAD1 | NHP_PTC | | | |
| 2573570 | TFCP2L1 | NHP_PTC | | | |
| 3933536 | TFF3 | NHP_PTC | | | |
| 2591421 | TFPI | | | NHP_FVPTC | |
| 2558612 | TGFA | NHP_PTC | | | |
| 2380590 | TGFB2 | NHP_PTC | | | |
| 3181728 | TGFBR1 | NHP_PTC | | | |
| 3976341 | TIMP1 | NHP_PTC | FA_FVPTC | | |
| 2649113 | TIPARP | NHP_PTC | | | |
| 3615579 | TJP1 | NHP_PTC | | | |
| 3173880 | TJP2 | NHP_PTC | | | |
| 3751042 | TLCD1 | NHP_PTC | | | |
| 3969115 | TLR8 | NHP_PTC | | | |
| 2700365 | TM4SF1 | NHP_PTC | | | |
| 2647315 | TM4SF4 | NHP_PTC | | | |
| 3110608 | TM7SF4 | NHP_PTC | | | |
| 3763390 | TMEM100 | NHP_PTC | | | |
| 3412345 | TMEM117 | NHP_PTC | | | |
| 3346147 | TMEM133 | NHP_PTC | | | |
| 2577482 | TMEM163 | NHP_PTC | | | |
| 2815220 | TMEM171 | | FA_FVPTC | NHP_FVPTC | |
| 3166644 | TMEM215 | NHP_PTC | | NHP_FVPTC | |
| 3571904 | TMEM90A | NHP_PTC | | | |
| 3717870 | TMEM98 | NHP_PTC | | | |
| 3351200 | TMPRSS4 | NHP_PTC | | | |
| 3222170 | TNC | NHP_PTC | | | |
| 3150455 | TNFRSF11B | | FA_FVPTC | | |
| 3645555 | TNFRSF12A | NHP_PTC | FA_FVPTC | NHP_FVPTC | |
| 3648391 | TNFRSF17 | | | | LCT_REST |

TABLE 4-continued

Top Subtype Analysis
This analysis resulted in 599 unique TCIDs, currently mapping to 681 genes.

| TCID | Gene Symbol (Affy vna29) | Subtype 1 | Subtype 2 | Subtype 3 | Subtype 4 |
|---|---|---|---|---|---|
| 3222128 | TNFSF15 | NHP_PTC | | | |
| 3907111 | TOMM34 | NHP_PTC | | | |
| 3136888 | TOX | | | | LCT_REST |
| 2924330 | TPD52L1 | NHP_PTC | | | |
| 2466554 | TPO | NHP_PTC | FA_FVPTC | NHP_FVPTC | |
| 3818515 | TRIP10 | NHP_PTC | | | |
| 4018327 | TRPC5 | NHP_PTC | FA_FVPTC | NHP_FVPTC | |
| 3512294 | TSC22D1 | NHP_PTC | | | |
| 2991150 | TSPAN13 | NHP_PTC | | | |
| 4015397 | TSPAN6 | NHP_PTC | | | |
| 3891342 | TUBB1 | NHP_PTC | | | |
| 3779579 | TUBB6 | NHP_PTC | | | |
| 3401217 | TULP3 | NHP_PTC | | | |
| 3087167 | TUSC3 | NHP_PTC | | | |
| 3809324 | TXNL1 | | FA_FVPTC | | |
| 3429460 | TXNRD1 | | | NHP_FVPTC | |
| 3775842 | TYMS | NHP_PTC | | | |
| 2448971 | UCHL5 | | | NHP_FVPTC | |
| 2974592 | VNN1 | | | NHP_FVPTC | |
| 2974635 | VNN2 | NHP_PTC | | | |
| 2974610 | VNN3 | NHP_PTC | | | |
| 3203855 | WDR40A | NHP_PTC | | | |
| 2489228 | WDR54 | NHP_PTC | | | |
| 3625052 | WDR72 | | FA_FVPTC | | |
| 3768474 | WIPI1 | | | NHP_FVPTC | |
| 2677356 | WNT5A | NHP_PTC | | | |
| 4015548 | XKRX | NHP_PTC | | | |
| 2370123 | XPR1 | NHP_PTC | | | |
| 3832280 | YIF1B | NHP_PTC | | | |
| 2413484 | YIPF1 | | FA_FVPTC | | |
| 4024373 | YTHDC2 | NHP_PTC | | | |
| 3989089 | ZBTB33 | NHP_PTC | | | |
| 3988596 | ZCCHC12 | NHP_PTC | FA_FVPTC | NHP_FVPTC | |
| 3987607 | ZCCHC16 | NHP_PTC | FA_FVPTC | NHP_FVPTC | |
| 3569754 | ZFP36L1 | NHP_PTC | | | |
| 2706791 | ZMAT3 | NHP_PTC | | | |
| 3132616 | ZMAT4 | NHP_PTC | FA_FVPTC | NHP_FVPTC | |
| 2331903 | ZNF643 | NHP_PTC | | | |
| 3011675 | ZNF804B | NHP_PTC | | | |

TABLE 5

Trident Analysis
This benign vs. malignant analysis resulted in 210 unique TCIDs, currently mapping to 237 genes. These genes represent the union of three statistically significant sub-analyses (Repeatable, Bayes, and Tissue) using a single dataset.

| TCID | Gene Symbol (Affy v.na29) | Repeatable | Bayes | Tissue | DE | P value |
|---|---|---|---|---|---|---|
| 3393720 | MPZL2 | TRUE | TRUE | TRUE | 1.49 | 1.87E−32 |
| 2400177 | CAMK2N1 | TRUE | TRUE | FALSE | 1.67 | 2.27E−29 |
| 3067478 | NRCAM | TRUE | TRUE | FALSE | 1.42 | 2.53E−29 |
| 3445908 | EPS8 | TRUE | TRUE | TRUE | 1.44 | 6.34E−29 |
| 3020343 | MET | TRUE | TRUE | FALSE | 1.49 | 1.47E−27 |
| 4012178 | CITED1 | TRUE | TRUE | FALSE | 1.50 | 2.37E−27 |
| 2710599 | CLDN1 | TRUE | TRUE | FALSE | 1.41 | 9.07E−27 |
| 3338192 | CCND1 | TRUE | TRUE | TRUE | 1.36 | 2.63E−26 |
| 3338192 | FLJ42258 | TRUE | TRUE | TRUE | 1.36 | 2.63E−26 |
| 3126191 | PSD3 | TRUE | TRUE | TRUE | 1.32 | 3.49E−25 |
| 2884845 | GABRB2 | TRUE | TRUE | FALSE | 1.73 | 4.07E−25 |
| 3087167 | TUSC3 | TRUE | TRUE | FALSE | 1.49 | 6.22E−25 |
| 3907234 | SDC4 | TRUE | TRUE | FALSE | 1.46 | 2.08E−24 |
| 2721959 | ROS1 | TRUE | TRUE | FALSE | 1.48 | 2.82E−24 |
| 2721959 | SLC34A2 | TRUE | TRUE | FALSE | 1.48 | 2.82E−24 |
| 3679959 | EMP2 | FALSE | TRUE | FALSE | 1.50 | 2.83E−24 |
| 2708855 | C11orf72 | TRUE | TRUE | TRUE | 1.59 | 1.31E−23 |
| 2708855 | LIPH | TRUE | TRUE | TRUE | 1.59 | 1.31E−23 |
| 3416895 | METTL7B | TRUE | TRUE | FALSE | 1.49 | 2.12E−23 |
| 3136178 | PLAG1 | FALSE | TRUE | TRUE | 1.41 | 2.37E−23 |
| 2442008 | RXRG | TRUE | TRUE | FALSE | 1.60 | 3.50E−23 |

TABLE 5-continued

Trident Analysis
This benign vs. malignant analysis resulted in 210 unique TCIDs, currently mapping
to 237 genes. These genes represent the union of three statistically significant
sub-analyses (Repeatable, Bayes, and Tissue) using a single dataset.

| TCID | Gene Symbol (Affy v.na29) | Repeatable | Bayes | Tissue | DE | P value |
|---|---|---|---|---|---|---|
| 2657808 | CLDN16 | TRUE | TRUE | TRUE | 1.51 | 2.63E−22 |
| 3984945 | ARMCX3 | TRUE | TRUE | FALSE | 1.45 | 3.13E−22 |
| 2567167 | LONRF2 | TRUE | TRUE | TRUE | 1.38 | 3.67E−22 |
| 2685304 | PROS1 | TRUE | TRUE | FALSE | 1.46 | 3.81E−22 |
| 3744463 | MYH10 | TRUE | TRUE | FALSE | 1.46 | 6.20E−22 |
| 3415744 | IGFBP6 | TRUE | TRUE | FALSE | 1.56 | 9.91E−22 |
| 2834282 | STK32A | TRUE | TRUE | TRUE | 1.27 | 1.03E−21 |
| 3554452 | KIAA0284 | TRUE | TRUE | FALSE | 1.32 | 1.38E−21 |
| 3040518 | MACC1 | TRUE | TRUE | FALSE | 1.47 | 1.42E−21 |
| 3587495 | SCG5 | TRUE | TRUE | FALSE | 1.34 | 1.74E−21 |
| 2686023 | DCBLD2 | TRUE | TRUE | FALSE | 1.18 | 1.83E−21 |
| 3335894 | CST6 | FALSE | TRUE | FALSE | 1.43 | 2.29E−21 |
| 2783596 | PDE5A | TRUE | TRUE | TRUE | 1.55 | 2.63E−21 |
| 3522398 | AIDA | TRUE | TRUE | FALSE | 1.38 | 2.99E−21 |
| 3522398 | DOCK9 | TRUE | TRUE | FALSE | 1.38 | 2.99E−21 |
| 3638204 | MFGE8 | TRUE | TRUE | FALSE | 1.51 | 5.35E−21 |
| 3638204 | QTRT1 | TRUE | TRUE | FALSE | 1.51 | 5.35E−21 |
| 3323052 | NAV2 | TRUE | TRUE | FALSE | 1.30 | 7.00E−21 |
| 2924492 | HEY2 | TRUE | TRUE | FALSE | 1.48 | 2.01E−20 |
| 3726154 | ITGA3 | TRUE | TRUE | FALSE | 1.35 | 2.16E−20 |
| 2924330 | TPD52L1 | TRUE | TRUE | FALSE | 1.17 | 2.21E−20 |
| 3988596 | ZCCHC12 | TRUE | TRUE | FALSE | 1.52 | 2.85E−20 |
| 3683377 | GPRC5B | TRUE | TRUE | FALSE | 1.28 | 4.84E−20 |
| 3417249 | ERBB3 | FALSE | TRUE | FALSE | 1.51 | 6.63E−20 |
| 2511820 | PKP4 | TRUE | TRUE | TRUE | 1.22 | 7.51E−20 |
| 4020655 | ODZ1 | TRUE | TRUE | FALSE | 1.34 | 8.32E−20 |
| 3628832 | DAPK2 | FALSE | TRUE | FALSE | 1.34 | 1.20E−19 |
| 3007960 | CLDN4 | TRUE | TRUE | FALSE | 1.20 | 1.42E−19 |
| 2598261 | FN1 | TRUE | TRUE | FALSE | 1.31 | 3.25E−19 |
| 2936857 | LOC730031 | TRUE | TRUE | TRUE | 1.12 | 5.16E−19 |
| 2936857 | MLLT4 | TRUE | TRUE | TRUE | 1.12 | 5.16E−19 |
| 3666366 | CDH3 | TRUE | TRUE | TRUE | 1.48 | 6.10E−19 |
| 3757108 | KRT19 | TRUE | TRUE | FALSE | 1.41 | 6.20E−19 |
| 3451375 | PRICKLE1 | FALSE | TRUE | TRUE | 1.42 | 8.79E−19 |
| 3338552 | CTTN | TRUE | TRUE | TRUE | 1.10 | 9.53E−19 |
| 2680046 | ADAMTS9 | TRUE | TRUE | FALSE | 1.40 | 1.06E−18 |
| 3867458 | PLEKHA4 | TRUE | TRUE | FALSE | 1.35 | 1.50E−18 |
| 3494629 | SCEL | TRUE | TRUE | FALSE | 1.39 | 1.57E−18 |
| 3978943 | KLF8 | TRUE | TRUE | FALSE | 1.35 | 3.66E−18 |
| 2397025 | DHRS3 | TRUE | TRUE | FALSE | 1.22 | 3.89E−18 |
| 3420316 | HMGA2 | TRUE | TRUE | TRUE | 1.48 | 4.63E−18 |
| 3126368 | PSD3 | TRUE | TRUE | FALSE | 1.19 | 5.77E−18 |
| 2809245 | ITGA2 | TRUE | TRUE | FALSE | 1.45 | 6.16E−18 |
| 2526806 | FN1 | TRUE | TRUE | TRUE | 1.19 | 7.55E−18 |
| 2827645 | SLC27A6 | FALSE | TRUE | FALSE | 1.49 | 8.33E−18 |
| 3217361 | ANKS6 | TRUE | TRUE | FALSE | 1.19 | 8.37E−18 |
| 3743551 | CLDN7 | TRUE | TRUE | FALSE | 1.07 | 1.80E−17 |
| 3571904 | NPC2 | FALSE | TRUE | FALSE | 0.99 | 2.53E−17 |
| 3571904 | TMEM90A | FALSE | TRUE | FALSE | 0.99 | 2.53E−17 |
| 2558612 | TGFA | TRUE | TRUE | FALSE | 1.35 | 2.71E−17 |
| 3987607 | CCDC121 | TRUE | TRUE | FALSE | 1.46 | 3.28E−17 |
| 3987607 | ZCCHC16 | TRUE | TRUE | FALSE | 1.46 | 3.28E−17 |
| 3088213 | SH2D4A | TRUE | TRUE | FALSE | 1.18 | 5.07E−17 |
| 3751002 | RAB34 | TRUE | TRUE | FALSE | 1.19 | 5.77E−17 |
| 3973891 | CXorf27 | TRUE | TRUE | FALSE | 1.52 | 6.03E−17 |
| 3973891 | SYTL5 | TRUE | TRUE | FALSE | 1.52 | 6.03E−17 |
| 3044072 | NOD1 | TRUE | TRUE | TRUE | 1.45 | 6.85E−17 |
| 2370123 | XPR1 | TRUE | TRUE | FALSE | 1.26 | 7.13E−17 |
| 3174816 | ANXA1 | FALSE | TRUE | TRUE | 1.08 | 7.85E−17 |
| 2966193 | C6orf168 | TRUE | TRUE | FALSE | 1.37 | 1.01E−16 |
| 2525533 | LOC648149 | TRUE | TRUE | FALSE | 1.24 | 1.02E−16 |
| 2525533 | MAP2 | TRUE | TRUE | FALSE | 1.24 | 1.02E−16 |
| 3154002 | KCNQ3 | TRUE | TRUE | FALSE | 1.41 | 1.09E−16 |
| 3590164 | SPINT1 | TRUE | TRUE | FALSE | 1.17 | 1.35E−16 |
| 3329343 | MDK | TRUE | TRUE | TRUE | 1.28 | 1.58E−16 |
| 2875193 | P4HA2 | TRUE | TRUE | FALSE | 1.10 | 1.80E−16 |
| 3726691 | ABCC3 | TRUE | TRUE | FALSE | 1.17 | 1.86E−16 |
| 2451870 | ETNK2 | TRUE | TRUE | TRUE | 1.33 | 1.91E−16 |
| 4018327 | TRPC5 | TRUE | TRUE | TRUE | 1.48 | 2.43E−16 |
| 3046197 | ELMO1 | TRUE | TRUE | TRUE | −1.26 | 2.80E−16 |
| 2460817 | SIPA1L2 | TRUE | TRUE | TRUE | 1.17 | 3.16E−16 |
| 3976341 | TIMP1 | TRUE | TRUE | TRUE | 1.15 | 3.39E−16 |

TABLE 5-continued

Trident Analysis
This benign vs. malignant analysis resulted in 210 unique TCIDs, currently mapping to 237 genes. These genes represent the union of three statistically significant sub-analyses (Repeatable, Bayes, and Tissue) using a single dataset.

| TCID | Gene Symbol (Affy v.na29) | Repeatable | Bayes | Tissue | DE | P value |
|---|---|---|---|---|---|---|
| 2973232 | C6orf174 | TRUE | TRUE | FALSE | 1.42 | 3.78E-16 |
| 2973232 | KIAA0408 | TRUE | TRUE | FALSE | 1.42 | 3.78E-16 |
| 3417809 | NAB2 | TRUE | TRUE | FALSE | 1.25 | 5.50E-16 |
| 2751936 | GALNT7 | TRUE | TRUE | FALSE | 1.17 | 5.95E-16 |
| 2648535 | SGEF | TRUE | FALSE | FALSE | 1.16 | 1.33E-15 |
| 3759587 | LOC100129115 | TRUE | TRUE | FALSE | 1.34 | 1.47E-15 |
| 3759587 | PLCD3 | TRUE | TRUE | FALSE | 1.34 | 1.47E-15 |
| 3994710 | MAMLD1 | FALSE | TRUE | FALSE | 1.37 | 1.80E-15 |
| 3581221 | AHNAK2 | TRUE | TRUE | FALSE | 1.31 | 2.29E-15 |
| 3259253 | C10orf131 | FALSE | TRUE | TRUE | 1.01 | 4.17E-15 |
| 3259253 | ENTPD1 | FALSE | TRUE | TRUE | 1.01 | 4.17E-15 |
| 2562435 | EDNRB | FALSE | TRUE | FALSE | 1.37 | 5.28E-15 |
| 2562435 | SFTPB | FALSE | TRUE | FALSE | 1.37 | 5.28E-15 |
| 3489138 | CYSLTR2 | TRUE | TRUE | TRUE | 1.30 | 5.69E-15 |
| 3002640 | EGFR | TRUE | TRUE | TRUE | 1.11 | 8.20E-15 |
| 2578790 | LRP1B | FALSE | TRUE | FALSE | -0.95 | 1.06E-14 |
| 3768535 | FAM20A | FALSE | TRUE | FALSE | 1.25 | 1.11E-14 |
| 3044129 | GGCT | TRUE | TRUE | FALSE | 1.11 | 1.12E-14 |
| 2980449 | IPCEF1 | TRUE | TRUE | TRUE | -1.14 | 1.29E-14 |
| 4018454 | AMOT | TRUE | TRUE | FALSE | 1.34 | 1.47E-14 |
| 3763390 | TMEM100 | TRUE | TRUE | TRUE | 1.40 | 2.44E-14 |
| 2740067 | ANK2 | FALSE | TRUE | TRUE | -0.89 | 2.57E-14 |
| 3622934 | MYEF2 | TRUE | TRUE | TRUE | 1.03 | 4.13E-14 |
| 3622934 | SLC24A5 | TRUE | TRUE | TRUE | 1.03 | 4.13E-14 |
| 2414958 | TACSTD2 | FALSE | TRUE | FALSE | 1.29 | 5.50E-14 |
| 3321150 | ARNTL | TRUE | TRUE | TRUE | 1.18 | 7.68E-14 |
| 3464860 | DUSP6 | TRUE | TRUE | FALSE | 1.10 | 1.17E-13 |
| 3464860 | LOC100131490 | TRUE | TRUE | FALSE | 1.10 | 1.17E-13 |
| 3217242 | GABBR2 | TRUE | TRUE | TRUE | 1.21 | 1.22E-13 |
| 3110608 | TM7SF4 | TRUE | TRUE | TRUE | 1.23 | 2.16E-13 |
| 3110395 | RIMS2 | TRUE | TRUE | FALSE | 1.13 | 2.54E-13 |
| 3649714 | C16orf45 | TRUE | TRUE | FALSE | 1.10 | 7.74E-13 |
| 3867264 | CA11 | TRUE | TRUE | FALSE | 1.05 | 8.23E-13 |
| 3832280 | C19orf33 | TRUE | TRUE | FALSE | 1.20 | 8.77E-13 |
| 3832280 | YIF1B | TRUE | TRUE | FALSE | 1.20 | 8.77E-13 |
| 2452440 | KLHDC8A | TRUE | TRUE | FALSE | 1.08 | 1.39E-12 |
| 2608469 | ITPR1 | TRUE | TRUE | TRUE | -1.10 | 1.71E-12 |
| 3577612 | SERPINA1 | FALSE | TRUE | FALSE | 0.96 | 2.24E-12 |
| 3577612 | SERPINA2 | FALSE | TRUE | FALSE | 0.96 | 2.24E-12 |
| 4015548 | XKRX | TRUE | TRUE | FALSE | 1.12 | 2.68E-12 |
| 3451814 | MAFG | FALSE | TRUE | TRUE | 1.04 | 2.91E-12 |
| 3451814 | NELL2 | FALSE | TRUE | TRUE | 1.04 | 2.91E-12 |
| 2734421 | ARHGAP24 | FALSE | TRUE | FALSE | -1.05 | 3.17E-12 |
| 2816298 | IQGAP2 | TRUE | TRUE | FALSE | -1.10 | 5.75E-12 |
| 2524301 | NRP2 | FALSE | TRUE | FALSE | 0.93 | 7.41E-12 |
| 3132616 | ZMAT4 | FALSE | TRUE | TRUE | -0.89 | 1.03E-11 |
| 3365136 | SERGEF | FALSE | TRUE | TRUE | 0.98 | 1.04E-11 |
| 3367673 | MPPED2 | FALSE | TRUE | FALSE | -0.95 | 1.18E-11 |
| 2608309 | LRRN1 | FALSE | FALSE | TRUE | 0.84 | 1.66E-11 |
| 2820925 | RHOBTB3 | FALSE | TRUE | TRUE | 0.85 | 2.73E-11 |
| 3369931 | RAG2 | FALSE | TRUE | TRUE | -0.75 | 3.90E-11 |
| 2708922 | IGF2BP2 | FALSE | TRUE | TRUE | 0.90 | 5.15E-11 |
| 3868783 | KLK7 | TRUE | TRUE | TRUE | 1.19 | 7.94E-11 |
| 3006572 | AUTS2 | TRUE | TRUE | FALSE | 1.06 | 1.02E-10 |
| 3411810 | PDZRN4 | TRUE | TRUE | FALSE | 1.20 | 1.21E-10 |
| 2876897 | SPOCK1 | TRUE | FALSE | FALSE | 1.05 | 1.39E-10 |
| 3166644 | TMEM215 | FALSE | FALSE | TRUE | 0.98 | 1.49E-10 |
| 3933536 | TFF3 | FALSE | TRUE | FALSE | -0.80 | 2.50E-10 |
| 3159330 | DOCK8 | FALSE | TRUE | TRUE | -0.90 | 2.53E-10 |
| 3279058 | ACBD7 | FALSE | TRUE | TRUE | 1.03 | 2.83E-10 |
| 3593931 | GLDN | TRUE | TRUE | FALSE | 1.13 | 3.46E-10 |
| 3404030 | KLRG1 | FALSE | TRUE | TRUE | -0.88 | 5.39E-10 |
| 2373842 | PTPRC | FALSE | FALSE | TRUE | -0.90 | 9.75E-10 |
| 3010503 | CD36 | FALSE | TRUE | TRUE | -0.81 | 3.46E-09 |
| 2583374 | PLA2R1 | FALSE | TRUE | TRUE | -0.72 | 6.14E-09 |
| 3856646 | ZNF208 | FALSE | FALSE | TRUE | 0.77 | 6.91E-09 |
| 3692999 | MT1G | FALSE | TRUE | TRUE | -0.82 | 1.01E-08 |
| 2587790 | GPR155 | FALSE | TRUE | TRUE | -0.86 | 1.12E-08 |
| 2362351 | PYHIN1 | FALSE | FALSE | TRUE | -0.76 | 1.46E-08 |
| 2727587 | KIT | FALSE | TRUE | FALSE | -0.75 | 1.50E-08 |
| 2427619 | KCNA3 | FALSE | FALSE | TRUE | -0.78 | 1.50E-08 |
| 3142381 | FABP4 | FALSE | TRUE | FALSE | -0.72 | 1.82E-08 |

TABLE 5-continued

Trident Analysis
This benign vs. malignant analysis resulted in 210 unique TCIDs, currently mapping
to 237 genes. These genes represent the union of three statistically significant
sub-analyses (Repeatable, Bayes, and Tissue) using a single dataset.

| TCID | Gene Symbol (Affy v.na29) | Repeatable | Bayes | Tissue | DE | P value |
| --- | --- | --- | --- | --- | --- | --- |
| 2584018 | DPP4 | FALSE | TRUE | TRUE | 0.78 | 2.22E−08 |
| 2387126 | RYR2 | FALSE | TRUE | TRUE | −0.64 | 2.26E−08 |
| 2823880 | CAMK4 | FALSE | FALSE | TRUE | −0.72 | 2.67E−08 |
| 3410384 | C12orf35 | FALSE | FALSE | TRUE | −0.78 | 2.74E−08 |
| 2466554 | TPO | FALSE | TRUE | FALSE | −0.77 | 5.30E−08 |
| 2806468 | IL7R | FALSE | FALSE | TRUE | −0.78 | 1.04E−07 |
| 2730746 | SLC4A4 | FALSE | TRUE | TRUE | −0.73 | 1.12E−07 |
| 3467949 | SLC5A8 | FALSE | FALSE | TRUE | −0.74 | 1.23E−07 |
| 2518272 | CERKL | FALSE | FALSE | TRUE | −0.74 | 1.58E−07 |
| 2518272 | ITGA4 | FALSE | FALSE | TRUE | −0.74 | 1.58E−07 |
| 3450861 | ABCD2 | FALSE | FALSE | TRUE | −0.66 | 1.63E−07 |
| 3389450 | CARD16 | FALSE | FALSE | TRUE | −0.78 | 1.66E−07 |
| 3389450 | CASP1 | FALSE | FALSE | TRUE | −0.78 | 1.66E−07 |
| 2657831 | IL1RAP | FALSE | TRUE | FALSE | 0.78 | 1.85E−07 |
| 3059667 | SEMA3D | FALSE | TRUE | TRUE | −0.71 | 2.04E−07 |
| 4013460 | CYSLTR1 | FALSE | FALSE | TRUE | −0.71 | 2.12E−07 |
| 3126504 | CSGALNACT1 | FALSE | TRUE | TRUE | −0.65 | 2.29E−07 |
| 3811339 | BCL2 | FALSE | TRUE | TRUE | −0.76 | 2.29E−07 |
| 2724671 | RHOH | FALSE | FALSE | TRUE | −0.69 | 2.37E−07 |
| 3160895 | JAK2 | FALSE | FALSE | TRUE | −0.74 | 2.48E−07 |
| 2486811 | PLEK | FALSE | FALSE | TRUE | −0.75 | 2.66E−07 |
| 3443804 | KLRB1 | FALSE | FALSE | TRUE | −0.73 | 2.84E−07 |
| 3576704 | TC2N | FALSE | TRUE | TRUE | −0.74 | 3.29E−07 |
| 3742627 | C17orf87 | FALSE | FALSE | TRUE | −0.70 | 4.80E−07 |
| 3347658 | ATM | FALSE | FALSE | TRUE | −0.65 | 4.89E−07 |
| 3347658 | NPAT | FALSE | FALSE | TRUE | −0.65 | 4.89E−07 |
| 2815220 | TMEM171 | FALSE | FALSE | TRUE | −0.60 | 5.00E−07 |
| 3960174 | LGALS2 | FALSE | FALSE | TRUE | −0.70 | 5.58E−07 |
| 2462329 | ERO1LB | FALSE | TRUE | TRUE | −0.67 | 6.74E−07 |
| 2608725 | BHLHE40 | FALSE | TRUE | TRUE | 0.72 | 8.08E−07 |
| 3389353 | CARD17 | FALSE | FALSE | TRUE | −0.72 | 1.09E−06 |
| 3389353 | CASP1 | FALSE | FALSE | TRUE | −0.72 | 1.09E−06 |
| 3062082 | PDK4 | FALSE | FALSE | TRUE | 0.67 | 1.22E−06 |
| 2593159 | STK17B | FALSE | FALSE | TRUE | −0.65 | 1.88E−06 |
| 2353669 | CD2 | FALSE | FALSE | TRUE | −0.67 | 2.06E−06 |
| 2428796 | PTPN22 | FALSE | FALSE | TRUE | −0.66 | 2.70E−06 |
| 2422035 | GBP5 | FALSE | FALSE | TRUE | −0.69 | 3.37E−06 |
| 2766289 | TMEM156 | FALSE | FALSE | TRUE | −0.57 | 4.55E−06 |
| 3060450 | C7orf62 | FALSE | FALSE | TRUE | −0.61 | 5.81E−06 |
| 2439554 | AIM2 | FALSE | FALSE | TRUE | −0.60 | 6.78E−06 |
| 3443891 | CLEC2B | FALSE | FALSE | TRUE | −0.58 | 3.51E−05 |
| 2766192 | TLR10 | FALSE | FALSE | TRUE | −0.51 | 3.87E−05 |
| 3536706 | LGALS3 | FALSE | TRUE | FALSE | 0.52 | 4.67E−05 |
| 3009838 | CCDC146 | FALSE | FALSE | TRUE | −0.56 | 7.30E−05 |
| 3009838 | POLR2J4 | FALSE | FALSE | TRUE | −0.56 | 7.30E−05 |
| 2412312 | TTC39A | FALSE | FALSE | TRUE | 0.51 | 7.45E−05 |
| 2548699 | CYP1B1 | FALSE | TRUE | FALSE | 0.49 | 3.52E−04 |
| 3443868 | CD69 | FALSE | FALSE | TRUE | −0.47 | 4.85E−04 |
| 3461981 | TSPAN8 | FALSE | FALSE | TRUE | −0.44 | 7.33E−04 |
| 3648391 | TNFRSF17 | FALSE | FALSE | TRUE | −0.44 | 7.66E−04 |
| 3018605 | SLC26A4 | FALSE | TRUE | TRUE | −0.46 | 9.81E−04 |
| 3107828 | PLEKHF2 | FALSE | FALSE | TRUE | −0.42 | 1.19E−03 |
| 2372812 | RGS13 | FALSE | FALSE | TRUE | −0.38 | 1.66E−03 |
| 3197955 | GLDC | FALSE | FALSE | TRUE | −0.37 | 5.51E−03 |
| 2796995 | SORBS2 | FALSE | FALSE | TRUE | −0.32 | 1.01E−02 |
| 3135567 | LYPLA1 | FALSE | FALSE | TRUE | −0.32 | 1.78E−02 |
| 2732508 | CXCL13 | FALSE | FALSE | TRUE | −0.30 | 1.94E−02 |
| 3200982 | MLLT3 | FALSE | FALSE | TRUE | −0.30 | 2.03E−02 |
| 2735027 | SPP1 | FALSE | FALSE | TRUE | 0.25 | 6.47E−02 |
| 2554018 | EFEMP1 | FALSE | FALSE | TRUE | −0.20 | 1.55E−01 |
| 2945882 | CMAH | FALSE | FALSE | TRUE | −0.21 | 1.65E−01 |
| 2767378 | ATP8A1 | FALSE | FALSE | TRUE | 0.20 | 1.79E−01 |
| 4016193 | TMSB15A | FALSE | FALSE | TRUE | −0.16 | 2.27E−01 |
| 4016193 | TMSB15B | FALSE | FALSE | TRUE | −0.16 | 2.27E−01 |
| 3019158 | LRRN3 | FALSE | FALSE | TRUE | 0.16 | 2.57E−01 |
| 2700244 | CP | FALSE | FALSE | TRUE | 0.12 | 4.37E−01 |
| 2700244 | HPS3 | FALSE | FALSE | TRUE | 0.12 | 4.37E−01 |
| 2855285 | CCDC152 | FALSE | FALSE | TRUE | −0.10 | 4.49E−01 |
| 2855285 | SEPP1 | FALSE | FALSE | TRUE | −0.10 | 4.49E−01 |
| 2773947 | CXCL9 | FALSE | FALSE | TRUE | −0.10 | 4.56E−01 |

TABLE 5-continued

Trident Analysis
This benign vs. malignant analysis resulted in 210 unique TCIDs, currently mapping to 237 genes. These genes represent the union of three statistically significant sub-analyses (Repeatable, Bayes, and Tissue) using a single dataset.

| TCID | Gene Symbol (Affy v.na29) | Repeatable | Bayes | Tissue | DE | P value |
|---|---|---|---|---|---|---|
| 3108226 | PGCP | FALSE | TRUE | TRUE | 0.04 | 7.65E−01 |
| 2773972 | CXCL11 | FALSE | FALSE | TRUE | 0.02 | 8.93E−01 |

Algorithms for Disease Diagnostics

The goal of algorithm development is to extract biological information from high-dimensional transcription data in order to accurately classify benign vs. malignant biopsies. In some embodiments, disclosed herein is a molecular classifier algorithm, which combines the process of upfront pre-processing of exon data, followed by exploratory analysis, technical factor removal (when necessary), feature (i.e. marker or gene) selection, classification, and finally, performance measurements. Other embodiments also describe the process of cross-validation within and outside the feature selection loop as well as an iterative gene selection method algorithm to combine three analytical methods of marker extraction (tissue, Bayesian, repeatability).

The nature of the training set represents the biggest obstacle to the creation of a robust classifier. Often, a given clinical cohort is limited by the prevalence of disease subtypes that are represented, and/or there is no clear phenotypic, biological, and/or molecular distinction between disease subtypes. Theoretically, the training set can be improved by increasing the number and nature of samples in a prospective clinical cohort, however this approach is not always feasible. Joining of multiple datasets to increase the overall size of the cohort used for training the classifier can be accompanied by analytical challenges and experimental bias.

In one aspect, the present invention overcomes limitations in the current art by joining multiple datasets and applying a technical factor removal normalization approach to the datasets either prior to and/or during classification. In another aspect, the present invention provides methods for gene selection. In another aspect, the present invention introduces a novel ROC-based method for obtaining more accurate subtype-specific classification error rates. Multiple datasets belonging to distinct experiments can be combined and analyzed together. This increases the number of samples available for model training and the overall accuracy of the predictive algorithm.

1. Quality Control

Affymetrix Power Tools (APT, version 1.10.2) software can be used to process, normalize and summarize output (post-hybridization) microarray data (.CEL) files. Quantile normalization, detection above background (DABG), and robust multichip average (RMA) determination of AIX can be done using APT, a program that has been written and streamlined for the automatic processing of post-hybridization data. This automated processing script produces a probeset-level intensity matrix and a gene-level intensity matrix. DABG can be computed as the fraction of probes having smaller than $p<1e-4$ when compared with background probes of the similar GC content (Affymetrix). Accurate classification may be encumbered by a variety of technical factors including failed or suboptimal hybridization. Post-Hybridization QC metrics can be correlated with Pre-Hybridization QC variables to identify the technical factors that may obscure or bias signal intensity.

i. Classification Version

In some embodiments, Classification is used to analyze data in the subject method. The version of the engine used to generate reports at the end of discovery has been tagged as Release-Classification-1.0 in SVN. In one example, the data analyzed by Classification are .CEL files generated from Thyroid Tissue and FNA samples run on Affymetrix Human Exon 1 ST array with NA26 annotations.

In one example, the overall workflow after scanning the microarrays is as follows: output .CEL files→APT Intensity Matrix→pDABG/AUC→remove samples with AUC≤0.73 and DABG≤xPlot→PCAs of each categorical technical factor→Plot variance component as function of each technical factor→Determine if additional samples need to be removed or flagged→Determine if factor needs removal globally or within cross-validation→run classification.

Two common QC metrics used to pass or fail a sample in order to enter it into the molecular classifier are Intron/Exon separation AUC and pDABG or pDET. The threshold for AUC can be, for example, around 0.73. The threshold for pDET (percentage of genes or probe sets that are detected above background) can be adjusted for different data sets as learning continues during marker discovery.

2. Exploratory Analysis

In some embodiments, the present invention utilizes one or more exploratory methods to generate a broad preliminary analysis of the data. These methods are used in order to assess whether technical factors exist in the datasets that may bias downstream analyses. The output from exploratory analyses can be used to flag any suspicious samples, or batch effects. Flagged samples or subsets of samples can then be processed for technical factor removal prior to, and/or during feature selection and classification. Technical factor removal is described in detail in section 3. The methods used for exploratory analyses include but are not limited to:

Principal component analysis (PCA) can be used to assess the effects of various technical factors, such as laboratory processing batches or FNA sample collection media, on the intensity values, To assess the effects of technical factors, the projection of the normalized intensity values to the first few principal components can be visualized in a pair-wise manner, color coded by the values of the technical variable. If a significant number of samples are affected by any given technical factor and the first few principal components show separation according to the factor, this factor can be considered a candidate for computational removal during subsequent phases of analysis.

In addition to PCA visualization, the present invention can utilize analysis of variance (variance components) as a quantitative measure to isolate technical factors that have significant effect on normalized intensity values, Variance decomposition can be achieved by fitting a linear model to the normalized intensity values for each of the genes that passes non-specific filtering criteria. The explanatory variables in the linear model include biological factors as well as technical factors of interest. When categorical technical factors are represented sparsely in the data, combinations of these factors can be explored as explanatory variables in the model to reduce the number of parameters and enable estimation of effect sizes due to individual variables. In one embodiment, once the linear model is fitted for gene n, the omega squared measure ($\omega^2$) is used to provide an unbiased assessment of the effect size for each of the explanatory variables j on the individual gene (Bapat, R. B. (2000). Linear Algebra and Linear Models (Second ed.) Springer):

$$\omega 2 = (S\,S\text{ effect} - df\text{ effect} * M\,S\text{ error})(M\,S\text{ error} + S\,S\text{ total})$$

Figure 23:
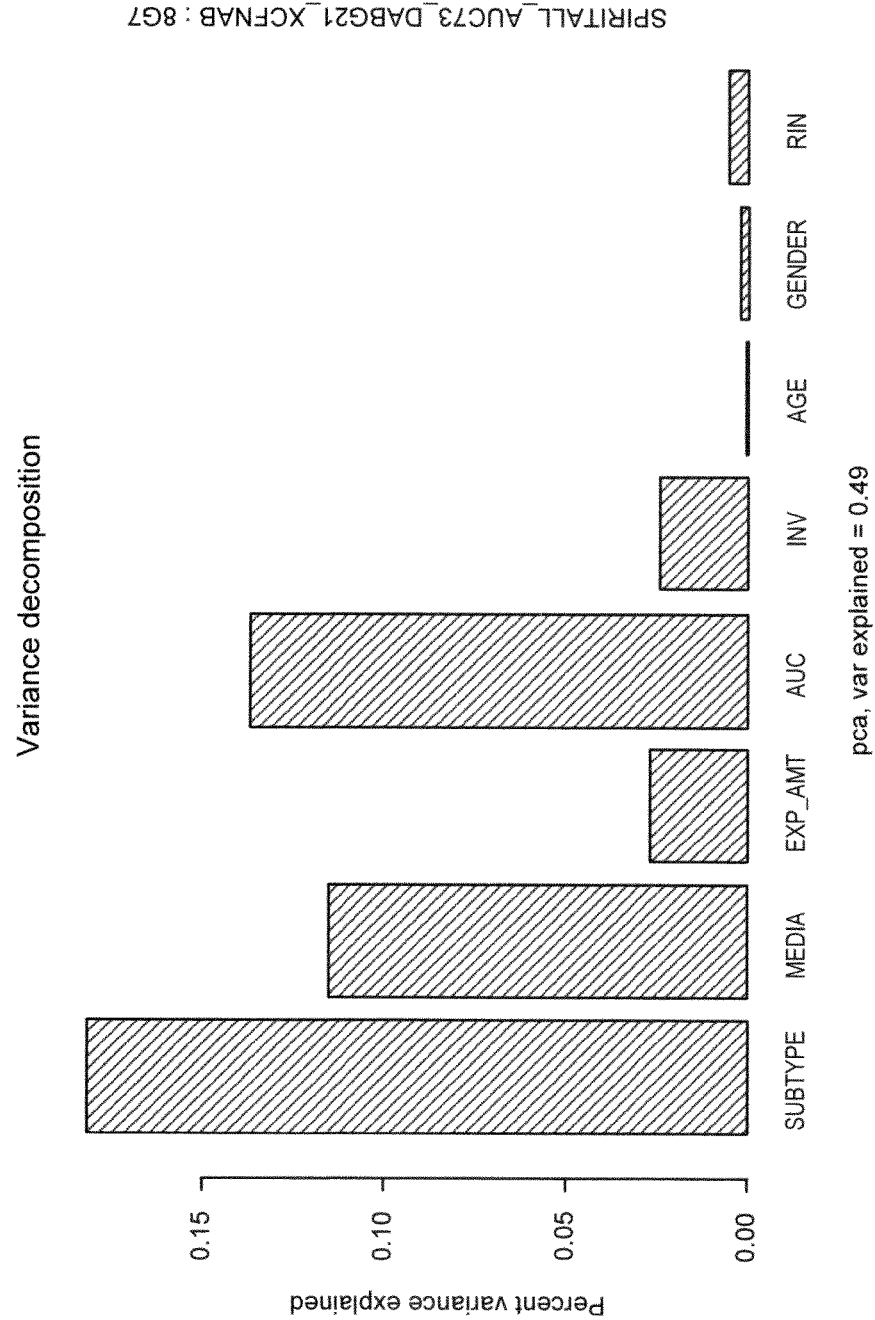
FIG. 23 shows an example of technical factor effects using variance decomposition analysis.
Figure 24:
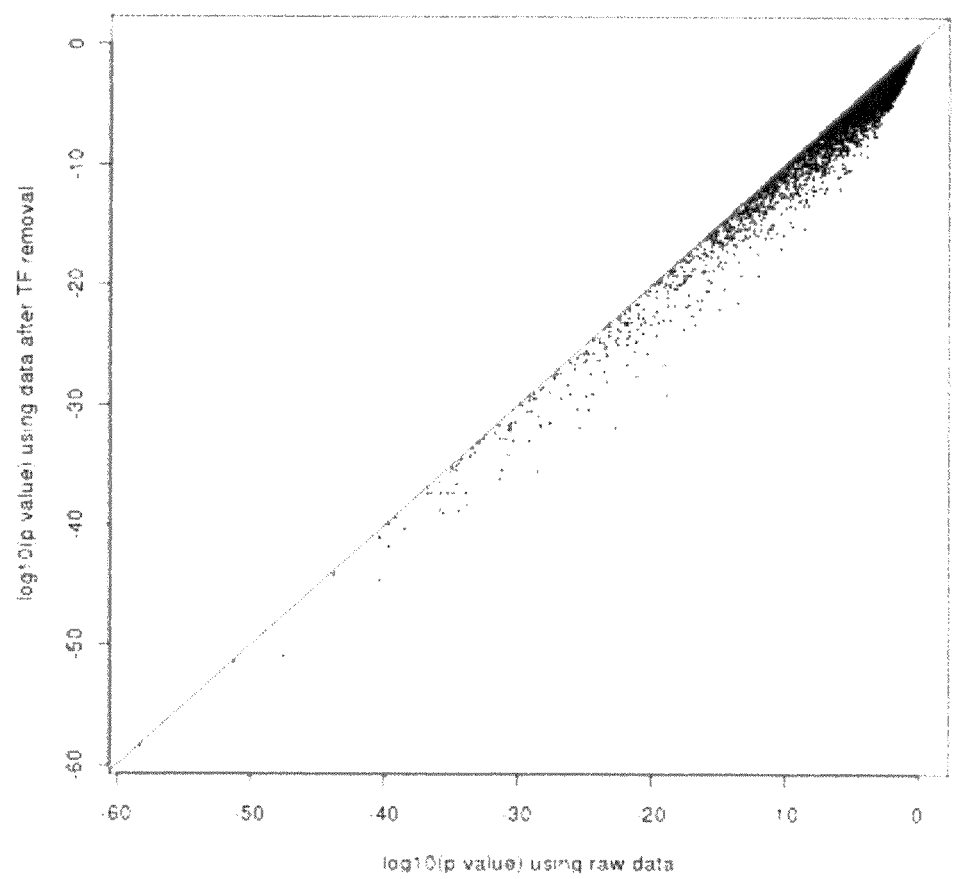
FIG. 24 shows that P-values improve after technical factor removal. In this example the technical factor removed was sample collection fluid. Two chemically distinct fluids were used for sample preservation at the time of collection in the clinic. This technical factor obscured the biological signal present during standard analysis. The 45-degree line in the graph indicates that the p-values calculated from the raw data (log 10 scale) were lower than the p-values calculated after the technical factor removal method was used on the same dataset. P-values become more significant with technical factor removal. Here technical factor is collection fluid. A large number of samples came from another collection fluid and that effect obscures the biological signal present in the markers.

Here $SS_{effect}$ is the sum of squares due to the explanatory variable, MS., is the mean squared error, $SS_{total}$ is the total sum of squares, and $df_{effect}$ is the degrees of freedom associated with a particular variable, To assess average effect size across all genes passing non-specific filtering criteria, average values of $\omega^2$ are calculated across all genes and visualized either as raw effect sizes or proportions of total variance explained. FIG. 23 shows an example plot with average effect sizes assessed across one biological factor (pathology class) and three technical factors (one continuous and categorical). Non-biological explanatory variables with effect sizes greater than or comparable to the biological factors are considered candidates for computational removal as technical factors.

3. Technical Factor Removal

PCA and Variance components can be used to assess the magnitude and significance of the technical variability in the data relative to the biological signal. If it was deemed that technical sources of variability must be removed, then the regression method can be used to remove that effect.

(a) Details on the regression method: In a supervised setting, this method can be used to adjust the probe intensities for variation due to technical reasons (e.g. sample collection media) in the presence of the primary variable of interest (the disease label). Adjustments for technical factors can be made both in gene/feature selection, as well as in feature adjustment necessary for correct classification. For example:

(I) Feature Selection Linear Model:

$$E(y) = \beta 0 + \beta 1\ \beta M + \beta 2 TF1 + \beta 3\ BM*TF2 + \ldots + \varepsilon$$

where TF1 is technical factor 1; and BM is the variable which contains the label 'B' or 'M'. The current call to LIMMA for feature selection would be extended to support the adjustment by technical factors (up to 3) and corresponding 2-way interaction terms with the BM variable, if needed.

Feature Adjustment: The features themselves can be adjusted in the following way:

$$Y - \hat{Y} - X\{\text{circumflex over }(\beta)\}$$

where {circumflex over ($\beta$)} are the estimated coefficients from the terms in the feature selection linear model equation which involve technical factors. In some instances, the model matrix will contain only the variables containing the technical factor and will not contain the column of 1's (the intercept term).

In unsupervised correction, the technical factor (TF) covariate can be used to shift the means between samples of one type (e.g., banked FNA) and those of another (e.g., prospective FNA). A boxplot of all the probe intensities for each sample will show whether such a "shift in means" exists due to known factors of technical variation.

In some embodiments, only if the technical source of variability is simply a global "shift in means" or linear and is not confounded by disease subtype then the regression method in an unsupervised setting will be applied. This would be an unsupervised correction, i.e., no disease labels will be used in the correction step.

In some embodiments, if evidence of technical variability is present in the data, but biological signal overwhelms it, no correction is applied to the data sets. A list of co-variables that can be examined by the subject algorithm is shown in Table 7.

TABLE 7

Technical factors or variables considered in the algorithm

| Variable | Values |
| --- | --- |
| Collection source | OR vs. Clinic |
| Collection method | Banked FNA vs. Prospective FNA |
| Collection media | Trizol vs. RNAProtect |
| RNA RIN | Continuous |
| WTA yield | Continuous |
| ST yield | Continuous |
| Hybridization site | Laboratory 1 vs. Laboratory 2 |
| Hybridization quality (AUC) | Continuous |
| General pathology | Benign vs. Malignant |
| Subtype pathology | LCT, NHP, FA, HA, FC, FVPTC, PTC, MTC |
| Experiment batch | FNA TRIzol 1-4 vs. FNA RNAprotect 1-4 or FNA TRIzol vs. FNA RNAprotect |
| Lab contamination | Dominant peak, band seen, both |

Classification accuracy, sensitivity, specificity, ROC curves, error vs number of markers curves, positive predictive value (PPV) and negative predictive value (NPV) can be reported using these approaches. The methods of the present invention have sensitivity required to detect rare transcripts, which are expressed at a few copies per cell, and to reproducibly detect at least approximately two-fold differences in the expression levels. In some embodiments, the subject methods provide a high sensitivity of detecting gene expression and therefore detecting a genetic disorder or cancer that is greater than 60%, 65%, 70%, 75%, 80%, 85%, 90%, 91%, 92%, 93%, 94%, 95%, 95.5%, 96%, 96.5%, 97%, 97.5%, 98%, 98.5%, 99%, 99.5% or more. Therefore, the sensitivity of detecting and classifying a genetic disorder or cancer is increased. The classification accuracy of the subject methods in classifying genetic disorders or cancers can be greater than 70%, 75%, 80%, 85%, 90%, 91%, 92%, 93%, 94%, 95%, 95.5%, 96%, 96.5%, 97%, 97.5%, 98%, 98.5%, 99%, 99.5% or more. In some embodiments, the subject methods provide a high specificity of detecting and classifying gene expression that is greater than, for example, 80%, 85%, 90%, 91%, 92%, 93%, 94%, 95%, 95.5%, 96%, 96.5%, 97%, 97.5%, 98%, 98.5%, 99%, 99.5% or more. In some embodiments, the nominal specificity is greater than or equal to 70%. The nominal negative predictive value (NPV) is greater than or equal to 95%. In some embodiments, the NPV is about 95%, 95.5%, 96%, 96.5%, 97%, 97.5%, 98%, 98.5%, 99%, 99.5% or more.

In some embodiments, feature selection (gene selection) can also be combined with technical factor removal, Often a variable, such as the sample collection media, provides a distinct shift at the intensity level. If the variable is associated with the disease subtype (Benign vs Malignant) then feature selection can account for this variable (a confounder) in the regression model (LIMMA). The details of accounting for technical factor effects on the intensities in feature selection are described in Section 3 above. Repeatable feature selection can be carried out together with correction/removal of relevant technical factors present in the data set for each regression model applied to the genes.

In cross-validation mode at least two methods can be used, either one at a time, or in succession. The cross-validation methods are K-fold cross-validation and leave-one-out cross-validation (LOOCV). In one embodiment, feature selection (with or without technical factor removal) is incorporated within each loop of cross-validation. This enables the user to obtain unbiased estimates of error rates. Further, feature selection can also be performed within certain classifiers (e.g., random forest) in a multivariate setting. The classifier takes the features selected and the previously built training-set model and makes a classification call (Benign or not Benign) on the test set. This procedure of repeatedly splitting the data into training and test sets and providing a single averaged error rate at the end gives an unbiased error rate in the cross-validation mode, Training and validation data sets can be normalized and processed together (APT, RMA with quantile normalization) including removal of technical factors when necessary. The data can be split into training and validation sets based on specific criteria (e.g., balancing each set by relevant covariate levels).

In several embodiments, algorithm training can be conducted on a sample of surgical tissue, FNA's collected in TRIzol, and/or FNAs collected in RNAProtect. In testing of algorithm performance results, results were obtained where approximately 90% non-benign percent agreement (a.k.a. sensitivity) and 93% benign agreement (a.k.a. specificity) on a select set of samples that pass certain pre- and post-chip metrics.

Training of the algorithm can include feature (i.e. Gene) selection. Each round of training can result in a de novo set of markers, for example, 5, 10, 25, 50, 100, 200, 300 or 500 markers. In one example, comparison of marker lists across the three key discovery training sets (surgical tissue, FNA's collected in TRIzol, and FNAs collected in RNAProtect) revealed a total of 338 non-redundant markers; of these 158 markers are in all three marker lists.

In some embodiments, the exon array platform used in the present invention measures mRNA levels of all known human genes (24,000) and all known transcripts (>200,000). This array is used on every sample run in feasibility (i.e. gene discovery), therefore the algorithm is trained on the full complement of genes at every step. Throughout algorithm training, feature (i.e. gene) selection occurs de novo for every experimental set. Thus, features may be selected from multiple experiments and later combined.

Marker panels can be chosen to accommodate adequate separation of benign from non-benign expression profiles. Training of this multi-dimensional classifier, i.e., algorithm, was performed on over 500 thyroid samples, including>300 thyroid FNAs. Many training/test sets were used to develop the preliminary algorithm. First the overall algorithm error rate is shown as a function of gene number for benign vs non-benign samples. All results are obtained using a support vector machine model which is trained and tested in a cross-validated mode (30-fold) on the samples.

In some embodiments, the difference in gene expression level is at least 10%, 15%, 20%, 25%, 30%, 35%, 40%, 45% or 50% or more. In some embodiments, the difference in gene expression level is at least 2, 3, 4, 5, 6, 7, 8, 9, 10 fold or more. In some embodiments, the biological sample is identified as cancerous with an accuracy of greater than 75%, 80%, 85%, 90%, 95%, 99% or more. In some embodiments, the biological sample is identified as cancerous with a sensitivity of greater than 95%. In some embodiments, the biological sample is identified as cancerous with a specificity of greater than 95%. In some embodiments, the biological sample is identified as cancerous with a sensitivity of greater than 95% and a specificity of greater than 95%. In some embodiments, the accuracy is calculated using a trained algorithm.

In some embodiments of the present invention, results are classified using a trained algorithm. Trained algorithms of the present invention include algorithms that have been developed using a reference set of known malignant, benign, and normal samples. The classification scheme using the algorithms of the present invention is shown in FIG. 23. Algorithms suitable for categorization of samples include but are not limited to k-nearest neighbor algorithms, concept vector algorithms, naive bayesian algorithms, neural network algorithms, hidden markov model algorithms, genetic algorithms, and mutual information feature selection algorithms or any combination thereof. In some cases, trained algorithms of the present invention may incorporate data other than gene expression or alternative splicing data such as but not limited to scoring or diagnosis by cytologists or pathologists of the present invention, information provided by the pre-classifier algorithm of the present invention, or information about the medical history of the subject of the present invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for processing or analyzing a sample of tissue of a subject comprising:
   (a) obtaining said sample of tissue of said subject, wherein said subject has or is suspected of having a thyroid cancer, and wherein said sample of tissue comprises gene expression products;
   (b) subjecting a first portion of said sample of tissue to cytological testing that indicates that said first portion of said sample of tissue is indeterminate;
   (c) upon identifying said first portion of said sample of tissue as indeterminate, assaying by sequencing, array hybridization, or nucleic acid amplification, said gene expression products from a second portion of said sample of tissue, to yield a data set including data corresponding to levels of said gene expression products, wherein said data does not include a plurality of technical factor variables;
   (d) in a programmed computer, inputting said data including said levels of said gene expression products from (c) to a trained algorithm to generate a classification of said sample of tissue as positive or negative for said thyroid cancer at an accuracy of at least 90%; and
   (e) electronically outputting a report that identifies said classification of said sample of tissue as positive or negative for said thyroid cancer.

2. The method of claim 1, wherein said gene expression products include messenger ribonucleic acid (mRNA).

3. The method of claim 2, wherein said mRNA has a ribonucleic acid integrity number (RIN) of 2.0 or more.

4. The method of claim 2, wherein a portion of said mRNA is used for multi-gene microarray analysis, and wherein said sample of tissue has an RIN of equal to or less than 5.0.

5. The method of claim 1, wherein said assaying comprises using one or more of the following: microarray, SAGE, blotting, reverse transcriptase polymerase chain reaction (PCR), or quantitative PCR.

6. The method of claim 1, wherein said trained algorithm is trained with multiple datasets of levels of gene expression products obtained from a plurality of training samples.

7. The method of claim 1, wherein said sample of tissue has a benign condition, and wherein said trained algorithm does not classify said sample of tissue as positive for said thyroid cancer.

8. The method of claim 1, wherein said sample of tissue has a malignant condition, and wherein said trained algorithm classifies said sample of tissue as positive for said thyroid cancer.

9. The method of claim 1, wherein said trained algorithm generates said classification at an accuracy of at least about 90% for at least two subtypes of said thyroid cancer.

10. The method of claim 9, wherein said trained algorithm generates said classification at a specificity of at least about 80%.

11. The method of claim 10, wherein said trained algorithm generates said classification at a specificity of at least about 90%.

12. The method of claim 1, wherein said trained algorithm generates said classification at a sensitivity of at least about 70%.

13. The method of claim 12, wherein said trained algorithm generates said classification at a sensitivity of at least about 80%.

14. The method of claim 1, wherein said trained algorithm is trained for a subset of genes corresponding to said gene expression products.

15. The method of claim 1, wherein said gene expression products are selected based on a plurality of technical factor variables.

16. The method of claim 1, wherein said sample of tissue is a sample of thyroid tissue.

17. The method of claim 16, wherein, (i) when said classification identifies said sample of thyroid tissue as negative for said thyroid cancer, obtaining another sample of thyroid tissue from said subject and repeating (b)-(e) to monitor a change over time in said levels of said gene expression products, or (ii) when said classification identifies said sample of thyroid tissue as positive for said thyroid cancer, treating said subject by a thyroidectomy.

18. The method of claim 1, wherein said trained algorithm is trained with a training set comprising cytologically indeterminate samples.

19. The method of claim 1, wherein said trained algorithm is trained with a training set comprising fine needle aspirate (FNA) samples.

20. The method of claim 19, wherein said training set comprises greater than 300 FNA samples.

21. The method of claim 19, wherein said training set comprises surgical biopsy samples.

22. The method of claim 1, wherein said first portion is different from said second portion.

23. The method of claim 1, further comprising, upon identifying said first portion of said sample of tissue as indeterminate, (i) identifying one or more variants in a third portion of said sample of tissue, and (ii) using said one or more variants and said levels of said gene expression products to generate said classification of said sample of tissue as positive or negative for said thyroid cancer at an accuracy of at least 90%.

24. The method of claim 23, wherein said third portion is the same as said second portion.

25. The method of claim 1, wherein said gene expression products comprise micro ribonucleic acid (microRNA).

26. The method of claim 25, wherein said gene expression products comprise a plurality of microRNAs.

27. The method of claim 1, wherein (c) comprises processing said gene expression products to generate complementary deoxyribonucleic acid (cDNA) molecules, and sequencing said cDNA molecules to yield said data corresponding to said levels of said gene expression products.

28. The method of claim 1, further comprising processing said data to remove said plurality of technical factor variables, thereby yielding said data that does not include said plurality of technical factor variables.

29. The method of claim 28, wherein said plurality of technical factor variables includes one or more members selected from the group consisting of: collection source, collection method, collection media, ribonucleic acid integrity number, whole transcriptome amplification yield, sense strand yield, hybridization site, hybridization quality and experiment batch.

* * * * *